US009328154B2

(12) United States Patent
Chilkoti

(10) Patent No.: US 9,328,154 B2
(45) Date of Patent: May 3, 2016

(54) THERAPEUTIC AGENTS COMPRISING FUSIONS OF GROWTH HORMONE AND ELASTIC PEPTIDES

(71) Applicant: Duke University, Durham, NC (US)

(72) Inventor: Ashutosh Chilkoti, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 14/254,660

(22) Filed: Apr. 16, 2014

(65) Prior Publication Data
US 2015/0080306 A1 Mar. 19, 2015

Related U.S. Application Data

(63) Continuation of application No. 12/852,365, filed on Aug. 6, 2010, now Pat. No. 8,841,255, which is a continuation-in-part of application No. 12/493,912, filed on Jun. 29, 2009, now Pat. No. 8,178,495, said application No. 12/852,365 is a continuation-in-part of application No. 12/158,190, filed as application No. PCT/US2006/048572 on Dec. 20, 2006, now Pat. No. 8,334,257.

(60) Provisional application No. 61/076,221, filed on Jun. 27, 2008, provisional application No. 60/751,896, filed on Dec. 20, 2005.

(51) Int. Cl.
| *A61K 38/27* | (2006.01) |
| *A61K 38/17* | (2006.01) |
| *C07K 14/61* | (2006.01) |
| *C07K 14/00* | (2006.01) |
| *A61K 38/48* | (2006.01) |
| *A61K 45/06* | (2006.01) |
| *A61K 47/48* | (2006.01) |
| *C07K 14/52* | (2006.01) |
| *C07K 14/605* | (2006.01) |
| *C07K 14/62* | (2006.01) |
| *C07K 14/71* | (2006.01) |
| *C07K 14/745* | (2006.01) |
| *C07K 14/78* | (2006.01) |
| *A61K 38/22* | (2006.01) |
| *A61K 38/28* | (2006.01) |
| *A61K 38/00* | (2006.01) |

(52) U.S. Cl.
CPC .............. *C07K 14/61* (2013.01); *A61K 38/2278* (2013.01); *A61K 38/28* (2013.01); *A61K 38/4846* (2013.01); *A61K 45/06* (2013.01); *A61K 47/48246* (2013.01); *A61K 47/48292* (2013.01); *A61K 47/48315* (2013.01); *C07K 14/52* (2013.01); *C07K 14/605* (2013.01); *C07K 14/62* (2013.01); *C07K 14/71* (2013.01); *C07K 14/745* (2013.01); *C07K 14/78* (2013.01); *A61K 38/00* (2013.01); *C07K 2319/31* (2013.01)

(58) Field of Classification Search
None
See application file for complete search history.

(56) References Cited

U.S. PATENT DOCUMENTS

| 4,132,746 A | 1/1979 | Urry et al. |
| 4,187,852 A | 2/1980 | Urry et al. |
| 4,474,851 A | 10/1984 | Urry |
| 4,500,700 A | 2/1985 | Urry |
| 4,589,882 A | 5/1986 | Urry |
| 4,749,647 A | 6/1988 | Thomas et al. |
| 4,752,638 A | 6/1988 | Nowinski et al. |
| 4,783,523 A | 11/1988 | Urry et al. |
| 4,870,055 A | 9/1989 | Urry et al. |
| 4,898,926 A | 2/1990 | Urry |
| 5,147,855 A | 9/1992 | Gozes et al. |
| 5,235,041 A | 8/1993 | Cappello et al. |
| 5,236,904 A | 8/1993 | Gerstenberg et al. |
| 5,243,038 A | 9/1993 | Ferrari et al. |
| 5,288,514 A | 2/1994 | Ellman |
| 5,445,934 A | 8/1995 | Fodor et al. |
| 5,447,912 A | 9/1995 | Gerstenberg et al. |
| 5,496,712 A | 3/1996 | Cappello et al. |
| 5,514,581 A | 5/1996 | Ferrari et al. |
| 5,519,004 A | 5/1996 | Urry |
| 5,520,672 A | 5/1996 | Urry |

(Continued)

FOREIGN PATENT DOCUMENTS

| EP | 0449592 B1 | 11/1994 |
| EP | 0978565 B1 | 10/2006 |

(Continued)

OTHER PUBLICATIONS

AntiThrombin III Deficiency < http://emedicine.medscape.com/article/954688-overview >downloaded Jan. 6, 2010.
Clotting Factor Definition < http://medical-dictionary.thefreedictionary.com/Ciotting+factors > -downloaded Jan. 6, 2012.
"What are Rare Clotting Factor Deficiencies?", published by World Federation of Hemophilia, 2009, pp. 1-29.
Baggio et al., "A Recombinant Human Glucagon-Like Peptide (GLP)-1-Albumin Protein (Albugon) Mimics Peptidergic Activation of GLP-1 Receptor-Dependent Pathways Coupled with Satiety, Gastrointestinal Motility, and Glucose Homeostasis," Diabetes, 53: 2492-2500 (2004).

(Continued)

*Primary Examiner* — Christine J Saoud
*Assistant Examiner* — Jon M Lockard
(74) *Attorney, Agent, or Firm* — Cooley LLP

(57) ABSTRACT

The present invention provides therapeutic agents and compositions comprising elastic peptides and therapeutic proteins. Such peptides exhibit a flexible, extended conformation. In some embodiments, the therapeutic protein is a GLP-1 receptor agonist (e.g., GLP-1, exendin), insulin, or Factor VII/VIIa, including functional analogs. The present invention further provides encoding polynucleotides, as well as methods of making and using the therapeutic agents. The therapeutic agents have improvements in relation to their use as therapeutics, including, inter alia, one or more of half-life, clearance and/or persistance in the body, solubility, and bioavailability.

21 Claims, 33 Drawing Sheets

(56) References Cited

U.S. PATENT DOCUMENTS

| | | | |
|---|---|---|---|
| 5,527,610 A | 6/1996 | Urry | |
| 5,545,617 A | 8/1996 | Dartt et al. | |
| 5,624,711 A | 4/1997 | Sundberg et al. | |
| 5,641,648 A | 6/1997 | Ferrari et al. | |
| 5,646,016 A | 7/1997 | McCoy et al. | |
| 5,681,816 A | 10/1997 | Korman | |
| 5,700,914 A | 12/1997 | Jorgensen et al. | |
| 5,702,717 A | 12/1997 | Cha et al. | |
| 5,747,646 A | 5/1998 | Hakimi et al. | |
| 5,770,570 A | 6/1998 | Paul et al. | |
| 5,770,697 A | 6/1998 | Ferrari et al. | |
| 5,773,249 A | 6/1998 | Cappello et al. | |
| 5,816,259 A | 10/1998 | Rose | |
| 5,830,713 A | 11/1998 | Ferrari et al. | |
| 5,849,535 A | 12/1998 | Cunningham et al. | |
| 5,854,387 A | 12/1998 | Urry et al. | |
| 5,900,405 A | 5/1999 | Urry | |
| 5,958,881 A | 9/1999 | Korman | |
| 5,972,406 A | 10/1999 | Urry et al. | |
| 5,972,883 A | 10/1999 | Gozes et al. | |
| 5,998,588 A | 12/1999 | Hoffman et al. | |
| 6,004,782 A | 12/1999 | Daniell et al. | |
| 6,018,030 A | 1/2000 | Ferrari et al. | |
| 6,037,321 A | 3/2000 | Cox et al. | |
| 6,063,061 A | 5/2000 | Wallace et al. | |
| 6,140,072 A | 10/2000 | Ferrari et al. | |
| 6,153,655 A | 11/2000 | Martinez et al. | |
| 6,184,348 B1 | 2/2001 | Ferrari et al. | |
| 6,200,598 B1 | 3/2001 | Needham | |
| 6,238,916 B1 | 5/2001 | El Halawani | |
| 6,258,562 B1 | 7/2001 | Salfield et al. | |
| 6,328,996 B1 | 12/2001 | Urry | |
| 6,329,209 B1 | 12/2001 | Wagner et al. | |
| 6,355,776 B1 | 3/2002 | Ferrari et al. | |
| 6,380,154 B1 | 4/2002 | Cappello et al. | |
| 6,429,188 B1 | 8/2002 | Perez et al. | |
| 6,503,534 B1 | 1/2003 | Pellet et al. | |
| 6,537,521 B2 | 3/2003 | Uzgiris | |
| 6,541,033 B1 | 4/2003 | Shah | |
| 6,582,926 B1 | 6/2003 | Chilkoti | |
| 6,583,272 B1 | 6/2003 | Bailon | |
| 6,593,394 B1 | 7/2003 | Li et al. | |
| 6,699,294 B2 | 3/2004 | Urry | |
| 6,852,834 B2 | 2/2005 | Chilkoti | |
| 6,998,387 B1 | 2/2006 | Goke et al. | |
| 7,084,243 B2 | 8/2006 | Glaesner et al. | |
| 7,094,755 B2 | 8/2006 | Burman et al. | |
| 7,101,843 B2 | 9/2006 | Glaesner et al. | |
| 7,138,486 B2 | 11/2006 | Habener et al. | |
| 7,141,547 B2 | 11/2006 | Rosen et al. | |
| 7,144,863 B2 | 12/2006 | DeFelippis et al. | |
| 7,176,278 B2 | 2/2007 | Prior | |
| 7,226,910 B2 | 6/2007 | Wilson et al. | |
| 7,232,879 B2 | 6/2007 | Galloway et al. | |
| 7,259,233 B2 | 8/2007 | Dodd et al. | |
| 7,271,149 B2 | 9/2007 | Glaesner et al. | |
| 7,332,473 B2 | 2/2008 | Onoue et al. | |
| 7,364,859 B2 | 4/2008 | Chilkoti | |
| 7,429,458 B2 | 9/2008 | Chilkoti | |
| 7,442,680 B2 | 10/2008 | Yong et al. | |
| 7,459,441 B2 | 12/2008 | Minagawa et al. | |
| 7,468,353 B2 | 12/2008 | Bevec | |
| 7,566,691 B2 | 7/2009 | Nestor | |
| 7,723,472 B2 | 5/2010 | Szoka | |
| 7,776,815 B2 | 8/2010 | Vanderby et al. | |
| 8,178,495 B2 | 5/2012 | Chilkoti | |
| 8,334,257 B2 | 12/2012 | Chilkoti | |
| 8,703,717 B2 * | 4/2014 | Schellenberger et al. | ... 514/21.2 |
| 8,729,018 B2 | 5/2014 | Chilkoti | |
| 8,841,255 B2 | 9/2014 | Chilkoti | |
| 9,127,047 B2 | 9/2015 | Chilkoti | |
| 2001/0034050 A1 | 10/2001 | Chilkoti | |
| 2002/0081309 A1 | 6/2002 | Pettit | |
| 2002/0142964 A1 | 10/2002 | Nissen et al. | |
| 2002/0151458 A1 | 10/2002 | Gomariz et al. | |
| 2003/0059840 A1 | 3/2003 | Chilkoti | |
| 2003/0059841 A1 | 3/2003 | Chilkoti | |
| 2003/0199445 A1 | 10/2003 | Knudsen et al. | |
| 2003/0211094 A1 | 11/2003 | Nelsestuen | |
| 2004/0053370 A1 | 3/2004 | Glaesner | |
| 2004/0063631 A1 | 4/2004 | Block | |
| 2004/0110296 A1 | 6/2004 | Vargeese et al. | |
| 2004/0234609 A1 | 11/2004 | Collier et al. | |
| 2005/0026826 A1 | 2/2005 | Hoenig | |
| 2005/0118109 A1 | 6/2005 | Block et al. | |
| 2005/0203009 A1 | 9/2005 | Pan et al. | |
| 2005/0249730 A1 | 11/2005 | Goetsch et al. | |
| 2005/0255554 A1 | 11/2005 | Chilkoti | |
| 2006/0019347 A1 | 1/2006 | Cho et al. | |
| 2006/0130158 A1 | 6/2006 | Turner | |
| 2006/0247156 A1 | 11/2006 | Vanderby et al. | |
| 2007/0009602 A1 | 1/2007 | Setton et al. | |
| 2008/0108573 A1 | 5/2008 | Duggan | |
| 2008/0207492 A1 | 8/2008 | Polt et al. | |
| 2008/0221041 A1 | 9/2008 | Block et al. | |
| 2008/0261863 A1 | 10/2008 | Whelan et al. | |
| 2008/0274961 A1 | 11/2008 | Bevec | |
| 2008/0318865 A1 | 12/2008 | Juul-Mortensen | |
| 2009/0004104 A1 | 1/2009 | Chilkoti | |
| 2009/0005315 A1 | 1/2009 | Duggan | |
| 2009/0092582 A1 | 4/2009 | Bogin et al. | |
| 2009/0175821 A1 | 7/2009 | Bridon et al. | |
| 2009/0220455 A1 | 9/2009 | Chilkoti | |
| 2009/0227493 A1 | 9/2009 | Nakashima et al. | |
| 2009/0270317 A1 | 10/2009 | Chilkoti | |
| 2010/0016212 A1 | 1/2010 | Rubin et al. | |
| 2010/0022455 A1 | 1/2010 | Chilkoti | |
| 2010/0184651 A1 | 7/2010 | Maithal et al. | |
| 2010/0189643 A1 | 7/2010 | Chilkoti et al. | |
| 2011/0039776 A1 | 2/2011 | Chilkoti | |
| 2011/0123487 A1 | 5/2011 | Chilkoti | |
| 2011/0178017 A1 | 7/2011 | Sadeghi et al. | |
| 2011/0236384 A1 | 9/2011 | Setton et al. | |
| 2013/0005664 A1 | 1/2013 | Chilkoti | |
| 2013/0079277 A1 | 3/2013 | Chilkoti | |
| 2013/0085099 A1 | 4/2013 | Chilkoti | |
| 2013/0085104 A1 | 4/2013 | Chilkoti | |
| 2013/0143802 A1 | 6/2013 | Chilkoti | |
| 2013/0150291 A1 | 6/2013 | Jowett et al. | |
| 2013/0172274 A1 | 7/2013 | Chilkoti | |
| 2013/0178411 A1 | 7/2013 | Chilkoti | |
| 2013/0178416 A1 | 7/2013 | Chilkoti | |
| 2013/0310538 A1 | 11/2013 | Chilkoti | |
| 2014/0024600 A1 | 1/2014 | Chilkoti et al. | |
| 2014/0213516 A1 | 7/2014 | Chilkoti | |
| 2014/0364371 A1 | 12/2014 | Setton et al. | |

FOREIGN PATENT DOCUMENTS

| | | |
|---|---|---|
| EP | 2307038 A4 | 12/2009 |
| JP | 6-206898 A | 7/1994 |
| JP | 2004-528014 A | 9/2004 |
| JP | 2006-503588 A | 2/2006 |
| WO | WO 86/06492 A1 | 11/1986 |
| WO | WO 96/32406 A1 | 10/1996 |
| WO | WO 99/11661 A1 | 3/1999 |
| WO | WO 99/38984 | 5/1999 |
| WO | WO 00/56774 A1 | 9/2000 |
| WO | WO 01/79271 A1 | 10/2002 |
| WO | WO 03/041493 A1 | 5/2003 |
| WO | WO 03/099835 A1 | 12/2003 |
| WO | WO 2004/020454 A2 | 3/2004 |
| WO | WO 2004/104020 A2 | 12/2004 |
| WO | WO 2005/000892 A2 | 1/2005 |
| WO | WO 2006/001806 A2 | 1/2006 |
| WO | WO 2006/078629 A2 | 7/2006 |
| WO | WO 2006/110292 A2 | 10/2006 |
| WO | WO 2007/002362 A2 | 1/2007 |
| WO | WO 2007/039140 A1 | 4/2007 |
| WO | WO 2007/073486 A2 | 6/2007 |
| WO | WO 2007/100535 A2 | 9/2007 |
| WO | WO 2007/103515 A2 | 9/2007 |
| WO | WO 2007/104493 A1 | 9/2007 |
| WO | WO 2008/030968 A2 | 3/2008 |

(56) References Cited

FOREIGN PATENT DOCUMENTS

| WO | WO 2008/141786 A2 | 11/2008 |
|---|---|---|
| WO | WO 2008/155134 A1 | 12/2008 |
| WO | WO 2009/059278 A1 | 5/2009 |
| WO | WO 2009/158704 A2 | 12/2009 |
| WO | WO 2010/042997 A1 | 4/2010 |
| WO | WO 2013/028989 A1 | 2/2013 |

OTHER PUBLICATIONS

Bidwell et al., "Application of thermally responsive polypeptides directed against c-Myc transcriptional function for cancer therapy," Mol. Cancer Ther., 4(7): 1076-1085 (2005).
Chang et al., "Role of Disulfide Bonds in the Structure and Activity of Human Insulin," Mol. Cells., 16(3): 323-330 (2003).
Chen et al., "A new temperature-and pH-responsive copolymer for possible use protein conjugation," Macromol. Chem. Phys., 196: 1251-1259 (1995).
Chen, J.P., et al., "Polymer-protein conjugates, II. Affinity precipitation separation of human immunogammaglobulin by a poly(N-isopropylacrylamide)-protein A conjugate," Biomaterials, 11: 631-634 (1990).
Chilkoti, A. et al., "Targeted drug delivery by thermally responsive polymers," Adv. Drug Deliv. Rev., 54: 613-630 (2002).
Chilkoti, A., "Biomedical Applications of Genetically Encoded Elastin Biopolymers," Abstracts of Papers, 222nd ACS National Meeting, Chicago, IL, US, Aug. 26-30, 2001, MACR-019, see abstract.
Chilkoti, A., et al., "Site-Specific Conjugation of a Temperature-Sensitive Polymer to a Genetically-Engineered Protein," Bioconjugate Chemistry, 5: 504-507 (1994).
Chow et al., "Ultra-High Expression of a Thermally Responsive Recombinant Fusion Protein in *E. coli*," Biotechnol. Prog., 22: 638-646 (2006).
Domschke et al., "Vasoactive intestinal peptide in man: pharmacokinetics, metabolic and circulatory effects," Gut, 19: 1049-1053 (1978).
Dreher et al., "Evaluation of an elastin-like polypeptide-doxorubicin conjugate for cancer therapy," J. Controlled Release, 91: 31-43 (2003).
Dreher et al., "Nitroxide conjugate of a thermally responsive elastin-like polypeptide for noninvasive thermometry," American Association of Physicists in Medicine, Medical Physics, 31(10): 2755-2762 (2004).
EP Application No. 06848713.1, Extended European Search Report dated Nov. 26, 2012, 10 pages.
EP Application No. 07814724.6, Extended European Search Report dated Mar. 4, 2010, 6 pages.
EP Application No. 09771235.0, Extended European Search Report dated Feb. 21, 2013, 6 pages.
EP Application No. 15163709.7, Extended European Search Report, dated Jun. 17, 2015, 8 pages.
Estall and Drucker, "Glucagon and Glucagon-Like Peptide REceptors as Drug Targets," Curr. Pharm. Design, 12(14): 1731-1750 (2006).
Furgeson et al., "Structural optimization of a "smart" doxorubicin-polypeptide conjugate for thermally targeted delivery to solid tumors," J. Control. Rel., 110(2): 362-369 (2005).
Hattori et al., "Intravenous Administration of Thioredoxin Decreases Brain Damage Following Transient Focal Cerebral Ischemia in Mice," Antioxid. Redox Signal. 6:81-87 (2004).
He, X., "Scandium and Albumin" —Definition http://www.springerreference.com/docs/html/chapterdbid/358272.html downloaded Apr. 30, 2013.
Henning and Sawmiller, "Vasoactive intestinal peptide: cardiovascular effect," Cardiovascular Res., 49: 27-37 (2001).
Hoffman, A.S., "Applications of Thermally Reversible Polymers and Hydrogels in Therapeutics and Diagnostics," Journal of Controlled Release, 6: 297-305 (1987).

Holleman, Frits. Regular human insulin [internet]. Aug. 13, 2014; Diapedia 81040961114 rev. No. 9. Available from: http://dx.doi.org/1 0.14496/dia.81 040961114.9—Retrieved Aug. 24, 2015.
Hui et al., "Structure and function studies of glucagon-like peptide-1 (GLP-1): the designing of a novel pharmacological agent for the treatment of diabetes," Diabetes/Metab. Res. Rev., 21(4): 313-331 (2005).
Hyun et al., "Capture and Release of Protein on the Nanoscale by Stimuli-Responsive Elastin-Like Polypeptide Switches", J. Am. Chem. Soc., 126(23): 7330-7335 (2004).
Kim, Jin-Soo et al., "Ribonuclease S-peptide as a carrier in fusion proteins," Protein Science, 2: 348-356 (1993).
Kobatake, Eiry et al., "Design and Gene Engineering Synthesis of an Extremely Thermostable Protein with Biological Activity," Biomacromolecules, 1: 382-386 (2000).
MacArthur and Thornton, "Influence of Proline Residues on Protein Conformation," J. Mol. Biol., 218: 397-412 (1991).
McPherson et al., "Product Purification by Reversible Phase Transition Following *Escherichia coli* Expression of Genes Encoding up to 251 Repeats of the Elastomeric Pentapeptide GVGVP," Protein Expression and Purification, 7: 51-57 (1996).
McPherson, D. et al., "Production and purification of a recombinant elastomeric polypeptide, G-(VPGVG)19-VPGV from *Escherichia coli*," Biotechnol. Prog., 8: 347-352 (1992).
Meyer et al. "Purification of Recombinant Proteins by Fusion with Thermally-Responsive Polypeptides," Nat. Biotechnol., 17: 1112-1115 (1999).
Meyer et al., "Polypeptide Fusion Tag for Thermal Purification of Recombinant Proteins," Abstracts of Papers, 217th ACS National Meeting, Anaheim, CA, US, Mar. 21-25, 1999, BIOT-078, see abstract.
Meyer et al., "Protein Purification by Fusion with an Environmentally Responsive Elastin-Like Polypeptide: Effect of Polypeptide Length on the Purification of Thioredoxin," Biotechnol. Prog., 17: 720-728 (2001).
Meyer, Dan E. et al., "Drug targeting using thermally responsive polymers and local hyperthermia," Journal of Controlled Release, 74: 213-224 (2001).
Meyer, Dan E. et al., "Targeting a Genetically Engineered Elastin-like Polypeptide to Solid Tumors by Local Hypothermia," Cancer Res., 61(4): 1548-1554 (2001).
Mirmira et al., "Importance of the Character and Configuration of Residues B24, B25, and B26 in Insulin-Receptor Interactions," J. Biol. Chem., 266(3): 1428-1436 (1991).
Nath and Chilkoti, "Interfacial Phase Transition of an Environmentally Responsive Elastin Biopolymer Adsorbed on Functionalized Gold Nanoparticles Studied by Colloidal Surface Plasmon Resonance," J. Am. Chem. Soc., 123(34): 8197-8202 (2001).
Ngo et al., "Computational Complexity, Protein Structure Prediction, and the Levinthal Paradox," Chapter 14, pp. 491-495, in The Protein Folding Problem and Tertiary Structure Prediction, Marz, Jr. and LeGrand, Editors, Birkhauser, Boston (1994).
Nilsson, B. et al., "Fusion proteins in biotechnology and structural biology," Curr. Opin. Struct. Biol., 2: 569-575 (1992).
Nilsson, J. et al., "Affinity Fusion Strategies for Detection, Purification and Immobilization of Recombinant Proteins," Protein Expression and Purification, 11: 1-16 (1997).
Önyüksel et al., "Human VIP-α: A long-acting, biocompatible and biodegradable peptide nanomedicine for essential hypertension," Peptides, 27: 2271-2275 (2006).
Önyüksel et al., "A Novel Formulation of VIP in Sterically Stabilized Micelles Amplifies Vasodilation In Vivo," Pharmaceutical Research, 16(1): 155-160 (1999).
PCT/US2007/077767, International Search Report and Written Opinion, mailed Aug. 11, 2008.
PCT/US2007/077767, International Preliminary Report on Patentability, dated Mar. 10, 2009.
PCT/US2006/048572, International Search Report and Written Opinion, mailed May 9, 2008.
PCT/US2006/048572, International Preliminary Report on Patentability, dated Jun. 24, 2008.
PCT/US2009/049059, International Search Report of the International Searching Authority, mailed Nov. 13, 2009, 4 pages.

(56) References Cited

OTHER PUBLICATIONS

PCT/US2009/049059, Written Opinion of the International Searching Authority, mailed Nov. 13, 2009.
PCT/US2009/049059, International Preliminary Report on Patentability, dated Jan. 5, 2011.
Richter et al. "The Impact of Reducing Dose Frequency on Health Outcomes" Clinical Therapeutics (2003), 25(8): 2307-2335.
Rubinstein et al., "Intratracheal and subcutaneous liposomal VIP normalizes arterial pressure in spontaneously hypertensive hamsters," International Journal of Pharmaceutics, 316: 144-147 (2006).
Santi et al., "Predictable and tunable half-life extension of therapeutic agents by controlled chemical release from macromolecular conjugates," Proc. Natl. Acad. Sci. USA, 109(16): 6211-6216 (2012).
Sejourne et al., "Development of a Novel Bioactive Formulation of Vasoactive Intestinal Peptide in Sterically Stabilized Liposomes," Pharmaceutical Research, 14(3): 362-365 (1997).
Sharma and Sharma, "Liposomes in drug delivery: progress and limitations," Int. J. Pharm., 154: 123-140 (1997).
Shimazu, et al, "Thermally triggered purification and immobilization of elastin-OPH fusions", Biotechnol Bioeng., 81(1): 74-79 (2003).
Sojikul et al., "A plant signal peptide-hepatitis B surface antigen fusion protein with enhanced stability and immunogenicity expressed in plant cells", PNAS, vol. 100 No. 5 pp. 2209-2214 (2003).
Simoncsits et al., "Synthesis, cloning and expression in *Escherichia coli* of artificial genes coding for biologically active elongated precursors of the vasoactive intestinal polypeptide," Eur. J. Biochem., 178: 343-350 (1988).
Suzuki, et al., "Encapsulation of VIP into liposomes restores vasorelaxation in hypertension in situ," Am. J. Physiol., 271(40): H282-H287 (1996).
Urry, D.W. et al., "Phase-structure Transitions of the Elastin Polypentapeptide-water system within the framework of composition-temperature studies," Biopolymers, 24: 2345-2346 (1985).
Urry, D.W. et al., "Temperature of Polypeptide Inverse Temperature Transition Depends on Mean Residue Hydrophobicity," J. Am. Chem. Soc., 113: 4346-4348 (1991).
Urry, D.W., "Entropic Elastic Processes in Protein Mechanisms, I. Elastic Structure Due to an Inverse Temperature Transition and Elasticity Due to Internal Chain Dynamics," Journal of Protein Chemistry, 7(1): 1-34 (1988).
Urry, D.W., "Free Energy Transduction in Polypeptides and Proteins Based on Inverse Temperature Transitions," Prog. Biophys. Molec. Biol., 57: 23-57 (1992).
Urry, D.W., "Physical Chemistry of Biological Free Energy Transduction as Demonstrated by Elastic Protein-Based Polymers," J. Phys. Chem. B., 101(51): 11007-11028 (1997).
Walsh, "Therapeutic insulins and their large-scale manufacture," Appl. Microbiol. Biotechnol., 67: 151-159 (2005).
Wells, "Additivity of Mutational Effects in Proteins," Biochem. 29(37):8509-8517 (1990).
Wilmot and Thornton, "Analysis and prediction of the different types of β-turn in proteins", J. Mol. Biol., 203(1): 221-232 (1988).
Yasuda H., et al., "Expression of the small peptide GLP-1 in transgenic plants", Transgenic Res., 14(5): 677-684 (2005).

\* cited by examiner

FIGURE 2B

```
1       aattaatacg actcactata ggggaattgt gagcggataa caattcccct
        ttaattatgc tgagtgatat cccctttaaca ctcgcctatt gttaagggga
        >>...T7 prom....>>

XbaI                                          NdeI
        -+----                                        ---+---
                                                      P1--------
51      ctagaaataa ttttgtttaa ctttaagaag gagatataca tatgcatggc
        gatctttatt aaaacaaatt gaaattcttc ctctatatgt atacgtaccg
                                                      <-------
                                                      m  h  g
                                                      > Ex-4>

----------------------->P2---------------------------
101     gaaggcacct ttaccagcga tctgagcaaa cagatggaag aagaagcggt
        cttccgtgga aatggtcgct agactcgttt gtctaccttc ttcttcgcca
        ----------------P6<----------------------------------
        >..................Ex-4..............................>
           e   g   t   f   t   s   d   l   s   k   q   m   e   e   e   a AscI
                                                       --+-----
        ------------------------------------->P3---------------
151     gcgcctgttt attgaatggc tgaaaaacgg cggcccgagc agcggcgcgc
        cgcggacaaa taacttaccg acttttttgcc gccgggctcg tcgccgcgcg
        ------------------------------P5         <---------
        >....................Ex-4............................>
           v   r   l   f   i   e   w   l   k   n   g   g   p   s   g   a XhoI
                  -+----
        ------------>
201     cgccgcgag cctcgagggc atgggtgggc cgggcgtggg tgttccgggc
        gcggcggctc ggagctcccg tacccacccg gcccgcaccc acaaggcccg
        --------------P4
        >.........>......................>ELP1-90>
           p   p   p   s   l   e   g   m   g   g   p   g   v   g   v   p   g 251     gtgggtgttc cgggtggcgg tgtgccgggc gcaggtgttc ctggtgtagg   (SEQ ID NO.23)
        cacccacaag gcccaccgcc acacggcccg cgtccacaag gaccacatcc
        >........................ELP1-90....................>
           v   g   v   p   g   g   g   v   p   g   a   g   v   p   g   v   (SEQ ID NO.24)

P1: SEQ ID NO.: 35
        P2: SEQ ID NO.: 36
        P3: SEQ ID NO.: 37
        P4: SEQ ID NO.: 38
        P5: SEQ ID NO.: 39
        P6: SEQ ID NO.: 40
```

FIGURE 3A

```
    NdeI
    ----
    P7------------------------------------------------------------
1   tatggaaaac ctgtatttcc aacatggcga aggcaccttt accagcgatc
    accttttg gacataaagg ttgtaccgct tccgtggaaa tggtcgctag
    <-----------------------------------------------P8
    >>................Ex-4 ELP1-90....................>
      m   e   n   l   y   f   q   h   g   e   g   t   f   t   s   d
      >>......Tev........>>

>
51  tgagcaaaca gatggaagaa gaagcggtgc gcctgtttat tgaatggctg
    actcgtttgt ctaccttctt cttcgccacg cggacaaata acttaccgac
    >...................Ex-4 ELP1-90'...................>
      l   s   k   q   m   e   e   e   a   v   r   l   f   i   e   w   l AscI
                        --+-----
101 aaaaacggcg gcccgagcag cggcgcgccg ccgccgagcc  (SEQ ID NO.: 25)
    tttttgccgc cgggctcgtc gccgcgcggc ggcggctcgg agct
              <----------------------------------P4
    >..............Ex-4 ELP1-90..............>>
      k   n   g   g   p   s   s   g   a   p   p   p   s  (SEQ ID NO.: 26)

P4: SEQ ID NO.: 38
    P7: SEQ ID NO.: 41
    P8: SEQ ID NO.: 42
```

FIGURE 3B

```
    NdeI
    ----
    P9-----------------------------------------------------------
  1 tatggatatc ccaacgaccg aaaacctgta tttccaacat ggcgaaggca
       acctatag ggttgctggc ttttggacat aaaggttgta ccgcttccgt
       <------------------------------------------------------
    >>.................Ex-4 ELP1-90.....................>
       m  d  i  p  t  t  e  n  l  y  f  q  h  g  e  g
       >>...........Linker Tev...........>>

---------------->
 51 cctttaccag cgatctgagc aaacagatgg aagaagaagc ggtgcgcctg
    ggaaatggtc gctagactcg tttgtctacc ttcttcttcg ccacgcggac
    ---------P10
    >....................Ex-4 ELP1-90......................>
      t  f  t  s  d  l  s  k  q  m  e  e  e  a  v  r  l AscI
                                                  --+------
101 tttattgaat ggctgaaaaa cggcggcccg agcagcggcg cgccgccgcc
    aaataactta ccgactttt gccgccgggc tcgtcgccgc gcggcggcgg
                                     <-------------------------
    >....................Ex-4 ELP1-90......................>
       f  i  e  w  l  k  n  g  g  p  s  s  g  a  p  p 151 gagcc (SEQ ID NO.: 27)
    ctcggagct
    -------P4
    >..>> Ex-4 ELP1-90
     p  s    (SEQ ID NO.: 28)

P4: SEQ ID NO.: 38
    P9: SEQ ID NO.: 43
    P10: SEQ ID NO.: 44
```

FIGURE 4A

```
    NdeI
    ----
    P11------------------------------------------------------
 1  tatgaaaaag atttggctgg cgctggctgg tttagtttta gcgtttagcg
    acttttttc taaaccgacc gcgaccgacc aaatcaaaat cgcaaatcgc
    <-------------------------------------------------------
    >>.....................DsbA........................>
      m  k  k  i  w  l  a  l  a  g  l  v  l  a  f  s ----------------------------------------------->
 51 catcggcgca tggcgaaggc acctttacca gcgatctgag caaacagatg
    gtagccgcgt accgcttccg tggaaatggt cgctagactc gtttgtctac
    ------------------------------P12
    >.DsbA>>>>..............Ex-4 ELP1-90.................>
      a  s  a  h  g  e  g  t  f  t  s  d  l  s  k  q  m 101 gaagaagaag cggtgcgcct gtttattgaa tggctgaaaa acggcggccc
    cttcttcttc gccacgcgga caaataactt accgactttt tgccgccggg
                                                      <----
    >..................Ex-4 ELP1-90.....................>
       e  e  e  a  v  r  l  f  i  e  w  l  k  n  g  g AscI
              --+------
151 gagcagcggc gcgccgccgc cgagcc (SEQ ID NO.: 29)
    ctcgtcgccg cgcggcggcg gctcggagct
    ------------------------------P4
    >......Ex-4 ELP1-90.......>>
      p  s  s  g  a  p  p  p  s  (SEQ ID NO.: 30)

P4:  SEQ ID NO.: 38
    P11: SEQ ID NO.: 45
    P12: SEQ ID NO.: 46
``` pET24d-DsbA-Ex-4 ELP1-90

FIGURE 5B

```
                                                                  XbaI
                                                                  -+----
  1   taatacgact cactataggg gaattgtgag cggataacaa ttcccctcta NdeI
                                                      --+----
 51   gaaataattt tgtttaactt taagaaggag atatacatat ggagaacctg
                                                       m   e   n   l KpnI
                      ------+
101   tatttccaac atggcgaagg taccttaca agcgatgtta gttcatatct
               >>>>................GLP-1(7-37)................>
                y   f   q   h   g   e   g   t   f   t   s   d   v   s   s   y 151   ggagggccag gcggcaaagg aattcattgc gtggctggtg aaaggccgcg
      >....................GLP-1(7-37)................>
       l   e   g   q   a   a   k   e   f   i   a   w   l   v   k   g   r XhoI
      -+----
201   gcctcgaggg catgggtggg ccgggcgtgg gtgttccggg cgtgggtgtt
      >>                      >>....ELP1-90.....>
       g   l   e   g   m   g   g   p   g   v   g   v   p   g   v   g   v 251   ccgggtggcg gtgtgccggg cgcaggtgtt cctggtgtag gtgtgccggg
      >.....................ELP1-90................>
        p   g   g   g   v   p   g   a   g   v   p   g   v   g   v   p 301   tgttggtgtg ccgggtgttg gtgtaccagg tggcggtgtt ccgggtgcag
      >.....................ELP1-90................>
        g   v   g   v   p   g   v   g   v   p   g   g   g   v   p   g   a 351   gcgttccggg tggcggtgtg ccgggcgtgg gtgttccggg cgtgggtgtt
      >.....................ELP1-90................>
        g   v   p   g   g   g   v   p   g   v   g   v   p   g   v   g   v 401   ccgggtggcg gtgtgccggg cgcaggtgtt cctggtgtag gtgtgccggg
      >.....................ELP1-90................>
        p   g   g   g   v   p   g   a   g   v   p   g   v   g   v   p 451   tgttggtgtg ccgggtgttg gtgtaccagg tggcggtgtt ccgggtgcag
      >.....................ELP1-90................>
        g   v   g   v   p   g   v   g   v   p   g   g   g   v   p   g   a 501   gcgttccggg tggcggtgtg ccgggcgtgg gtgttccggg cgtgggtgtt
      >.....................ELP1-90................>
        g   v   p   g   g   g   v   p   g   v   g   v   p   g   v   g   v 551   ccgggtggcg gtgtgccggg cgcaggtgtt cctggtgtag gtgtgccggg
      >.....................ELP1-90................>
        p   g   g   g   v   p   g   a   g   v   p   g   v   g   v   p 601   tgttggtgtg ccgggtgttg gtgtaccagg tggcggtgtt ccgggtgcag
      >.....................ELP1-90................>
        g   v   g   v   p   g   v   g   v   p   g   g   g   v   p   g   a
```

FIGURE 5B cont.

```
 651   gcgttccggg tggcggtgtg ccgggcgtgg gtgttccggg cgtgggtgtt
       >........................ELP1-90........................>
         g  v  p  g  g  g  v  p  g  v  g  v  p  g  v  g  v 701   ccgggtggcg gtgtgccggg cgcaggtgtt cctggtgtag gtgtgccggg
       >........................ELP1-90........................>
          p  g  g  g  v  p  g  a  g  v  p  g  v  g  v  p 751   tgttggtgtg ccgggtgttg gtgtaccagg tggcggtgtt ccgggtgcag
       >........................ELP1-90........................>
         g  v  g  v  p  g  v  g  v  p  g  g  g  v  p  g  a 801   gcgttccggg tggcggtgtg ccgggcgtgg gtgttccggg cgtgggtgtt
       >........................ELP1-90........................>
         g  v  p  g  g  g  v  p  g  v  g  v  p  g  v  g  v 851   ccgggtggcg gtgtgccggg cgcaggtgtt cctggtgtag gtgtgccggg
       >........................ELP1-90........................>
          p  g  g  g  v  p  g  a  g  v  p  g  v  g  v  p 901   tgttggtgtg ccgggtgttg gtgtaccagg tggcggtgtt ccgggtgcag
       >........................ELP1-90........................>
         g  v  g  v  p  g  v  g  v  p  g  g  g  v  p  g  a 951   gcgttccggg tggcggtgtg ccgggcgtgg gtgttccggg cgtgggtgtt
       >........................ELP1-90........................>
         g  v  p  g  g  g  v  p  g  v  g  v  p  g  v  g  v 1001   ccgggtggcg gtgtgccggg cgcaggtgtt cctggtgtag gtgtgccggg
       >........................ELP1-90........................>
          p  g  g  g  v  p  g  a  g  v  p  g  v  g  v  p 1051   tgttggtgtg ccgggtgttg gtgtaccagg tggcggtgtt ccgggtgcag
       >........................ELP1-90........................>
         g  v  g  v  p  g  v  g  v  p  g  g  g  v  p  g  a 1101   gcgttccggg tggcggtgtg ccgggcgtgg gtgttccggg cgtgggtgtt
       >........................ELP1-90........................>
         g  v  p  g  g  g  v  p  g  v  g  v  p  g  v  g  v 1151   ccgggtggcg gtgtgccggg cgcaggtgtt cctggtgtag gtgtgccggg
       >........................ELP1-90........................>
          p  g  g  g  v  p  g  a  g  v  p  g  v  g  v  p 1201   tgttggtgtg ccgggtgttg gtgtaccagg tggcggtgtt ccgggtgcag
       >........................ELP1-90........................>
         g  v  g  v  p  g  v  g  v  p  g  g  g  v  p  g  a 1251   gcgttccggg tggcggtgtg ccgggcgtgg gtgttccggg cgtgggtgtt
       >........................ELP1-90........................>
         g  v  p  g  g  g  v  p  g  v  g  v  p  g  v  g  v 1301   ccgggtggcg gtgtgccggg cgcaggtgtt cctggtgtag gtgtgccggg
       >........................ELP1-90........................>
          p  g  g  g  v  p  g  a  g  v  p  g  v  g  v  p
```

FIGURE 5B cont.

```
1351   tgttggtgtg  ccgggtgttg  gtgtaccagg  tggcggtgtt  ccgggtgcag
       >......................ELP1-90.......................>
        g  v  g  v  p  g  v  g  v  p  g  g  g  v  p  g  a 1401   gcgttccggg  tggcggtgtg  ccgggcgtgg  gtgttccggg  cgtgggtgtt
       >......................ELP1-90.......................>
        g  v  p  g  g  g  v  p  g  v  g  v  p  g  v  g  v 1451   ccgggtggcg  gtgtgccggg  cgcaggtgtt  cctggtgtag  gtgtgccggg
       >......................ELP1-90.......................>
         p  g  g  g  v  p  g  a  g  v  p  g  v  g  v  p 1501   tgttggtgtg  ccgggtgttg  gtgtaccagg  tggcggtgtt  ccgggtgcag
       >......................ELP1-90.......................>
        g  v  g  v  p  g  v  g  v  p  g  g  g  v  p  g  a NheI
                                          -+------
1551   gcgttccggg  tggcggtgtg  ccgggctggc  cgtgataagc  tagcatgact
       >..............ELP1-90.............>>
        g  v  p  g  g  g  v  p  g  w  p  -  -  (SEQ ID NO: 54)

1601   ggtggacagc  aaatgggtcg  gatccgaatt  cgagctccgt  cgagcaccac 1651   caccaccacc  actgagatcc  ggctgctaac  aaagcccgaa  aggaagctga (SEQ ID NO: 53)
```

FIGURE 6B

```
                                                                    XbaI
                                                                  -+----
  1   taatacgact cactataggg gaattgtgag cggataacaa ttcccctcta NdeI
                                            --+----
 51   gaaataattt tgtttaactt taagaaggag atatacatat ggagaacctg
                                                  >>...Tev....>
                                                    m  e  n  l KpnI
                     ------+
101   tatttccaac atggcgaagg tacctttaca agcgatgtta gttcatatct
      >..Tev.>>
         y  f  q
                 >>.................GLP-1....................>
                    h  g  e  g  t  f  t  s  d  v  s  s  y 151   ggagggccag gcggcaaagg aatttattgc gtggctggtg aaaggccgcg
      >.....................GLP-1............................>
         l  e  g  q  a  a  k  e  f  i  a  w  l  v  k  g  r 201   gcgtgccggg cgtgggtgtt ccgggcgtgg gtgttccggg tggcggtgtg
      >> GLP-1
         g
                 >>..................ELP1-120..................>
                    v  p  g  v  g  v  p  g  v  g  v  p  g  g  v 251   ccgggcgcag gtgttcctgg tgtaggtgtg ccgggtgttg gtgtgccggg
      >..........................ELP1-120.....................>
         p  g  a  g  v  p  g  v  g  v  p  g  v  g  v  p 301   tgttggtgta ccaggtggcg gtgttccggg tgcaggcgtt ccgggtggcg
      >..........................ELP1-120.....................>
         g  v  g  v  p  g  g  g  v  p  g  a  g  v  p  g  g 351   gtgtgccggg cgtgggtgtt ccgggcgtgg gtgttccggg tggcggtgtg
      >..........................ELP1-120.....................>
         g  v  p  g  v  g  v  p  g  v  g  v  p  g  g  g  v 401   ccgggcgcag gtgttcctgg tgtaggtgtg ccgggtgttg gtgtgccggg
      >..........................ELP1-120.....................>
         p  g  a  g  v  p  g  v  g  v  p  g  v  g  v  p 451   tgttggtgta ccaggtggcg gtgttccggg tgcaggcgtt ccgggtggcg
      >..........................ELP1-120.....................>
         g  v  g  v  p  g  g  g  v  p  g  a  g  v  p  g  g 501   gtgtgccggg cgtgggtgtt ccgggcgtgg gtgttccggg tggcggtgtg
      >..........................ELP1-120.....................>
         g  v  p  g  v  g  v  p  g  v  g  v  p  g  g  g  v 551   ccgggcgcag gtgttcctgg tgtaggtgtg ccgggtgttg gtgtgccggg
      >..........................ELP1-120.....................>
         p  g  a  g  v  p  g  v  g  v  p  g  v  g  v  p
```

FIGURE 6B cont.

```
 601  tgttggtgta ccaggtggcg gtgttccggg tgcaggcgtt ccgggtggcg
      >........................ELP1-120......................>
        g  v  g  v  p  g  g   g  v  p   g  a  g  v  p  g  g 651  gtgtgccggg cgtgggtgtt ccgggcgtgg gtgttccggg tggcggtgtg
      >........................ELP1-120......................>
        g  v  p  g  v  g  v   p  g  v   g  v  p  g  g  g  v 701  ccgggcgcag gtgttcctgg tgtaggtgtg ccgggtgttg gtgtgccggg
      >........................ELP1-120......................>
        p  g  a  g  v  p  g   v  g  v   p  g  v  g  v  p 751  tgttggtgta ccaggtggcg gtgttccggg tgcaggcgtt ccgggtggcg
      >........................ELP1-120......................>
        g  v  g  v  p  g  g   g  v  p   g  a  g  v  p  g  g 801  gtgtgccggg cgtgggtgtt ccgggcgtgg gtgttccggg tggcggtgtg
      >........................ELP1-120......................>
        g  v  p  g  v  g  v   p  g  v   g  v  p  g  g  g  v 851  ccgggcgcag gtgttcctgg tgtaggtgtg ccgggtgttg gtgtgccggg
      >........................ELP1-120......................>
        p  g  a  g  v  p  g   v  g  v   p  g  v  g  v  p 901  tgttggtgta ccaggtggcg gtgttccggg tgcaggcgtt ccgggtggcg
      >........................ELP1-120......................>
        g  v  g  v  p  g  g   g  v  p   g  a  g  v  p  g  g 951  gtgtgccggg cgtgggtgtt ccgggcgtgg gtgttccggg tggcggtgtg
      >........................ELP1-120......................>
        g  v  p  g  v  g  v   p  g  v   g  v  p  g  g  g  v 1001  ccgggcgcag gtgttcctgg tgtaggtgtg ccgggtgttg gtgtgccggg
      >........................ELP1-120......................>
        p  g  a  g  v  p  g   v  g  v   p  g  v  g  v  p 1051  tgttggtgta ccaggtggcg gtgttccggg tgcaggcgtt ccgggtggcg
      >........................ELP1-120......................>
        g  v  g  v  p  g  g   g  v  p   g  a  g  v  p  g  g 1101  gtgtgccggg cgtgggtgtt ccgggcgtgg gtgttccggg tggcggtgtg
      >........................ELP1-120......................>
        g  v  p  g  v  g  v   p  g  v   g  v  p  g  g  g  v 1151  ccgggcgcag gtgttcctgg tgtaggtgtg ccgggtgttg gtgtgccggg
      >........................ELP1-120......................>
        p  g  a  g  v  p  g   v  g  v   p  g  v  g  v  p 1201  tgttggtgta ccaggtggcg gtgttccggg tgcaggcgtt ccgggtggcg
      >........................ELP1-120......................>
        g  v  g  v  p  g  g   g  v  p   g  a  g  v  p  g  g 1251  gtgtgccggg cgtgggtgtt ccgggcgtgg gtgttccggg tggcggtgtg
      >........................ELP1-120......................>
        g  v  p  g  v  g  v   p  g  v   g  v  p  g  g  g  v
```

FIGURE 6B cont.

```
1301  ccgggcgcag gtgttcctgg tgtaggtgtg ccgggtgttg gtgtgccggg
      >................ELP1-120....................>
         p  g  a   g  v  p   g  v  g  v   p  g  v   g  v  p 1351  tgttggtgta ccaggtggcg gtgttccggg tgcaggcgtt ccgggtggcg
      >................ELP1-120....................>
         g  v  g  v   p  g  g   g  v  p   g  a  g  v   p  g  g 1401  gtgtgccggg cgtgggtgtt ccggcgtgg gtgttccggg tggcggtgtg
      >................ELP1-120....................>
         g  v  p   g  v  g  v   p  g  v   g  v  p   g  g  g  v 1451  ccgggcgcag gtgttcctgg tgtaggtgtg ccgggtgttg gtgtgccggg
      >................ELP1-120....................>
         p  g  a   g  v  p   g  v  g  v   p  g  v   g  v  p 1501  tgttggtgta ccaggtggcg gtgttccggg tgcaggcgtt ccgggtggcg
      >................ELP1-120....................>
         g  v  g  v   p  g  g   g  v  p   g  a  g  v   p  g  g 1551  gtgtgccggg cgtgggtgtt ccggcgtgg gtgttccggg tggcggtgtg
      >................ELP1-120....................>
         g  v  p   g  v  g  v   p  g  v   g  v  p   g  g  g  v 1601  ccgggcgcag gtgttcctgg tgtaggtgtg ccgggtgttg gtgtgccggg
      >................ELP1-120....................>
         p  g  a   g  v  p   g  v  g  v   p  g  v   g  v  p 1651  tgttggtgta ccaggtggcg gtgttccggg tgcaggcgtt ccgggtggcg
      >................ELP1-120....................>
         g  v  g  v   p  g  g   g  v  p   g  a  g  v   p  g  g 1701  gtgtgccggg cgtgggtgtt ccggcgtgg gtgttccggg tggcggtgtg
      >................ELP1-120....................>
         g  v  p   g  v  g  v   p  g  v   g  v  p   g  g  g  v 1751  ccgggcgcag gtgttcctgg tgtaggtgtg ccgggtgttg gtgtgccggg
      >................ELP1-120....................>
         p  g  a   g  v  p   g  v  g  v   p  g  v   g  v  p 1801  tgttggtgta ccaggtggcg gtgttccggg tgcaggcgtt ccgggtggcg
      >................ELP1-120....................>
         g  v  g  v   p  g  g   g  v  p   g  a  g  v   p  g  g 1851  gtgtgccggg cgtgggtgtt ccggcgtgg gtgttccggg tggcggtgtg
      >................ELP1-120....................>
         g  v  p   g  v  g  v   p  g  v   g  v  p   g  g  g  v 1901  ccgggcgcag gtgttcctgg tgtaggtgtg ccgggtgttg gtgtgccggg
      >................ELP1-120....................>
         p  g  a   g  v  p   g  v  g  v   p  g  v   g  v  p 1951  tgttggtgta ccaggtggcg gtgttccggg tgcaggcgtt ccgggtggcg
      >................ELP1-120....................>
         g  v  g  v   p  g  g   g  v  p   g  a  g  v   p  g  g
```

FIGURE 6B cont.

```
           BglI                  NheI
      -----------+---         -+-----
2001  gtgtgccggg ctggccgtga taagctagca tgactggtgg acagcaaatg  (SEQ ID NO:55)
      >.......ELP1-120.......>>
        g   v   p    g   w   p   -   -  (SEQ ID NO: 56)
```

FIGURE 7B

```
              BglII
              -+----
   1  gacggatcgg gagatctccc gatcccctat ggtgcactct cagtacaatc 51  tgctctgatg ccgcatagtt aagccagtat ctgctccctg cttgtgtgtt 101  ggaggtcgct gagtagtgcg cgagcaaaat ttaagctaca acaaggcaag 151  gcttgaccga caattgcatg aagaatctgc ttagggttag gcgttttgcg 201  ctgcttgcgc atgtacgggc cagatatacg cgttgacatt gattattgac 251  tagttattaa tagtaatcaa ttacggggtc attagttcat agcccatata 301  tggagttccg cgttacataa cttacggtaa atggcccgcc tggctgaccg 351  cccaacgacc cccgcccatt gacgtcaata atgacgtatg ttcccatagt 401  aacgccaata gggactttcc attgacgtca atgggtggag tatttacggt 451  aaactgccca cttggcagta catcaagtgt atcatatgcc aagtacgccc 501  cctattgacg tcaatgacgg taaatggccc gcctggcatt atgcccagta 551  catgacctta tgggactttc ctacttggca gtacatctac gtattagtca 601  tcgctattac catggtgatg cggttttggc agtacatcaa tgggcgtgga 651  tagcggtttg actcacgggg atttccaagt ctccacccca ttgacgtcaa 701  tgggagtttg ttttggcacc aaaatcaacg ggactttcca aatgtcgta 751  acaactccgc cccattgacg caaatgggcg gtaggcgtgt acggtgggag 801  gtctatataa gcagagctct ctggctaact agagaaccca ctgcttactg NheI
                                                      -+----
 851  gcttatcgaa attaatacga ctcactatag ggagacccaa gctggctagc 901  atggtctccc aggccctcag gctcctctgc cttctgcttg gcttcaggg
      >>...............signal prepropetide..................>
         m  v  s  q  a  l  r  l  l  c  l  l  l  g  l  q 951  ctgcctggct gcagtcttcg taacccagga ggaagcccac ggcgtcctgc
      >...............signal prepropetide...................>
         g  c  l  a  a  v  f  v  t  q  e  e  a  h  g  v  l 1001  accggcgccg cgcgccaac gcgttcctgg aggagctacg gccgggctcc
      >...........>>>>............FVII-ELP1-90.............>
         h  r  r  r  a  n  a  f  l  e  e  l  r  p  g  s
                       >>...............FVII................>
```

FIGURE 7B cont.

```
1051   ctggagaggg agtgcaagga ggagcagtgc tccttcgagg aggcccggga
       >....................FVII-ELP1-90....................>
         l   e   r   e   c   k   e   e   q   c   s   f   e   e   a   r
       >.....................FVII..........................>

BglII
       -+----
1101   gatcttcaag gacgcggaga ggacgaagct gttctggatt tcttacagtg
       >....................FVII-ELP1-90....................>
         e   i   f   k   d   a   e   r   t   k   l   f   w   i   s   y   s
       >.....................FVII..........................>

1151   atggggacca gtgtgcctca agtccatgcc agaatggggg ctcctgcaag
       >....................FVII-ELP1-90....................>
         d   g   d   q   c   a   s   s   p   c   q   n   g   g   s   c   k
       >.....................FVII..........................>

1201   gaccagctcc agtcctatat ctgcttctgc ctccctgcct tcgagggccg
       >....................FVII-ELP1-90....................>
         d   q   l   q   s   y   i   c   f   c   l   p   a   f   e   g
       >.....................FVII..........................>

1251   gaactgtgag acgcacaagg atgaccagct gatctgtgtg aacgagaacg
       >....................FVII-ELP1-90....................>
         r   n   c   e   t   h   k   d   d   q   l   i   c   v   n   e   n
       >.....................FVII..........................>

1301   gcggctgtga gcagtactgc agtgaccaca cgggcaccaa gcgctcctgt
       >....................FVII-ELP1-90....................>
         g   g   c   e   q   y   c   s   d   h   t   g   t   k   r   s   c
       >.....................FVII..........................>

1351   cggtgccacg aggggtactc tctgctggca gacggggtgt cctgcacacc
       >....................FVII-ELP1-90....................>
         r   c   h   e   g   y   s   l   l   a   d   g   v   s   c   t
       >.....................FVII..........................>

XbaI
                                              -+----
1401   cacagttgaa tatccatgtg gaaaaatacc tattctagaa aaagaaatg
       >....................FVII-ELP1-90....................>
         p   t   v   e   y   p   c   g   k   i   p   i   l   e   k   r   n
       >.....................FVII..........................>

1451   ccagcaaacc ccaaggccga attgtggggg gcaaggtgtg ccccaaaggg
       >....................FVII-ELP1-90....................>
         a   s   k   p   q   g   r   i   v   g   g   k   v   c   p   k   g
       >.....................FVII..........................>

1501   gagtgtccat ggcaggtcct gttgttggtg aatggagctc agttgtgtgg
       >....................FVII-ELP1-90....................>
         e   c   p   w   q   v   l   l   v   n   g   a   q   l   c
       >.....................FVII..........................>
```

FIGURE 7B cont.

```
1551    ggggaccctg atcaacacca tctgggtggt ctccgcggcc cactgtttcg
        >..................FVII-ELP1-90.....................>
          g  g  t  l  i  n  t  i  w  v  v  s  a  a  h  c  f
        >........................FVII.......................>

1601    acaaaatcaa gaactggagg aacctgatcg cggtgctggg cgagcacgac
        >..................FVII-ELP1-90.....................>
          d  k  i  k  n  w  r  n  l  i  a  v  l  g  e  h  d
        >........................FVII.......................>

1651    ctcagcgagc acgacgggga tgagcagagc cggcgggtgg cgcaggtcat
        >..................FVII-ELP1-90.....................>
           l  s  e  h  d  g  d  e  q  s  r  r  v  a  q  v
        >........................FVII.......................>

1701    catccccagc acgtacgtcc cgggcaccac caaccacgac atcgcgctgc
        >..................FVII-ELP1-90.....................>
          i  i  p  s  t  y  v  p  g  t  t  n  h  d  i  a  l
        >........................FVII.......................>

1751    tccgcctgca ccagcccgtg gtcctcactg accatgtggt gccctctgc
        >..................FVII-ELP1-90.....................>
          l  r  l  h  q  p  v  v  l  t  d  h  v  v  p  l  c
        >........................FVII.......................>

1801    ctgcccgaac ggacgttctc tgagaggacg ctggccttcg tgcgcttctc
        >..................FVII-ELP1-90.....................>
          l  p  e  r  t  f  s  e  r  t  l  a  f  v  r  f
        >........................FVII.......................>

1851    attggtcagc ggctggggcc agctgctgga ccgtggcgcc acggccctgg
        >..................FVII-ELP1-90.....................>
          s  l  v  s  g  w  g  q  l  l  d  r  g  a  t  a  l
        >........................FVII.......................>

1901    agctcatggt cctcaacgtg ccccggctga tgacccagga ctgcctgcag
        >..................FVII-ELP1-90.....................>
          e  l  m  v  l  n  v  p  r  l  m  t  q  d  c  l  q
        >........................FVII.......................>

1951    cagtcacgga aggtgggaga ctccccaaat atcacggagt acatgttctg
        >..................FVII-ELP1-90.....................>
           q  s  r  k  v  g  d  s  p  n  i  t  e  y  m  f
        >........................FVII.......................>

2001    tgccggctac tcggatggca gcaaggactc ctgcaagggg gacagtggag
        >..................FVII-ELP1-90.....................>
          c  a  g  y  s  d  g  s  k  d  s  c  k  g  d  s  g
        >........................FVII.......................>

KpnI
                                                      ------+
2051    gcccacatgc cacccactac cggggcacgt ggtacctgac gggcatcgtc
        >..................FVII-ELP1-90.....................>
          g  p  h  a  t  h  y  r  g  t  w  y  l  t  g  i  v
        >........................FVII.......................>
```

FIGURE 7B cont.

```
2101  agctggggcc agggctgcgc aaccgtgggc cactttgggg tgtacaccag
      >....................FVII-ELP1-90....................>
        s  w  g  q  g  c  a  t  v  g  h  f  g  v  y  t
      >....................FVII..........................>

2151  ggtctcccag tacatcgagt ggctgcaaaa gctcatgcgc tcagagccac
      >....................FVII-ELP1-90....................>
        r  v  s  q  y  i  e  w  l  q  k  l  m  r  s  e  p
      >....................FVII..........................>

NotI
                                             --+------
2201  gcccaggagt cctcctgcga gccccatttc cgcggccgc tgaaaacctg
      >....................FVII-ELP1-90....................>
        r  p  g  v  l  l  r  a  p  f  p  a  a  a  e  n  l
      >...........FVII...............>>          >>.tev..>

2251  tattttcagg gtggggccgc tgggccgggc gtgggagttc ccggcgtggg
      >....................FVII-ELP1-90....................>
        y  f  q  g  g  a     a  g  p  g  v  g  v  p  g  v
      >....tev...>>           >>........ELP1-90..........>

2301  agttcccgga ggcggagtgc ccggcgcagg agttcctgga gtcggagtgc
      >....................FVII-ELP1-90....................>
        g  v  p  g     g  g  v     p  g  a     g  v  p  g  v  g  v
      >....................ELP1-90........................>

2351  ccggagttgg agtgcccgga gttggagtcc caggaggcgg agtccccgga
      >....................FVII-ELP1-90....................>
        p  g  v     g  v  p  g     v  g  v     p  g  g     g  v  p  g
      >....................ELP1-90........................>

2401  gcaggcgtcc ccggaggcgg agtgccgggc gtgggagttc ccggcgtggg
      >....................FVII-ELP1-90....................>
        a  g  v     p  g  g     g  v  p  g     v  g  v     p  g  v
      >....................ELP1-90........................>

2451  agttcccgga ggcggagtgc ccggcgcagg agttcctgga gtcggagtgc
      >....................FVII-ELP1-90....................>
        g  v  p  g     g  g  v     p  g  a     g  v  p  g  v  g  v
      >....................ELP1-90........................>

2501  ccggagttgg agtgcccgga gttggagtcc caggaggcgg agtccccgga
      >....................FVII-ELP1-90....................>
        p  g  v     g  v  p  g     v  g  v     p  g  g     g  v  p  g
      >....................ELP1-90........................>

2551  gcaggcgtcc ccggaggcgg agtgccgggc gtgggagttc ccggcgtggg
      >....................FVII-ELP1-90....................>
        a  g  v     p  g  g     g  v  p  g     v  g  v     p  g  v
      >....................ELP1-90........................>
```

FIGURE 7B cont.

```
2601  agttcccgga ggcggagtgc ccggcgcagg agttcctgga gtcggagtgc
      >.....................FVII-ELP1-90......................>
        g  v  p  g  g  g  v  p  g  a  g  v  p  g  v  g  v
      >.....................ELP1-90...........................>

2651  ccggagttgg agtgcccgga gttggagtcc caggaggcgg agtccccgga
      >.....................FVII-ELP1-90......................>
        p  g  v  g  v  p  g  v  g  v  p  g  g  g  v  p  g
      >.....................ELP1-90...........................>

2701  gcaggcgtcc ccggaggcgg agtgccgggc gtgggagttc ccggcgtggg
      >.....................FVII-ELP1-90......................>
         a  g  v  p  g  g  g  v  p  g  v  g  v  p  g  v
      >.....................ELP1-90...........................>

2751  agttcccgga ggcggagtgc ccggcgcagg agttcctgga gtcggagtgc
      >.....................FVII-ELP1-90......................>
        g  v  p  g  g  g  v  p  g  a  g  v  p  g  v  g  v
      >.....................ELP1-90...........................>

2801  ccggagttgg agtgcccgga gttggagtcc caggaggcgg agtccccgga
      >.....................FVII-ELP1-90......................>
        p  g  v  g  v  p  g  v  g  v  p  g  g  g  v  p  g
      >.....................ELP1-90...........................>

2851  gcaggcgtcc ccggaggcgg agtgccgggc gtgggagttc ccggcgtggg
      >.....................FVII-ELP1-90......................>
         a  g  v  p  g  g  g  v  p  g  v  g  v  p  g  v
      >.....................ELP1-90...........................>

2901  agttcccgga ggcggagtgc ccggcgcagg agttcctgga gtcggagtgc
      >.....................FVII-ELP1-90......................>
        g  v  p  g  g  g  v  p  g  a  g  v  p  g  v  g  v
      >.....................ELP1-90...........................>

2951  ccggagttgg agtgcccgga gttggagtcc caggaggcgg agtccccgga
      >.....................FVII-ELP1-90......................>
        p  g  v  g  v  p  g  v  g  v  p  g  g  g  v  p  g
      >.....................ELP1-90...........................>

3001  gcaggcgtcc ccggaggcgg agtgccgggc gtgggagttc ccggcgtggg
      >.....................FVII-ELP1-90......................>
         a  g  v  p  g  g  g  v  p  g  v  g  v  p  g  v
      >.....................ELP1-90...........................>

3051  agttcccgga ggcggagtgc ccggcgcagg agttcctgga gtcggagtgc
      >.....................FVII-ELP1-90......................>
        g  v  p  g  g  g  v  p  g  a  g  v  p  g  v  g  v
      >.....................ELP1-90...........................>

3101  ccggagttgg agtgcccgga gttggagtcc caggaggcgg agtccccgga
      >.....................FVII-ELP1-90......................>
        p  g  v  g  v  p  g  v  g  v  p  g  g  g  v  p  g
      >.....................ELP1-90...........................>
```

FIGURE 7B cont.

```
3151  gcaggcgtcc ccggaggcgg agtgccgggc gtgggagttc ccggcgtggg
      >...................FVII-ELP1-90.....................>
         a  g  v  p  g  g  g  v  p  g  v  g  v  p  g  v
      >......................ELP1-90......................>

3201  agttcccgga ggcggagtgc ccggcgcagg agttcctgga gtcggagtgc
      >...................FVII-ELP1-90.....................>
         g  v  p  g  g  g  v  p  g  a  g  v  p  g  v  g  v
      >......................ELP1-90......................>

3251  ccggagttgg agtgcccgga gttggagtcc caggaggcgg agtccccgga
      >...................FVII-ELP1-90.....................>
         p  g  v  g  v  p  g  v  g  v  p  g  g  g  v  p  g
      >......................ELP1-90......................>

3301  gcaggcgtcc ccggaggcgg agtgccgggc gtgggagttc ccggcgtggg
      >...................FVII-ELP1-90.....................>
         a  g  v  p  g  g  g  v  p  g  v  g  v  p  g  v
      >......................ELP1-90......................>

3351  agttcccgga ggcggagtgc ccggcgcagg agttcctgga gtcggagtgc
      >...................FVII-ELP1-90.....................>
         g  v  p  g  g  g  v  p  g  a  g  v  p  g  v  g  v
      >......................ELP1-90......................>

3401  ccggagttgg agtgcccgga gttggagtcc caggaggcgg agtccccgga
      >...................FVII-ELP1-90.....................>
         p  g  v  g  v  p  g  v  g  v  p  g  g  g  v  p  g
      >......................ELP1-90......................>

3451  gcaggcgtcc ccggaggcgg agtgccgggc gtgggagttc ccggcgtggg
      >...................FVII-ELP1-90.....................>
         a  g  v  p  g  g  g  v  p  g  v  g  v  p  g  v
      >......................ELP1-90......................>

3501  agttcccgga ggcggagtgc ccggcgcagg agttcctgga gtcggagtgc
      >...................FVII-ELP1-90.....................>
         g  v  p  g  g  g  v  p  g  a  g  v  p  g  v  g  v
      >......................ELP1-90......................>

3551  ccggagttgg agtgcccgga gttggagtcc caggaggcgg agtccccgga
      >...................FVII-ELP1-90.....................>
         p  g  v  g  v  p  g  v  g  v  p  g  g  g  v  p  g
      >......................ELP1-90......................>

XbaI
                                                      -+----
                                               XhoI
                                               -+----
3601  gcaggcgtcc ccggaggcgg agtgccgggc tggccttgat gactcgagtc
      >...................FVII-ELP1-90................>>
         a  g  v  p  g  g  g  v  p  g  w  p  -  -  (SEQ ID NO: 59)
      >......................ELP1-90................>>

3651  tagagggccc gtttaaaccc gctgatcagc ctcgactgtg ccttctagtt (SEQ ID NO:57)
```

FIGURE 8A

```
      XbaI                                          NdeI
      -+----                                        ---+---
                                    P15----------------------
  51  ctagaaataa ttttgtttaa ctttaagaag gagatataca tatgtttgtg
                                      Insulin ELP1-90 >>......>
                                                       m   f   v
                                                    B chain >>...>
      ---------------->
 101  aaccaacacc tgtgcggctc acacctggtg gaagctctct acctagtgtg
      >................Insulin ELP1-90....................>
        n   q   h   l   c   g   s   h   l   v   e   a   l   y   l   v
      >...............B chain........................>

151  cggggaacga ggcttcttct acacacccaa gacccgccgg gaggcagagg
      >................Insulin ELP1-90....................>
        c   g   e   r   g   f   f   y   t   p   k   t   r   r   e   a   e
      >..............B chain.............>>
                                                    C chain >>.......>

201  acctgcaggt ggggcaggtg gagctgggcg ggggccctgg tgcaggcagc
      >................Insulin ELP1-90....................>
        d   l   q   v   g   q   v   e   l   g   g   g   p   g   a   g   s
      >......................C chain.........................>

251  ctgcagccct tggccctgga ggggtccctg cagaagcgtg gcattgtgga
      >................Insulin ELP1-90....................>
        l   q   p   l   a   l   e   g   s   l   q   k   r   g   i   v
      >............C chain.............>>
                                                        >>A chain..>
                                                    <------------------
 301  acaatgctgt accagcatct gctccctcta ccagctggag aactactgca
                                                        cctc ttgatgacgt >................Insulin ELP1-90....................>
        e   q   c   c   t   s   i   c   s   l   y   q   l   e   n   y   c
      >....................A chain....................>
        e   q   c   c   t   s   i   c   s   l   y   q   l   e   n   y   c XhoI
      -+----
 351  acctcgaggg catgggtggg ccgggcgtgg gtgttccggg cgtgggtgtt
      tggagctccc gtaccc
      --------------P16

>................Insulin ELP1-90....................>
        n   l   e   g   m   g   g   p   g   v   g   v   p   g   v   g   v
      >> A chain 401  ccgggtggcg gtgtgccggg cgcaggtgtt cctggtgtag gtgtgccggg(SEQ ID NO:31)
      >................Insulin ELP1-90....................>
        p   g   g   g   v   p   g   a   g   v   p   g   v   g   v   p   (SEQ ID NO:32)

P15: SEQ ID NO.: 47
      P16: SEQ ID NO.: 48
``` pET24d Insulin-ELP1-90

$T_{1/2}$ FVIIa = 45-60 min $T_{1/2}$ FVIIa-ELP = 690 min $T_{1/2}$ IV= 12.9 hours
$T_{1/2}$ SQ= 8.6 hours Long Half Life of GLP-1 ELP in Rabbits $T_{1/2}$ IV= 12.920 hours
$T_{1/2}$ SQ= 8.624 hours

THERAPEUTIC AGENTS COMPRISING FUSIONS OF GROWTH HORMONE AND ELASTIC PEPTIDES

PRIORITY

This application is a continuation of U.S. application Ser. No. 12/852,365, filed Aug. 6, 2010, which is a continuation-in-part of, U.S. application Ser. No. 12/493,912, filed Jun. 29, 2009, now U.S. Pat. No. 8,178,495, which claims priority to U.S. Provisional Application No. 61/076,221, filed Jun. 27, 2008, each of which is hereby incorporated by reference in its entirety. U.S. application Ser. No. 12/852,365 is also a continuation-in-part of U.S. application Ser. No. 12/158,190, now U.S. Pat. No. 8,334,257, which is a U.S. national stage of PCT/US06/048572, filed Dec. 20, 2006, which claims priority to U.S. Provisional Application No. 60/751,896, filed Dec. 20, 2005, each of which is hereby incorporated by reference in its entirety.

GOVERNMENT SUPPORT

This invention was made with Government support under grant number EB00188 and GM-061232 from National Institutes of Health. The US Government has certain rights to this invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PHAS_021_04US_SeqList_ST25.txt, date recorded: Apr. 14, 2014, file size 50 kb).

BACKGROUND OF THE INVENTION

Therapeutic proteins or peptides in their native state or when recombinantly produced can be labile molecules exhibiting, inter alia, short periods of serum stability, serum half-life (i.e., circulatory half-life), or limited persistence in the body. Such molecules can also be extremely labile when formulated, such as when formulated in aqueous solutions.

In some instances, polyethylene glycol (PEG) conjugated to a proteinaceous molecule results in a longer-acting, sustained activity of the molecule. PEG attachment, however, can often substantially reduce or even destroy the protein's therapeutic activity. Therapeutic proteins and/or peptides have also been stabilized by fusion to certain proteins that are capable of extending serum half-life. For example, in some instances, therapeutic proteins fused to albumin, transferrin, and antibody fragments exhibit extended serum half-life when compared to the therapeutic protein in the unfused state. See U.S. Pat. No. 7,238,667 (particularly with respect to albumin conjugates), U.S. Pat. No. 7,176,278 (particularly with respect to transferrin conjugates), and U.S. Pat. No. 5,766,883, which are each hereby incorporated by reference in their entireties.

There remains a need in the art for more stable, longer acting, and/or effective proteinaceous molecules.

SUMMARY OF THE INVENTION

The present invention provides therapeutic agents comprising an elastic peptide component and a therapeutic proteinacious component. The elastic peptide component may form a spiral conformation, and/or may have an extended structure relative to an alpha helix. The elastic peptide component may be structurally related to, or derived from, sequences of the elastin protein (elastin-like-peptide or ELP). Such elastic peptide components provide certain therapeutic advantages to the therapeutic agent, such as comparatively better stability, solubility, bioavailability, half-life, persistence, and/or biological action of the therapeutic proteinaceous component. Such properties may be determined, for example, with respect to the therapeutic component's unfused or unconjugated counterpart. In some embodiments, the elastic peptide is an ELP that undergoes a reversible inverse phase transition, which may impart additional practical and/or therapeutic advantages. The invention further provides polynucleotides encoding the therapeutic agents of the invention, as well as methods of treatment or prophylaxis for certain biological conditions.

In a first aspect, the invention provides a therapeutic agent comprising an elastic peptide component and a therapeutic proteinacious component, as well as pharmaceutical compositions containing the same for delivery to a subject or patient in need. The therapeutic component may be selected from active portions of the therapeutic proteins described herein, including those listed in Table 1, or functional analogs thereof. In certain embodiments, the therapeutic component is a GLP-1 receptor agonist, such as GLP-1, exendin-4, or a functional analog thereof. Such therapeutic components are generally effective for, among other things, increasing insulin secretion from the pancreas in a glucose-dependent manner. In other embodiments, the therapeutic component is an insulin or functional analog thereof, which is generally effective for promoting glucose uptake from the blood and storage within cells. In still other embodiments, the therapeutic component is a Factor VII/VIIa or functional analog thereof, which is generally effective for promoting coagulation by activation of Factor X or Factor IX.

The elastic peptide and therapeutic components may be covalently coupled by various means, including chemical coupling (e.g., conjugation) and recombinant fusion technology. In addition, the number of elastic peptide or therapeutic components per molecule, and their respective positions within the molecule, may vary as needed. The therapeutic agent may further include one or more spacer or linker moieties, which in addition to providing the desired functional independence of the elastic peptide and therapeutic components, may optionally provide for additional functionalities, such as a protease-sensitive feature to allow for proteolytic release or activation of the therapeutic component. The therapeutic agent may further include one or more targeting components such as, for example, a peptide or protein to target the therapeutic agent to a particular cell type, e.g., a cancer cell, or to a particular organ.

In a second aspect, the invention provides polynucleotides, such polynucleotides comprising a nucleotide sequence encoding a therapeutic agent of the invention. For example, the nucleotide sequence encodes an elastic peptide fusion with a functional portion of at least one therapeutic protein described herein, including those listed in Table 1 (or functional analog thereof). In certain embodiments, the therapeutic component is a GLP-1 receptor agonist (including GLP-1 and exendin-4), insulin, Factor VII/VIIa, or functional analog thereof. Such polynucleotides may further comprise additional control element(s) operably linked to the nucleotide sequence, such as promoter elements and/or other transcription or expression-related signals. The polynucleotide may be inserted into various vectors, which may be useful for production of the therapeutic agent in host cells, including, for example, bacterial and eukaryotic host cells.

In a third aspect, the invention provides a method for treating or preventing a disease, disorder, or condition in a subject, such as in a mammalian patient, including a human patient. The method comprises administering an effective amount of the therapeutic agent of the invention (or pharmaceutical composition containing the same) to a subject or patient in need thereof. For example, the patient may be in need of an agent having a biological activity or preferred indication listed herein (e.g., in Table 1). In certain embodiments employing a GLP-1 receptor agonist/elastic peptide compound or employing an insulin/elastic peptide compound, the invention provides a method for treating one or more disorders including type 1 or type 2 diabetes, hyperglycemia, and impaired glucose tolerance. In certain other embodiments employing Factor VII/VIIa/elastic peptide compound, the invention provides a method for treating one or more disorders including hemophilia, post-surgical bleeding, anticoagulation-induced bleeding, thrombocytopenia, factor VII deficiency, factor XI deficiency, and intracranial hemorrhage.

Various other aspects, features and embodiments of the invention will be more fully apparent from the following disclosure and appended claims.

BRIEF DESCRIPTION OF THE FIGURES

FIG. 2B depicts the nucleotide and amino acid sequence of the exendin-4/ELP fusion (SEQ ID NOS: 23 and 24). Primer sequences are indicated (SEQ ID NOS:35-40).

FIG. 3A depicts the nucleotide and amino acid sequence of an exendin-4 construct having an N-terminal Tev (Tobacco Etch Virus cysteine protease) cleavage site (SEQ ID NOS: 25 and 26). Primer sequences are indicated (SEQ ID NOS:38, 41, 42). FIG. 3B also depicts the nucleotide and amino acid sequence of an exendin-4 construct having an N-terminal Tev cleavage site, but with an additional sequence N-terminal to the Tev cleavage site to provide a better target for the protease (SEC) ID NOS: 27 and 28). Primer sequences are indicated (SEQ ID NOS:38, 43,44).

FIG. 4A depicts the nucleotide and amino acid sequence of an exendin-4/ELP fusion as in FIGS. 1-3, but with a DsbA leader sequence to direct secretion into the periplasmic space (SEQ ID NOS: 29 and 30). Primer sequences are indicated (SEQ ID NOS:38, 45, 46).

FIG. 5B depicts the nucleotide and amino acid sequence of the encoded fusion protein (SEQ ID NOS: 53 and 54, respectively).

FIG. 6B depicts the nucleotide and amino acid sequence of the encoded fusion protein (SEQ ID NOS: 55 and 56, respectively).

FIG. 7B depicts the nucleotide and amino acid sequence of the encoded fusion protein (SEQ ID NOS: 57 and 58, respectively).

FIG. 8A depicts the nucleotide and amino acid sequence of an insulin (B, C, and A chains) having the ELP component cloned in frame (SEQ ID NOS: 31 and 32). Primer sequences are indicated (SEQ ID NOS: 47 and 48).

DETAILED DESCRIPTION OF THE INVENTION

Figure 1:
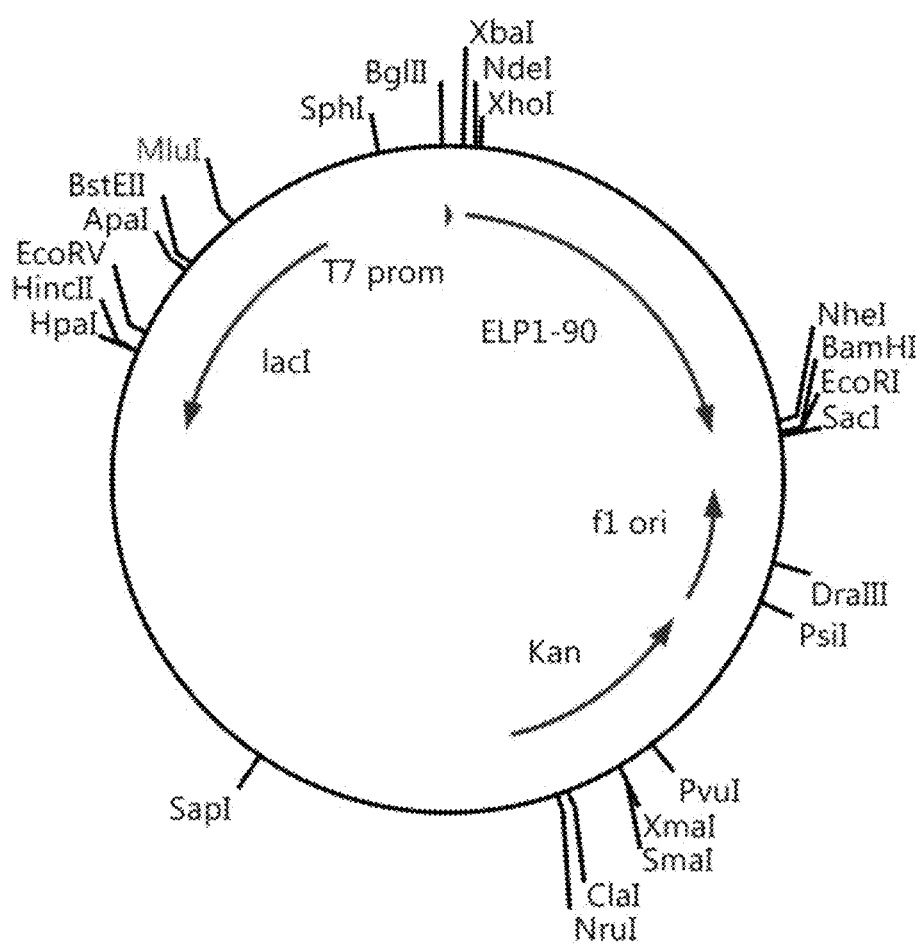
FIG. 1 depicts plasmid pET24d-ELP1-90, encoding an elastin-like-peptide (ELP) component with a 10 unit VPGXG (SEQ ID NO: 3) repeat motif, where guest position X is V, G, and A in the ratio of 5:3:2. This motif is repeated eight times with a final C-terminal 10-unit repeat where X is V, G, A, and W in the ratio 4:3:2:1. This ELP component is represented generally as [(VPGXG)$_{10}$]$_9$.

The present invention provides therapeutic agents comprising an elastic peptide component and a therapeutic component. The therapeutic component may be selected from Table 1 (e.g., selected from a Therapeutic Protein, or functional portion or functional analog thereof, listed in Table 1), or described herein. In certain embodiments, the therapeutic component is a GLP-1 receptor agonist, such as GLP-1 or exendin-4, or may be insulin, Factor VII/VIIa, or functional analog thereof. The elastic peptide component exhibits a flexibility and freedom of movement that results from its secondary structure characteristics, and overall or substantial lack of a rigid tertiary structure. The elastic peptide components may contain structural units related to, or derived from, sequences of the elastin protein. The elastic peptide provides certain therapeutic advantages, such as comparatively better persistence, stability, solubility, bioavailability, half-life, and/or biological action of the therapeutic component. Such properties may be determined with respect to, for example, an unfused or unconjugated counterpart of the therapeutic component. The invention further provides polynucleotides encoding the therapeutic agents of the invention, as well as methods of treatment or prophylaxis for certain biological conditions, including the preferred indications listed in Table 1, and including diabetes (e.g., Type I and Type II), hyperglycemia, bleeding, hemophilia, and hemorrhage, among others.

For ease of reference in the ensuing discussion, set out below are definitions of some terms appearing in the discussion.

As used herein, the term "therapeutic agent" or "therapeutic component" refers to an agent or component capable of inducing a biological effect in vivo and/or in vitro. The biological effect may be useful for treating and/or preventing a condition, disorder, or disease in a subject or patient.

As used herein, the term "coupled" means that the specified components are either directly covalently bonded to one another (e.g., via chemical conjugation or recombinant fusion technology), or indirectly covalently joined to one another (e.g., via chemical conjugation or recombinant fusion technology) through an intervening moiety or moieties, such as a bridge, spacer, or linker.

As used herein, "half-life" (which generally refers to in vivo half-life or circulatory half-life) is the period of time that is required for a 50% diminution of bioactivity of the active agent to occur. Such term is to be contrasted with "persistence," which is the overall temporal duration of the active agent in the body, and "rate of clearance" as being a dynamically changing variable that may or may not be correlative with the numerical values of half-life and persistence.

The term "functional analog" refers to a protein that is an active analog (e.g., either chemical or protein analog), derivative, fragment, truncation isoform or the like of a native protein. For example, the functional analog may be a functional analog of a therapeutic protein listed in Table 1, or may be a functional analog of a GLP-1 receptor agonist (e.g., GLP-1, exendin), insulin, or Factor VII/VIIa. A polypeptide is active when it retains some or all of the biological activity of the corresponding native polypeptide, as determined in vivo or in one or more indicative in vitro assays. Exemplary activity assays for certain therapeutic proteins, which are determinative of activity, are listed Table 1. Further, such biological activities and assays for GLP-1 receptor agonists, insulin, and Factor VII/VIIa, which are determinative of whether a given molecule is a "functional analog," are described in detail elsewhere herein.

As used herein, the term "native," as used in reference to an amino acid sequence, indicates that the amino acid sequence is found in a naturally-occurring protein.

As used herein, the term "spacer" refers to any moiety, peptide or other chemical entity, that may be interposed between the elastic peptide component and the therapeutic component. For example, the spacer may be a divalent group that is covalently bonded at one terminus to the elastic peptide component, and covalently bonded at the other terminus to the therapeutic component. The therapeutic agents may therefore be open to the inclusion of additional chemical structure that does not preclude the efficacy of the agent for its intended purpose. The spacer may, for example, be a protease-sensitive spacer moiety that is provided to control the pharmacokinetics of the agent, or the spacer may be a protease-resistant moiety.

The therapeutic component and the elastic peptide component may be coupled with one another in any suitable covalent manner, including chemical coupling and recombinant technology, such that the therapeutic agent is efficacious for its intended purpose, and such that the presence of the elastic peptide component enhances the therapeutic component in some functional, therapeutic or physiological aspect. For example, the elastic peptide-coupled therapeutic component may be enhanced in, e.g., its bioavailability, bio-unavailability, therapeutically effective dose, biological action, formulation compatibility, resistance to proteolysis or other degradative modality, solubility, half-life or other measure of persistence in the body subsequent to administration, rate of clearance from the body subsequent to administration, etc. Such enhancement may be determined, for example, in relation to a corresponding unconjugated or unfused counterpart therapeutic (e.g., determined relative to native GLP-1, exendin, insulin, or Factor VII/VIIa, or a therapeutic protein described herein).

In some embodiments, the therapeutic agent of the invention circulates or exists in the body in a soluble form, and escapes filtration by the kidney thereby persisting in the body in an active form. In some embodiments, the therapeutic agents of the invention have a molecular weight of less than the generally recognized cut-off for filtration through the kidney, such as less than about 60 kD, or in some embodiments less than about 55, 50, 45, 40, 30, or 20 kDa, and persist in the body by at least 2-fold, 3-fold, 4-fold, 5-fold, 10-fold, 20-fold, or 100-fold or longer than an uncoupled (e.g., unfused or unconjugated) therapeutic counterpart.

The number of elastic peptide and/or therapeutic components per molecule, and their respective positions within the molecule, may vary among embodiments of the invention. For example, in embodiments where the agent is a recombinant fusion, at least one elastic peptide component may be placed at one or both of the N-terminus and the C-terminus. Where the elastic peptide component is at both the N-terminus and C-terminus of the fusion, the elastic peptide components will flank the therapeutic component. Alternatively, the therapeutic component may be positioned at either or both of the N-terminus and C-terminus. Where the therapeutic component is at both the N-terminus and C-terminus, the therapeutic component will flank the elastic peptide component. In a further embodiment, different therapeutic components are positioned at the N-terminus and C-terminus of the molecule. As discussed in detail herein, in certain embodiments, such therapeutic component(s) may be released by proteolysis of a spacer moiety separating the elastic peptide and therapeutic components. In certain embodiments, the therapeutic component may be inactive in the fused state, and becoming active upon proteolytic release from the elastic peptide component(s). Alternatively, the therapeutic component remains active in the fused state, making proteolytic processing of the therapeutic agent unnecessary for biological activity.

When prepared as recombinant fusions, the therapeutic agent can be prepared by known recombinant expression techniques. For example, to recombinantly produce the therapeutic agent, a nucleic acid sequence encoding the chimeric gene is operatively linked to a suitable promoter sequence such that the nucleic acid sequence encoding such fusion protein will be transcribed and/or translated into the desired fusion protein in the host cells. Preferred promoters are those useful for expression in *E. coli*, such as the T7 promoter. Any commonly used expression system may be used, including eukaryotic or prokaryotic systems. Specific examples include yeast (e.g., *Saccharomyces* spp., *Pichia* spp.), baculovirus, mammalian, and bacterial systems, such as *E. coli*, and Caulobacter.

The various aspects and embodiments of the invention are described in greater detail in the following sections.

Elastic Peptide Component

The therapeutic agent of the invention may comprise one or more elastic peptide components. The elastic peptide components may comprise or consist of structural peptide units or sequences that are related to, or derived from, the elastin protein (e.g., elastin-like-peptides, or ELPs). Elastic peptides are useful for improving the properties of therapeutic proteins, such as those described herein (e.g., listed in Table 1), including GLP-1 receptor agonists (e.g., GLP-1 or exendin-4), insulin, and Factor VII/VIIa in one or more of bioavailability, therapeutically effective dose, biological action, formulation compatibility, resistance to proteolysis, solubility, half-life or other measure of persistence in the body subsequent to administration, and/or rate of clearance from the body.

The elastic peptide component may be constructed from structural units of from three to about twenty amino acids, or in some embodiments, from four to ten amino acids, such as five or six amino acids. The length of the individual structural units, may vary or may be uniform. In certain embodiments, the elastic peptide component is constructed of a polytetra-, polypenta-, polyhexa-, polyhepta-, polyocta, and polynonapeptide motif of repeating structural units. Exemplary structural units include units defined by SEQ ID NOS: 1-12 (below), which may be employed as repeating structural units, including tandem-repeating units, or may be employed in some combination, to create a peptide component effective for improving the properties of the therapeutic component. Thus, the elastic peptide component may comprise or consist essentially of structural unit(s) selected from SEQ ID NOS: 1-12, as defined below.

The elastic peptide component, comprising such structural units, may be of varying sizes. For example, the elastic peptide component may comprise or consist essentially of from about 10 to about 500 structural units, or in certain embodiments about 15 to about 150 structural units, or in certain embodiments from about 20 to about 100 structural units, or from about 50 to about 90 structural units, including one or a combination of units defined by SEQ ID NOS: 1-12. Thus, the elastic peptide component may have a length of from about 50 to about 2000 amino acid residues, or from about 100 to about 600 amino acid residues, or from about 200 to about 500 amino acid residues, or from about 200 to about 400 amino acid residues.

Elastic polymers (e.g., bioelastic polymers) are known and described in, for example, U.S. Pat. No. 5,520,672 to Urry et al. In general, elastic peptides comprise elastomeric units of bioelastic pentapeptides, tetrapeptides, and/or nonapeptides (e.g., elastin-like peptides). Thus, in some embodiments the elastomeric unit is a pentapeptide, in other embodiments the elastomeric unit is a tetrapeptide, and in still other embodiments the elastomeric unit is a nonapeptide. Bioelastic polymers that may be used to carry out the present invention are set forth in U.S. Pat. No. 4,474,851, which is hereby incorporated by reference in its entirety.

As disclosed in U.S. Pat. No. 4,474,851, elastomeric peptides may have a sequence of regularly appearing β-turns, forming an overall spiral conformation (e.g., a β-spiral, which is a series of regularly repeating β-turns). The spiral structures are more open than the more common α-helix. As a result, the atoms in the peptide backbone have a high freedom of movement (e.g., as compared to the freedom of movement for an α-helix). This is particularly true of librational motions involving peptide moieties. A libration is a torsional oscillation involving simultaneous rotational motions of the two single bonds on each side of a librating moiety. The moiety involved in a libration may be a single peptide bond or several peptide residues. For adequate freedom of motion to exist, it is important, however, that the carbonyl oxygen and the amino hydrogen of the peptide bond not be involved in hydrogen bonding to other parts of the molecule or to other molecules. Otherwise a greater energy barrier to the libration exists and motion will be restricted. Since non-hydrogen-bonded segments having freedom of motion exist in the β-spiral between the points of hydrogen bonding for the β-turns, these segments may be said to be librationally suspended. Librationally suspended segments therefore are a structural feature that exists in certain elastic peptides because of the repeating β-turns with relative infrequent hydrogen bonding. Librationally suspended segments resulting from the β-spiral structure are thought to give rise to elasticity, as will be further discussed.

Another factor leading to the high librational freedom of such molecules is the absence of significant polar interactions between the amino acid residues, either intrachain or interchain, other than a hydrogen bond within the β-turn. The amino acid residues present are mostly hydrophobic or glycine and accordingly do not exert significant forces on one another through space. If a significant number of charged or polar groups were present, electrostatic interactions might limit librational freedom and restrict the number of available states in the relaxed (non-extended) form of the molecules. Polar and charged amino acid residues are not strictly prohibited, however, if their presence does not destroy the elasticity of the eslatic peptide component as a whole. For example, an occasional serine residue is present in naturally occurring tropoelastin without destroying elasticity. Accordingly, hydrophobic amino acid residues and glycines are preferred in forming elastomeric polypeptides of the present type although other amino acids may be present to a some extent.

Although not intending to be bound by theory, the elasticity of polypeptides of the β-turn structure may be caused by thermodynamic drive toward greater entropy. The relaxed state of the β-spiral has a large degree of librational freedom and thus the atoms of the peptide chain can exist in a large number of positions. When the molecules are stretched, the degree of freedom is reduced, particularly for librational motions, and when the tension is released, a thermodynamic driving force toward higher entropy results in reformation of the contracted β-spiral.

Other specific bioelastic polymers that can be used to carry out the present invention are described in U.S. Pat. Nos. 4,132,746, 4,187,852, 4,500,700, 4,589,882, and 4,870,055, each of which are hereby incorporated by reference. Still other examples of bioelastic polymers are set forth in U.S. Pat. No. 6,699,294, U.S. Pat. No. 6,753,311, and U.S. Pat. No. 6,063,061, which are also incorporated by reference in their entirety.

In some embodiments, the β-turn may have the following structure, in the formation of a β-spiral:

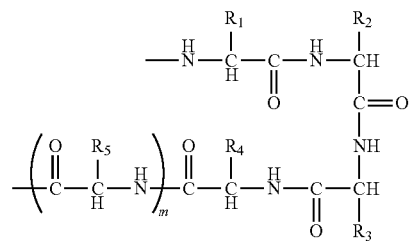

wherein R1-R5 represent side chains of amino acid residues 1-5, and m is 0 when the repeating unit is a tetrapeptide or 1 when the repeating unit is a pentapeptide. Nonapeptide repeating units generally consist of sequential tetra- and pentapeptides. The amino acid residues may be hydrophobic amino acid residues, such as those independently selected from alanine, valine, leucine, isoleucine, proline, phenylalanine, tryptophan, and methionine. In many cases, the first amino acid residue of the repeating unit is a residue of valine, leucine, isoleucine or phenylalanine; the second amino acid residue is a residue of proline; the third amino acid residue is a residue of glycine; and the fourth amino acid residue is glycine or a hydrophobic residue such as tryptophan, phenylalanine or tyrosine.

In some embodiments, the elastic peptide component, or in some cases the therapeutic agent, has a size of less than about 65 kDa, or less than about 60 kDa, or less than about 55 kDa, or less than about 50 kDa, or less than about 40 kDa, or less than about 30 or 25 kDa. Three major blood proteins, Human Serum Albumin (HSA), Transferrin (Tf) and IgG, or the Fc portion of IgGs in their glycosylated form, have been exploited to extend the half-lives of proteins and peptides for improved therapeutic use. These molecules are 585, 679 and 480 amino acids in length giving molecular weights of about 66, 77, and ~75 kDa (including glycosylations), respectively. They are each globular and relatively compact. The half life of these molecules is determined by a number of factors, including charge distribution, rescue of molecules by the neonatal Fc receptor (FcRn) (HSA and Fc) or cycling of Tf through the Tf receptor (TfR), and their size which prevents filtering through the kidney glomerulus. HSA is slightly below the generally regarded cut-off for filtration through the kidney (~70 kDa) but its charge distribution helps prevent this. It would be anticipated that, in order to achieve half-life extension of the same order as that achieved with HSA, Tf and Fc, a protein of at least this molecular weight range would be required or desirable, i.e. having over 550 amino acids and being over 65 kDa. However, an elastic peptide with a small number of amino acids relative to HSA, Tf and Fc (e.g., in the range of about 300 to 400) and around 30 to 40 kDa may have a half life that matches and/or exceeds that of HSA, Tf, and Fc.

Thus, in some embodiments, the elastic peptide component may have an extended, relatively unstructured (e.g., no definitive tertiary structure due to rotational and/or librational freedom of the peptide backbone) and non-globular form, and thus such molecules may have a large expanded structure in comparison to HSA, Tf and Fc, so as to escape kidney filtration. In such embodiments, the therapeutic agents of the invention have a molecular weight of less than the generally recognized cut-off for filtration through the kidney, such as less than about 60 kD, or in some embodiments less than about 55, 50, 45, 40, 30, or 25 kDa, and persist in the body by at least 2-fold, 3-fold, 4-fold, 5-fold, 10-fold, 20-fold, or 100-fold longer than an uncoupled (e.g., unfused or unconjugated) therapeutic counterpart.

In certain embodiments, the elastic peptide component is an ELP that undergoes a reversible inverse phase transition. ELP components are structurally disordered and highly soluble in water below a transition temperature (Tt), but exhibit a sharp (2-3° C. range) disorder-to-order phase transition when the temperature is raised above the Tt, leading to desolvation and aggregation of the ELP components. For example, the ELP forms insoluble polymers, when reaching sufficient size, which can be readily removed and isolated from solution by centrifugation. Such phase transition is reversible, and isolated insoluble ELPs can be completely resolubilized in buffer solution when the temperature is returned below the Tt of the ELPs. Thus, the therapeutic agents of the invention can, in some embodiments, be separated from other contaminating proteins to high purity using inverse transition cycling procedures, e.g., utilizing the temperature-dependent solubility of the therapeutic agent, or salt addition to the medium. Successive inverse phase transition cycles can be used to obtain a high degree of purity. In addition to temperature and ionic strength, other environmental variables useful for modulating the inverse transition of the therapeutic agents include pH, the addition of inorganic and organic solutes and solvents, side-chain ionization or chemical modification, and pressure.

In certain embodiments, the ELP component does not undergo a reversible inverse phase transition, or does not undergo such a transition at a biologically relevant Tt, and thus the improvements in the biological and/or physiological properties of the molecule (as described elsewhere herein), may be entirely or substantially independent of any phase transition properties. Nevertheless, such phase transition properties may impart additional practical advantages, for example, in relation to the recovery and purification of such molecules.

In certain embodiments, the ELP component(s) may be formed of structural units, including but not limited to:
  (a) the tetrapeptide Val-Pro-Gly-Gly, or VPGG (SEQ ID NO: 1);
  (b) the tetrapeptide Ile-Pro-Gly-Gly, or IPGG (SEQ ID NO: 2);
  (c) the pentapeptide Val-Pro-Gly-X-Gly (SEQ ID NO: 3), or VPGXG, where X is any natural or non-natural amino acid residue, and where X optionally varies among polymeric or oligomeric repeats;
  (d) the pentapeptide Ala-Val-Gly-Val-Pro, or AVGVP (SEQ ID NO: 4);
  (e) the pentapeptide Ile-Pro-Gly-X-Gly, or IPGXG (SEQ ID NO: 5), where X is any natural or non-natural amino acid residue, and where X optionally varies among polymeric or oligomeric repeats;
  (e) the pentapeptide Ile-Pro-Gly-Val-Gly, or IPGVG (SEQ ID NO: 6);
  (f) the pentapeptide Leu-Pro-Gly-X-Gly, or LPGXG (SEQ ID NO: 7), where X is any natural or non-natural amino acid residue, and where X optionally varies among polymeric or oligomeric repeats;
  (g) the pentapeptide Leu-Pro-Gly-Val-Gly, or LPGVG (SEQ ID NO: 8);
  (h) the hexapeptide Val-Ala-Pro-Gly-Val-Gly, or VAPGVG (SEQ ID NO: 9);
  (I) the octapeptide Gly-Val-Gly-Val-Pro-Gly-Val-Gly, or GVGVPGVG (SEQ ID NO: 10);
  (J) the nonapeptide Val-Pro-Gly-Phe-Gly-Val-Gly-Ala-Gly, or VPGFGVGAG (SEQ ID NO: 11); and
  (K) the nonapeptides Val-Pro-Gly-Val-Gly-Val-Pro-Gly-Gly, or VPGVGVPGG (SEQ ID NO: 12).

Such structural units defined by SEQ ID NOS:1-12 may form structural repeat units, or may be used in combination to form an ELP component in accordance with the invention. In some embodiments, the ELP component is formed entirely (or almost entirely) of one or a combination of (e.g., 2, 3 or 4) structural units selected from SEQ ID NOS: 1-12. In other embodiments, at least 75%, or at least 80%, or at least 90% of the ELP component is formed from one or a combination of structural units selected from SEQ ID NOS: 1-12, and which may be present as repeating units.

In certain embodiments, the ELP component(s) contain repeat units, including tandem repeating units, of the pentapeptide Val-Pro-Gly-X-Gly (SEQ ID NO:3), where X is as defined above, and where the percentage of Val-Pro-Gly-X-Gly (SEQ ID NO:3) pentapeptide units taken with respect to the entire ELP component (which may comprise structural units other than VPGXG (SEQ ID NO:3)) is greater than about 75%, or greater than about 85%, or greater than about 95% of the ELP component. The ELP component may contain motifs having a 5 to 15-unit repeat (e.g. about 10-unit repeat) of the pentapeptide of SEQ ID NO: 3, with the guest residue X varying among at least 2 or at least 3 of the units. The guest residues may be independently selected, such as from the amino acids V, I, L, A, G, and W (and may be selected so as to retain a desired inverse phase transition property). The repeat motif itself may be repeated, for example, from about 5 to about 12 times, such as about 8 to 10 times, to create an exemplary ELP component. The ELP component as described in this paragraph may of course be constructed from any one of the structural units defined by SEQ ID NOS: 1-12, or a combination thereof.

In some embodiments, the ELP component may include a β-turn structure. Exemplary peptide sequences suitable for creating a β-turn structure are described in International Patent Application PCT/US96/05186, which is hereby incorporated by reference in its entirety. For example, the fourth residue (X) in the elastin pentapeptide sequence, VPGXG (SEQ ID NO:3), can be altered without eliminating the formation of a β-turn. Alternatively, the ELP component may lack a β-turn, or otherwise have a different conformation and/or folding character.

In certain embodiments, the ELP components include polymeric or oligomeric repeats of the pentapeptide VPGXG (SEQ ID NO: 3), where the guest residue X is any amino acid. X may be a naturally occurring or non-naturally occurring amino acid. In some embodiments, X is selected from alanine, arginine, asparagine, aspartic acid, cysteine, glutamic acid, glutamine, glycine, histidine, isoleucine, leucine, lysine, methionine, phenylalanine, serine, threonine, tryptophan, tyrosine and valine. In some embodiments, X is a natural amino acid other than proline or cysteine.

The guest residue X (e.g., with respect to SEQ ID NO: 3, or other ELP structural unit) may be a non-classical (non-genetically encoded) amino acid. Examples of non-classical amino acids include: D-isomers of the common amino acids, 2,4-diaminobutyric acid, α-amino isobutyric acid, A-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

Selection of X is independent in each ELP structural unit (e.g., for each structural unit defined herein having a guest residue X). For example, X may be independently selected for each structural unit as an amino acid having a positively charged side chain, an amino acid having a negatively charged side chain, or an amino acid having a neutral side chain, including in some embodiments, a hydrophobic side chain.

In still other embodiments, the ELP component(s) may include polymeric or oligomeric repeats of the pentapeptides VPGXG (SEQ ID NO:3), IPGXG (SEQ ID NO:5) or LPGXG (SEQ ID NO:7), or a combination thereof, where X is as defined above.

In each embodiment, the structural units, or in some cases polymeric or oligomeric repeats, of the elastic peptide sequences may be separated by one or more amino acid residues that do not eliminate the overall effect of the molecule, that is, in imparting certain improvements to the therapeutic component as described. In certain embodiments, such one or more amino acids also do not eliminate or substantially affect the phase transition properties where ELP components are employed (relative to the deletion of such one or more amino acids).

For ELP sequences, in each repeat, X is independently selected. The structure of the resulting ELP components may be described using the notation ELPk [$X_iY_j$ n], where k designates a particular ELP repeat unit, the bracketed capital letters are single letter amino acid codes and their corresponding subscripts designate the relative ratio of each guest residue X in the structural units (where applicable), and n describes the total length of the ELP in number of the structural repeats. For example, ELP1 [$V_5A_2G_3$-10] designates an ELP component containing 10 repeating units of the pentapeptide VPGXG (SEQ ID NO:3), where X is valine, alanine, and glycine at a relative ratio of 5:2:3; ELP1 [$K_1V_2F_1$-4] designates an ELP component containing 4 repeating units of the pentapeptide VPGXG (SEQ ID NO:3), where X is lysine, valine, and phenylalanine at a relative ratio of 1:2:1; ELP1 [$K_1V_7F_1$-9] designates a polypeptide containing 9 repeating units of the pentapeptide VPGXG (SEQ ID NO:3), where X is lysine, valine, and phenylalanine at a relative ratio of 1:7:1; ELP1 [V-5] designates a polypeptide containing 5 repeating units of the pentapeptide VPGXG (SEQ ID NO:3), where X is exclusively valine; ELP1 [V-20] designates a polypeptide containing 20 repeating units of the pentapeptide VPGXG (SEQ ID NO:3), where X is exclusively valine; ELP2 [5] designates a polypeptide containing 5 repeating units of the pentapeptide AVGVP (SEQ ID NO:4); ELP3 [V-5] designates a polypeptide containing 5 repeating units of the pentapeptide IPGXG (SEQ ID NO:5), where X is exclusively valine; ELP4 [V-5] designates a polypeptide containing 5 repeating units of the pentapeptide LPGXG (SEQ ID NO:7), where X is exclusively valine. Such ELP components as described in this paragraph may be used in connection with the present invention to increase the therapeutic properties of the therapeutic component.

Further, the Tt is a function of the hydrophobicity of the guest residue. Thus, by varying the identity of the guest residue(s) and their mole fraction(s), ELPs can be synthesized that exhibit an inverse transition over a 0-100° C. range. Thus, the Tt at a given ELP length may be decreased by incorporating a larger fraction of hydrophobic guest residues in the ELP sequence. Examples of suitable hydrophobic guest residues include valine, leucine, isoleucine, phenylalanine, tryptophan and methionine. Tyrosine, which is moderately hydrophobic, may also be used. Conversely, the Tt may be increased by incorporating residues, such as those selected from the group consisting of: glutamic acid, cysteine, lysine, aspartate, alanine, asparagine, serine, threonine, glycine, arginine, and glutamine; preferably selected from alanine, serine, threonine and glutamic acid.

The ELP component in some embodiments is selected or designed to provide a Tt ranging from about 10 to about 80° C., such as from about 35 to about 60° C., or from about 38 to about 45° C. In some embodiments, the Tt is greater than about 40° C. or greater than about 42° C., or greater than about 45° C., or greater than about 50° C. The transition temperature, in some embodiments, is above the body temperature of the subject or patient (e.g., >37° C.) thereby remaining soluble in vivo, or in other embodiments, the Tt is below the body temperature (e.g., <37° C.) to provide alternative advantages, such as in vivo formation of a drug depot for sustained release of the therapeutic agent.

The Tt of the ELP component can be modified by varying ELP chain length, as the Tt generally increases with decreasing MW. For polypeptides having a molecular weight>100, 000, the hydrophobicity scale developed by Urry et al. (PCT/

US96/05186, which is hereby incorporated by reference in its entirety) is preferred for predicting the approximate Tt of a specific ELP sequence. However, in some embodiments, ELP component length can be kept relatively small, while maintaining a target Tt, by incorporating a larger fraction of hydrophobic guest residues (e.g., amino acid residues having hydrophobic side chains) in the ELP sequence. For polypeptides having a molecular weight<100,000, the Tt may be predicted or determined by the following quadratic function: $Tt=M_0+M_1X+M_2X^2$ where X is the MW of the fusion protein, and $M_0=116.21$; $M_1=-1.7499$; $M_2=0.010349$.

While the Tt of the ELP component, and therefore of the ELP component coupled to a therapeutic component, is affected by the identity and hydrophobicity of the guest residue, X, additional properties of the molecule may also be affected. Such properties include, but are not limited to solubility, bioavailability, persistence, and half-life of the molecule.

As described in PCT/US2007/077767 (published as WO 2008/030968), which is hereby incorporated by reference in its entirety, the ELP-coupled therapeutic component can retain the therapeutic component's biological activity. Additionally, ELPs themselves can exhibit long half-lives. Therefore, ELP components in accordance with the present invention substantially increase (e.g. by greater than 10%, 20%, 30%, 50%, 100%, 200%, 500% or more, in specific embodiments) the half-life of the therapeutic component when conjugated thereto. Such half-life (or in some embodiments persistance or rate of clearance) is determined in comparison to the half-life of the free (unconjugated or unfused) form of the therapeutic component. Furthermore, ELPs may target high blood content organs, when administered in vivo, and thus, can partition in the body, to provide a predetermined desired corporeal distribution among various organs or regions of the body, or a desired selectivity or targeting of a therapeutic agent. In sum, the therapeutic agents contemplated by the invention are administered or generated in vivo as active compositions having extended half-lives (e.g., circulatory half-life), among other potential benefits described herein.

The invention thus provides various agents for therapeutic (in vivo) application, where the therapeutic component is biologically active. Such therapeutic components include, without limitation, growth hormone (GH) particularly human and bovine growth hormone, growth hormone-releasing hormones; interferon including α-. β-, or γ-interferons, etc, interleukin-I; interleukin-II; erythropoietin including α- and β-erythropoietin (EPO), granulocyte colony stimulating factor (GCSF), granulocyte macrophage colony stimulating factor (GM-CSF), anti-agiogenic proteins (e.g., angiostatin, endostatin) PACAP polypeptide (pituitary adenylate cyclase activating polypeptide), vasoactive intestinal peptide (VIP), thyrotrophin releasing hormone (TRH), corticotropin releasing hormone (CRH), vasopressin, arginine vasopressin (AVP), angiotensin, calcitonin, atrial naturetic factor, somatostatin, adrenocorticotropin, gonadotropin releasing hormone, oxytocin, insulin, somatotropin, plasminogen tissue activator, coagulation factors including coagulation factors VIII and IX, glucosylceramidase, sargramostim, lenograstin, filgrastin, dornase-α, molgramostim, PEG-L-asparaginase, PEG-adenosine deaminase, hirudin, eptacog-α (human blood coagulation factor VIIa) nerve growth factors, transforming growth factor, epidermal growth factor, basic fibroblast growth factor, VEGF; heparin including low molecular weight heparin, calcitonin; antigens; monoclonal antibodies; vancomycin; desferrioxamine (DFO); parathyroid hormone, an immunogen or antigen, an antibody such as a monoclonal antibody.

Where the therapeutic component is an antibody or antibody sequence, the antibody may be of any isotype, including IgG, IgM, IgA, IgD, and IgE. Where the antibody is IgG, the subtype may be IgGi, IgG2, IgG3, or IgG4. The antibody sequence may be humanized or chimeric. The term "antibody" as used herein includes antibody fragments or segments that retain the capability of binding to a target antigen, for example, Fab, F(ab')2, and Fv fragments, and the corresponding fragments obtained from antibodies other than IgG. Examples of therapeutic antibodies include but are not limited to herceptin, rituxan, campath, gemtuzumab, herceptin, panorex, rituximab, bexxar, edrecolomab, alemtuzumab, mylotrag, IMC-C225, smartin 195, and mitomomab.

The therapeutic component may also be a therapeutic component listed in Table 1 (e.g., full length or functional portions or functional analogs thereof), as well as GLP-1 receptor agonists such as GLP-1 or exendin-4, insulin, or Factor VII/VIIa, and functional analogs thereof. The structure and activity of such therapeutic components are described in detail below. In some forms of the therapeutic agent, the coupling of the therapeutic component to the elastic peptide is effected by direct covalent bonding or indirect (through appropriate spacer groups) bonding (as described elsewhere herein). Further, the therapeutic component(s) and the elastic peptide component(s) can be structurally arranged in any suitable manner involving such direct or indirect covalent bonding, relative to one another.

Glucagon-Like Peptide (GLP)-1 Receptor Agonists

In certain embodiments of the invention, the therapeutic agent comprises an ELP component fused or conjugated to a GLP-1 receptor agonist, such as GLP-1, exendin-4, or functional analogs thereof.

Human GLP-1 is a 37 amino acid residue peptide originating from preproglucagon which is synthesized in the L-cells in the distal ileum, in the pancreas, and in the brain. Processing of preproglucagon to give GLP-1(7-36)amide, GLP-1(7-37) and GLP-2 occurs mainly in the L-cells. A simple system is used to describe fragments and analogs of this peptide. For example, $Gly^8$-GLP-1(7-37) designates a fragment of GLP-1 formally derived from GLP-1 by deleting the amino acid residues Nos. 1 to 6 and substituting the naturally occurring amino acid residue in position 8 (Ala) by Gly. Similarly, $Lys^{34}$ ($N^\epsilon$-tetradecanoyl)-GLP-1(7-37) designates GLP-1(7-37) wherein the ε-amino group of the Lys residue in position 34 has been tetradecanoylated. Where reference in this text is made to C-terminally extended GLP-1 analogues, the amino acid residue in position 38 is Arg unless otherwise indicated, the optional amino acid residue in position 39 is also Arg unless otherwise indicated and the optional amino acid residue in position 40 is Asp unless otherwise indicated. Also, if a C-terminally extended analogue extends to position 41, 42, 43, 44 or 45, the amino acid sequence of this extension is as in the corresponding sequence in human preproglucagon unless otherwise indicated.

The parent peptide of GLP-1, proglucagon (PG), has several cleavage sites that produce various peptide products dependent on the tissue of origin including glucagon (PG[32-62]) and GLP-1[7-36]$NH_2$ (PG[72-107]) in the pancreas, and GLP-1[7-37] (PG[78-108]) and GLP-1[7-36]$NH_2$ (PG [78-107]) in the L cells of the intestine where GLP-1[7-36]$NH_2$ (78-107 PG) is the major product. The GLP-1 component in accordance with the invention may be any biologically active product or derivative of proglocagon, or functional analog thereof, including: GLP-1(1-35), GLP-1(1-36), GLP-1(1-36) amide, GLP-1(1-37), GLP-1(1-38), GLP-1(1-39), GLP-1(1-40), GLP-1(1-41), GLP-1(7-35), GLP-1(7-36), GLP-1(7-36) amide, GLP-1(7-37), GLP-1(7-38), GLP-1(7-39), GLP-1(7-

40) and GLP-1(7-41), or a analog of the foregoing. Generally, the GLP-1 component in some embodiments may be expressed as GLP-1 (A-B), where A is an integer from 1 to 7 and B is an integer from 38 to 45, optionally with one or more amino acid substitutions as defined below.

As an overview, after processing in the intestinal L-cells, GLP-1 is released into the circulation, most notably in response to a meal. The plasma concentration of GLP-1 rises from a fasting level of approximately 15 pmol/L to a peak postprandial level of 40 pmol/L. For a given rise in plasma glucose concentration, the increase in plasma insulin is approximately threefold greater when glucose is administered orally compared with intravenously (Kreymann et al., 1987, *Lancet* 2(8571): 1300-4). This alimentary enhancement of insulin release, known as the incretin effect, is primarily humoral and GLP-1 is now thought to be the most potent physiological incretin in humans. GLP-1 mediates insulin production via binding to the GLP-1 receptor, known to be expressed in pancreatic β cells. In addition to the insulinotropic effect, GLP-1 suppresses glucagon secretion, delays gastric emptying (Wettergen et al., 1993, *Dig Dis Sci* 38: 665-73) and may enhance peripheral glucose disposal (D'Alessio et al., 1994, *J. Clin Invest* 93: 2293-6).

A combination of actions gives GLP-1 unique therapeutic advantages over other agents currently used to treat non-insulin-dependent diabetes mellitus (NIDDM). First, a single subcutaneous dose of GLP-1 can completely normalize post prandial glucose levels in patients with NIDDM (Gutniak et al., 1994, *Diabetes Care* 17: 1039-44). This effect may be mediated both by increased insulin release and by a reduction in glucagon secretion. Second, intravenous infusion of GLP-1 can delay postprandial gastric emptying in patients with NIDDM (Williams et al., 1996, *J. Clin Endo Metab* 81: 327-32). Third, unlike sulphonylureas, the insulinotropic action of GLP-1 is dependent on plasma glucose concentration (Holz et al., 1993, *Nature* 361:362-5). Thus, the loss of GLP-1-mediated insulin release at low plasma glucose concentration protects against severe hypoglycemia.

When given to healthy subjects, GLP-1 potently influences glycemic levels as well as insulin and glucagon concentrations (Orskov, 1992, *Diabetologia* 35:701-11), effects which are glucose dependent (Weir et al., 1989, *Diabetes* 38: 338-342). Moreover, it is also effective in patients with diabetes (Gutniak, M., 1992, *N. Engl J Med* 226: 1316-22), normalizing blood glucose levels in type 2 diabetic subjects and improving glycemic control in type 1 patients (Nauck et al., 1993, *Diabetologia* 36: 741-4, Creutzfeldt et al., 1996, *Diabetes Care* 19:580-6).

GLP-1 is, however, metabolically unstable, having a plasma half-life ($t_{1/2}$) of only 1-2 minutes in vivo. Moreover, exogenously administered GLP-1 is also rapidly degraded (Deacon et al., 1995, *Diabetes* 44: 1126-31). This metabolic instability has limited the therapeutic potential of native GLP-1.

GLP-1[7-36]NH$_2$ has the following amino acid sequence: HAEGTFTSDVSSYLEGQAAKEFIAWLVKGR (SEQ ID NO: 13), which may be employed as the GLP-1 component in accordance with the invention. Alternatively, the GLP-1 component may contain glycine (G) at the second position, giving, for example, the sequence HGEGTFTSDVS-SYLEGQAAKEFIAWLVKGR (SEQ ID NO: 17). The GLP-1 component may be a biologically active fragment of GLP-1, for example, as disclosed in US 2007/0041951, which is hereby incorporated by reference in its entirety. Other fragments and modified sequences of GLP-1 are known in the art (U.S. Pat. No. 5,614,492; U.S. Pat. No. 5,545,618; European Patent Application, Publication No. EP 0658568 A1; WO 93/25579, which are hereby incorporated by reference in their entireties). Such fragments and modified sequences may be used in connection with the present invention, as well as those described below.

Certain structural and functional analogs of GLP-1 have been isolated from the venom of the Gila monster lizards (*Heloderma suspectum* and *Heloderma horridum*) and have shown clinical utility. Such molecules find use in accordance with the present invention. In particular, exendin-4 is a 39 amino acid residue peptide isolated from the venom of *Heloderma suspectum* and shares approximately 52% homology with human GLP-1. Exendin-4 is a potent GLP-1 receptor agonist that stimulates insulin release, thereby lowering blood glucose levels. Exendin-4 has the following amino acid sequence: HGEGTFTSDLSKQMEEEAVRLFEWLKNG-GPSSGAPPPS (SEQ ID NO: 14). A synthetic version of exendin-4 known as exenatide (marketed as Byetta®) has been approved for the treatment of Type-2 Diabetes. Although exenatide is structurally analogous to native GLP-1, it has a longer half-life after injection.

While exenatide has the ability to lower blood glucose levels on its own, it can also be combined with other medications such as metformin, a thiozolidinedione, a sulfonylureas, and/or insulin to improve glucose control. Exenatide is administered by injection subcutaneously twice per day using a pre-filled pen device. Typical human responses to exenatide include improvements in the initial rapid release of endogenous insulin, an increase in β-cell growth and replication, suppression of pancreatic glucagon release, delayed gastric emptying, and reduced appetite—all of which function to lower blood glucose. Unlike sulfonylureas and meglitinides, exenatide increases insulin synthesis and secretion in the presence of glucose only, thus lessening the risk of hypoglycemia. Despite the therapeutic utility of exenatide, it has certain undesirable traits, including the requirement of twice daily injections, gastrointesional side effects, and similar to native GLP-1, a relatively short half-life (i.e. approximately 2 hr).

Various functional analogs of GLP-1 and exendin-4 are known, and which find use in accordance with the invention. These include liraglutide (Novo Nordisk, WO98/008871), R1583/taspoglutide (Roche, WO00/034331), CJC-1131 (ConjuChem, WO00/069911), ZP-10/AVE0010 (Zealand Pharma, Sanofi-Aventis, WO01/004156), and LY548806 (Eli Lilly, WO03/018516).

Liraglutide, also known as NN2211, is a GLP-1 receptor agonist analog that has been designed for once-daily injection (Harder et al., 2004, *Diabetes Care* 27: 1915-21). Liraglutide has been tested in patients with type-2 diabetes in a number of studies and has been shown to be effective over a variety of durations. In one study, treatment with liraglutide improved glycemic control, improved β-cell function, and reduced endogenous glucose release in patients with type-2 diabetes after one week of treatment (Degn et al., 2004, *Diabetes* 53: 1187-94). In a similar study, eight weeks of 0.6-mg liraglutide therapy significantly improved glycemic control without increasing weight in subjects with type 2 diabetes compared with those on placebo (Harder et al., 2004, *Diabetes Care* 27: 1915-21).

Thus, in certain embodiments, the GLP-1 receptor agonist in accordance with the invention is as described in WO98/008871, which is hereby incorporated by reference in its entirety. The GLP-1 receptor agonist may have at least one lipophilic substituent, in addition to one, two, or more amino acid substitutions with respect to native GLP-1. For example, the lipophilic substituent may be an acyl group selected from $CH_3(CH_2)_nCO$—, wherein n is an integer from 4 to 38, such as an integer from 4 to 24. The lipophilic substituent may be an acyl group of a straight-chain or branched alkyl or fatty acid (for example, as described in WO98/008871, which description is hereby incorporated by reference).

In certain embodiments, the GLP-1 component is $Arg^{26}$-GLP-1(7-37), $Arg^{34}$-GLP-1(7-37), $Lys^{36}$-GLP-1(7-37), $Arg^{26,34}Lys^{36}$-GLP-I (7-37), $Arg^{26,34}Lys^{38}$-GLP-I (7-38), $Arg^{28,34}\ Lys^{39}$-GLP-1(7-39), $Arg^{26,34}Lys^{40}$-GLP-1(7-40), $Arg^{26}Lys^{36}$-GLP-1(7-37), $Arg^{34}Lys^{36}$-GLP-1(7-37), $Arg^{26}Lys^{39}$-GLP-1(7-39), $Arg^{34}Lys^{40}$-GLP-1(7-40), $Arg^{26,34}Lys^{36,39}$-GLP-I (7-39), $Arg^{26,34}Lys^{36,40}$-GLP-1(7-40), $Gly^8Arg^{26}$-GLP-1(7-37); $Gly^8Arg^{34}$-GLP-1(7-37); $Gly^8Lys^{38}$-GLP-1(7-37); $Gly^8Arg^{26,34}Lys^{36}$-GLP-1(7-37), $Gly^8Arg^{26,34}Lys^{39}$-GLP-1(7-39), $Gly^8Arg^{26,34}Lys^{40}$-GLP-1(7-40), $Gly^8Arg^{26}Lys^{36}$-GLP-1(7-37), $Gly^8Arg^{34}Lys^{36}$-GLP-1(7-37), $Gly^8Arg^{26}Lys^{39}$-GLP-1(7-39); $Gly^8Arg^{34}Lys^{40}$-GLP-1(7-40), $Gly^8Arg^{28,34}Lys^{36,39}$-GLP-1(7-39) and $Gly^8Arg^{26,34}Lys^{35,40}$-GLP-1(7-40), each optionally having a lipophilic substituent. For example, the GLP-1 receptor agonist may have the sequence/structure $Arg^{34}Lys^{26}$-(N-ϵ-(γ-Glu(N-α-hexadecanoyl)))-GLP-I(7-37).

Taspoglutide, also known as R1583 or BIM 51077, is a GLP-1 receptor agonist that has been shown to improve glycemic control and lower body weight in subjects with type 2 diabetes mellitus treated with metformin (Abstract No. A-1604, Jun. 7, 2008, 68th American Diabetes Association Meeting, San Francisco, Calif.).

Thus, in certain embodiments, the GLP-1 receptor agonist is as described in WO00/034331, which is hereby incorporated by reference in its entirety. In certain exemplary embodiments, the GLP-1 receptor agonist has the sequence $[Aib^{8,35}]hGLP-1(7-36)NH_2$ (e.g. taspoglutide), wherein Aib is alpha-aminoisobutyric acid.

CJC-1131 is a GLP-1 analog that consists of a DPP-IV-resistant form of GLP-1 joined to a reactive chemical linker group that allows GLP-1 to form a covalent and irreversible bond with serum albumin following subcutaneous injection (Kim et al., 2003, *Diabetes* 52: 751-9). In a 12-week, randomized, double-blind, placebo-controlled multicenter study, CJC-1131 and metformin treatment was effective in reducing fasting blood glucose levels in type 2 diabetes patients (Ratner et al., Abstract No. 10-OR, Jun. 10-14, 2005, 65th American Diabetes Association Meeting, San Francisco, Calif.).

Thus, in certain embodiments, the GLP-1 receptor agonist is as described in WO00/069911, which is hereby incorporated by reference in its entirety. In some embodiments, the GLP-1 receptor agonist is modified with a reactive group which reacts with amino groups, hydroxyl groups or thiol groups on blood components to form a stable covalent bond. In certain embodiments, the GLP-1 receptor agonist is modified with a reactive group selected from the group consisting of succinimidyl and maleimido groups. In certain exemplary embodiments, the GLP-1 receptor agonist has the sequence/structure: $D-Ala^8Lys^{37}$-(2-(2-(2-maleimidopropionamido (ethoxy)ethoxy)acetamide))-GLP-1(7-37) (e.g. CJC-1131).

AVE0010, also known as ZP-10, is a GLP-1 receptor agonist that may be employed in connection with the invention. In a recent double-blind study, patients treated with once daily dosing of AVE0010 demonstrated significant reductions in HbA1c levels (Ratner et al., Abstract No. 433-P, 68th American Diabetes Association Meeting, San Francisco, Calif.). At the conclusion of the study, the percentages of patients with HbA1c <7% ranged from 47-69% for once daily dosing compared to 32% for placebo. In addition, AVE0010 treated patients showed dose-dependent reductions in weight and post-prandial plasma glucose.

Thus, in certain embodiments, the GLP-1 receptor agonist is as described in WO01/004156, which is hereby incorporated by reference in its entirety. For example, the GLP-1 receptor agonist may have the sequence: HGEGTFTSDL-SKQMEEEAVRLFIEWLKNGGPSSGAPPSKKKKKK-NH2 (SEQ ID NO: 18) (e.g. AVE0010).

LY548806 is a GLP-1 derivative designed to be resistant to proteolysis by dipeptidase-peptidyl IV (DPP-IV) (Jackson et al., Abstract No. 562, Jun. 10-14, 2005, 65th American Diabetes Association Meeting, San Francisco, Calif.). In an animal model of hyperglycemia, LY548806 has been shown to produce a significant lowering of blood glucose levels during the hyperglycemic phase (Saha et al., 2006, J. Pharm. Exp. Ther. 316: 1159-64). Moreover, LY548806 was shown to produce a significant increase in insulin levels consistent with its known mechanism of action, namely stimulation of insulin release in the presence of hyperglycemia.

Thus, in certain embodiments, the GLP-1 receptor agonist is as described in WO03/018516, which is hereby incorporated by reference in its entirety. In some embodiments, the therapeutic agents of the present invention comprise GLP-1 analogs wherein the backbone for such analogs or fragments contains an amino acid other than alanine at position 8 (position 8 analogs). The backbone may also include L-histidine, D-histidine, or modified forms of histidine such as desamino-histidine, 2-amino-histidine, β-hydroxy-histidine, homohistidine, α-fluoromethyl-histidine, or α-methyl-histidine at position 7. In some embodiments, these position 8 analogs may contain one or more additional changes at positions 12, 16, 18, 19, 20, 22, 25, 27, 30, 33, and 37 compared to the corresponding amino acid of native GLP-1. In other embodiments, these position 8 analogs may contain one or more additional changes at positions 16, 18, 22, 25 and 33 compared to the corresponding amino acid of native GLP-1. In certain exemplary embodiments, the GLP-1 receptor agonist has the sequence: HVEGTFTSDVSSYLEEQAAKEFIAW-LIKGRG-OH (SEQ ID NO: 19) (e.g. LY548806).

Thus, the present invention provides therapeutic agents comprising an elastic peptide (e.g., an ELP) and a GLP-1 receptor agonist. For example, in certain embodiments, the GLP-1 receptor agonist is GLP-1 (SEQ ID NO:13, 17, or 59) or a functional analog thereof. In other embodiments, the GLP-1 receptor agonist is exendin-4 (SEQ ID NO:14) or a functional analog thereof. Such functional analogs of GLP-1 or exendin-4 include functional fragments truncated at the C-terminus by from 1 to 10 amino acids, including by 1, 2, 3, or up to about 5 amino acids (with respect to SEQ ID NOS: 13, 14, 17, or 59). Such functional analogs may contain from 1 to 10 amino acid insertions, deletions, and/or substitutions (collectively) with respect to the native sequence (e.g., SEQ ID NOS 13, 14, and 59), and in each case retaining the activity of the peptide. For example, the functional analog of GLP-1 or exendin-4 may have from 1 to about 3, 4, or 5 insertions, deletions and/or substitutions (collectively) with respect to SEQ ID NOS: 13, 59 and 14, and in each case retaining the activity of the peptide. Such activity may be confirmed or assayed using any available assay, including those described herein. In these or other embodiments, the GLP-1 receptor agonist component has at least about 50%, 75%, 80%, 85%, 90%, or 95% identity with the native sequence (SEQ ID NOS: 13, 59, and 14). The determination of sequence identity between two sequences (e.g., between a native sequence and a functional analog) can be accomplished using any alignment tool, including Tatusova et al., *Blast 2 sequences—a new tool for comparing protein and nucleotide sequences, FEMS*

*Microbiol Lett.* 174:247-250(1999). Such functional analogs may further comprise additional chemical modifications, such as those described in this section and/or others known in the art.

In certain embodiments, the GLP1-ELP fusion has a sequence exemplified herein as SEQ ID NOS: 54 and 56. When processed, the mature form of such fusion protein will begin with the $His^7$ of GLP.

In another aspect, the present invention provides methods for the treatment or prevention of type 2 diabetes, impaired glucose tolerance, type 1 diabetes, hyperglycemia, obesity, binge eating, bulimia, hypertension, syndrome X, dyslipidemia, cognitive disorders, atheroschlerosis, non-fatty liver disease, myocardial infarction, coronary heart disease and other cardiovascular disorders. The method comprises administering the therapeutic agent comprising the elastin-like peptide (ELP) and the GLP-1 receptor agonist (as described above) to a patient in need of such treatment. In these or other embodiments, the present invention provides methods for decreasing food intake, decreasing β-cell apoptosis, increasing β-cell function and β-cell mass, and/or for restoring glucose sensitivity to β-cells. Generally, the patient may be a human or non-human animal patient (e.g., dog, cat, cow, or horse). Preferably, the patient is human.

The treatment with a ELP/GLP-1 receptor agonist compound according to the present invention may also be combined with one or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. In the present context, the expression "antidiabetic agent" includes compounds for the treatment and/or prophylaxis of insulin resistance and diseases wherein insulin resistance is the pathophysiological mechanism.

The ability of a GLP-1 or exendin-4 analog, or an GLP-1 receptor agonist/elastic peptide compound, to bind the GLP-1 receptor may be determined by standard methods, for example, by receptor-binding activity screening procedures which involve providing appropriate cells that express the GLP-1 receptor on their surface, for example, insulinoma cell lines such as RINmSF cells or INS-1 cells. In addition to measuring specific binding of tracer to membrane using radioimmunoassay methods, cAMP activity or glucose dependent insulin production can also be measured. In one method, a polynucleotide encoding the GLP-1 receptor is employed to transfect cells to thereby express the GLP-1 receptor protein. Thus, these methods may be employed for testing or confirming whether a suspected GLP-1 receptor agonist is active. An exemplary assay is described in greater detail herein.

In addition, known methods can be used to measure or predict the level of biologically activity of a GLP-1 receptor agonist or GLP-1 receptor agonist/elastic peptide in vivo (See e.g. Siegel, et al., 1999, *Regul Pept* 79(2-3): 93-102). In particular, GLP-1 receptor agonists or GLP-1 receptor agonist/elastic peptide compounds can be assessed for their ability to induce the production of insulin in vivo using a variety of known assays for measuring GLP-1 activity. For example, a GLP-1 receptor agonist/elastic peptide compound can be introduced into a cell, such as an immortalized β-cell, and the resulting cell can be contacted with glucose. If the cell produces insulin in response to the glucose, then the modified GLP-1 is generally considered biologically active in vivo (Fehmann et al., 1992, *Endocrinology* 130: 159-166). An exemplary assay is described in greater detail herein.

The ability of an GLP-1 receptor agonist/elastic peptide compound to enhance β-cell proliferation, inhibit β-cell apoptosis, and regulate islet growth may also be measured using known assays. Pancreatic β-cell proliferation may be assessed by $^3$H-tymidine or BrdU incorporation assays (See e.g. Buteau et al., 2003, *Diabetes* 52: 124-32), wherein pancreatic β-cells such as INS(832/13) cells are contacted with a GLP-1 receptor agonist/elastic peptide compound and analyzed for increases in $^3$H-thymidine or BrdU incorporation. The antiapoptotic activity of a GLP-1 receptor agonist/elastic peptide compound can be measured in cultured insulin-secreting cells and/or in animal models where diabetes occurs as a consequence of an excessive rate of beta-cell apoptosis (See e.g. Bulotta et al., 2004, *Cell Biochem Biophys* 40(3 suppl): 65-78).

In addition to GLP-1, other peptides of this family, such as those derived from processing of the pro-glucagon gene, such as GLP-2, GIP, and oxyntomodulin, could be conjugated or fused to the elastic peptide component (as described herein) to enhance the therapeutic potential.

Insulin

In other embodiments, the present invention provides a therapeutic agent comprising an elastin peptide component coupled to insulin (e.g., via fusion or conjugation). Insulin injections, e.g. of human insulin, can be used to treat diabetes. The insulin-making cells of the body are called β-cells, and they are found in the pancreas gland. These cells clump together to form the "islets of Langerhans", named for the German medical student who described them.

The synthesis of insulin begins at the translation of the insulin gene, which resides on chromosome 11. During translation, two introns are spliced out of the mRNA product, which encodes a protein of 110 amino acids in length. This primary translation product is called preproinsulin and is inactive. It contains a signal peptide of 24 amino acids in length, which is required for the protein to cross the cell membrane.

Once the preproinsulin reaches the endoplasmic reticulum, a protease cleaves off the signal peptide to create proinsulin. Proinsulin consists of three domains: an amino-terminal B chain, a carboxyl-terminal A chain, and a connecting peptide in the middle known as the C-peptide. Insulin is composed of two chains of amino acids named chain A (21 amino acids—GIVEQCCASVCSLYQLENYCN) (SEQ ID NO: 15) and chain B (30 amino acids FVNQHLCG-SHLVEALYLVCGERGFFYTPKA) (SEQ ID NO: 16) that are linked together by two disulfide bridges. There is a 3rd disulfide bridge within the A chain that links the 6th and 11th residues of the A chain together. In most species, the length and amino acid compositions of chains A and B are similar, and the positions of the three disulfide bonds are highly conserved. For this reason, pig insulin can replace deficient human insulin levels in diabetes patients. Today, porcine insulin has largely been replaced by the mass production of human proinsulin by bacteria (recombinant insulin).

Insulin molecules have a tendency to form dimers in solution, and in the presence of zinc ions, insulin dimers associate into hexamers. Whereas monomers of insulin readily diffuse through the blood and have a rapid effect, hexamers diffuse slowly and have a delayed onset of action. In the design of recombinant insulin, the structure of insulin can be modified in a way that reduces the tendency of the insulin molecule to form dimers and hexamers but that does not interrupt binding to the insulin receptor. In this way, a range of preparations are made, varying from short acting to long acting.

Within the endoplasmic reticulum, proinsulin is exposed to several specific peptidases that remove the C-peptide and generate the mature and active form of insulin. In the Golgi apparatus, insulin and free C-peptide are packaged into secretory granules, which accumulate in the cytoplasm of the β-cells. Exocytosis of the granules is triggered by the entry of glucose into the beta cells. The secretion of insulin has a broad impact on metabolism.

There are two phases of insulin release in response to a rise in glucose. The first is an immediate release of insulin. This is attributable to the release of preformed insulin, which is stored in secretory granules. After a short delay, there is a second, more prolonged release of newly synthesized insulin.

Once released, insulin is active for a only a brief time before it is degraded by enzymes. Insulinase found in the liver and kidneys breaks down insulin circulating in the plasma, and as a result, insulin has a half-life of only about 6 minutes. This short duration of action results in rapid changes in the circulating levels of insulin.

Insulin analogs have been developed with improved therapeutic properties (Owens et al., 2001, *Lancet* 358: 739-46; Vajo et al., 2001, *Endocr Rev* 22: 706-17), and such analogs may be employed in connection with the present invention. Various strategies, including elongation of the COOH-terminal end of the insulin B-chain and engineering of fatty acid-acylated insulins with substantial affinity for albumin are used to generate longer-acting insulin analogs. However, in vivo treatments with available longer-acting insulin compounds still result in a high frequency of hypo- and hyperglycemic excursions and modest reduction in $HbA_{1c}$. Accordingly, development of a truly long-acting and stable human insulin analog still remains an important task.

Functional analogs of insulin that may be employed in accordance with the invention include rapid acting analogs such as lispro, aspart and glulisine, which are absorbed rapidly (<30 minutes) after subcutaneous injection, peak at one hour, and have a relatively short duration of action (3 to 4 hours). In addition, two long acting insulin analogs have been developed: glargine and detemir, and which may be employed in connection with the invention. The long acting insulin analogs have an onset of action of approximately two hours and reach a plateau of biological action at 4 to 6 hours, and may last up to 24 hours.

Thus, in one embodiment, the insulin component may contain the A and/or B chain of lispro (also known as Humalog, Eli Lilly). Insulin lispro differs from human insulin by the substitution of proline with lysine at position 28 and the substitution of lysine with proline at position 29 of the insulin B chain. Although these modifications do not alter receptor binding, they help to block the formation of insulin dimers and hexamers, allowing for larger amounts of active monomeric insulin to be available for postprandial injections.

In another embodiment, the insulin may contain an A and/or B chain of aspart (also known as Novolog, Novo Nordisk). Insulin aspart is designed with the single replacement of the amino acid proline by aspartic acid at position 28 of the human insulin B chain. This modification helps block the formation for insulin hexamers, creating a faster acting insulin.

In yet another embodiment, the insulin may contain an A and/or B chain of glulisine (also known as Apidra, Sanofi-Aventis). Insulin glulisine is a short acting analog created by substitution of asparagine at position 3 by lysine and lysine at position 29 by glutamine of human insulin B chain. Insulin glulisine has more rapid onset of action and shorter duration of action compared to regular human insulin.

In another embodiment, the insulin may contain an A and/or B chain of glargine (also known as Lantus, Sanofi-Aventis). Insulin glargine differs from human insulin in that the amino acid asparagine at position 21 of the A chain is replaced by glycine and two arginines are added to the C-terminus of the B-chain. Compared with bedtime neutral protamine Hagedorn (NPH) insulin (an intermediate acting insulin), insulin glargine is associated with less nocturnal hypoglycemia in patients with type 2 diabetes.

In yet another embodiment, the insulin may contain an A and/or B chain from detemir (also known as Levemir, Novo Nordisk). Insulin detemir is a soluble (at neutral pH) long-acting insulin analog, in which the amino acid threonine at B30 is removed and a 14-carbon, myristoyl fatty acid is acetylated to the epsilon-amino group of LysB29. After subcutaneous injection, detemir dissociates, thereby exposing the free fatty acid which enables reversible binding to albumin molecules. So at steady state, the concentration of free unbound insulin is greatly reduced resulting in stable plasma glucose levels.

In some embodiments, the insulin may be a single-chain insulin analog (SIA) (e.g. as described in U.S. Pat. No. 6,630,438 and WO08/019368, which are hereby incorporated by reference in their entirety). Single-chain insulin analogs encompass a group of structurally-related proteins wherein the A and B chains are covalently linked by a polypeptide linker. The polypeptide linker connects the C-terminus of the B chain to the N-terminus of the A chain. The linker may be of any length so long as the linker provides the structural conformation necessary for the SIA to have a glucose uptake and insulin receptor binding effect. In some embodiments, the linker is about 5-18 amino acids in length. In other embodiments, the linker is about 9-15 amino acids in length. In certain embodiments, the linker is about 12 amino acids long. In certain exemplary embodiments, the linker has the sequence KDDNPNLPRLVR (SEQ ID NO.: 20) or GAGSSSRRAPQT (SEQ ID NO.: 21). However, it should be understood that many variations of this sequence are possible such as in the length (both addition and deletion) and substitutions of amino acids without substantially compromising the effectiveness of the produced SIA in glucose uptake and insulin receptor binding activities. For example, several different amino acid residues may be added or removed from either end without substantially decreasing the activity of the produced SIA.

An exemplary single-chain insulin analog currently in clinical development is albulin (Duttaroy et al., 2005, Diabetes 54: 251-8). Albulin can be produced in yeast or in mammalian cells. It consists of the B and A chain of human insulin (100% identity to native human insulin) linked together by a dodecapeptide linker and fused to the $NH_2$ terminals of the native human serum albumin. For expression and purification of albulin, Duttaroy et al. constructed a synthetic gene construct encoding a single-chain insulin containing the B- and A-chain of mature human insulin linked together by a dodecapeptide linker using four overlapping primers and PCR amplification. The resulting PCR product was ligated in-frame between the signal peptide of human serum albumin (HSA) and the $NH_2$ terminus of mature HSA, contained within a pSAC35 vector for expression in yeast. In accordance with the present invention, the HSA component of abulin may be replaced with an ELP component as described herein.

Thus, in one aspect, the present invention provides therapeutic agents comprising an elastic peptide and an insulin or functional analog thereof. For example, in certain embodiments, the insulin is a mammalian insulin, such as human insulin or porcine insulin. In accordance with the invention, the elastic peptide component may be coupled (e.g., via recombinant fusion or chemical conjugation) to the insulin A chain, or B chain, or both. The insulin may comprise each of chains A, B, and C (SEQ ID NOS: 51 and 52), or may contain a processed form, containing only chains A and B. In some embodiments, chains A and B are connected by a short linking peptide, to create a single chain insulin. The insulin may be a functional analog of human insulin, including functional fragments truncated at the N-terminus and/or C-terminus (of either or both of chains A and B) by from 1 to 10 amino acids, including by 1, 2, 3, or about 5 amino acids. Functional analogs may contain from 1 to 10 amino acid insertions, deletions, and/or substitutions (collectively) with respect to the native sequence (e.g., SEQ ID NOS 15 and 16), and in each case retaining the activity of the peptide. For example, functional analogs may have 1, 2, 3, 4, or 5 amino acid insertions, deletions, and/or substitutions (collectively) with respect to the native sequence (which may contain chains A and B, or chains A, B, and C). Such activity may be confirmed or assayed using any available assay, including those described herein. In these or other embodiments, the insulin component has at least about 75%, 80%, 85%, 90%, 95%, or 98% identity with each of the native sequences for chains A and B (SEQ ID NOS:15 and 16). The determination of sequence identity between two sequences (e.g., between a native sequence and a functional analog) can be accomplished using any alignment tool, including Tatusova et al., *Blast 2 sequences—a new tool for comparing protein and nucleotide sequences FEMS Microbiol Lett.* 174:247-250 (1999). The insulin component may contain additional chemical modifications known in the art.

In another aspect, the present invention provides methods for the treatment or prevention of diabetes, including type I and II diabetes. The method comprises administering an effective amount of the therapeutic agent comprising an elastic peptide (e.g., ELP) component and an insulin (or functional analog thereof) component to a patient in need thereof. Generally, the patient may be a human or non-human animal (e.g., dog, cat, cow, or horse) patient. Preferably, the patient is human.

To characterize the in vitro binding properties of an insulin analog or an elastic peptide-containing insulin analog, competition binding assays may be performed in various cell lines that express the insulin receptor (Jehle et al., 1996, *Diabetologia* 39: 421-432). For example, competition binding assays using CHO cells overexpressing the human insulin receptor may be employed. Insulin can also bind to the IGF-1 receptor with a lower affinity than the insulin receptor. To determine the binding affinity of an ELP-containing insulin analog, a competition binding assay can be performed using $^{125}$I-labeled IGF-1 in L6 cells.

The activities of insulin include stimulation of peripheral glucose disposal and inhibition of hepatic glucose production. The ability of an elastic peptide-containing insulin analog to mediate these biological activities can be assayed in vitro using known methodologies. For example, the effect of an elastic peptide-containing analog on glucose uptake in 3T3-L1 adipocytes can be measured and compared with that of insulin. Pretreatment of the cells with a biologically active analog will generally produce a dose-dependent increase in 2-deoxyglucose uptake. The ability of an elastic peptide-containing insulin analog to regulate glucose production may be measured in any number of cells types, for example, H4IIe hepatoma cells. In this assay, pretreatment with a biologically active analog will generally result in a dose-dependent inhibition of the amount of glucose released.

Factor VII (VIIa)

In certain embodiments, the invention provides therapeutic agents comprising an elastic peptide component coupled (e.g., via fusion or conjugation) to a Factor VII/VIIa. Coagulation is the biological process of blood clot formation involving many different serine proteases as well as their essential cofactors and inhibitors. It is initiated by exposure of Factor VII (FVII) and Factor VIIa (FVIIa) to its membrane bound cofactor, tissue factor (TF), resulting in production of Factor Xa (FXa) and more FVIIa. The process is propagated upon production of Factor IXa (FIXa) and additional FXa that, upon binding with their respective cofactors FVIIIa and FVa, form platelet bound complexes, ultimately resulting in the formation of thrombin and a fibrin clot. Thrombin also serves to further amplify coagulation by activation of cofactors such as FV and FVII and zymogens such as Factor XI. Moreover, thrombin activates platelets leading to platelet aggregation, which is necessary for the formation of a hemostatic plug.

Factor VII circulates in the blood in a zymogen form, and is converted to its active form, Factor VIIa, by either factor IXa, factor Xa, factor XIIa, or thrombin by minor proteolysis. Factor VIIa is a two-chain, 50 kilodalton (kDa) plasma serine protease. The active form of the enzyme comprises a heavy chain (254 amino acid residues) containing a catalytic domain and a light chain (152 residues) containing 2 epidermal growth factor (EGF)-like domains. The mature factor VII/VIIa that circulates in plasma is composed of 406 amino acid residues (SEQ ID NO: 33). The light and heavy chains are held together by a disulfide bond.

As noted above, Factor VIIa is generated by proteolysis of a single peptide bond from its single chain zymogen, Factor VII, which is present at approximately 0.5 µg/ml in plasma. The conversion of zymogen Factor VII into the activated two-chain molecule occurs by cleavage of an internal peptide bond. In human Factor VII, the cleavage site is at Arg152-Ile153 (Hagen et al., 1986, *PNAS USA* 83: 2412-6).

"Factor VII/VIIa" as used in this application means a product consisting of either the unactivated form (factor VII) or the activated form (factor VIIa) or mixtures thereof. "Factor VII/VIIa" within the above definition includes proteins that have an amino acid sequence of native human factor VII/VIIa. It also includes proteins with a slightly modified amino acid sequence, for instance, a modified N-terminal end including N-terminal amino acid deletions or additions so long as those proteins substantially retain the activity of factor VIIa. "Factor VII" within the above definition also includes natural allelic variations that may exist and occur from one individual to another. Also, degree and location of glycosylation or other post-translation modifications may vary depending on the chosen host cells and the nature of the host cellular environment.

In the presence of calcium ions, Factor VIIa binds with high affinity to TF. TF is a 263 amino acid residue glycoprotein composed of a 219 residue extracellular domain, a single transmembrane domain, and a short cytoplasmic domain (Morrissey et al., 1987, *Cell* 50: 129-35). The TF extracellular domain is composed of two fibronectin type III domains of about 105 amino acids each. The binding of FVIIa is mediated entirely by the TF extracellular domain (Muller et al., 1994, *Biochem.* 33:10864-70). Residues in the area of amino acids 16-26 and 129-147 contribute to the binding of FVIIa as well as the coagulant function of the molecule. Residues Lys20, Trp45, Asp58, Tyr94, and Phe140 make a large contribution (1 kcal/mol) to the free energy (ΔG) of binding to FVIIa.

TF is expressed constitutively on cells separated from plasma by the vascular endothelium. Its expression on endothelial cells and monocytes is induced by exposure to inflammatory cytokines or bacterial lipopolysaccharides (Drake et al., 1989, *J. Cell Biol.* 109: 389). Upon tissue injury, the exposed extracellular domain of TF forms a high affinity, calcium dependent complex with FVII. Once bound to TF, FVII can be activated by peptide bond cleavage to yield serine protease FVIIa. The enzyme that catalyzes this step in vivo has not been elucidated, but in vitro FXa, thrombin, TF:FVIIa and FIXa can catalyze this cleavage. FVIIa has only weak activity upon its physiological substrates FX and FIX whereas the TF:FVIIa complex rapidly activates FX and FIX.

The TF:FVIIa complex constitutes the primary initiator of the extrinsic pathway of blood coagulation. The complex initiates the extrinsic pathway by activation of FX to Factor Xa (FXa), FIX to Factor IXa (FIXa), and additional FVII to FVIIa. The action of TF:FVIIa leads ultimately to the conversion of prothrombin to thrombin, which carries out many biological functions. Among the most important activities of thrombin is the conversion of fibrinogen to fibrin, which polymerizes to form a clot. The TF:FVIIa complex also participates as a secondary factor in extending the physiological effects of the contact activation system.

The initiation and subsequent regulation of coagulation is complex, since maintenance of hemostasis is crucial for survival. There is an exquisite balance between hemostasis (normal clot formation and dissolution) and thrombosis (pathogenic clot formation). Serious clinical conditions involving aberrations in coagulation include deep vein thrombosis, myocardial infarction, pulmonary embolism, stroke and disseminated intravascular coagulation (in sepsis). There are also many bleeding coagulopathies where there is insufficient clot formation. These include hemophilia A (FVIII deficiency) or hemophilia B (FIX deficiency), where procoagulant therapy is required. The challenge in this therapeutic area is to operate in the narrow window between too much and too little coagulation.

The use of exogenous FVIIa as a therapeutic agent has been shown to induce hemostasis in patients with hemophilia A and B (Hedner, 2001, *Seminars Hematol.* 38 (suppl. 12): 43-7; Hedner, 2004, *Seminars Hematol.* 41 (suppl. 1): 35-9). It also has been used to treat bleeding in patients with liver disease, anticoagulation-induced bleeding, surgery, thrombocytopenia, thrombasthenia, Bemard-Soulier syndrome, von Willebrand disease, and other bleeding disorders (See e.g. Roberts et al., 2004, *Blood* 104: 3858-64).

Commercial preparations of human recombinant FVIIa are sold as NovoSeven.™ NovoSeven™ is indicated for the treatment of bleeding episodes in hemophilia A or B patients and is the only recombinant FVIIa effective for bleeding episodes currently available. A circulating recombinant FVIIa half-life of 2.3 hours was reported in "Summary Basis for Approval for NovoSeven™" FDA reference number 96-0597. Moreover, the half-life of recombinant FVIIa is shorter in pediatric patients (~1.3 hours), suggesting that higher doses of recombinaint FVIIa may be required in this population (Roberts et al., 2004, *Blood* 104: 3858-64). Accordingly, relatively high doses and frequent administration are necessary to reach and sustain the desired therapeutic or prophylactic effect. As a consequence, adequate dose regulation is difficult to obtain and the need of frequent intravenous administrations imposes restrictions on the patient's way of living.

A molecule with a longer circulation half-life would decrease the number of necessary administrations. Given the frequent injections associated with currently available FVIIa therapy and the potential for obtaining more optimal therapeutic FVIIa levels with concomitant enhanced therapeutic effect, there is a clear need for improved FVII or FVIIa-like molecules with a longer half-life in vivo.

Recombinant human coagulation factor VIIa (rFVIIa, NovoSeven; Novo Nordisk A/S, Copenhagen, Denmark) has proven to be efficacious for the treatment of bleeding episodes in hemophilia patients with inhibitors. A small fraction of patients may be refractory to rFVIIa treatment and could potentially benefit from genetically modified FVIIa molecules with increased potencies. To this end, FVIIa analogs with increased intrinsic activity have been investigated that exhibit superior hemostatic profiles in vitro (see e.g. WO02/077218 or WO05/074975, which are hereby incorporated by reference in their entirety, and Tranholm et al., 2003, *Blood* 102(10): 3615-20, which is also incorporated by reference). These analogs may also be used as more efficacious hemostatic agents in other indications where efficacy of rFVIIa has been observed, including in thrombocytopenia and trauma.

Thus, in some embodiments, the Factor VIIa analog that may be used in accordance with the invention is as described in WO02/077218 or WO05/074975. For example, the FVIIa analog may have a glutamine substituted for methionine at position 298 (i.e. M298Q-FVIIa). In certain exemplary embodiments, the FVIIa analog contains two additional mutations, valine at position 158 replaced by aspartic acid and glutamic acid at position 296 replaced by valine (i.e. V158D/E296V/M298Q-FVIIa). Additionally or alternatively, the Factor VIIa analog may have an alanine residue substitution for lysine at position 337 (i.e. V158D/E296V/M298Q/K337A-FVIIa). In still other embodiments, the Factor VIIa analog has a substitution or insertion selected from Q250C; P406C; and 407C, wherein a cysteine has also been introduced in the C-terminal sequence (see, e.g. U.S. Pat. No. 7,235,638, which is hereby incorporated by reference in its entirety). The Factor VIIa analog may further comprise a substitution or insertion at one or more of positions 247, 260, 393, 396, and/or 405.

In these or other embodiments, the Factor VIIa analog comprises a substitution relative to the sequence of native Factor VIIa selected from: (a) a substitution of Lys157 with an amino acid selected from the group consisting of Gly, Val, Ser, Thr, Asp, and Glu; (b) a substitution of Lys337 with ah amino acid selected from the group consisting of Ala, Gly, Val, Ser, Thr, Gin, Asp, and Glu; (c) a substitution of Asp334 with any amino acid other than Ala or Asn; and (d) a substitution of Ser336 with any amino acid other than Ala or Cys (see e.g. U.S. Pat. No. 7,176,288, which is hereby incorporated by reference in its entirety). Additionally or alternatively, the Factor VIIa analog comprises a substitution of the Leu at position 305 of Factor VII with an amino acid residue selected from the group consisting of Val, Ile, Met, Phe, Trp, Pro, Gly, Ser, Thr, Cys, Tyr, Asn, Glu, Lys, Arg, His, Asp and Gln (see e.g. U.S. Pat. No. 6,905,683, which is hereby incorporated by reference in its entirety).

Thus, in one aspect, the present invention provides therapeutic agents comprising an elastic peptide, e.g., an elastin-like peptide (ELP) and a Factor VII/VIIa, or functional analog thereof. For example, in certain embodiments, the Factor VII/VIIa is human Factor VII/VIIa (e.g., SEQ ID NO: 33). The Factor VII/VIIa may be a functional analog of human Factor VII/VIIa, including functional fragments truncated at the N-terminus and/or C-terminus by from 1 to 10 amino acids, including by 1, 2, 3, or about 5 amino acids. Functional analogs may contain from 1 to 10 amino acid insertions, deletions, and/or substitutions (collectively) with respect to the native sequence (e.g., SEQ ID NO: 33), and in each case retaining the activity of the peptide. For example, such analogs may have from 1 to about 5 amino acid insertions, deletions, and/or substitutions (collectively) with respect to the native full length sequence, or with respect to one or both of the heavy and light chains. Such activity may be confirmed or assayed using any available assay, including those described herein. In these or other embodiments, the Factor VII/VIIa component has at least about 75%, 80%, 85%, 90%, 95%, or 98% identity with the native sequence (SEQ ID NO:33). The determination of sequence identity between two sequences (e.g., between a native sequence and a functional analog) can be accomplished using any alignment tool, including Tatusova et al., *Blast 2 sequences—a new tool for comparing protein and nucleotide sequences, FEMS Microbiol Lett.* 174: 247-250(1999).

In exemplary embodiments, the FactorVII-ELP fusion has the amino acid sequence of SEQ ID NO:58. SEQ ID NO:58 further comprises a TEV protease cleavage site between the FactorVII and ELP sequences, which may be beneficial for removing the ELP sequence post expression where desired. However, in accordance with the invention, the tev sequence may be entirely removed, or replaced with another linking sequence as disclosed herein.

In another aspect, the present invention provides methods for the treatment or prevention of bleeding-related disorders. The method comprises administering an effective amount of the therapeutic agent comprising an elastic peptide and a Factor VII/VIIa or functional analog thereof to a patient in need. In certain embodiments, the bleeding-related disorder is one or more of hemophilia (A or B), post-surgical bleeding, anticoagulation-induced bleeding, thrombocytopenia, Factor VII deficiency, Factor XI deficiency, bleeding in patients with liver disease, thrombasthenia, Bernard-Soulier syndrome, von Willebrand disease, and intracranial hemorrhage. Generally, the patient is a human or non-human animal (e.g., dog, cat, cow, or horse) patient. Preferably, the patient is human.

To characterize the in vitro binding properties of a suspected Factor VII/VIIa analog, or an elastic peptide-containing Factor VIIa analog, TF binding assays can be performed as described previously (See, e.g., Chaing et al., 1994, Blood 83(12): 3524-35). Briefly, recombinant human TF can be coated onto Immulon II plates in carbonate antigen buffer overnight at 4° C. BSA is also coated onto the plates for use as a control. Elastic peptide-containing Factor VIIa analogs may be added at various concentrations in TBS-T buffer. After several washes, monospecific polyclonal rabbit anti-human FVIIa sera is added and incubated for approximately an hour at room temperature. Next, goat anti-rabbit IgG conjugated to alkaline phosphatase is added, followed by the alkaline phosphatase substrate PNPP, which is used for detection. After subtraction of background, the absorbance at ~405 nm is taken to be directly proportional to the degree of Factor VIIa binding to the immobilized TF. These values can then be compared to control plasma containing Factor VIIa.

The clotting ability of a Factor VII/VIIa analog or an elastic peptide-containing Factor VIIa analog can be measured in human FVII deficient plasma. In this assay, the elastic peptide-containing Factor VIIa analog diluted to varying concentrations directly into FVII deficient plasma. In a coagulometer, one part plasma±a FVIIa analog can be mixed with 2 parts Innovin™ (Dade, Miami, Fla.) prothrombin time reagent (recombinant human tissue factor with phospholipids and $CaCl_2$). Clot formation is detected optically and time to clotting measured. Clotting time (seconds) is compared to the mean clotting time of FVII-deficient plasma alone and plotted as the fractional clotting time versus FVIIa analog concentration.

Therapeutic Proteins

The present invention further provides therapeutic agents comprising an elastic peptide component and at least one therapeutic protein selected from Table 1. The elastic peptide (e.g., ELP) component and therapeutic protein may be coupled by recombinant fusion or chemical conjugation as described herein. Such therapeutic proteins are listed in Table 1 by protein name and GeneSeq Accession No. The amino acid sequence of each Therapeutic Protein, which is known in the art, is hereby incorporated by reference for each Therapeutic Protein listed in Table 1. Such therapeutic proteins are further described in US patent or PCT publications that are also listed in Table 1, and such US patent and PCT publications are hereby incorporated by reference, especially with respect to the structure of such therapeutic proteins and described functional analogs.

Table 1 further describes the biological activity of each listed Therapeutic Protein, as well as an exemplary assay for determining the activity of functional analogs or agents of the invention (e.g., fusion with an elastic peptide component). Generally, functional analogs of therapeutic proteins listed in Table 1 may include functional fragments truncated at the N-terminus and/or C-terminus by from 1 to 10 amino acids, including by 1, 2, 3, 4 or about 5 amino acids. Functional analogs may contain from 1 to 10 amino acid insertions, deletions, and/or substitutions (collectively) with respect to the base sequence (e.g., as listed in Table 1), and in each case retaining the full or partial biological activity (as listed in Table 1) of the therapeutic protein. For example, functional analogs may have 1, 2, 3, 4, or 5 amino acid insertions, deletions, and/or substitutions (collectively) with respect to the base sequence. Such activity may be confirmed or assayed using any available assay, including those described in the Table. In these or other embodiments, the therapeutic protein has at least about 75%, 80%, 85%, 90%, 95%, or 98% identity with the corresponding base sequence. The molecules may further comprise additional chemical modifications known for each in the art.

In some embodiments, the therapeutic protein (e.g., as selected from Table 1) has a size of less than about 25 kDa, or less than about 10 kDa, or less than about 5 kDa, and the corresponding therapeutic agent of the invention (e.g., comprising the ELP component) has a molecular weight of less than about 60 kDa, 55 kDa, 50 kDa, or 40 kDa.

Table 1 further lists preferred indications for each therapeutic protein, for which the corresponding therapeutic agent finds use, such as in a method for treatment or prevention related to such indication.

TABLE 1

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| BMP-1 | GeneSeq Acession P80618 | WO8800205 | BMP1 belongs to the transforming growth factor-beta (TGFB) superfamily. Bone morphogenic proteins induce cartilage and bone formation, play important role in nephrogesis, and play an important role in the development of many organs, including lung, heart, teeth, gut, skin, and particularly the kidney. | BMP-1 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902. Apr. 16, 1999; and Hogan, B. L. M. (1996) Genes Dev. 10, 1580-1594. | Induction of Cartilage, Tissue and Bone Growth, and Diabetes |
| BMP-2 | GeneSeq Accession P80619 | WO8800205 | BMP-2 belongs to the transforming growth factor-beta (TGFB) superfamily. Bone morphogenic protein induces bone formation. | BMP-2 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| BMP-2B | GeneSeq Accession W24850 | U.S. Pat. No. 5,631,142 | BMP-2b belongs to the transforming growth factor-beta (TGFB) superfamily. Bone morphogenic protein induces bone formation. | BMP-2b activity can be determined using the following assays known in the art: Nat Genet. 2001 January; 27(1): 84-8; Eur J Biochem 1996 Apr. 1; 237(1): 295-302; J Biol Cbcre, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| BMP-4 | GeneSeq Accession B02796 | WO0020591 | BMP-4 belongs to the transforming growth factor-beta (TGFB) superfamily. Bone morphogenic protein induces bone formation. | BMP-4 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902. Apr. 16, 1999; and Hogan, B. L. M. (1996) Genes Dev. 10, 1580-1594. | Induction of Cartilage, Tissue and Bone Growth, and Diabetes |
| BMP-5 | GeneSeq Accession B02797 | WO0020591 | BMP-5 belongs to the transforming growth factor-beta (TGFB) superfamily. Bone morphogenic protein induces bone formation. | BMP-5 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897- | Induction of Cartilage, Tissue and Bone Growth, and Diabetes |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| BMP-6 | GeneSeq Accession R32904 | U.S. Pat. No. 5,187,076 | BMP-6 belongs to the transforming growth factor-beta (TGFB) superfamily. Bone morphogenic protein induces bone formation. | 10902. Apr. 16, 1999; and Hogan, B. L. M. (1996) Genes Dev. 10, 1580-1594. BMP-6 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902. Apr. 16, 1999; and Hogan, B. L. M. (1996) Genes Dev. 10, 1580-1594. | Induction of Cartilage, Tissue and Bone Growth, and Diabetes |
| Osteogenic Protein-1; OP-1; BMP-7 | GeneSeq Accession W34783 | WO973462 | OP-1 belongs to the transforming growth factor-beta (TGFB) superfamily. Bone morphogenic protein induces bone formation. | OP-1 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902. Apr. 16, 1999; and Hogan, B. L. M. (1996) Genes Dev. 10, 1580-1594. | Induction of Cartilage, Tissue and Bone Growth, and Diabetes |
| Osteogenic Protein-2 | GeneSeq Accession R57973 | WO9406399 | OP-2 belongs to the transforming growth factor-beta (TGFB) superfamily. Bone morphogenic protein induces bone formation. | OP-2 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902. Apr. 16, 1999; and Hogan, B. L. M. (1996) Genes Dev. 10, 1580-1594. | Induction of Cartilage, Tissue and Bone Growth, and Diabetes |
| GDP-1 | GeneSeq Accession R60961 | WO9406449 | Members of the TGF-beta family of proteins initiate cell signaling by binding to heteromeric receptor complexes of type I (TbetaRI) and type II (TbetaRII) serine/threonine kinase receptors (reviewed by Massague, J. et al. (1994) Trends Cell Biol. 4: 172 178; Miyazono, K. et al. (1994) Adv. Immunol. 55: 181-220). Activation of this heteromeric receptor complex occurs when TGF-beta binds to TbetaRII, which then recruits and phosphorylates TbetaRI. Activated TbetaRI then propagates the signal to downstream targets (Chen, F. and | The effect of GDF-1 on signaling can be assayed by treating Primary BAECs transferred with a construct called p3TP-Lux, containing a TGF-beta responsive promoter fused to a luciferase reporter gene, and measuring luciferase gene expression (Wrana et al, 1994, Nature 370: 341-347). | Developmental disorders, Induction of Cartilage, Tissue and Bone Growth, and Diabetes |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | Weinberg, R. A. (1995) PNA892: 1565-1569; Wrana, J. L. et al. (1994) Nature 370: 341 347). | | |
| BMP-9 | GeneSeq Accession R86903 | WO9533830 | BMP-9 belongs to the transforming growth factor-beta (TGFB) superfamily. Bone morphogenic protein induces bone formation. | BMP-9 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902. Apr. 16, 1999; and Hogan, B. L. M. (1996) Genes Dev. 10, 1580-1594. | Induction of Cartilage, Tissue and Bone Growth, and Diabetes |
| BMP-10 | GeneSeq Accession R66202 | WO9426893 | BMP-10 belongs to the transforming growth factor-beta (TGFB) superfamily. Bone morphogenic protein induces bone formation. | BMP-10 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902. Apr. 16, 1999; and Hogan, B. L. M (1996) Genes Dev. 10, 1580-1594. | Induction of Cartilage, Tissue and Bone Growth, and Diabetes |
| BMP-12 | GeneSeq Accession R78734 | WO9516035 | BMP-12 belongs to the transforming growth factor-beta (TGFB) superfamily. Bone morphogenic protein induces bone formation. | BMP-12 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902. Apr. 16, 1999; and Hogan, B. L. M. (1996) Genes Dev. 10, 1580-1594. | Induction of Cartilage, Tissue and Bone Growth, and Diabetes |
| BMP-15 | GeneSeq Accession W11261 | WO9636710 | BMP-15 belongs to the transforming growth factor-beta (TGFB) superfamily. Bone morphogenic protein induces bone formation. | BMP-15 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902. Apr. 16, 1999; and Hogan, B. L. M. (1996) Genes Dev. 10, 1580-1594. | Induction of Cartilage, Tissue and Bone Growth, and Diabetes |
| BMP-17 | GeneSeq Accession Y17870 | WO9929718 | BMP-17 belongs to the transforming growth factor-beta (TGFB) superfamily. Bone morphogenic protein induces bone formation. | BMP-17 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902. Apr. 16, 1999; and Hogan, | Induction of Cartilage, Tissue and Bone Growth, and Diabetes |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| BMP-18 | GeneSeq Accession Y17871 | WO9929718 | BMP-18 belongs to the transforming growth factor-beta (TGFB) superfamily. Bone morphogenic protein induces bone formation. | B. L. M. (1996) Genes Dev. 10, 1580-1594. BMP-18 activity can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | Induction of Cartilage, Tissue and Bone Growth, and Diabetes |
| Inhibin alpha | GeneSeq Accession B02806 | WO0020591 | The inhibin beta A subunit joins the alpha subunit to form a pituitary FSH secretion inhibitor. Inhibin has been shown to regulate gonadal stromal cell proliferation negatively and to have tumour-suppressor activity. In addition, serum levels of inhibin have been shown to reflect the size of granulosa-cell tumors and can therefore be used as a marker for primary as well as recurrent disease. | Tumor suppressor activity of inhibin can be determined using assays known in the art: Matzuk et al., Nature 1992 Nov. 26: 360 (6402); 313-9. | Tumor suppression. |
| Inhibin beta | GeneSeq Accession H02808 | WO0020591 | The inhibin beta A subunit joins the alpha subunit to form a pituitary FSH secretion inhibitor. Inhibin has been shown to regulate gonadal stromal cell proliferation negatively and to have tumour-suppressor activity. In addition, serum levels of inhibin have been shown to reflect the size of granulosa-cell tumors and can therefore be used as a marker for primary as well as recurrent disease. | Tumor suppressor activity of inhibin can be determined using assays known in the art: Matzuk et al., Nature 1992 Nov. 26: 360 (6402); 313-9. | Tumor suppression. |
| Cerebus Protein | GeneSeq Accession W86032 | WO9849296 | Cerebus is believed to be involved in the inhibition of BMP activity | BMP activity, in the presence of the antagonist Cerebus, can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902, Apr. 16, 1999; and Hogan, B. L. M. (1996) Genes Dev. 10, 1580-1594. | BMP Antagonist useful for Osteosarcoma, abnormal bone growth. |
| Soluble BMP Receptor Kinase Protein-3 | GeneSeq Accession R95227 | WO9614579 | Soluble BMP receptor kinase protein-3 is involved in the binding of BMPs. Soluble BMP receptor kinase protein-3 is useful as an antagonist for the inhibition of BMP activity. | BMP activity, in the presence of the soluble antagonist BMP receptor kinase protein-3, can be determined using the following assays known in the art: Nat Genet. 2001 January; | BMP Antagonist useful for Osteosarcoma, abnormal bone growth. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | | 27(1): 84-8; Eur J Biochem 1996 Apr. 1; 237(1): 295-302; J Biol Chem, Vol. 274, Issue 16, 10897-10902. Apr. 16, 1999; and Hogan, B. L. M. (1996) Genes Dev. 10, 1580-1594. | |
| BMP Processing Enzyme Furin | GeneSeq Accession W36099 | WO9741250 | BMPs belong to the transforming growth factor-beta (TGFB) superfamily. Bone morphogenic protein induces bone formation. | BMP activity, in the presence of the Furin, can be determined using the following assays known in the art: Nat Genet. 2001 January; 27(1): 84-8; Eur J Biochem 1996 Apr. 1; 237(1): 295-302; J Biol Chem, Vol. 274, Issue 16, 10897-10902. Apr. 16, 1999; and Hogan, B. L. M. (1996) Genes Dev. 10, 1580-1594. | Bone formation or Regeneration Abnormalities |
| TGF-beta 1 | GeneSeq Accession R29657 | WO9216228 | Members of the TGF-beta family of proteins initiate cell signaling by binding to heteromeric receptor complexes of type I (TbetaRI) and type II (TbetaRII) serine/threonine kinase receptors (reviewed by Massague, J. et al. (1994) Trends Cell Biol. 4: 172 178; Miyazono, K. et al. (1994) Adv. Immunol. 55: 181-220). Activation of this heteromeric receptor complex occurs when TGF-beta. binds to TbetaRII, which then recruits and phosphorylates TbetaRI. Activated TbetaRI then propagates the signal to downstream targets (Chen, F. and Weinberg. R. A. (1995) PNA892: 1565-1569; Wrana, J. L. et al. (1994) Nature 370: 341. | The effect of TGF betas on signaling can be assayed by treating Primary BAECs transfected with a construct called p3TP-Lux, containing a TGF-beta responsive promoter fused to a reporter gene, and measuring luciferase gene expression (Wrana et al., 1994, Nature 370: 341-347). | Useful for treating cancer and to promote wound healing. |
| TGF-beta 2 | GeneSeq Accession R39659 | EP542679 | Members of the TGF-beta family of proteins initiate cell signaling by binding to heteromeric receptor complexes of type I (TbetaRI) and type II (TbetaRII) serine/threonine kinase receptors (reviewed by Massague, J. et al. (1994) Trends Cell Biol. 4: 172 178; Miyazono, K. et al. (1994) Adv. Immunol. 55: 181-220). Activation of this heteromeric receptor complex occurs when TGF-beta. binds to TbetaRII, which then recruits and phosphorylates TbetaRI. Activated TbetaRI then propagates the signal to downstream targets (Chen, F. and | The effect of TGF betas on signaling can be assayed by treating Primary BAECs transfected with a construct called p3TP-Lux, containing a TGF-beta responsive promoter fused to a reporter gene, and measuring luciferase gene expression (Wrana et al., 1994, Nature 370: 341-347). | Useful for treating cancer and to promote wound healing. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| ZTGF-beta 9 | GeneSeq Accession Y70654 | WO0015798 | Weinberg. R. A. (1995) PNA892: 1565-1569; Wrana, J. L. et al. (1994) Nature 370: 341. Members of the TGF-beta family of proteins initiate cell signaling by binding to heteromeric receptor complexes of type I (TbetaRI) and type II (TbetaRII) serine/threonine kinase receptors (reviewed by Massague, J. et al. (1994) Trends Cell Biol. 4: 172 178; Miyazono, K. et al. (1994) Adv. Immunol. 55: 181-220). Activation of this heteromeric receptor complex occurs when TGF-beta. binds to TbetaRII, which then recruits and phosphorylates TbetaRI. Activated TbetaRI then propagates the signal to downstream targets (Chen, F. and Weinberg. R. A. (1995) PNA892: 1565-1569; Wrana, J. L. et al. (1994) Nature 370: 341. | The effect of TGF betas on signaling can be assayed by treating Primary BAECs transfected with a construct called p3TP-Lux, containing a TGF-beta responsive promoter fused to a reporter gene, and measuring luciferase gene expression (Wrana et al., 1994, Nature 370: 341-347). | Useful for treating cancer and to promote wound healing. |
| Anti-TGF beta family antibodies | | GB2305921 | Members of the TGF-beta family of proteins initiate cell signaling by binding to heteromeric receptor complexes of type I (TbetaRI) and type II (TbetaRII) serine/threonine kinase receptors (reviewed by Massague, J. et al. (1994) Trends Cell Biol. 4: 172 178; Miyazono, K. et al. (1994) Adv. Immunol. 55: 181-220). Activation of this heteromeric receptor complex occurs when TGF-beta. binds to TbetaRII, which then recruits and phosphorylates TbetaRI. Activated TbetaRI then propagates the signal to downstream targets (Chen, F. and Weinberg. R. A. (1995) PNA892: 1565-1569; Wrana, J. L. et al. (1994) Nature 370: 341. | The effect of TGF betas on signaling in the presence of an anti-TGF beta antibody, can be assayed by treating Primary BAECs transfected with a construct called p3TP-Lux, containing a TGF-beta responsive promoter fused to a reporter gene, and measuring luciferase gene expression (Wrana et al., 1994, Nature 370: 341-347). | Useful for control of fibrosis, immune, and inflammatory disease. |
| Latent TGF beta binding protein II | GeneSeq Accession Y70552 | WO0012551 | Members of the TGF-beta family of proteins initiate cell signaling by binding to heteromeric receptor complexes of type I (TbetaRI) and type II (TbetaRII) serine/threonine kinase receptors (reviewed by Massague, J. et al. (1994) Trends Cell | The effect of TGF betas on signaling in the presence of a TGF beta binding protein, can be assayed by treating Primary BAECs transfected with a construct called p3TP-Lux, containing a TGF-beta responsive promoter fused to a reporter gene, | Useful for inhibiting tissue or tumor growth. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | Biol. 4: 172 178; Miyazono, K. et al. (1994) Adv. Immunol. 55: 181-220). Activation of this heteromeric receptor complex occurs when TGF-beta. binds to TbetaRII, which then recruits and phosphorylates TbetaRI. Activated TbetaRI then propagates the signal to downstream targets (Chen, F. and Weinberg. R. A. (1995) PNA892: 1565-1569; Wrana, J. L. et al. (1994) Nature 370: 341. | and measuring luciferase gene expression (Wrana et al., 1994, Nature 370: 341-347). | |
| MP52 | GeneSeq Accession W36100 | WO9741250 | Members of the TGF-beta family of proteins initiate cell signaling by binding to heteromeric receptor complexes of type I (TbetaRI) and type II (TbetaRII) serine/threonine kinase receptors (reviewed by Massague, J. et al. (1994) Trends Cell Biol. 4: 172 178; Miyazono, K. et al. (1994) Adv. Immunol. 55: 181-220). Activation of this heteromeric receptor complex occurs when TGF-beta. binds to TbetaRII, which then recruits and phosphorylates TbetaRI. Activated TbetaRI then propagates the signal to downstream targets (Chen, F. and Weinberg. R. A. (1995) PNA892: 1565-1569; Wrana, J. L. et al. (1994) Nature 370: 341. | The effect of TGF betas on signaling can be assayed by treating Primary BAECs transfected with a construct called p3TP-Lux, containing a TGF-beta responsive promoter fused to a reporter gene, and measuring luciferase gene expression (Wrana et al., 1994, Nature 370: 341-347). | Bone formation or Regeneration Abnormalities |
| b57 Protein | GeneSeq Accession W69293 | WO9837195 | BMPs are involved in the induction of bone formation. Specific antagonists are useful in preventing this activity from occurring. | BMP activity, in the presence of b57 protein, can be determined using the following assays known in the art: Nat Genet. 2001 January; 27(1): 84-8; Eur J Biochem 1996 Apr. 1; 237(1): 295-302; J Biol Chem, Vol. 274, Issue 16, 1089-10902, Apr. 16, 1999; and Hogan, B. L. M. (1996) Genes Deve. 10, 1580-1594. | BMP Antagonist useful for Osteosarcoma, abnormal bone growth. |
| Resistin | GeneSeq Accession W69293 | WO0064920 | This gene belongs to the family defined by mouse FIZZ1 and FIZZ3/Resistin genes. The characteristic feature of this family is the C-terminal stretch of 10 cys residues with identical spacing. The mouse homolog of this protein is secreted by adipocytes, may be the hormone potanitly linking obesity to type II diabetes. | Ability of resistin to influence type II diabetes can be determined using assays known in the art: Pontoglio et al., J Clin Invest 1998 May 15; 101(10): 2215-22. | Type II diabetes and Syndrome X. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Galectin-4 | GeneSeq Accession W11841 | WO9703190 | Galectins are a family of carbohydrate-binding proteins characterized by an affinity for beta-galactoside containing glycoconjugates. | Ability of Galectin-4 polypeptides to bind lactose can be determined using assays known in the art: Wada, et al., J Biol Chem 1997 Feb. 28; 272(9): 6078-86. | Lactose intolerance. |
| APM-I; ACRP-30; Famoxin | GeneSeq Accession Y71035 | WO0026363 | ACPR30 gene is exclusively expressed in adipose tissue. ACRP30 is thought to increase fatty acid oxidation by muscle tissue. | Ability of ACRP30 polypeptides to influence obesity and fat oxidation can be determined using assays known in the art: Fruebis et al., Proc Nat'l Acad Sci USA 2001 Feb. 13; 98(4): 2005-10. | Obesity, Metabolic disorders, Lipid Metabolism; Hormone Secretion. |
| ACRP-30 Homologue; Complement Component C1q C | GeneSeq Accession B30234 | WO0063376 | ACPR30 gene is exclusively expressed in adipose tissue. ACRP30 is thought to increase fatty acid oxidation by muscle tissue. | Ability of ACRP30 homologue polypeptides to influence obesity and fat oxidation can be determined using assays known in the art: Fruebis et al., Proc Nat'l Acad Sci USA 2001 Feb. 13; 98(4): 2005-10. | Obesity, Metabolic disorders, Lipid Metabolism; Hormone Secretion. |
| Calpain-10a | GeneSeq Accession Y79567 | WO0023603 | Calpain is believed to play a role in insulin secretion and insulin activity, and therefore may be useful in the treatment of type II diabetes. | Ability of Calpain-10 to influence type II diabetes can be determined using assays known in the art: Pontoglio et al., J Clin Invest 1998 May 15; 101(10): 2215-22. | Diabetes mellitus; Regulation of Insulin secretory response; Insulin mediated glucose transport disorders. |
| Calpain-10b | GeneSeq Accession Y79568 | WO0023603 | Calpain is believed to play a role in insulin secretion and insulin activity, and therefore may be useful in the treatment of type II diabetes. | Ability of Calpain-10 to influence type II diabetes can be determined using assays known in the art: Pontoglio et al., J Clin Invest 1998 May 15; 101(10): 2215-22. | Diabetes mellitus; Regulation of Insulin secretory response; Insulin mediated glucose transport disorders. |
| Calpain-10c | GeneSeq Accession Y79569 | WO0023603 | Calpain is believed to play a role in insulin secretion and insulin activity, and therefore may be useful in the treatment of type II diabetes. | Ability of Calpain-10 to influence type II diabetes can be determined using assays known in the art: Pontoglio et al., J Clin Invest 1998 May 15; 101(10): 2215-22. | Diabetes mellitus; Regulation of Insulin secretory response; Insulin mediated glucose transport disorders. |
| PDGF-D | GeneSeq Accession Y71130 | WO0027879 | Vascular Endothelial Growth Factor. | Proliferation assay using NR6R-3T3 cells (Rizzino 1988 Cancer Res. 48: 4266). | Wound Healing; Atherosclerosis. |
| FasL | GeneSeq Accession Y28594 | WO9936079 | Activities associated with apoptosis and immune system functions. | Activity can be determined using Apoptosis assays known in the art: Walczak et al. (1996) EMBOJ 16: 5386-5397. | Apoptosis-related disorders; Autoimmune disorders; Graft v-Host disorders. |
| Chondro modulin-like protein | GeneSeq Accession Y71262 | WO0029579 | Chondromodulin proteins are cartilage proteins thought to confer resistance to angiogeneis, and thus may be useful as anti-angiogenic agents that may have utility in combating cancer. | Ability of Chondromodulin-like protein to inhibit vascularization can be determined using assays known in the art: Hirakie et al., J Biol Chem 1997 Dec. 19; 272(51): 32419-26. | Antianglogenic agent; Osteoblast proliferation stimulator; prevents vascularization of cartilage tissue; Useful to treat cancer. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Patched | GeneSeq Accession W72969 | U.S. Pat. No. 5,837,538 | Patched is a tumour-suppressor receptor for Sonic hedgehog (shh), which is a protein that controls developmental patterning and growth. | Ability of soluble Patched to bind to and inhibit the activities of shh can be determined using assays known in the art: Stone et al., Nature 1996 Nov. 14; 384(6605): 129-34. | Receptor for Hedgehog cellular proliferation signaling molecule. This receptor is useful as a means of preventing cellular proliferation via the shh signaling pathway, thus useful for cancers. |
| Patched-2 | GeneSeq Accession Y43261 | WO9953058 | Patched is a tumour-suppressor receptor for Sonic hedgehog (shh), which is a protein that controls developmental patterning and growth. | Ability of soluble Patched to bind to and inhibit the activities of shh can be determined using assays known in the art: Stone et al., Nature 1996 Nov. 14; 384(6605): 129-34. | Receptor for Hedgehog cellular proliferation signaling molecule. This receptor is useful as a means of preventing cellular proliferation via the shh signaling pathway, thus useful for cancers. |
| Maspin; Protease Inhibitor 5 | GeneSeq Accession R50938 | WO9405804 | Maspin is a member of the serpin family of serine protease inhibitors that is thought to suppress tumor metastasis. | The inhibitory effects of Maspin and other protease inhibitors can be assayed using methods known in the art such as a labeled protease substrate, for example, Universal Protease Substrate (casein, resorufin-labeled): Roche Molecular Biochemicals, Cat. No. 1080733. | Tumor suppressor which is down-regulated in breast cancers. The maspin protein has tumour suppressing and invasion suppressing activity. |
| Endostatin | GeneSeq Accession B28399 | WO0064946 | Endostatin is believed to inhibit effects of capillary endothelial cell proliferation. | The inhibitory effects of endostatin can be assayed using assays disclosed by Cao et al. (1996) J. Biol. Chem. 271 29461-29467. | Anti-angiogenic activity. Useful in the prevention and/or treatment of cancers. |
| aFGF; FGF-1 | GeneSeq Accession P94037 | EP298723 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| bFGF; FGF-2 | GeneSeq Accession R06685 | FR2642086 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| FGF-3; INT-2 | GeneSeq Accession R07824 | WO9503831 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| FGF-4; HST-1; HBGF-4 | GeneSeq Accession R07825 | WO9503831 | Fibroblast Growth Factor | Proliferation assay using NR6R-3T3 cells (Rizzino 1988 Cancer Res. 48: 4266); Examples 23 and 39 disclosed herein. | may be useful as anti-cancer agents. Promotion of growth and proliferation of cells, such as epithelial cells and keratinocytes. Antagonists may be useful as anti-cancer agents. |
| FGF-5 | GeneSeq Accession W22600 | WO9730155 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| FGF-6; Heparin binding secreted transforming factor-2 | GeneSeq Accession R58555 | EP613946 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents |
| FGF-8 | GeneSeq Accession R80783 | WO9524928 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| FGF-9; Glia activating factor | GeneSeq Accession R70822 | WO9503831 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| FGF-12; Fibroblast growth factor homologous factor-1 | GeneSeq Accession W06309 | WO9635708 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| FGF-15 | GeneSeq Accession Y08582 | WO9927100 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| FGF-16 | GeneSeq Accession Y05474 | WO9918128 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| FGF-18 | GeneSeq Accession Y08590 | WO9927100 | Fibroblast Growth Factor | Proliferation assay using NR6R-3T3 cells (Rizzino 1988 Cancer Res. 48: 4266); Examples 23 and 39 disclosed herein. | Promotion of growth and proliferation of cells, such as epithelial cells and keratinocytes. Antagonists may be useful as anti-cancer agents. |
| flt-3 ligand | GeneSeq Accession R67541 | EP627487 | Stem Cell Progenitor | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ. | Promotion of immune cell growth and/or differentiation. |
| VEGF-110 | GeneSeq Accession Y69417 | WO0013702 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGB-121 | GeneSeq Accession B50432 | WO0071713 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-138 | GeneSeq Accession Y43483 | WO9940197 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-145 | GeneSeq Accession Y69413 | WO0013702 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| VEGF-162 | GeneSeq Accession Y43484 | WO9940197 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-165 | GeneSeq Accession Y69414 | WO0013702 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-182 | GeneSeq Accession Y43483 | WO9940197 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-189 | GeneSeq Accession Y69415 | WO0013702 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-206 | GeneSeq Accession Y69416 | WO0013702 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-D | GeneSeq Accession W53240 | WO9807832 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF-E; VEGF-X | GeneSeq Accession Y33679 | WO9947677 | Promotes the growth and/or proliferation of endothelial cells. | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| VEGF Receptor; KDR; flk-1 | GeneSeq Accession W69679 | WO9831794 | Receptor for VEGF polypeptides | VEGF activity, in the presence of flk-1 polypeptides, can be determined using assays known in the art, such as those disclosed in | VEGF Receptor. Fusion protein with the extracellular domain is useful as an anti-angiogenic agent. Antagonists |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Soluble VEGF Receptor | GeneSeq Accession W47037 | U.S. Pat. No. 5,712,380 | Receptor for VEGF polypeptides | International Publication No. WO0045835, for example. | may be useful in the promotion of angiogenesis. VEGF Receptor. Fusion protein with the extracellular domain is useful as an anti-angiogenic agent. Antagonists may be useful in the promotion of angiogenesis. |
| flt-1 | GeneSeq Accession Y70751 | WO0021560 | Receptor for VEGF polypeptides | VEGF activity, in the presence of VEGF Receptor polypeptides, can be determined using assays known in the art, such as those disclosed in International Publication No. WO0045835, for example. | VEGF Receptor. Fusion protein with the extracellular domain is useful as an anti-angiogenic agent. Antagonists may be useful in the promotion of angiogenesis. |
| VEGF R-3; flt-4 | GeneSeq Accession B29047 | WO0058511 | Receptor for VEGF polypeptides | VEGF activity, in the presence of flt-1 polypeptides, can be determined using assays known in the art, such as those disclosed in International Publication No. WO0045835, for example. | VEGF Receptor. Fusion protein with the extracellular domain is useful as an anti-angiogenic agent. Antagonists may be useful in the promotion of angiogenesis. |
| Neuropilin-1 | GeneSeq Accession Y06319 | WO9929858 | Vascular Endothelial Growth Factor | VEGF activity, in the presence of flt-4 polypeptides, can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| Neuropilin-2 | GeneSeq Accession Y03618 | WO9929858 | Vascular Endothelial Growth Factor | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| Human fast twitch skeletal muscle troponin C | GeneSeq Accession W22597 | WO9730085 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art.: Proc Natl Acad Sci USA 1999 Mar 16; 96(6): 2645-50. | Anti-angiogenesis |
| Human fast twitch skeletal muscle troponin I | GeneSeq Accession W18054 | WO9730085 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art.: Proc Natl Acad Sci USA 1999 Mar 16; 96(6): 2645-50. | Anti-angiogenesis |
| Human fast twitch | GeneSeq Accession | WO9730085 | Troponins are contractile proteins that are thought to inhibit angiogenesis. High levels | Ability of soluble Troponins to inhibit angiogenesis can be | Anti-angiogenesis |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| skeletal muscle troponin T fragment. | W22599 | | may contribute to the difficulty encountered in revascularizing the ischemic myocardium after cardiovascular injury. | determined using assays known in the art: . Proc Natl Acad Sci USA 1999 Mar 16; 96(6): 2645-50. | |
| myofibrillar protein troponin I | GeneSeq Accession W18053 | WO9719955 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art: . Proc Natl Acad Sci USA 1999 Mar 16; 96(6): 2645-50. | Anti-angiogenesis |
| myofibrillar protein troponin I | GeneSeq Accession W18054 | WO9719955 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art: . Proc Natl Acad Sci USA 1999 Mar 16; 96(6): 2645-50. | Anti-angiogenesis |
| Troponin peptides | GeneSeq Accessions Y29581, Y29582, Y29583, Y29584, Y29585, and Y29586 | WO9933874 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art: . Proc Natl Acad Sci USA 1999 Mar 16; 96(6): 2645-50. | Anti-angiogenesis |
| Human fast twitch skeletal muscle Troponin subunit C | GeneSeq Accession B00134 | WO0054770 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art: . Proc Natl Acad Sci USA 1999 Mar 16; 96(6): 2645-50. | Anti-angiogenesis |
| Human fast twitch skeletal muscle Troponin subunit I Protein | GeneSeq Accession B00135 | WO0054770 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art: . Proc Natl Acad Sci USA 1999 Mar 16; 96(6): 2645-50. | Anti-angiogenesis |
| Human fast twitch skeletal muscle Troponin subunit T | GeneSeq Accession B00136 | WO0054770 | Troponins are contractile proteins that are thought to inhibit angiogenesis. High levels may contribute to the difficulty encountered in revascularizing the ischemic myocardium after cardiovascular injury. | Ability of soluble Troponins to inhibit angiogenesis can be determined using assays known in the art: . Proc Natl Acad Sci USA 1999 Mar 16; 96(6): 2645-50. | Anti-angiogenesis |
| Activator Inhibitor-1; PAI-1 | GeneSeq Accession R08411 | WO9013648 | PAIs are believed to play a role in cancer, and cardiovascular disease and blood-clotting disorders. | Methods that measure plasminogen activator inhibitor (PA1) activity are known in the art, for example, assay the ability of PA1 to inhibit tissue plasminogen activator (tPA) | Anti-angiogenesis; blood-clotting disorders. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | | or urokinase (uPA): J Biochem Biophys Methods 2000 Sep. 11; 45(2): 127-40, Breast Cancer Res Treat 1996; 41(2): 141-6. Methods that measure anti-angiogenesis activity are known in the art, for example, Proc Natl Acad Sci USA 1999 Mar. 16; 96(6): 2645-50. | |
| Plasminogen Activator Inhibitor-2; PAI-2 | GeneSeq Accession P94160 | DE3722673 | PAIs are believed to play a role in cancer, and cardiovascular disease and blood-clotting disorders. | Methods that measure plasminogen activator inhibitor (PA1) activity are known in the art, for example, assay the ability of PA1 to inhibit tissue plasminogen activator (tPA) or urokinase (uPA): J Biochem Biophys Methods 2000 Sep. 11; 45(2): 127-40, Breast Cancer Res Treat 1996; 41(2): 141-6. Methods that measure anti-angiogenesis activity are known in the art, for example, Proc Natl Acad Sci USA 1999 Mar. 16; 96(6): 2645-50. | Anti-angiogenesis; blood-clotting disorders. |
| Activator Inhibitor-2; PAI-2 | GeneSeq Accession R10921 | WO9102057 | PAIs are believed to play a role in cancer, and cardiovascular disease and blood-clotting disorders. | Methods that measure plasminogen activator inhibitor (PA1) activity are known in the art, for example, assay the ability of PA1 to inhibit tissue plasminogen activator (tPA) or urokinase (uPA): J Biochem Biophys Methods 2000 Sep. 11; 45(2): 127-40, Breast Cancer Res Treat 1996; 41(2): 141-6. Methods that measure anti-angiogenesis activity are known in the art, for example, Proc Natl Acad Sci USA 1999 Mar. 16; 96(6): 2645-50. | Anti-angiogenesis; blood-clotting disorders. |
| Human PAI-1 mutants | GeneSeq Accessions R11755, R11756, R11757, R11758, R11759, R11760, R11761, R11762 | WO9105048 | PAIs are believed to play a role in cancer, and cardiovascular disease and blood-clotting disorders. | Methods that measure plasminogen activator inhibitor (PA1) activity are known in the art, for example, assay the ability of PA1 to inhibit tissue plasminogen activator (tPA) or urokinase (uPA): J Biochem Biophys Methods 2000 Sep. 11; 45(2): 127-40, Breast Cancer Res Treat 1996; 41(2): 141-6. Methods that measure anti-angiogenesis | Anti-angiogenesis; blood-clotting disorders. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | and R11763 | | | activity are known in the art, for example, Proc Natl Acad Sci USA 1999 Mar 16; 96(6): 2645-50. | |
| CXCR3; CXC | GeneSeq Accession Y79372 | WO0018431 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ. | Soluble CXCR3 polypeptides may be useful for inhibiting chemokine activities and viral infection. |
| Modified Rantes | GeneSeq Accession W38129 | WO9737005 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ. | Immune disorders. |
| RANTES | GeneSeq Accession Y05299 | EP905240 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ. | Immune disorders. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| MCI-1a | GeneSeq Accession R73914 | WO9509232 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ. | Immune disorders. |
| MCP-1b | GeneSeq Accession Y26176 | WO9929728 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ. | Immune disorders. |
| MCP-1 receptor | GeneSeq Accession R79165 | WO9519436 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ. | Soluble MCP-1 Receptor polypeptides may be useful for inhibiting chemokine activities and viral infection. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| MCP-3 | GeneSeq Accession R73915 | WO9509232 | Over 40 human chemokines have been described, which bind to ~17 receptors thus far identified. | | Immune disorders. |
| MCP-4 receptor | GeneSeq Accession W56689 | WO9809171 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ. | Soluble MCP-4 Receptor polypeptides may be useful for inhibiting chemokine activities and viral infection. |
| RANTES receptor | GeneSeq Accession W29588 | U.S. Pat. No. 5,652,133 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ. | Soluble RANTES Receptor polypeptides may be useful for inhibiting chemokine activities and viral infection. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| CCR5 variant | GeneSeq Accession W88238 | WO9854317 | described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ. | Soluble CCR5 polypeptides may be useful for inhibiting chemokine activities and viral infection. |
| CCR7 | GeneSeq Accession B50859 | U.S. Pat. No. 6,153,441 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ. | Soluble CCR7 polypeptides may be useful for inhibiting chemokine activities and viral infection. |
| CXC3 | GeneSeq Accession W23345 | WO9727299 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ. | Immune disorders. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Eotaxin | GeneSeq Accession W10099 | WO9700960 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ. | Immune disorders. |
| Neurotactin | GeneSeq Accessions Y77537, W34307, Y53259, and, Y77539 | U.S. Pat. No. 6,013,257 WO9742224 | Neurotactin may play a role in chemotactic leukocyte migration and brain inflammation processes. | Chemotactic leukocyte migration assays are known in the art, for example: J. Immunol. Methods 33, ((1980)); Nature 1997 Jun. 5; 387(6633): 611-7. | Immune disorders. |
| Human CKbeta-9 | GeneSeq Accession B50860 | U.S. Pat. No. 6,153,441 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | chemokine activities can be determined using assays known in the art: Methods in Molecular Biology, 2000, vol. 138: chemokine Protocols. Edited by: A. E. I. Proudfoot, T. N. C. Wells, and C. A. Power. Humana Press Inc, Totowa, NJ. | Immune disorders. |
| Lymphotactin | GeneSeq Accession B50052 | WO0073320 | Chemokines are a family of related small, secreted proteins involved in biological processes ranging from hematopoiesis, angiogenesis, and leukocyte trafficking. Members of this family are involved in a | chemokine activities can be determined using assays known in the art: Methods in Molecular Biology, 2000, vol. 138: Chemokine Protocols. Edited by: A. E. I. Proudfoot, T. N. C. Wells, | Immune disorders. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | similarly diverse range of pathologies including inflammation, allergy, tissue rejection, viral infection, and tumor biology. The chemokines exert their effects by acting on a family of seven transmembrane G. | and C. A. Power. Humana Press Inc., Totowa, NJ. | |
| MIP-3 alpha | GeneSeq Accession W44398 | WO9801557 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G. | chemokine activities can be determined using assays known in the art: Methods in Molecular Biology, 2000, vol. 138: Chemokine Protocols. Edited by: A. E. I Proudfoot, T. N. C. Wells, and C. A. Power. Humana Press Inc., Totowa, NJ. | Immune disorders. |
| MIP-3 beta | GeneSeq Accession W44399 | WO9801557 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G. | Chemokine activities can be determined using assays known in the art: Methods in Molecular Biology, 2000, vol. 138: Chemokine Protocols. Edited by: A. E. I Proudfoot, T. N. C. Wells, and C. A. Power. Humana Press Inc., Totowa, NJ. | Immune disorders. |
| MIP-Gamma | GeneSeq Accession R70798 | WO9504158 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G. | Chemokine activities can be determined using assays known in the art: Methods in Molecular Biology, 2000, vol. 138: Chemokine Protocols. Edited by: A. E. I Proudfoot, T. N. C. Wells, and C. A. Power. Humana Press Inc., Totowa, NJ. | Immune disorders. |
| Stem Cell Inhibitory Factor | GeneSeq Accession R11553 | WO9104274 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue | Chemokine activities can be determined using assays known in the art: Methods in Molecular Biology, 2000, vol. 138: Chemokine Protocols. Edited by: A. E. I Proudfoot, T. N. C. Wells, and C. A. Power. Humana Press Inc., Totowa, NJ. | Hematopoietic growth factors. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | rejection, viral infection, and tumor biology. The chemokines exert their effects by acting on a family of seven transmembrane G. | | |
| thrombo-poietin | GeneSeq Accession R79905 | WO9521920 | Thrombopoietin is involved in the regulation of the growth and differentiation of megakaryocytes and preceptors thereof. | Thrombopoietin (TPO) can be assayed to determine regulation of growth and differentiation of megakaryocytes. Mol Cell Biol 2001 Apr; 21(8): 2659-70; Exp Hematol 2001 January; 29(1): 51-8 and within. | Hematopoietic growth factors. |
| c-kit ligand; SCF; Mast cell growth factor; MGF; Fibro-sarcoma-derived stem cell factor | GeneSeq Accession Y53284, R83978 and R83977 | EP992579 and EP676470 | C-kit ligan is thought to stimulate the proliferation of mast cells, and is able to augment the proliferation of both myeloid and lymphoid hematopoietic progenitors in bone marrow culture. C-kit ligand is also thought to act synergistically with other cytokines. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ. | Hematopoietic growth factors. |
| Platelet derived growth factor | GeneSeq Accession B48653 | WO0066736 | Vascular Endothelial Growth Factor | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| Melanoma inhibiting protein | GeneSeq Accession R69811 | WO9503328 | Melanoma inhibiting protein has melanoma-inhibiting activity and can be used to treat cancer (melanoma, glioblastoma, neuroblastoma, small cell lung cancer, neuroectodermal tumors) or as an immunosuppressant (it inhibits IL-2 or phytohaemagglutinin induced proliferation of peripheral blood lymphocytes. | Tumor suppressor activity of melanoma inhibiting protein can be determined using assays known in the art: Matzuk et al., Nature 1992 Nov. 26; 360(6402): 313-9. | Cancer; melanoma |
| Glioma-derived growth factor | GeneSeq Accession R08120 | EP399816 | Vascular Endothelial Growth Factor | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| Platelet derived growth | GeneSeq Accession R84759 | EP682110 | Vascular Endothelial Growth Factor | VEGF activity can be determined using assays known in the art, such as those disclosed in International | Promotion of growth and proliferation of cells, such as vascular endothelial cells. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| factor precursor A | | | | Publication No. WO0045835, for example. | Antagonists may be useful as anti-angiogenic agents, and may be applicable for cancer. |
| Platelet derived growth factor precursor B | GeneSeq Accession R84760 | EP682110 | Vascular Endothelial Growth Factor | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| Platelet derived growth factor Bv-sis | GeneSeq Accession P80595 and P80596 | EP282317 | Vascular Endothelial Growth Factor | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| Placental Growth Factor | GeneSeq Accessions R23059 and R23060 | WO9206194 | Vascular Endothelial Growth Factor | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| Placental Growth Factor-2 | GeneSeq Accession Y08289 | DE19748734 | Vascular Endothelial Growth Factor | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer. |
| Thrombopoietin derivative1 | GeneSeq Accession Y77244 | WO0000612 | Thrombopoietin is involved in the regulation of the growth and differentiation of megakaryocytes and preceptors thereof. | Thrombopoietin (TPO) can be assayed to determine regulation of growth and differentiation of megakaryocytes. Mol Cell Biol 2001 Apr; 21(8): 2659-70; Exp Hematol 2001 January; 29(1): 51-8 and within. | Thrombocytopenia, cancer. |
| Thrombopoietin derivative2 | GeneSeq Accession Y77255 | WO0000612 | Thrombopoietin is involved in the regulation of the growth and differentiation of megakaryocytes and preceptors thereof. | Thrombopoietin (TPO) can be assayed to determine regulation of growth and differentiation of megakaryocytes. Mol Cell Biol 2001 Apr; 21(8): 2659-70; Exp Hematol 2001 January; 29(1): 51-8 and within. | Thrombocytopenia, cancer. |
| Thrombopoietin derivative3 | GeneSeq Accession Y77262 | WO0000612 | Thrombopoietin is involved in the regulation of the growth and differentiation of megakaryocytes and preceptors thereof. | Thrombopoietin (TPO) can be assayed to determine regulation of growth and differentiation of megakaryocytes. Mol Cell Biol 2001 Apr; 21(8): 2659-70; Exp | Thrombocytopenia, cancer. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Thrombo-poietin derivative4 | GeneSeq Accession Y77267 | WO0000612 | Thrombopoietin is involved in the regulation of the growth and differentiation of megakaryocytes and precursors thereof. | Thrombopoietin (TPO) can be assayed to determine regulation of growth and differentiation of megakaryocytes. Mol Cell Biol 2001 Apr;; 21(8): 2659-70; Exp Hematol 2001 January; 29(1): 51-8 and within. | Thrombocytopenia, cancer. |
| Thrombo-poietin derivative5 | GeneSeq Accession Y77246 | WO0000612 | Thrombopoietin is involved in the regulation of the growth and differentiation of megakaryocytes and precursors thereof. | Thrombopoietin (TPO) can be assayed to determine regulation of growth and differentiation of megakaryocytes. Mol Cell Biol 2001 Apr;; 21(8): 2659-70; Exp Hematol 2001 January; 29(1): 51-8 and within. | Thrombocytopenia, cancer. |
| Thrombo-poietin derivative6 | GeneSeq Accession Y77253 | WO0000612 | Thrombopoietin is involved in the regulation of the growth and differentiation of megakaryocytes and precursors thereof. | Thrombopoietin (TPO) can be assayed to determine regulation of growth and differentiation of megakaryocytes. Mol Cell Biol 2001 Apr;; 21(8): 2659-70; Exp Hematol 2001 January; 29(1): 51-8 and within. | Thrombocytopenia, cancer. |
| Thrombo-poietin derivative7 | GeneSeq Accession Y77256 | WO0000612 | Thrombopoietin is involved in the regulation of the growth and differentiation of megakaryocytes and precursors thereof. | Thrombopoietin (TPO) can be assayed to determine regulation of growth and differentiation of megakaryocytes. Mol Cell Biol 2001 Apr;; 21(8): 2659-70; Exp Hematol 2001 January; 29(1): 51-8 and within. | Thrombocytopenia, cancer. |
| Fract-alkine | GeneSeq Accession Y53255 | U.S. Pat. No. 6,043,086 | Fractalkine is believed to play a role in chemotactic leukocyte migration and neurological disorders. | Fractalkine activity can be determined using Chemotactic leukocyte migration assays known in the art, for example: J. Immunol. Methods 33, ((1980)); Nature 1997 Jun. 5; 387(6633): 611-7. | Immune disorders. |
| CXC3 | GeneSeq Accession W23345 | WO9757599 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ. | Immune disorders. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | biology. The chemokines exert their effects by acting on a family of seven transmembrane G-protein coupled receptors. Over 40 human chemokines have been described, which bind to ~17 receptors thus far identified. | | |
| CCR7 | GeneSeq Accession B50859 | U.S. Pat. No. 6,153,441 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ. | Soluble CCR7 polypeptides may be useful for inhibiting chemokine activities and viral infection. |
| Nerve Growth Factor-beta | GeneSeq Accession R11474 | EP414151 | Nerve Growth Factor | Proliferation assay using NR6R-3T3 cells (Rizzino 1988 Cancer Res. 48: 4266) | Neurological disorders, cancer |
| Nerve Growth Factor-beta2 | GeneSeq Accession W69725 | EP859056 | Nerve Growth Factor | Proliferation assay using NR6R 3T3 cells (Rizzino 1988 Cancer Res. 48: 4266 | Neurological disorders, cancer |
| Neurotrophin-3 | GeneSeq Accession W8889 | WO9821234 | Neurotrophins regulate neuronal cell survival and synaptic plasticity. | Trk tyrosine kinase activation assays known in the art can be used to assay for neurotrophin activity, for example, Proc Natl Acad Sci USA 2001 Mar. 13; 98(6): 3555-3560. | Neurological disorders, cancer |
| Neurotrophin-3 | GeneSeq Accession R47100 | WO9325684 | Neurotrophins regulate neuronal cell survival and synaptic plasticity. | Trk tyrosine kinase activation assays known in the art can be used to assay for neurotrophin activity, for example, Proc Natl Acad Sci USA 2001 Mar. 13; 98(6): 3555-3560. | Neurological disorders, cancer |
| Neurotrophin-4a | GeneSeq Accession R47101 | WO9325684 | Neurotrophins regulate neuronal cell survival and synaptic plasticity. | Trk tyrosine kinase activation assays known in the art can be used to assay for neurotrophin activity, for example, Proc Natl Acad Sci USA 2001 Mar. 13; 98(6): 3555-3560. | Neurological disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Neurotrophin-4b | GeneSeq Accession R47102 | WO9325684 | Neurotrophins regulate neuronal cell survival and synaptic plasticity, tyrosine kinases. | Trk tyrosine kinase activation assays known in the art can be used to assay for neurotrophin activity, for example, Proc Natl Acad Sci USA 2001 Mar. 13; 98(6): 3555-3560. | Neurological disorders, cancer |
| Neurotrophin-4c | GeneSeq Accession R47103 | WO9325684 | Neurotrophins regulate neuronal cell survival and synaptic plasticity, tyrosine kinases. | Trk tyrosine kinase activation assays known in the art can be used to assay for neurotrophin activity, for example, Proc Natl Acad Sci USA 2001 Mar. 13; 98(6): 3555-3560. | Neurological disorders, cancer |
| Neurotrophin-4d | GeneSeq Accession R47102 | WO9325684 | Neurotrophins regulate neuronal cell survival and synaptic plasticity, tyrosine kinases. | Trk tyrosine kinase activation assays known in the art can be used to assay for neurotrophin activity, for example, Proc Natl Acad Sci USA 2001 Mar. 13; 98(6): 3555-3560. | Neurological disorders, cancer |
| Platelet-Derived Growth Factor A chain | GeneSeq Accession R38918 | U.S. Pat. No. 5,219,739 | Vascular Endothelial Growth Factor | VEGF activity can be determined using assays known in the art, such as those disclosed in International Publication No. WO0045835, for example. | Promotion of growth and proliferation of cells, such as vascular endothelial cells. Hematopoietic and immune disorders. Antagonists may be useful as anti-angiogenic agents, and may be applicable for cancer |
| Platelet-Derived Growth Factor B chain | GeneSeq Accession R38919 | U.S. Pat. No. 5,219,739 | Vascular Endothelial Growth Factor | VEGF activity can be determined using assays known in the art, such as those disclosed in International Publication No. WO0045835, for example. | Promotion of growth and proliferation of cells, such as vascular endothelial cells. Hematopoietic and immune disorders. Antagonists may be useful as anti-angiogenic agents, and may be applicable for cancer |
| Stromal Derived Factor-1 alpha | GeneSeq Accession Y39995 | WO9948528 | Stromal Growth Factor | Proliferation assay using NR6R-3T3 cells (Rizzino 1988 Cancer Res. 48: 4266) | Hematopoietic, immune disorders, cancer |
| Stromal Derived Factor-1 beta | GeneSeq Accession R75420 | CA2117953 | Stromal Growth Factor | Proliferation assay using NR6R-3T3 cells (Rizzino 1988 Cancer Res. 48: 4266) | Hematopoietic, immune disorders, cancer |
| Tarc | GeneSeq Accession W14917 | WO9711969 | Chemotactic for T lymphocytes. May play a role in T-cell development. Thought to bind CCR8 and CCR4 | Chemotactic leukocyte migration assays are known in the art, for example: J. Immunol. Methods 33 ((1980)) | Antiinflammatory. Immune disorders, cancer |
| Prolactin | GeneSeq Accession R78691 | WO9521625 | Prolactin is involved in immune cell proliferation and apoptosis. | Immune cell proliferation and suppression of apoptosis by prolactin can be assayed by methods | Reproductive system disorders, cancer. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Prolactin2 | GeneSeq Accession Y31764 | U.S. Pat. No. 5,955,346 | Prolactin is involved in immune cell proliferation and apoptosis. | Immune coil proliferation and suppression of apoptosis by prolactin can be assayed by methods well-known in the art, for example, Buckley, AR and Buckley DJ, Ann NY Acad Sci 2000; 917: 522-33, and within. | Reproductive system disorders, cancer. |
| Follicle stimulating hormone Alpha subunit | GeneSeq Accession Y54160 | EP974359 | FSH stimulates secretion of interleukin-1 by cells isolated from women in the follicular phase | FSH activities can be determined using assays known in the art; J Gend Specif Med 1999 Nov.-Dec.; 2(6): 30-4; Mol Cell Endocrinol. 1997 Nov. 15; 134(2): 109-18. | Reproductive system disorders, cancer. |
| Follicle stimulating hormone Beta subunit | GeneSeq Accession Y54161 | EP974359 | FSH stimulates secretion of interleukin-1 by cells isolated from women in the follicular phase | FSH activities can be determined using assays known in the art; J Gend Specif Med 1999 Nov.-Dec.; 2(6): 30-4; Mol Cell Endocrinol. 1997 Nov. 15; 134(2): 109-18. | Reproductive system disorders, cancer. |
| Substance P (tachykinin) | GeneSeq Accession B23027 | WO0054053 | Substance P is associated with immunoregulation. | Immuneregulation and bone marrow, cell proliferation by substance P can be assayed by methods well-known in the art, for example, Lai et al. Proc Natl Acad Sci USA 2001 Mar. 27; 98(7): 3970-5; Jallat-Daloz et al. Allergy Asthma Proc 2001 Jan.-Feb.; 22(1): 17-23; Kahler et al. Exp Lung Res 2001 Jan.-Feb.; 27(1): 25-46; and Adamus M A and Dabrowski Z J. J Cell Biochem 2001; 81(3)499-506. | diabetes mellitus, hypertension, cancer |
| Ocytocin (Neurophysin I) | GeneSeq Accession B24085 and B24086 | WO0053755 | Oxytocin is involved in the induction of prostaglandin (E2) release as well as an increased amount of calcium release by smooth muscle cells. | Oxytocin and prostaglandin E(2) release and Ocytocin (Ca2+) increase can be assayed by methods well-known in the art, for example, Pavan et al., AM J Obset Gynecol 2000 Jul.; 183(1): 76-82 and Holdaet al., Cell Calcium 1996 Jul.; 20(1): 43 51. | inflammatory disorders immunologic disorders, cancer |
| Vasopressin | GeneSeq Accession | WO0053755 | Vasopressinis believed to have a direct antidiuretic action on the kidney, and it is | Vasopressin activity can be determined using assays known in | inflammatory disorders immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| (Neurophysin II) | B24085 and B24086 | | thought to cause vasoconstriction of the peripheral vessels. | the art, for example, Endocr Regul 1996 Mar; 30(1): 13-17. | |
| IL-1 | GeneSeq Accession P60326 | EP165654 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens A Practical Approach, Clemens et al., eds, IRL Press, Washington, D.C. 1987, pp. 221-225; and Orencole & Dinarelio (1989) Cytokine 1, 14-20. | inflammatory disorders, immunologic disorders, cancer |
| IL-1-mature | GeneSeq Accession R14855 | EP456332 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens A Practical Approach, Clemens et al., eds, IRL Press, Washington, D.C. 1987, pp. 221-225; and Orencole & Dinarelio (1989) Cytokine 1, 14-20. | inflammatory disorders, immunologic disorders, cancer |
| IL-1 beta | GeneSeq Accession Y08322 | WO9922763 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens A Practical Approach, Clemens et al., eds, IRL Press, Washington, D.C. 1987, pp. 221-225; and Orencole & Dinarelio (1989) Cytokine 1, 14-20. | inflammatory disorders, immunologic disorders, cancer |
| IL-3 variants | GeneSeq Accession P80382, P80383, P80384, and P80381 | WO8806161 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Kitamura et al (1989) J Cell Physiol. 140 323-334. | inflammatory disorders, immunologic disorders, cancer |
| IL-4 | GeneSeq Accession P70615 | WO8702990 | Interleukins are a group of multifunctional cytokines synthesized by lymphocytes, | Interleukin activity can be determined using assays known in the art: Matthews et al., in | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Lymphokines and Interferons A Practical Approach, Clemens et al., eds, IRL Press, Washington, D.C. 1987, pp. 221-225; and Siegel & Mostowski (1990) J Immunol Methods 132, 287-295. | |
| IL-4 muteins | GeneSeq Accession W52151 W52152 W52153 W52154 W52155 W52156 W52157 W52158 W52159 W52160 W52161 W52162 W52163 W52164 and W52165 | WO9747744 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Siegel & Mostowski (1990) J Immunol Methods 132, 287-295. | inflammatory disorders, immunologic disorders, cancer |
| IL-1 alpha | GeneSeq Accession P90108 | EP324447 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Orencole & Dinarello (1989) Cytokine 1, 14-20. | inflammatory disorders, immunologic disorders, cancer |
| IL-3 variants | GeneSeq Accession R38561, R38562, R38563, R38564, R38565, R38566, R38567, R38568, R38569, | WO9307171 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Aarden et al (1987) Eur. J. Immunol 17, 1411-16. | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| IL-6 | R38570, R38571, and R38572 GeneSeq Accession R45717 and R45718 | WO9402512 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Aarden et al (1987) Eur. J. Immunol 17, 1411-16. | inflammatory disorders, immunologic disorders, cancer |
| IL-13 | GeneSeq Accession R48624 | WO9404680 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Boutelier et al (1995) J. Immunol. Methods 181, 29. | inflammatory disorders, immunologic disorders, cancer |
| IL-4 mutein | GeneSeq Accession R47182 | DE4137333 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Siegel & Mostowski (1990) J Immunol Methods 132, 287-295. | inflammatory disorders, immunologic disorders, cancer |
| IL-4 mutein Y124X | GeneSeq Accession R47183 | DE4137333 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Siegel & Mostowski (1990) J Immunol Methods 132, 287-295. | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| IL-4 mutein Y124G | GeneSeq Accession R47184 | DE4137333 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Siegel & Mostowski (1990) J Immunol Methods 132, 287-295. | inflammatory disorders, immunologic disorders, cancer |
| Human Interleukin-10 (precursor) | GeneSeq Accession R41664 | WO9317698 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Thompson-Snipes et al (1991) J. Exp. Med. 173, 507-510. | inflammatory disorders, immunologic disorders, cancer |
| Human Interleukin-10 | GeneSeq Accession R42642 | WO9318783-A | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Thompson-Snipes et al (1991) J. Exp. Med. 173, 507-510. | inflammatory disorders, immunologic disorders, cancer |
| Human interleukin-1 beta precursor. | GeneSeq Accession R42447 | EP569042 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Orencole & Dinarello (1989) Cytokine 1, 14-20. | inflammatory disorders, immunologic disorders, cancer |
| Interleukin-1 alpha | GeneSeq Accession R45364 | EP578278 | Interleukins are a group of multifunctional cytokines synthesized by lymphocytes, monocytes, and macrophages. Known functions include stimulating | Interleukin activity can be determined using assays known in the art: Matthews et al., in Lymphokines and Interferens A Practical Approach, Clemens et al., | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | proliferation of immune cells (e.g., T helper cells, B cells, eosinophils, and lymphocytes), chemotaxis of neutrophils and T lymphocytes, and/or inhibition of interferons. | eds, IRL Press, Washington, D.C. 1987, pp. 221-225. | |
| Human interleukin-3 variant | GeneSeq Accession R22814 | JP04063595 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Kitamura et al (1989) J Cell Physiol. 140 323-334. | inflammatory disorders, immunologic disorders, cancer |
| IL-1i fragments | GeneSeq Accession R35484 and R35485 | EP541920 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Orencole & Dinarelio (1989) Cytokine 1, 14-20. | inflammatory disorders, immunologic disorders, cancer |
| IL-1 inhibitor (IL-1i) | GeneSeq Accession R35486 and R35484 | EP541920 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Orencole & Dinarelio (1989) Cytokine 1, 14-20. | inflammatory disorders, immunologic disorders, cancer |
| ICE 22 kD subunit. | GeneSeq Accession R33780 | EP533350 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| ICE 20 kD subunit | GeneSeq Accession R33781 | EP533350 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225. | inflammatory disorders, immunologic disorders, cancer |
| ICE 10 kD subunit | GeneSeq Accession R33782 | EP533350 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225. | inflammatory disorders, immunologic disorders, cancer |
| Human Interleukin-10 (precursor) | GeneSeq Accession R41664 | WO9317698 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Thompson-Snipes et al (1991) J. Exp. Med. 173, 507-510. | inflammatory disorders, immunologic disorders, cancer |
| Human Interleukin-10 | GeneSeq Accession R42642 | WO9318783 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Thompson-Snipes et al (1991) J. Exp. Med. 173, 507-510. | inflammatory disorders, immunologic disorders, cancer |
| Human Interleukin-1 beta precursor | GeneSeq Accession R42447 | EP569042 | Interleukins are a group of multifunctional cytokines synthesized by lymphocytes, monocytes, and macrophages. Known functions include stimulating proliferation of immune cells (e.g., | Interleukin activity can be determined using assays known in the art: Matthews et al., in Lymphokines and Interferens: A Practical Approach, Clemens et al., eds, IRL Press, Washington, D.C. | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human interleukin-6 | GeneSeq Accession R49041 | WO9403492 | T helper cells, B cells, eosinophils, and lymphocytes), chemotaxis of neutrophils and T lymphocytes, and/or inhibition of interferons. | 1987, pp. 221-225; and Kitamura et al (1989) J Cell Physiol. 140 323-334. | |
| | | | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Aarden et al (1987) Eur. J. Immunol 17, 1411-16. | inflammatory disorders, immunologic disorders, cancer |
| Mutant Interleukin 6 S176R | GeneSeq Accession R54990 | WO9411402 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Aarden et al (1987) Eur. J. Immunol 17, 1411-16. | inflammatory disorders, immunologic disorders, cancer |
| Interleukin 6 | GeneSeq Accession R55256 | JP06145063 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Aarden et al (1987) Eur. J. Immunol 17, 1411-16. | inflammatory disorders, immunologic disorders, cancer |
| Interleukin 8 (IL-8) receptor | GeneSeq Accession R53932 | JP06100595 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Holmes et al (1991) Science 253, 1278-80. | Soluble IL-8 receptor polypeptides may be useful for inhibiting interleukin activities. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human interleukin-7 | GeneSeq Accession R59919 | U.S. Pat. No. 5,328,988 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Park et al (1990) J. Exp. Med. 171, 1073-79. | inflammatory disorders, immunologic disorders, cancer |
| IL-3 containing fusion protein. | GeneSeq Accession R79342 and R79344 | WO9521254 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Kitamura et al (1989) J Cell Physiol. 140 323-334. | inflammatory disorders, immunologic disorders, cancer |
| IL-3 mutant proteins | GeneSeq Accession R79254, R79255, R79256, R79257, R79258, R79259, R79260, R79261, R79262, R79263, R79264, R79265, R79266, R79267, R79268, R79269, R79270, R79271, R79272, R79273, R79274, R79275, R79276, R79277, | ZA9402636 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Giri et al (1994) EMBO J. 13 2822-2830. | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | R79278, R79279, R79280, R79281, R79282, R79283, R79284, and R79285 | | | | |
| IL-12 p40 subunit. | GeneSeq Accession R63018 | AU9466072 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225. | inflammatory disorders, immunologic disorders, cancer |
| AGF | GeneSeq Accession R64240 | WO9429344 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225. | inflammatory disorders, immunologic disorders, cancer |
| Human interlaukin-12 40 kD subunit | GeneSeq Accession R79187 | WO9519786 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Hori et al (1987), Blood 70, 1069-1078. | inflammatory disorders, immunologic disorders, cancer |
| Human interleukin-15 receptor from clone P1 | GeneSeq Accession R90843 | WO9530695 | Interleukins are a group of multifunctional cytokines synthesized by lymphocytes, monocytes, and macrophages. Known functions include stimulating proliferation of immune cells (e.g., | Interleukin activity can be determined using assays known in the art: Matthews et al., in Lymphokines and Interferens: A Practical Approach, Clemens et al., eds, IRL Press, Washington, D.C. | Soluble IL-8 receptor polypeptides may be useful for inhibiting interleukin activities. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human interleukin-7 | GeneSeq Accession R92796 | WO9604306 | T helper cells, B cells, eosinophils, and lymphocytes), chemotaxis of neutrophils and T lymphocytes, and/or inhibition of interferons. Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | 1987, pp. 221-225; and Giri et al (1994) EMBO J. 13 2822-2830. Interleukin activity can be determined using assays known in the art: Matthews et al., in Lymphokines and Interferens: A Practical Approach, Clemens et al., eds, IRL Press, Washington, D.C. 1987, pp. 221-225; and Park et al (1990) J. Exp. Med. 171, 1073-79. | inflammatory disorders, immunologic disorders, cancer |
| interleukin-9 | GeneSeq Accession R92797 | WO9604306 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Yang et al (1989) Blood 74, 1880-84. | inflammatory disorders, immunologic disorders, cancer |
| interleukin-3 | GeneSeq Accession R92801 | WO9604306 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Kitamura et al (1989) J Cell Physiol. 140 323-334. | inflammatory disorders, immunologic disorders, cancer |
| Human interleukin-5 | GeneSeq Accession R92802 | WO9604306 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Kitamura et al (1989) J Cell Physiol. 140 323-334. | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Recombinant interleukin-16 | GeneSeq Accession W33373 | DE19617202 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Lim et al (1996) J. Immunol. 156, 2566-70. | inflammatory disorders, immunologic disorders, cancer |
| Human IL-16 protein | GeneSeq Accession W33234 | DE19617202 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Lim et al (1996) J. Immunol. 156, 2566-70. | inflammatory disorders, immunologic disorders, cancer |
| Thr1 17 human interleukin 9 | GeneSeq Accession W27521 | WO9708321 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225. | inflammatory disorders, immunologic disorders, cancer |
| Met1 17 human interleukin 9 | GeneSeq Accession W27522 | WO9708321 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferens: A Practical Approach, Clemens et al., eds, IRL Press, Washington, D.C. 1987, pp. 221-225; and Yang et al (1989) Blood 74, 1880-84. | inflammatory disorders, immunologic disorders, cancer |
| Human intracellular IL-1 receptor antagonist. | GeneSeq Accession W77158 | EP86-4585 | Interleukins are a group of multifunctional cytokines synthesized by lymphocytes, monocytes, and macrophages. Known functions include stimulating proliferation of immune cells (e.g., | Interleukin activity can be determined using assays known in the art: Matthews et al., in Lymphokines and Interferens: A Practical Approach, Clemens et al., eds, IRL Press, Washington, D.C. | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human interleukin-18 protein (IL-18) | GeneSeq Accession W77158 | EP864585 | T helper cells, B cells, eosinophils, and lymphocytes), chemotaxis of neutrophils and T lymphocytes, and/or inhibition of interferons. | 1987, pp. 221-225; and Orencole & Dinarello (1989) Cytokine 1, 14-20. | |
| Human interleukin-18 | GeneSeq Accession W77077 | EP861663 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and USHIO et al (1996) J. Immunol. 156, 4274-79. | inflammatory disorders, immunologic disorders, cancer |
| Human interleukin 18 derivatives | GeneSeq Accessions W77083, W77084, W77085, W77086, W77087, W77088, and W77089 | EP861663 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and USHIO et al (1996) J. Immunol. 156, 4274-79. | inflammatory disorders, immunologic disorders, cancer |
| Interleukin-9 (IL-9) mature protein (Thr117 version). | GeneSeq Accession W68158 | WO9827997 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yang et al (1989) Blood 74, 1880-84. | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| IL-9 mature protein variant (Met17 version) | GenSeq Accession W68157 | WO9827997 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yang et al (1989) Blood 74, 1880-84. | inflammatory disorders, immunologic disorders, cancer |
| Human IL-9 receptor protein variant #3. | GenSeq Accession W64058 | WO9824904 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yang et al (1989) Blood 74, 1880-84. | inflammatory disorders, immunologic disorders, cancer |
| Human IL-9 receptor protein variant fragment | GenSeq Accession W64060 | WO9824904 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yang et al (1989) Blood 74, 1880-84. | Soluble IL-9 receptor polypeptides may be useful for inhibiting interleukin activities. |
| Human IL-9 receptor protein variant #3. | GenSeq Accession W64061 | WO9824904 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yang et al (1989) Blood 74, 1880-84. | Soluble IL-9 receptor polypeptides may be useful for inhibiting interleukin activities. |
| Human Interleukin-12 p40 protein | GenSeq Accession W51311 | WO9817689 | Interleukins are a group of multifunctional cytokines synthesized by lymphocytes, monocytes, and macrophages. Known functions include stimulating proliferation of immune cells (e.g., | Interleukin activity can be determined using assays known in the art: Matthews et al., in Lymphokines and Interferons: A Practical Approach, Clemens et al., eds, IRL Press, Washington, D.C. | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human interleukin-12 p35 protein | GeneSeq Accession W51312 | WO9817689 | T helper cells, B cells, eosinophils, and lymphocytes), chemotaxis of neutrophils and T lymphocytes, and/or inhibition of interferons. | 1987, pp. 221-225; and Hori et al (1987), Blood 70, 1069-1078. | |
| Human protein with IL-16 activity | GeneSeq Accession W63753 | DE19649233- | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Hori et al (1987), Blood 70, 1069-1078. | inflammatory disorders, immunologic disorders, cancer |
| Human protein with IL-16 activity | GeneSeq Accession W59425 | DE19649233- | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Lim et al (1996) J. Immunol. 156, 2566-70. | inflammatory disorders, immunologic disorders, cancer |
| Human protein with IL-16 activity | GeneSeq Accession W53878 | U.S. Pat. No. 5,747,024 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Lim et al (1996) J. Immunol. 156, 2566-70. | inflammatory disorders, immunologic disorders, cancer |
| Human interleukin-15 | | | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Giri et al (1994) EMBO J. 13 2822-2830. | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human wild-type inter-leukin-4 (hIL-4) protein | GeneSeq Accession W52149 | WO9747744 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Siegel & Mostowski (1990) J Immunol Methods 132, 287-295. | inflammatory disorders, immunologic disorders, cancer |
| inter-leukin-4 muteins | GeneSeq Accessions W52150, W52151, W52153, W52154, W52155, W52156, W52157, W52158, W52159, W52160, W52161, W52162, W52163, W52164, W52165, W52166, and W52167 | WO9747744 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Siegel & Mostowski (1990) J Immunol Methods 132, 287-295. | inflammatory disorders, immunologic disorders, cancer |
| Human inter-leukin 1 delta | GeneSeq Accession Y28408 | WO9935268 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Orencole & Dinarello (1989) Cytokine 1, 14-20. | inflammatory disorders, immunologic disorders, cancer |
| Human inter-leukin-1 receptor antagonist beta | GeneSeq Accession Y24395 | WO9935268 | Interleukins are a group of multifunctional cytokines synthesized by lymphocytes, monocytes, and macrophages. Known functions include stimulating proliferation of immune cells (e.g., | Interleukin activity can be determined using assays known in the art: Matthews et al., in Lymphokines and Interferons: A Practical Approach, Clemens et al., eds, IRL Press, Washington, D.C. | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human EDIRF II protein sequence | GeneSeq Accession Y22199 | WO9932632 | T helper cells, B cells, eosinophils, and lymphocytes), chemotaxis of neutrophils and T lymphocytes, and/or inhibition of interferons. Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | 1987, pp. 221-225; and Orencole & Dinarello (1989) Cytokine 1, 14-20. Interleukin activity can be determined using assays known in the art: Matthews et al., in Lymphokines and Interferons: A Practical Approach, Clemens et al., eds, IRL Press, Washington, D.C. 1987, pp. 221-225. | inflammatory disorders, immunologic disorders, cancer |
| Human EDIRF I protein sequence | GeneSeq Accession Y22197 | WO9932632 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | inflammatory disorders, immunologic disorders, cancer |
| Human IL-1RD10 protein sequence | GeneSeq Accession Y14131 | WO9919480 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Orencole & Dinarello (1989) Cytokine 1, 14-20. | Soluble IL-1RD10 receptor polypeptides may be useful for inhibiting interleukin activities. |
| Human IL-1RD9 | GeneSeq Accession Y14122 | WO9919480 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons A Practical Approach, Clemens et al., eds, IRL Press, Washington, D.C. 1987, pp. 221-225; and Orencole & Dinarello (1989) Cytokine 1, 14-20. | Soluble IL-1RD10 receptor polypeptides may be useful for inhibiting interleukin activities. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human DNAX interleukin-40 | GeneSeq Accession Y09196 | WO9919491 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | inflammatory disorders, immunologic disorders, cancer |
| (DIL-40) alternative sequence | GeneSeq Accession Y09197 | WO9919491 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | inflammatory disorders, immunologic disorders, cancer |
| IL-11 | GeneSeq Accession R50176 | WO9405318 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Lu et al (1994) J immunol. Methods 173, 19. | inflammatory disorders, immunologic disorders, cancer |
| Human adipogenesis inhibitory factor | GeneSeq Accession R43260 | EP566410 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | inflammatory disorders, immunologic disorders, cancer |
| IL-11 | GeneSeq Accession W02202 | JP08127539 | Interleukins are a group of multifunctional cytokines synthesized by lymphocytes, monocytes, and macrophages. Known functions include stimulating proliferation of immune cells (e.g., | Interleukin activity can be determined using assays known in the art: Matthews et al., in Lymphokines and Interferons: A Practical Approach, Clemens et al., eds, IRL Press, Washington, D.C. | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | T helper cells, B cells, eosinophils, and lymphocytes), chemotaxis of neutrophils and T lymphocytes, and/or inhibition of interferons. | 1987, pp. 221-225; and Lu et al (1994) J immunol. Methods 173, 19. | |
| IL-14 | GeneSeq Accession R55800 | WO9416074 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Ambrus et al (1993) PNAS 90, 63330-34. | inflammatory disorders, immunologic disorders, cancer |
| IL-17 receptor | GeneSeq Accession B03807 | U.S. Pat. No. 6,072,033 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yao et al (1995) J. Immunol. 155, 5483-86. | Soluble IL-17 receptor polypeptides may be useful for inhibiting interleukin activities. |
| IL-17 | GeneSeq Accession R76573 | WO9518826 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yao et al (1995) J. Immunol. 155, 5483-86. | inflammatory disorders, immunologic disorders, cancer |
| CTLA-8 | GeneSeq Accession W13651 | WO9704097 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| IL-19 | GeneSeq Accession W37935 | WO9808870 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Gallagher et al (2000) Genes Immun. 1, 442-50. | inflammatory disorders, immunologic disorders, cancer |
| IL-21 (TIF) | GeneSeq Accession Y92879 | WO0024758 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Parrish-Novak et al (2000) Nature 408, 57-63. | inflammatory disorders, immunologic disorders, cancer |
| IL-8 receptor | GeneSeq Accession R33420 | WO9306229 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Holmes et al (1991) Science 253, 1278-80.. | Soluble IL-8 receptor polypeptides may be useful for inhibiting interleukin activities. |
| Human type II interleukin-1 receptor | GeneSeq Accession R85480 | U.S. Pat. No. 5,464,937 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Orencole & Dinarello (1989) Cytokine 1, 14-20. | Soluble type II interleukin-1 receptor polypeptides may be useful for inhibiting interleukin activities. |
| Human interleukin-12 receptor | GeneSeq Accession R69632 | EP638644 | Interleukins are a group of multifunctional cytokines synthesized by lymphocytes, monocytes, and macrophages. Known functions include stimulating proliferation of immune cells (e.g., | Interleukin activity can be determined using assays known in the art: Matthews et al., in Lymphokines and Interferons: A Practical Approach, Clemens et al., eds, IRL Press, Washington, D.C. | Soluble IL-12 receptor polypeptides may be useful for inhibiting interleukin activities. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | T helper cells, B cells, eosinophils, and lymphocytes), chemotaxis of neutrophils and T lymphocytes, and/or inhibition of interferons. | 1987, pp. 221-225; and Hori et al (1987), Blood 70, 1069-1078. | |
| Inter-leukin 8 receptor B | GeneSeq Accession R80758 | U.S. Pat. No. 5,440,021 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Holmes et al (1991) Science 253, 1278-80. | Soluble IL-8 receptor B polypeptides may be useful for inhibiting interleukin activities. |
| Human IL-8 receptor protein hIL8RA | GeneSeq Accession B09989 | JP08103276 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Holmes et al (1991) Science 253, 1278-80. | Soluble IL-8 receptor A polypeptides may be useful for inhibiting interleukin activities. |
| Human IL-8 receptor protein hIL8R | GeneSeq Accession B09990 | JP08103276 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Holmes et al (1991) Science 253, 1278-80. | Soluble IL-8 receptor polypeptides may be useful for inhibiting interleukin activities. |
| Inter-leukin-2 receptor associated protein p43 | GeneSeq Accession R97569 | WO9621732- | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Gillis et al (1978) J. Immunol. 120, 2027. | Soluble IL-2 receptor polypeptides may be useful for inhibiting interleukin activities. |
| Human inter- | GeneSeq Accession | WO9629408 | Interleukins are a group of multifunctional | Interleukin activity can be determined using assays known in | Soluble IL-17 receptor polypeptides may be useful for |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| leukin-17 receptor | W04185 | | cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | the art: Matthews et al., in Lymphokines and Interferons: A Practical Approach, Clemens et al., eds, IRL Press, Washington, D.C. 1987, pp. 221-225; and Yao et al (1995) J. Immunol. 155, 5483-86. | inhibiting interleukin activities. |
| Human interleukin-11 receptor | GeneSeq Accession R99090 | WO9619574 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Lu et al (1994) J immunol. Methods 173, 19. | Soluble IL-11 receptor polypeptides may be useful for inhibiting interleukin activities. |
| Human interleukin-1 receptor accessory protein | GeneSeq Accession W01911 | WO9623067 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Orencole & Dinarello (1989) Cytokine 1, 14-20. | Inflammatory disorders, immunologic disorders, cancer |
| AGF Protein | U.S. Pat. No. 5,488,032 | | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | Inflammatory disorders, immunologic disorders, cancer |
| Human interleukin-1 type-3 receptor | GeneSeq Accession R91064 | WO9607739 | Interleukins are a group of multifunctional cytokines synthesized by lymphocytes, monocytes, and macrophages. Known functions include stimulating proliferation of immune cells (e.g., T helper cells, B cells, eosinophils, | Interleukin activity can be determined using assays known in the art: Matthews et al., in Lymphokines and Interferons: A Practical Approach, Clemens et al., eds, IRL Press, Washington, D.C. 1987, pp. 221-225; and Orencole & | Soluble IL-type-3 receptor polypeptides may be useful for inhibiting interleukin activities |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | and lymphocytes), chemotaxis of neutrophils and T lymphocytes, and/or inhibition of interferons. | Dinarello (1989) Cytokine 1, 14-20. | |
| Human interleukin-13 beta receptor | GeneSeq Accession W24972 | WO9720926 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Bouteiler et al (1995) J. Immunol. Methods 181, 29. | Soluble IL-13 beta receptor polypeptides may be useful for inhibiting interleukin activities. |
| Human interleukin-13 alpha receptor | GeneSeq Accession W24973 | WO9720926 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Bouteiler et al (1995) J. Immunol. Methods 181, 29. | Soluble IL-13 alpha receptor polypeptides may be useful for inhibiting interleukin activities. |
| Human interleukin-4 receptor | GeneSeq Accession W13499 | U.S. Pat. No. 5,599,905 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Siegel & Mostowski (1990) J Immunol Methods 132, 287-295. | Soluble IL-4 receptor polypeptides may be useful for inhibiting interleukin activities. |
| Human interleukin-12 beta-2 receptor | GeneSeq Accession W12771 | EP759466 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Hori et al (1987), Blood 70, 1069-1078. | Soluble IL-12 beta-2 receptor polypeptides may be useful for inhibiting interleukin activities. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human interleukin-12 beta-1 receptor. | GeneSeq Accession W12772 | EP759466 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Hori et al (1987), Blood 70, 1069-1078. | Soluble IL-12 beta-1 receptor polypeptides may be useful for inhibiting interleukin activities. |
| Human IL-9 receptor protein | GeneSeq Accessions W64055, W64056, and W64057 | WO9824904 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yang et al (1989), Blood 74, 1880-84.. | Soluble IL-9 receptor polypeptides may be useful for inhibiting interleukin activities. |
| IL-10 receptor | GeneSeq Accession W41804 | U.S. Pat. No. 5,716,804 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Thompson-Snipes et al (1991) J. Exp. Med. 173, 507-510. | Soluble IL-10 receptor polypeptides may be useful for inhibiting interleukin activities. |
| Human IL-6 receptor | GeneSeq Accession Y30938 | JP11196867 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Aarden et al(1987) Eur. J. Immunol 17, 1411-16. | Soluble IL-6 receptor polypeptides may be useful for inhibiting interleukin activities. |
| Il-17 receptor | GeneSeq Accession Y97181 | U.S. Pat. No. 6,096,305 | Interleukins are a group of multifunctional cytokines synthesized by lymphocytes, monocytes, and macrophages. Known functions include stimulating proliferation of immune cells (e.g., | Interleukin activity can be determined using assays known in the art: Matthews et al., in Lymphokines and Interferons: A Practical Approach, Clemens et al., eds, IRL Press, Washington, D.C. | Soluble IL-17 receptor polypeptides may be useful for inhibiting interleukin activities. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| IL-17 receptor | GeneSeq Accession Y97131 | U.S. Pat. No. 6,100,235 | T helper cells, B cells, eosinophils, and lymphocytes), chemotaxis of neutrophils and T lymphocytes, and/or inhibition of interferons. | 1987, pp. 221-225; and Yao et al (1995) J. Immunol. 155, 5483-86. | Soluble IL-17 receptor polypeptides may be useful for inhibiting interleukin activities. |
| Human interleukin-3 receptor | GeneSeq Accession R25300 | EP509826 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Yao et al (1995) J. Immunol. 155, 5483-86. | Soluble IL-3 receptor polypeptides may be useful for inhibiting interleukin activities. |
| Human GM-CSF receptor | GeneSeq Accession R10919 | WO9102063 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Kitamura et al (1989) J Cell Physiol. 140 323-334. | Soluble GM-CSF receptor polypeptides may be useful for inhibiting interleukin activities. |
| Human IL-5 receptor alpha chain | GeneSeq Accession R25064 | EP492214 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | Soluble IL-5 receptor alpha polypeptides may be useful for inhibiting interleukin activities. |
| | | | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Kitamura et al (1989) J Cell Physiol. 140, 323-334. | |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| IL-5 receptor | GeneSeq Accession W82842 | WO9847923 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Kitamura et al (1989) J Cell Physiol. 140, 323-334. | Soluble IL-5 receptor polypeptides may be useful for inhibiting interleukin activities. |
| IL-6 receptor | GeneSeq Accession R37215 | JP05091892 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons A Practical Approach, Clemens et al., eds, IRL Press, Washington, D.C. 1987, pp. 221-225; and Aarden et al (1987) Eur. J. Immunol 17, 1411-16. | Soluble IL-6 receptor polypeptides may be useful for inhibiting interleukin activities. |
| Human B cell stimulating factor-2 receptor | GeneSeq Accession P90525 | AU8928720 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225. | Soluble B cell stimulating factor-2 receptor polypeptides may be useful for inhibiting interleukin activities. |
| IL-7 receptor clone | GeneSeq Accession R08330 | EP403114 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons. A Practical Approach, Clemens et al., eds, IRL Press, Washington, D.C. 1987, pp. 221-225; and Park et al (1990) J. Exp. Med. 171, 1073-79. | Soluble IL-7 receptor polypeptides may be useful for inhibiting interleukin activities. |
| EPO receptor; EPOR | GeneSeq Accession R06512 | WO9908822 | EPO Receptor is involved in the proliferation and differentiation of erythroblasts. | EPO Receptor activity can be determined using assays known in the art, such as, J Biol Chem 2001 Mar. 23; 276(12: 8995-9002; JAK2 protein tyrosine kinase activity: Blood 1994 Sep. 1; 84(5): 1501-7 | Inflammatory disorders, immunologic disorders, cancer, erythroblast proliferation and differentiation |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| IL-15 receptor | GeneSeq Accession R90843 | WO9530695 | Interleukins are a group of multifunctional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. | Interleukin activity can be determined using assays known in the art: Matthews et al., in Lymphokines and Interferons: A Practical Approach, Clemens et al., eds, IRL Press, Washington, D.C. 1987, pp. 221-225; and Giri et al (1994) EMBO J. 13 2822-2830. and Mol Cell Biol. 1994 Oct; 14(10: 6506-14. | Soluble IL-15 receptor polypeptides may be useful for inhibiting interleukin activities. |
| CD137; 4-1BB Receptor Protein | GeneSeq Accession R70977 | WO9507984 | Activities associated with apoptosis, NF-kB activation, and co-stimulation of immune cells such as T and B cells. | Apoptosis activity, NF-kB activation, and B and T cell co-stimulation can be determined using assays known in the art: Moore et al, 1999, Science, 285(5425): 260-3; Song H Y et al., 1997 Proc Natl Acad Sci USA 94(18): 9792-6; Epsevik and Nissen-Meyer, 1986, J. Immunol. Methods. | Soluble 4-1BB receptor polypeptides may be useful for inhibiting apoptosis, NF-kB activation, and/or co-stimulation of immune cells such as B and T cells. |
| BCMA | GeneSeq Accession Y71979 | WO0068378 | Activities associated with apoptosis, NF-kB activation, and co-stimulation of immune cells such as T and B cells. | Apoptosis activity, NF-kB activation, and B and T cell co-stimulation can be determined using assays known in the art: Moore et al, 1999, Science, 285(5425): 260-3; Song H Y et al., 1997 Proc Natl Acad Sci USA 94(18): 9792-6; Epsevik and Nissen-Meyer, 1986, J. Immunol. Methods. | Soluble BCMA receptor polypeptides may be useful for inhibiting apoptosis, NF-kB activation, and/or co-stimulation of immune cells such as B and T cells. |
| CD27 | GeneSeq Accession R20814 | WO9201049 | Activities associated with apoptosis, NF-kB activation, and co-stimulation of immune cells such as T and B cells. | Apoptosis activity, NF-kB activation, and B and T cell co-stimulation can be determined using assays known in the art: Moore et al, 1999, Science, 285(5425): 260-3; Song H Y et al., 1997 Proc Natl Acad Sci USA 94(18): 9792-6; Epsevik and Nissen-Meyer, 1986, J. Immunol. Methods. | Soluble CD27 polypeptides may be useful for inhibiting apoptosis, NF-kB activation, and/or co-stimulation of immune cells such as B and T cells. |
| CD30 | GeneSeq Accession R35478 | DE4200043 | Activities associated with apoptosis, NF-kB activation, and co-stimulation of immune cells such as T and B cells. | Apoptosis activity, NF-kB activation, and B and T cell co-stimulation can be determined using assays known in the art | Soluble CD30 polypeptides may be useful for inhibiting apoptosis, NF-kB activation, and/or co-stimulation of |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | | Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | immune cells such as B and T cells. |
| CD40 | GeneSeq Accession Y33499 | WO9945944 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science 285(5425): 260-3; Song HY et al., 1997 Proc Natl Acad Sci USA 94(18): 9792-6; Epsevik and Nissen-Meyer, 1986, J. Immunol. Methods. | Soluble CD40 polypeptides may be useful for inhibiting apoptosis, NF-kB activation, and/or co-stimulation of immune cells such as B and T cells. |
| EDAR | Genbank Accession AAD50077 | | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Immune Disorders, Lymphomas, X-linked hypohidrotic ectodermal dysplasia |
| OX40; ACT-4 | GeneSeq Accession R74737 | WO9512673 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Immune Disorders, Lymphomas, T cell disorders |
| TACI | GeneSeq Accession W75783 | WO9839361 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science. 285(5425): 260-3; Song HY et al., 1997 Proc Natl Acad Sci USA 94(18): 9792-6; Epsevik and Nissen-Meyer, 1986, J. Immunol. Methods. | Soluble TACI receptor polypeptides may be useful for inhibiting apoptosis, NF-kB activation, and/or co-stimulation of immune cells such as B and T cells. |
| TNF-R | GeneSeq Accession R10986 | AU9058976 | Activities associates with apoptosis, NF-kB activation, and co-stimulation of immune cells such as T and B cells. | Apoptosis activity, NF-kB activation, and B and T cell co-stimulation can be determined using | Soluble TNF-R receptor polypeptides may be useful for inhibiting apoptosis, NF-kB |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | | assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | activation, and/or co-stimulation of immune cells such as B and T cells. |
| TNF-RII; TNF p75 receptor; Death Receptor | GeneSeq Accession R11141 | EP418014 | Activities associated with apoptosis, NF-kB activation, and B and T cell co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18) 9792-6; Epsevik and Nissen-Meyer, 1986, J. Immunol. Methods. | Soluble TNFR-II receptor polypeptides may be useful for inhibiting apoptosis, NF-kB activation, and/or co-stimulation of immune cells such as B and T cells. |
| hAPO-4; TROY | GeneSeq Accession W93581 | WO9911791 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Immune Disorders, Cancers |
| TNF-alpha precursor | GeneSeq Accession P60074 | EP205038 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| Human TNF-alpha | GeneSeq Accession R62463 | EP619372 | Activities associated with apoptosis, NF-kB activation, and co-stimulation of immune cells such as T and B cells | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| Human TNF-alpha | GeneSeq Accession R42679 | EP563714 | Activities associated with apoptosis, NF-kB activation, and co-stimulation of immune cells such as T and B cells. | Apoptosis activity, NF-kB activation, and B and T cell co-stimulation can be determined using assays known in the art: Moore et | Inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human TNF-beta (LT-alpha) | GeneSeq Accession B37799 | WO0064479 | Activities associated with apoptosis, NF-kB activation, and co-stimulation of immune cells such as T and B cells. | al, 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| LT-alpha | GeneSeq Accession P70107 | EP250000 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| LT-beta | GeneSeq Accession R56869 | WO9413808 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18)9792-6; Epsevik and Nissen-Meyer, 1986, J. Immunol. Methods. | Inflammatory disorders, immunologic disorders, cancer |
| OPGL | GeneSeq Accession W83195 | WO9846751 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18)9792-6; Epsevik and Nissen-Meyer, 1986, J. Immunol. Methods. | Inflammatory disorders, immunologic disorders, cancer, loss of bone mass |
| FasL | GeneSeq Accession W98071 | WO9903999 | Activities associated with apoptosis, NF-kB activation, and co-stimulation of immune cells such as T and B cells. | Apoptosis activity, NF-kB activation, and B and T cell co-stimulation can be determined using assays known in the art: Moore, et al., 1999, Science, 285(5425): 260-3; | Inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| FasL | GeneSeq Accession W95041 | WO9903998 | Activities associated with apoptosis, NF-kB activation, and co-stimulation of immune cells such as T and B cells. | Song HY et al., 1997 Proc Natl Acad Sci USA 94(18)9792-6; Epsevik and Nissen-Meyer, 1986, J. Immunol. Methods. | Inflammatory disorders, immunologic disorders, cancer |
| CD27L | GeneSeq Accession R50121 | WO9405691 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| CD30 ligand | GeneSeq Accession R45007 | WO9324135 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| CD40L | GeneSeq Accession R85486 | WO9529935 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| 4-1BB ligand | GeneSeq Accession W26657 | U.S. Pat. No. 5,674,704 | Activities associated with apoptosis, NF-kB activation, and co-stimulation of immune cells such as T and B cells. | Apoptosis activity, NF-kB activation, and B and T cell co-stimulation can be determined using assays known in the art: Moore et al., 1999, Science, 285(5425): 260-3; Song HY et al, 1997 Proc Natl | Inflammatory disorders, immunologic disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| FAS Ligand Inhibitory Protein (DcR3) | GeneSeq Accession B19335 | WO0058465 | Activities associated with apoptosis, NF-kB activation, and co-stimulation of immune cells such as T and B cells. | Acad Sci USA 94(18): 9792-6; Epsevik and Nissen-Meyer, 1986, J. Immunol. Methods. Apoptosis activity, NF-kB activation, and B and T cell co-stimulation can be determined using assays known in the art: Moore et al., 1999, Science, 285(5425): 260-3; Song HY et al., 1997 Proc Natl Acad Sci USA 94(18): 9792-6; Epsevik and Nissen-Meyer, 1986, J. Immunol. Methods | Soluble DcR3 polypeptides may be useful for inhibiting apoptosis, NF-kB activation, and/or co-stimulation of immune cells such as B and T cells. |
| OX40L | GeneSeq Accession R79903 | WO9521915 | Activities associated with apoptosis, NF-kB activation, and co-stimulation of immune cells such as T and B cells. | Apoptosis activity, NF-kB activation, and B and T cell co-stimulation can be determined using assays known in the art: Moore et al, 1999, Science, 285(5425): 260-3; Song HY et al., 1997 Proc Natl Acad Sci USA 94(18): 9792-6; Epsevik and Nissen-Meyer, 1986, J. Immunol. Methods. | Inflammatory disorders, immunologic disorders, cancer |
| Protease inhibitor peptides | GeneSeq Accessions R12435, R12436, R12437, R12438, R12439, R12440, and R1244 | WO9106561 | Peptides that inhibit the function/binding of HIV | HIV protease activities are known in the art: HIV protease assays: EP087231. One can modify the assay to look for inhibition using any of the disclosed protease inhibitor polypeptides. | HIV, inflammatory disorders, immunologic disorders, cancer, viral infections |
| Retro viral protease inhibitors | GeneSeq Accessions R06660, R06661, R06662, R06663, R06664, R06665, R06666, R06667, R06668, R06669, R06670, R06671, R06672, | EP387231 | Peptides that inhibit the function/binding of HIV | HIV protease activities are known in the art: HIV protease assays: EP087231. One can modify the assay to look for inhibition using any of the disclosed protease inhibitor polypeptides. | HIV, inflammatory disorders, immunologic disorders, cancer, viral infections |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | R06673, R06674, R06675, and R06676 | | | | |
| HIV protease inhibiting peptides | GeneSeq Accessions R59293, R59294, R59295, R59296, R59297, R59298, R59299, R59300, R59301, R59302, R59301, R59302, R59303, R59304, R59305, R59306, R59307, R59308, R59309, R59310, R59311, R59312, R59313, R59314, R59315, R59316, R59317, R59318, R59319, R59320, R59321, R59322, R59323, R59324, R59325, R59326, R59327, R59328, R59329, | WO9301828 | Peptides that inhibit the function/binding of HIV | HIV protease activities are known in the art. HIV protease assays EP0387231. One can modify the assay to look for inhibition using any of the disclosed protease inhibitor polypeptides | HIV, inflammatory disorders, immunologic disorders, cancer, viral infections |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | R59330, R59331, R59332, R59333, R59334, R59335, R59336, R59337, R59338, R59339, R59340, R59341, R59342, R59343, R59344, R59345, R59346, R59347, R59348, R59349, and R59350 | | | | |
| HIV-1 protease inhibitors | GeneSeq Accessions R86326, R86327, R86328, R86329, R86330, R86331, R86332, R86333, R86334, R86335, R86336, R86337, R86338, R86339, R86340, R86341, R86342, R86343, R86344, R86345, R86346, R86347, | DE4412174 | Peptides that inhibit the function/binding of HIV | HIV protease activities are known in the art: HIV protease assays: EP0387231. One can modify the assay to look for inhibition using any of the disclosed protease inhibitor polypeptides | HIV, inflammatory disorders, immunologic disorders, cancer, viral infections |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | R86348, R86349, R86350, R86351, R86352, R86353, R86354, R86355, R86356, R86357, R86358, R86359, R86360, R86361, R86362, R86363, R86364, R86365, R86366, R86367, R86368, R86369, R86370, and R86371 | | | | |
| HIV Inhibitor Peptide | GeneSeq Accession Y89687 | WO9959615 | Peptides that inhibit the function/binding of HIV | HIV protease activities are known in the art: HIV protease assays: EP0387231. One can modify the assay to look for inhibition using any of the disclosed protease inhibitor polypeptides. | HIV, inflammatory disorders, immunologic disorders, cancer, viral infections |
| HIV Inhibitor Peptide | GenSeq Accession Y31955 | WO9948513 | Peptides that inhibit the function/binding of HIV | HIV Protease activities are known in the art; HIV protease assays: EP0387231. One can modify the assay to look for inhibition using any of the disclosed protease inhibitor polypeptides. | HIV, inflammatory disorders, immunologic disorders, cancer, viral infections |
| HIV Inhibitor Peptide | www.sciencex press.org; Published online 12 Jan. 2001; 10.1126/scienc e.1057453 | | Peptides that inhibit the function/binding of HIV | HIV protease activities are known in the art: HIV protease assays: EP0387231. One can modify the assay to look for inhibition using any of the disclosed protease inhibitor polypeptides. | HIV, inflammatory disorders, immunologic disorders, cancer, viral infections |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human monocyte chemo attractant factor hMCP-3 | GeneSeq Accession R73915 | WO9509232 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Immune disorders, particularly useful for treating bacterial and/or viral menigitis |
| Human monocyte chemo-attractant factor hMCP-1 | GeneSeq Accession R73914 | WO9509232 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Immune disorders, particularly useful for treating bacterial and/or viral menigitis |
| Human gro-beta chemo-kine | GeneSeq Accessions R66699 and W17671 | WO9429341 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Immune disorders, inflammatory disorders, blood-related disorders, stem cell transplantation, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human gro-gamma chemokine | GeneSeq Accessions R66700 and W17672 | WO9429341 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Immune disorders, inflammatory disorders, blood-related disorders, stem cell transplantation, cancer |
| Human gro-alpha chemokine | GeneSeq Accessions R66698 and W18024 | WO9429341 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Immune disorders, inflammatory disorders, blood-related disorders, stem cell transplantation, cancer |
| Human eosinophil-expressed chemokine (EEC) | GeneSeq Accession W05186 | WO9963481 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Immune disorders, particularly treatment of eosinophilia, inflammation, allergies, asthma, leukaemia and lymphoma |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Chemo-kine-like protein PF4-414 Full-Length and Mature | GeneSeq Accessions R92318 and R99809 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Cancer and blood-related disorders, particularly myelosuppression |
| Chemo-kine-like protein IL-8M3 | GeneSeq Accession R99812 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ; and Holmes et al (1991) Science 253, 1278-80. | Cancer and blood-related disorders, particularly myelosuppression |
| Human inter-leukin-8 (IL-8) | GeneSeq Accession R99814 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ; and Holmes et al (1991) Science 253, 1278-80. | Cancer and blood-related disorders, particularly myelosuppression |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Chemo-kine-like protein IL-8M1 Full-Length and Mature | GeneSeq Accessions R99815 and R99803 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ; and Holmes et al (1991) Science 253, 1278-80. | Cancer and blood-related disorders, particularly myelosuppression |
| Chemo-kine-like protein IL - 8M8 Full-Length and Mature | GeneSeq Accessions R99816 and R99805 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ; and Holmes et al (1991) Science 253, 1278-80. | Cancer and blood-related disorders, particularly myelosuppression. |
| Chemo-kine-like protein IL - 8M8 Full-Length and Mature | GeneSeq Accessions R99817 and R99806 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ; and Holmes et al (1991) Science 253, 1278-80. | Cancer and blood-related disorders, particularly myelosuppression. |

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Chemo-kine-like protein IL - 8M8 Full-Length and Mature | GeneSeq Accessions R99818 and R99804 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. Humana Press Inc., Totowa, NJ; and Holmes et al (1991) Science 253, 1278-80. | Cancer and blood-related disorders, particularly myelosuppression. |
| Chemo-kine-like protein IL - 8M8 Full-Length and Mature | GeneSeq Accessions R99819 and R99807 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. Humana Press Inc, Totowa, NJ | Cancer and blood-related disorders, particularly myelosuppression. |
| Chemo-kine-like protein IL - 8M8 Full-Length and Mature | GeneSeq Accessions R99822 and R9807 | WO9613587 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. Humana Press Inc, Totowa, NJ | Cancer and blood-related disorders, particularly myelosuppression. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human foetal spleen expressed chemokine, FSEC | GeneSeq Accession R98499 | WO9622374 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. Humana Press Inc, Totowa, NJ | Immune disorders |
| Liver expressed chemokine-1 (LVEC-1) | GeneSeq Accession R95689 | WO9616979 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. Humana Press Inc, Totowa, NJ | Inflammation of the liver |
| Liver expressed chemokine-2 (LVEC-2) | GeneSeq Accession R95690 | WO9616979 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. Humana Press Inc, Totowa, NJ | Inflammation of the liver |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Pituitary expressed chemokine (PGEC) | GeneSeq Accession R95691 | WO9616979 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. Humana Press Inc, Totowa, NJ | Inflammation, particularly of the liver |
| Adenoid-expressed chemokine (ADEC) | GeneSeq Accession R97664 | WO9617868 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power. Humana Press Inc, Totowa, NJ | Inflammation, angiogenesis, tumorigenesis, musculoskeletal disorders |
| Human chemokine CC-2 | GeneSeq Accession W38170 | WO9741230 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138; Chemokine protocols. Edited by: A. E. I Proudfoot, T. N. C. Wells, and C. A. Power. Humana Press Inc. Totowa, NJ | Immune disorders, cell migration, proliferation, and differentiation disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human chemokine HCC-1 | GeneSeq Accession W38171 | WO9741230 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in molecular Biology 2000, vol. 138: Chemokine Protocols. Edited by A. E. I. Proudfoot, T. N. C. Wells and C. A. Power Humana Press Inc, Totowa, NJ | Immune disorders, cell migration, proliferation, and differentiation disorders |
| Human chemokine CC-3 | GeneSeq Accession W38172 | WO9741230 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in molecular Biology, 2000, vol. 138: Chemokine Protocols. Edited by A. E. I. Proudfoot, T. N. C. Wells, and C. A. Power Humana Press Inc, Totowa, NJ | Immune disorders, cell migration, proliferation and differentiation disorders |
| Novel beta-chemokine designated PTEC | GeneSeq Accession W27271 | WO9739126 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in molecular Biology, 2000, vol. 138: Chemokine Protocols. Edited by A. E. I. Proudfoot, T. N. C. Wells, and C. A. Power Humana Press Inc, Totowa, NJ | Immune disorders, vascular disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human CX3C 111 amino acid chemokine | GeneSeq Accession W23344 | WO9727299 | Chemokines are a family of related small, secreted proteins involved in biological processes ranging from hematopoiesis, anglogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in molecular Biology, 2000, vol. 138: Chemokine Protocols. Edited by A. E. I. Proudfoot, T. N. C. Wells, and C. A. Power Humana Press Inc., Totowa, NJ | Immune disorders, inflammatory diseases, abnormal proliferation, regeneration, degeneration, and atrophy |
| Human CCF18 chemokine | GeneSeq Accession W25942 | WO9721812 | Chemokines are a family of related small, secreted proteins involved in biological processes ranging from hematopoiesis, anglogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in molecular Biology, 2000, vol. 138: Chemokine Protocols. Edited by A. E. I. Proudfoot, T. N. C. Wells, and C. A. Power Humana Press Inc, Totowa, NJ | Abnormal physiology and development disorders, can also be used as an anti-viral agent |
| Human beta-chemokine H1305 (MCP-2) | GeneSeq Accession W26655 | WO9725427 | Chemokines are a family of related small, secreted proteins involved in biological processes ranging from hematopoiesis, anglogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in molecular Biology, 2000, vol. 138: Chemokine Protocols. Edited by A. E. I. Proudfoot, T. N. C. Wells, and C. A. Power Humana Press Inc., Totowa, NJ | Chemotaxis, blood-related disorders, viral infection, HIV, wound healing, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human eosinocyte CC type chemokine eotaxin | GeneSeq Accession W14990 | WO9712914 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in molecular Biology, 2000, vol. 138: Chemokine Protocols. Edited by A. E. I. Proudfoot, T. N. C. Wells, and C. A. Power Humana Press Inc., Totowa, NJ | Inflammatory and immune disorders |
| Human thymus and activation regulated cytokine (TARC) | GeneSeq Accession W14018 | WO9711969 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in molecular Biology, 2000, vol. 138: Chemokine Protocols. Edited by A. E. I. Proudfoot, T. N. C. Wells, and C. A. Power Humana Press Inc., Totowa, NJ | Inflammatory and immune disorders |
| Human chemokine beta-8 short forms | GeneSeq Accession W16315 | WO9712041 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in molecular Biology, 2000, vol. 138: Chemokine Protocols. Edited by A. E. I. Proudfoot, T. N. C. Wells, and C. A. Power Humana Press Inc., Totowa, NJ | Cancer, wound healing, immune disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Macrophage derived chemokine, MDC | GeneSeq Accession W20058 | WO9640923 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power Humana Press Inc, Totowa, NJ | Inflammatory diseases, wound healin, angiogenesis |
| Human chemokine ZSIG-35 | GeneSeq Accession W30565 | WO9844117 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power Humana Press Inc, Totowa, NJ | Inflammatory and immune diseases |
| Primate CC chemokine "ILINCK" | GeneSeq Accesssion W69990 | WO9832658 | Chemokines are a family of related small, secreted proteins involved in biological processes ranging from hematopoiesis, angiogenesis, and leukocyte trafficking. | Chemokine activities can be determined using assays known in the art: Methods in Molecular Biology, 2000, vol. 138: Chemokine Protocols. Edited by: A. E. I. Proudfoot, T. N. C. Wells, and C. A. Power Humana Press Inc., Totowa, NJ | Immune and inflammatory disorders, abnormal proliferation, regeneration, generation and atrophy disorders |
| Primate CXC chemokine "IBICK" | GeneSeq Accession W69989 | WO9832858 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue | Chemokine activities can be determined using assays known in the art: Methods in Molecular Biology, 2000, vol. 138: Chemokine Protocols. Editd by. A. E. I. Proudfoot, T. N. C. Wells, and C. A. Power. Humana Press Inc, Totowa, NJ | Immune and inflammatory disorders, abnormal proliferation, regeneration, generation and atrophy disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human CC-type chemokine protein designated SLC (secondary lymphoid chemokine) | GeneSeq Accession W69163 | WO9831809 | rejection, viral infection, and tumor biology. The chemokines exert their effects by acting on a family of seven transmembrane G-protein coupled receptors. Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Immune, inflammatory, and infectious disorders, cancer |
| Human CC chemokine ELC protein | GeneSeq Accession W62542 | WO9826071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Cancer and infectious diseases, particularly herpes virus |
| Human DVic-1 C-C chemokine | GeneSeq Accession W60649 | WO9823750 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Abnormal proliferation, regeneration, degeneration, and atrophy disorders, including cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | biology. The chemokines exert their effects by acting on a family of seven transmembrane G-protein coupled receptors. Over 40 human chemokines have been described, which bind to ~17 receptors thus far identified. | | |
| Human C-C chemokine DGWCC | GeneSeq Accession W60650 | WO9823750 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Immune disorders, cell proliferation disorders, cancer |
| Human STCP-1 | GeneSeq Accession W62783 | WO9824907 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Immune disorders, particularly T cell related disorders, viral infection, and inflammation, especially joint |
| Exodua protein | GeneSeq Accession W61279 | WO9821330 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their | Chemokine activities can be determined using assays known in the art: Methods in Molecular Biology, 2000, vol.138: Chemokine Protocols. Edited by. A. E. I. Proudfoot, T. N. C. Wells. and C. A. Power. Humana Press Inc, Totowa, NJ | Immune and inflammatory disorders, angiogenesis, cancer, and proliferation disorders, particularly myeloproliferative diseases |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human Chemokine protein | GeneSeq Acession W50887 | WO9814581 | effects by acting on a family of seven transmembrane G-protein coupled receptors. Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Cancer and degenerative disorders |
| Human T cell mixed lymphocyte reaction expressed chemokine (TMEC) | GeneSeq Acession W58703 | U.S. Pat. No. 5,780,268 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Meltods of Molecular Biology, 2000, vol. 138: Chemokine Protocols. Edited by: A. E. I. Proudfoot, T. N. C. Wells, and C. A. Power Humana Press Inc, Totowa, NJ | Immune, inflammatory, and infectious disorders, cancer |
| Human 6CKine protein | GeneSeq Acession W50885 | WO9814581 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven | Chemokine activities can be determined using assays known in the art: Meltods of Molecular Biology, 2000, vol. 138: Chemokine Protocols. Edited by: A. E. I. Proudfoot, T. N. C. Wells, and C. A. Power Humana Press Inc., Totowa, NJ | Cancer and degenerative disorders |

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| human liver and activation regulated chemokine (LARC) | GeneSeq Accession W57475 | WO9817800 | transmembrane G-protein coupled receptors. Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power Humana Press Inc, Totowa, NJ | Immune, inflammatory, and infectious disorders, cancer |
| RANTES peptide | GeneSeq Accession W29538 | WO9744462 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power Humana Press Inc, Totowa, NJ | Infectious diseases, particularly HIV |
| RANTES 8-68 | GeneSeq Accession W29529 | WO9744462 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power Humana Press Inc, Totowa, NJ | Infectious diseases, particularly HIV |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| RANTES 9-68 | GeneSeq Accession W29528 | WO9744462 | Over 40 human chemokines have been described, which bind to ~17 receptors thus far identified. | | Infectious diseases, particularly HIV |
| Human chemokine protein 331D5 | GeneSeq Accession W59433 | WO9811226 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power Humana Press Inc., Totowa, NJ | Abnormal proliferation, regeneration, degeneration or atrophy, including cancer |
| Human chemokine protein 61164 | GeneSeq Accession W59430 | WO9811226 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Mehtods of Molecular Biology, 2000, vol. 138: Chemokine Protocols. Edited by: A. E. I. Proudfoot, T. N. C. Wells, and C. A. Power Humana Press Inc., Totowa, NJ | Abnormal proliferation, regeneration, degeneration or atrophy, including cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Chemokine MCP-4 | GeneSeq Accession W56690 | WO9809171 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods of Molecular Biology, 2000, vol. 138: Chemokine Protocols. Edited by: A. E. I. Proudfoot, T. N. C. Wells, and C. A. Power Humana Press Inc., Totowa, NJ | Immune, Inflammatory, and infectious diseases |
| Human stromal cell-derived chemokine, SDF-1 | GeneSeq Accession W50766 | FR2751658 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | HIV infections |
| Thymus expressed chemokine (TECK) | GeneSeq Accession W44397 | WO9801557 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc., Totowa, NJ | Immune and inflammatory disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human chemokine MIP-3 alpha | GeneSeq Accession W44398 | WO9801557 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Immune and inflammatory disorders |
| Human chemokine MIP-3beta | GeneSeq Accession W44399 | WO9801557 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Immune and inflammatory disorders |
| Human monocyte chemotactic proprotein (MCPP) sequence | GeneSeq Accession W42072 | WO9802459 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Immune disorders, respiratory disorders, cancer |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Macrophage-derived chemokine (MDC) | GeneSeq Accessions W40811 and Y24414 | U.S. Pat. No. 5,688,927/ U.S. Pat. No. 5,932,703 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Immune, and inflammatory disorders, cancer |
| Macrophage derived chemokine analogue MDC-eyfy | GeneSeq Accession Y24416 | U.S. Pat. No. 5,932,703 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Immune and inflammatory disorders |
| Macrophage derived chemokine analogue MDC (n+1) | GeneSeq Accession Y24413 | U.S. Pat. No. 5,932,703 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Immune and inflammatory disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Macrophage derived chemokine analogue MDC-yl | GeneSeq Accession Y24415 | U.S. Pat. No. 5,932,703 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Immune and inflammatory disorders |
| Human type CC chemokine eotaxin 3 protein sequence | GeneSeq Accession Y43178 | JP11243

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human IP-10 and human Muc-1 core epitope (VNT) fusion protein | GeneSeq Accession Y29894 | WO9946392 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Tim-1 protein | GeneSeq Accession Y28290 | WO9933990 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Inflammation due to stimuli such as heart attacks and stroke, infection, physical trauma, UV or ionizing radiation, burns, frostbite or corrosive chemicals |
| Human Lkn-1 Full-Length and Mature protein | GeneSeq Accessions Y17280, Y17274, Y17281, and Y17275 | WO9928473 and WO9928472 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | HIV infection and cancer, particularly leukemia |
| N-terminal modified chemokine met-hSDF-1 alpha | GeneSeq Accession Y05818 | WO9920759 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Inhibit or stimulate angiogenesis, inhibit the binding of HIV |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| N-terminal modified chemokine met-hSDF-1beta | GeneSeq Accession Y05819 | WO9920759 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: chemokine Protocols. Edited by: A. E. I. Proudfoot, T. N. C. Wells, and C. A. Power. Humana Press Inc., Totowa, NJ | Inhibit or stimulate angiogenesis, inhibit the binding of HIV, antiinflammatory; immunosuppressant |
| N-terminal modified chemokine GroHEK/hSDF-1alpha | GeneSeq Accession Y05820 | WO9920759 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Inhibit or stimulate angiogenesis, inhibit the binding of HIV, antiinflammatory; immunosuppressant |
| N-terminal modified chemokine GroHEK/hSDF-1beta. | GeneSeq Accession Y05821 | WO9920759 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Inhibit or stimulate angiogenesis, inhibit the binding of HIV, antiinflammatory; immunosuppressant |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Chemokine Eotaxin | GeneSeq Accession Y14230 | WO9912968 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power. Humana Press Inc, Totowa, NJ | Increase or enhance an inflammatory response, an immune response orhaematopoietic cell-associated activity; treat a vascular indication; Cancer; enhance wound healing, to prevent or treat asthma, organ transplant rejection, rheumatoid arthritis or allergy |
| Chemokine hMCP1a | GeneSeq Accession Y14225 | WO9912968 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power. Humana Press Inc, Totowa, NJ | Immune disorders, Vascular disorders, Wound healing, cancer, prevent organ transplant rejection, Increase or enhance an inflammatory response, |
| Chemokine hMCP1b | GeneSeq Accession Y14226 | WO9912968 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power. Humana Press Inc, Totowa, NJ | Immune disorders, Vascular disorders, Wound healing, cancer, prevent organ transplant rejection, Increase or enhance an inflammatory response, |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Chemokine hSDF1b | GeneSeq Accession Y14228 | WO9912968 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power, Humana Press Inc, Totowa, NJ | Immune disorders, Vascular disorders, Wound healing, cancer, prevent organ transplant rejection, Increase or enhance an inflammatory response, |
| Chemokine hIL-8 | GeneSeq Accession Y14229 | WO9912968 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power, Humana Press Inc., Totowa, NJ; and Holmes et al (1991) Science 253, 1278-80. | Immune disorders, Vascular disorders, Wound healing, cancer, prevent organ transplant rejection, Increase or enhance an inflammatory response, |
| Chemokine hMCP1 | GeneSeq Accession Y14222 | WO9912968 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power, Humana Press Inc., Totowa, NJ | Immune disorders, Vascular disorders, Wound healing, cancer, prevent organ transplant rejection, Increase or enhance an inflammatory response, |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | Over 40 human chemokines have been described, which bind to ~17 receptors thus far identified. | | |
| Chemokine hMCP2 | GeneSeq Accession Y14223 | WO9912968 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power, Humana Press Inc., Totowa, NJ | Immune disorders, Vascular disorders, Wound healing, cancer, prevent organ transplant rejection, Increase or enhance an inflammatory response, |
| Chemokine hMCP3 | GeneSeq Accession Y14224 | WO9912968 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power, Humana Press Inc., Totowa, NJ | Immune disorders, Vascular disorders, Wound healing, cancer, prevent organ transplant rejection, Increase or enhance an inflammatory response, |
| C-C chemokine, MCP2 | GeneSeq Accession Y05300 | EP905240 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viralk infection, and tumor biology. The chemokines exert their effects by acting on a family of seven transmembrane G-protein-coupled receptors. Over 40 human chemokines have | Chemokine activities can be determined using assays known in the art: Methods in Molecular Bilogy, 2000, vol. 138: Chemokine Protocols. Edited by: A. E. I. Proudfoot, T. N. C. Wells, and C. A. Power, Humana Press Inc., Totowa, NJ | Inflammatory, Immune and infectious diseases; pulmonary diseases and skin disorders; tumours, and angiogenesis-and haematopoiesis-related diseases |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | been described, which bind to ~17 receptors thus far identified. | | |
| Wild type monocyte chemotactic protein 2 | GeneSeq Accession Y07233 | EP906954 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, virakl infection, and tumor biology. The chemokines exert their effects by acting on a family of seven transmembrane G-protein-coupled receptors. Over 40 human chemokines have been described, which bind to ~17 receptors thus far identified. | Chemokine activities can be determined using assays known in the art: Methods in Molecular Bilogy, 2000, vol. 138: Chemokine Protocols. Edited by: A. E. I. Proudfoot, T. N. C. Wells, and C. A. Power, Humana Press Inc, Totowa, NJ | Inflammatory, Immune and infectious diseases; pulmonary diseases and skin disorders; tumours, and angiogenesis- and haematopoiesis-related diseases |
| Truncated monocyte chemotactic protein 2 (6-76) | GeneSeq Accession Y07234 | EP906954 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc, Totowa, NJ | Inflammatory, immune and infectious diseases; pulmonary diseases and skin disorders; tumours, and angiogenesis-and haematopoiesis-related diseases |
| Truncated RANTES protein (3-68) | GeneSeq Accessions Y07236 and Y07232 | EP905241; EP906954 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc, Totowa, NJ | Inflammatory, immune and infectious diseases; pulmonary diseases and skin disorders; tumours, and angiogenesis-and haematopoiesis-related diseases |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | Over 40 human chemokines have been described, which bind to ~17 receptors thus far identified. | | |
| Wild type monocyte chemotactic protein 2 | GeneSeq Accession Y07237 | EP905241 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc., Totowa, NJ | Inflammatory, immune and infectious diseases; pulmonry diseases and skin disorders; tumours, and angiogenesis-and haematopoiesis-related diseases |
| Truncated monocyte chemotactic protein 2 (6-76) | GeneSeq Accession Y07238 | EP905241 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc., Totowa, NJ | Inflammatory, immune and infectious diseases; pulmonry diseases and skin disorders; tumours, and angiogenesis-and haematopoiesis-related diseases |
| A partial CXCR4B protein | GeneSeq Accession W97363 | EP897980 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc., Totowa, NJ | Soluble CXCR4B receptor polypeptides may be useful for inhibiting chemokine activities and viral infection. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | Over 40 human chemokines have been described, which bind to ~17 receptors thus far identified. | | |
| Interferon gamma-inducible protein (IP-10) | GeneSeq Accession W96709 | U.S. Pat. No. 5,871,723 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc, Totowa, NJ | Angiogenesis, Cancer, Inflammatory and Immune disorders, Cardio-Vascular disorders, Musco-skeletal disorders |
| A mono-kine induced by gamma-interferon (MIG) | GeneSeq Accession W96710 | U.S. Pat. No. 5,871,723 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc, Totowa, NJ | Angiogenesis, Cancer, Inflammatory and Immune disorders, Cardio-Vascular disorders, Musco-skeletal disorders |
| Inter-leukin-8 (IL-8) protein. | GeneSeq Accession W96711 | U.S. Pat. No. 5,871,723 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc., Totowa, NJ; and Holmes et al (1991) Science 253, 1278-80. | Angiogenesis, Cancer, Inflammatory and Immune disorders, Cardio-Vascular disorders, Musco-skeletal disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Epithelial neutrophil activating protein-78 (ENA-78) | GeneSeq Accession W96712 | U.S. Pat. No. 5,871,723 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc., Totowa, NJ | Angiogenesis, Cancer, Inflammatory and Immune disorders, Cardio-Vascular disorders, Musco-skeletal disorders |
| Growth related oncogene-alpha (GRO-alpha). | GeneSeq Accession W96713 | U.S. Pat. No. 5,871,723 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokines activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc., Totowa, NJ | Angiogenesis, Cancer, Inflammatory and Immune disorders, Cardio-Vascular disorders, Musco-skeletal disorders |
| Growth related oncogene-beta (GRO-beta). | GeneSeq Accession W96714 | U.S. Pat. No. 5,871,723 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc., Totowa, NJ | Angiogenesis, Cancer, Inflammatory and Immune disorders, Cardio-Vascular disorders, Musco-skeletal disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | Over 40 human chemokines have been described, which bind to ~17 receptors thus far identified. | | |
| Growth related oncogene-gamma (GRO-gamma) | GeneSeq Accession W96715 | U.S. Pat. No. 5,871,723 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc, Totowa, NJ | Angiogenesis, Cancer, Inflammatory and Immune disorders, Cardio-Vascular disorders, Musco-skeletal disorders |
| A platelet basic protein (PBP) | GeneSeq Accession W96716 | U.S. Pat. No. 5,871,723 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc, Totowa, NJ | Angiogenesis, Cancer, Inflammatory and Immune disorders, Cardio-Vascular disorders, Musco-skeletal disorders |
| Connective tissue activating protein-III (CTAP-III) | GeneSeq Accession S96717 | U.S. Pat. No. 5,871,723 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc, Totowa, NJ | Angiogenesis, Cancer, Inflammatory and Immune disorders, Cardio-Vascular disorders, Musco-skeletal disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Beta-thromboglobulin protein (beta-TG) | GeneSeq Accession W96718 | U.S. Pat. No. 5,871,723 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc., Totowa, NJ | Angiogenesis, Cancer, Inflammatory and Immune disorders, Cardio-Vascular disorders, Musco-skeletal disorders |
| Neutrophil activating peptide-2 (NAP-2) | GeneSeq Accession W96719 | U.S. Pat. No. 5,871,723 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc., Totowa, NJ | Angiogenesis, Cancer, Inflammatory and Immune disorders, Cardio-Vascular disorders, Musco-skeletal disorders |
| Granulocyte chemotactic protein-2 (GCP-2) | GeneSeq Accession W96720 | U.S. Pat. No. 5,871,723 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc., Totowa, NJ | Angiogenesis, Cancer, Inflammatory and Immune disorders, Cardio-Vascular disorders, Musco-skeletal disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human chemokine MIG-beta protein | GeneSeq Accession W90124 | EP887409 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | | Immune disorders, viral, parasitic, fungal or bacterial infections, Cancer; autoimmune diseases or transplant rejection |
| Human ZCHEMO-8 | GeneSeq Accession W82716 | WO9854326 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc, Totowa, NJ | Immune disorders, cancer, myelopoietic disorders, autoimmune disorders and immunodeficiencies, Inflammatory and infectious diseases, Vascular disorders, wound healing |
| Human Act-2 protein | GeneSeq Accession W82717 | WO9854326 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power, Humana Press Inc, Totowa, NJ | Immune disorders, cancer, myelopoietic disorders, autoimmune disorders and immunodeficiencies, Inflammatory and infectious diseases, Vascular disorders, wound healing |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | Over 40 human chemokines have been described, which bind to ~17 receptors thus far identified. | | |
| Human SISD protein | GeneSeq Acession W82720 | WO9854326 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Immune disorders, cancer, myelopoietic disorders, autoimmune disorders and immunodeficiencies, Inflammatory and infectious diseases, Vascular disorders, wound healing |
| Human M110 protein | GeneSeq Acession W82721 | WO9854326 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods of Molecular Biology, 2000, vol. 138: Chemokine Protocols. Edited by: A. E. I. Proudfoot, T. N. C. Wells, and C. A. Power Humana Press Inc, Totowa, NJ | Immune disorders, cancer, myelopoietic disorders, autoimmune disorders and immunodeficiencies, Inflammatory and infectious diseases, Vascular disorders, wound healing |
| Human M11A protein | GeneSeq Acession W82722 | WO9854326 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods of Molecular Biology, 2000, vol. 138: Chemokine Protocols. Edited by: A. E. I. Proudfoot, T. N. C. Wells, and C. A. Power Humana Press Inc, Totowa, NJ | Immune disorders, cancer, myelopoietic disorders, autoimmune disorders and immunodeficiencies, Inflammatory and infectious diseases, Vascular disorders, wound healing |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human CCC3 protein | GeneSeq Accession W82723 | WO9854326 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Meltods of Molecular Biology, 2000, vol. 138: Chemokine Protocols. Edited by: A. E. I. Proudfoot, T. N. C. Wells, and C. A. Power Humana Press Inc., Totowa, NJ | Immune disorders, cancer, myelopoietic disorders, autoimmune disorders and immunodeficiencies, Inflammatory and infectious diseases, Vascular disorders, wound healing |
| A human L105 chemokine designated huL105_3. | GeneSeq Accession W87588 | WO9856818 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Meltods of Molecular Biology, 2000, vol. 138: Chemokine Protocols. Edited by: A. E. I. Proudfoot, T. N. C. Wells, and C. A. Power Humana Press Inc., Totowa, NJ | Cancer, wound healing |
| A human L105 chemokine designated huL105_7. | GeneSeq Accession W87589 | WO9856818 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Meltods of Molecular Biology, 2000, vol. 138: Chemokine Protocols. Edited by: A. E. I. Proudfoot, T. N. C. Wells, and C. A. Power Humana Press Inc., Totowa, NJ | Cancer, wound healing |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human mature gro-alpha polypeptide used to treat sepsis | GeneSeq Accession W81498 | WO9848828 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Meltods of Molecular Biology, 2000, vol. 138: Chemokine Protocols. Edited by: A. E. I. Proudfoot, T. N. C. Wells, and C. A. Power Humana Press Inc, Totowa, NJ | Infectious diseases, sepsis |
| Human mature gro-gamma polypeptide used to treat sepsis | GeneSeq Accession W81500 | WO9848828 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Meltods of Molecular Biology, 2000, vol. 138: Chemokine Protocols. Edited by: A. E. I. Proudfoot, T. N. C. Wells, and C. A. Power Humana Press Inc, Totowa, NJ | Infectious diseases, sepsis |
| Human thymus expressed chemokine TECK and TECK variant | GeneSeq Accessions B19607 and B19608 | WO0053635 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Meltods of Molecular Biology, 2000, vol. 138: Chemokine Protocols. Edited by: A. E. I. Proudfoot, T. N. C. Wells, and C. A. Power Humana Press Inc, Totowa, NJ | Inflammatory disorders, cancer, Immune and vascular disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human chemokine SDF1alpha | GeneSeq Accession B15791 | WO0042071 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods of Molecular Biology, 2000, vol. 138: Chemokine Protocols. Edited by: A. E. I. Proudfoot, T. N. C. Wells, and C. A. Power Humana Press Inc., Totowa, NJ | Autoimmune disorders, Immune, Vascular and Inflammatory disorders |
| Human chemokine GROalpha | GeneSeq Accession B15793 | WO0042071 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Autoimmune disorders, Immune, Vascular and Inflammatory diorders |
| Human chemokine eotaxin | GeneSeq Accession B15794 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot; T. N. C. Wells, and C. A. Power. Humana Press Inc., Totowa, NJ | Autoimmune disorders, Immune, Vascular and Inflammatory disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human chemokine MIG | GeneSeq Accession B15803 | WO0042071 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C.A Power. Humana Press Inc, Totowa, NJ | Autoimmune disorders, Immune, Vascular and Inflammatory disorders |
| Human chemokine PF4 | GeneSeq Accession B15804 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot; T. N. C. Wells, and C. A. Power, Humana Press Inc, Totowa, NJ | Autoimmune disorders, Immune, Vascular and Inflammatory disorders |
| Human chemokine I-309 | GeneSeq Accession B15805 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot; T. N. C. Wells, and C. A. Power, Humana Press Inc, Totowa, NJ | Autoimmune disorders, Immune, Vascular and Inflammatory disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human chemokine HCC-1 | GeneSeq Accession B15806 | WO0042071 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot; T. N. C. Wells, and C. A. Power. Humana Press Inc., Totowa, NJ | Autoimmune disorders, Immune, Vascular and Inflammatory disorders |
| Human chemokine C10 | GeneSeq Accession B15807 | WO0042071 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot; T. N. C. Wells, and C. A. Power. Humana Press Inc., Totowa, NJ | Autoimmune disorders, Immune, Vascular and Inflammatory disorders |
| Human chemokine CCR-2 | GeneSeq Accession B15808 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot; T. N. C. Wells, and C. A. Power. Humana Press Inc., Totowa, NJ | Autoimmune disorders, Immune, Vascular and Inflammatory disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human chemokine ENA-78 | GeneSeq Accession B15809 | WO0042071 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot; T. N. C. Wells, and C. A. Power. Humana Press Inc, Totowa, NJ | Autoimmune disorders, Immune, Vascular and Inflammatory disorders |
| Human chemokine GRObeta | GeneSeq Accession B15810 | WO0042071 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot; T. N. C. Wells, and C. A. Power. Humana Press Inc, Totowa, NJ | Autoimmune disorders, Immune, Vascular and Inflammatory disorders |
| Human chemokine IP-10 | GeneSeq Accession B15811 | WO0042071 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Autoimmune disorders, Immune, Vascular and Inflammatory disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | Over 40 human chemokines have been described, which bind to ~17 receptors thus far identified. | | |
| Human chemokine SDF1beta | GeneSeq Accession B15812 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Autoimmune disorders, Immune, Vascular and Inflammatory disorders |
| Human chemokine GRO alpha | GeneSeq Accession B15813 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Autoimmune disorders, Immune, Vascular and Inflammatory disorders |
| Human chemokine MIP1beta | GeneSeq Accession B15831 | WO0042071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Autoimmune disorders, Immune, Vascular and Inflammatory disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| A human C-C chemokine designated exodus | GeneSeq Accession B07939 | U.S. Pat. No. 6,096,300 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | | Cancer |
| Human chemokine L105_7 | GeneSeq Accession Y96922 | U.S. Pat. No. 6,084,071 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Chemotaxis, Gene Therapy, Wound healing |
| Human chemokine L105_3 | GeneSeq Accession Y96923 | U.S. Pat. No. 6,084,071 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Chemotaxis, Gene Therapy, Wound healing |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human secondary lymphoid chemokine (SLC) | GeneSeq Accession B01434 | WO0038706 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Cancer, Vascular and Immune disorders |
| Human non-ELR CXC chemokine H174 | GeneSeq Accession Y96310 | WO0029439 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Immune and Inflammatory disorders, Cancer, Haemostatic and thrombolytic activity |
| Human non-ELR CXC chemokine IP10 | GeneSeq Accession Y96311 | WO0029439 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Immune and Inflammatory disorders, Cancer, haemostatic and thrombolytic activity |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human non-ELR CXC chemokine Mig | GeneSeq Accession Y96313 | WO0029439 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc., Totowa, NJ | Immune and Inflammatory disorders, Cancer, haemostatic and thrombolytic activity |
| Human chemokine Ckbeta-7 | GeneSeq Accession Y96280 | WO0028035 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Cancer, wound healing, inflammatory and immunoregulatory disorders |
| Human chemokine MIP-1alpha | GeneSeq Accession Y96281 | WO0028035 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Cancer, wound healing, inflammatory and immunoregulatory disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| | | | Over 40 human chemokines have been described, which bind to ~17 receptors thus far identified. | | |
| Human mature chemokine Ckbeta-7 (optionally truncated) | GenSeq Accession Y96282 | WO0028035 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. Over 40 human chemokines have been described, which bind to ~17 receptors thus far identified. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Cancer, wound healing, inflammatory and immunoregulatory disorders |
| Human chemokine receptor CXCR3 | GenSeq Accession Y79372 | WO0018431 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Soluble CXCR3 polypeptides may be useful for inhibiting chemokine activities and viral infection. |
| Human neurotactin chemokine like domain | GenSeq Accession Y53259 | U.S. Pat. No. 6,043,086 | Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I. Proudfoot, T. N. C. Wells, and C. A. Power. Humana Press Inc, Totowa, NJ | Neurological disorders, Immune and respiratory disorders |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Human CC type chemokine interleukin C | GeneSeq Accession Y57771 | JP11302298 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I Proudfoot, T. N. C. Wells, and C. A. Power. Humana Press Inc., Totowa, NJ | Cancer and infectious diseases |
| Human CKbeta-9 | GeneSeq Accession B50860 | U.S. Pat. No. 6,153,441 | Over 40 human chemokines have been described, which bind to ~17 receptors thus far identified. Chemokines are a family of related small, secreted proteins involved in biological processes ranging from hematopoiesis, angiogenesis, and leukocyte trafficking. Members of this family are involved in a similarly diverse range of pathologies including inflammation, allergy, tissue rejection, viral infection, and tumor biology. The chemokines exert their effects by acting on a family of seven transmembrane G-protein coupled receptors. | Chemokine activities can be determined using assays known in the art: Methods in Molecular Biology, 2000, vol. 138: Chemokine Protocols. Edited by: A. E. I Proudfoot, T. N. C. Wells, and C. A. Power. Humana Press Inc., Totowa, NJ | Cancer, Auto-immune and inflammatory disorders, Cardiovascular disorders |
| Preproapolipoprotein "paris" variant | GeneSeq Accession W08602 | WO9637608 | Apoa-1 participates in the reverse transport of cholesterol from tissues to the liver for excretion by promoting cholesterol efflux from tissues and by acting as a cofactor for the lecithin cholesterol acyltransferase (lcat). | Lipid binding activity can be determined using assays known in the art, such as, for example, the Cholesterol Efflux Assays of Takahaski et al., P.N.A.S., Vol. 96, Issue 20, 11358-11363, Sep. 28, 1999. | Useful for cardiovascular disorders, cholesterol disorders, and Hyperlipidaemia |
| Preproapolipoprotein "milano" variant | | 5,721,114 | Apoa-1 participates in the reverse transport of cholesterol from tissues to the liver for excretion by promoting cholesterol efflux from tissues and by acting as a | Lipid binding activity can be determined using assays known in the art, such as, for example, the Cholesterol Efflux Assays of Takahaski et al., P.N.A.S., Vol. 96, | Useful for cardiovascular disorders, cholesterol disorders, and Hyperlipidaemia |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Glycodelin-A; Progesterone-associated endometrial protein | GeneSeq Accession W00289 | WO9628169 | cofactor for the lecithin cholesterol acyltransferase (lcat). Naturally produced female contraceptive that is removed rapidly from the body following 2-3 days production. Uses include contraception | Issue 20, 11358-11363, Sep. 28, 1999. Glycodelin-A activity can be determined using the hemizona assay as described in Oehninger, S., Coddington, C. C., Hodgen, G. D., and Seppala, M (1995) Fertil. Steril. 63, 377-383. | Naturally derived contraceptive useful for the prevention of pregnancy. |
| NOGO-A | Genbank Accession CAB99248 | | NOGO polypeptides are potent inhibitors of neurite growth. | Inhibition of Neurite outgrowth. Antagonists to NOGO polypeptides may promote the outgrowth of neurites, thus inducing regeneration of neurons. | NOGO-A polypeptide antagonists are useful for the promotion of neural growth, which could be useful in the treatment of neural disorders and dysfunction due to degenerative diseases or trauma; useful in the treatment of neoplastic diseases of the CNS; induce regeneration of neurons or to promote the structural plasticity of the CNS. |
| NOGO-B | Genbank Accession CAB99249 | | NOGO polypeptides are potent inhibitors of neurite growth. | Inhibition of Neurite outgrowth. Antagonists to NOGO polypeptides may promote the outgrowth of neurites, thus inducing regeneration of neurons. | NOGO-B polypeptide antagonists are useful for the promotion of neural growth, which could be useful in the treatment of neural disorders and dysfunction due to degenerative diseases or trauma; useful in the treatment of neoplastic diseases of the CNS; induce regeneration of neurons or to promote the structural plasticity of the CNS. |
| NOGO-C | Genbank Accession CAB99250 | | NOGO polypeptides are potent inhibitors of neurite growth. | Inhibition of Neurite outgrowth. Antagonists to NOGO polypeptides may promote the outgrowth of neurites, thus inducing regeneration of neurons. | NOGO-C polypeptide antagonists are useful for the promotion of neural growth, which could be useful in the treatment of neural disorders and dysfunction due to degenerative diseases or trauma; useful in the treatment of neoplastic diseases of the CNS; induce regeneration of neurons or to promote the |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| NOGO-66 Receptor | Genbank Accession AAG53612 | | NOGO polypeptides are potent inhibitors of neurite growth, and are thought to mediate their effects through the NOGO-66 Receptor. | Inhibition of Neurite outgrowth by mediating the biological effects of NOGO polypeptides. Soluble NOGO-66 receptor polypeptides may promote the outgrowth of neurites, thus inducing regeneration of neurons. | structural plasticity of the CNS. NOGO-66 receptor polypeptides are useful for the promotion of neural growth, which could be useful in the treatment of neural disorders and dysfunction due to degenerative diseases or trauma; useful in the treatment of neoplastic diseases of the CNS; induce regeneration of neurons or to promote the structural plasticity of the CNS. |
| Antibodies specific for collapsin | | U.S. Pat. No. 5,416,197 | These antibodies are useful for the promotion of neurite outgrowth | Collapsin activity, which is thought to inhibit the outgrowth of neurites, can be assayed in the presence of antibodies specific for collapsing using assays known in the art, such as, for example, the collapse assay disclosed by Luo et al., Cell 1993 Oct. 22; 75(2): 217-27 | Useful for the promotion of neural growth, which could be useful in the treatment of neural disorders and dysfunction due to degenerative diseases or trauma. |
| Humanized Anti-VEGF Antibodies, and fragments thereof | | WO9845331 | These agents have anti-inflammatory and anti-cancer applications | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer |
| Humanized Anti-VEGF Antibodies, and fragments thereof | | WO0029584 | These agents have anti-inflammatory and anti-cancer applications | VEGF activity can be determined using assays known in the art, such as those disclosed in International Publication No. WO0045835, for example. | Promotion of growth and proliferation of cells, such as vascular endothelial cells. Antagonists may be useful as anti-angiogenic agents, and may be applicable for cancer |
| Membrane bound proteins | GeneSeq. Accession Y66631-Y66765 | WO9963088 | Cancer, Immune Disorders | These proteins can be used for linking bioactive molecules to cells and for modulating biological activities of cells, using the polypeptide targeting for specific targeting. The polypeptide targeting can be used to kill the target cells, e.g. for the treatment of cancers. These proteins are useful for the treatment | Activities can be determined using assay known in the art, such as, for example, the assays disclosed in International Publication No. WO0121658. |

TABLE 1-continued

| Therapeutic Protein X | Exemplary Identifier (the sequences listed in this column are each hereby incorporated by reference) | PCT/Patent Reference (the patents and publications listed in this column are each hereby incorporated by reference) | Biological Activity | Exemplary Activity Assay (the publications listed in this column are each hereby incorporated by reference) | Preferred Indication Y |
|---|---|---|---|---|---|
| Secreted and Transmembrane polypeptides | GenSeq Accession B44241-B44334 | WO0053756 | Cancer, Immune Disorders | of immune system disorders. These proteins can be used for linking bioactive molecules to cells and for modulating biological activities of cells, using the polypeptides for specific targeting. The polypeptide targeting can be used to kill the target cells, e.g. for the treatment of cancers. These proteins are useful for the treatment of immune system disorders. | Activities can be determined using assay known in the art, such as, for example, the assays disclosed in International Publication No. WO0121658 |
| Secreted and Transmembrane polypeptides | GeneSeq Accession Y41685-Y41774 | WO9946281 | Cancer, Immune Disorders | These proteins can be used for linking bioactive molecules to cells and for modulating biological activities of cells, using the polypeptides for specific targeting. The polypeptide targeting can be used to kill the target cells, e.g. for the treatment of cancers. These proteins are useful for the treatment of immune system disorders. | Activities can be determined using assay known in the art, such as, for example, the assays disclosed in International Publication No. WO0121658 |

Conjugation and Coupling

The present invention provides therapeutic agents comprising an elastic peptide component and a therapeutic component, such as therapeutic proteins listed in herein, including Table 1, as well as a GLP-1 receptor agonists, insulin, Factor VII/VIIa, and functional analogs as described. Such agents may be prepared by recombinant technology and/or chemical coupling (e.g., conjugation).

A recombinantly-produced elastic peptide fusion protein, in accordance with certain embodiments of the invention, includes the elastic peptide component and the therapeutic component associated with one another by genetic fusion. For example, the fusion protein may be generated by translation of a polynucleotide encoding the therapeutic component cloned in-frame with the elastic peptide component (or vice versa). Such an elastic peptide fusion protein may contain one or more copies of the therapeutic component attached to the N-terminus and/or the C-terminus of the elastic peptide component. In some embodiments, the therapeutic proteinacious component is attached to both the N- and C-terminus of the elastic peptide component and the fusion protein may contain one or more equivalents of the therapeutic component on either or both ends of the elastic peptide component.

In certain embodiments, the elastic peptide component and the therapeutic components can be fused using a linker peptide of various lengths to provide greater physical separation and allow more spatial mobility between the fused portions, and thus maximize the accessibility of the therapeutic component, for instance, for binding to its cognate receptor. The linker peptide may consist of amino acids that are flexible or more rigid. For example, a flexible linker may include amino acids having relatively small side chains, and which may be hydrophilic. Without limitation, the flexible linker may contain a stretch of glycine and/or serine residues. More rigid linkers may contain, for example, more sterically hindering amino acid side chains, such as (without limitation) tyrosine or histidine. The linker may be less than about 50, 40, 30, 20, 10, or 5 amino acid residues. The linker can be covalently linked to and between an elastic peptide component and a therapeutic component, for example, via recombinant fusion.

The linker or peptide spacer may be protease-cleavable or non-cleavable. By way of example, cleavable peptide spacers include, without limitation, a peptide sequence recognized by proteases (in vitro or in vivo) of varying type, such as Tev, thrombin, factor Xa, plasmin (blood proteases), metalloproteases, cathepsins (e.g., GFLG, etc.), and proteases found in other corporeal compartments. In some embodiments employing cleavable linkers, the fusion protein ("the therapeutic agent") may be inactive, less active, or less potent as a fusion, which is then activated upon cleavage of the spacer in vivo. Alternatively, where the therapeutic agent is sufficiently active as a fusion, a non-cleavable spacer may be employed. The non-cleavable spacer may be of any suitable type, including, for example, non-cleavable spacer moieties having the formula [(Gly)n-Ser]m (SEQ ID NO.: 22) where n is from 1 to 4, inclusive, and m is from 1 to 4, inclusive. Alternatively, a short elastic peptide sequence different than the backbone elastic peptide could be employed instead of a linker or spacer, while accomplishing the necessary effect.

In still other embodiments, the therapeutic agent is a recombinant fusion having a therapeutic component flanked on each terminus by an elastic peptide component. At least one of said elastic peptide components may be attached via a cleavable spacer, such that the therapeutic component is inactive, but activated in vivo by proteolytic removal of a single elastic peptide component. The resulting single elastic peptide fusion being active, and having an enhanced half-life (or other property described herein) in vivo.

In other embodiments, the present invention provides chemical conjugates of the elastic peptide component and the therapeutic component. The conjugates can be made by chemically coupling an elastic peptide component to a therapeutic component by any number of methods well known in the art (See e.g. Nilsson et al., 2005, Ann Rev Biophys Bio Structure 34: 91-118). In some embodiments, the chemical conjugate can be formed by covalently linking the therapeutic component to the elastic peptide component, directly or through a short or long linker moiety, through one or more functional groups on the therapeutic proteinacious component, e. g., amine, carboxyl, phenyl, thiol or hydroxyl groups, to form a covalent conjugate. Various conventional linkers can be used, e. g., diisocyanates, diisothiocyanates, carbodiimides, bis (hydroxysuccinimide) esters, maleimide-hydroxysuccinimide esters, glutaraldehyde and the like.

Non-peptide chemical spacers can additionally be of any suitable type, including for example, by functional linkers described in Bioconjugate Techniques, Greg T. Hermanson, published by Academic Press, Inc., 1995, and those specified in the Cross-Linking Reagents Technical Handbook, available from Pierce Biotechnology, Inc. (Rockford, Ill.), the disclosures of which are hereby incorporated by reference, in their respective entireties. Illustrative chemical spacers include homobifunctional linkers that can attach to amine groups of Lys, as well as heterobifunctional linkers that can attach to Cys at one terminus, and to Lys at the other terminus.

In certain embodiments, relatively small ELP components (e.g., ELP components of less than about 30 kDa, 25 kDa, 20 kDa, 15 kDa, or 10 kDa), that do not transition at room temperature (or human body temperature, e.g., Tt>37° C.), are chemically coupled or crosslinked. For example, two relatively small ELP components, having the same or different properties, may be chemically coupled. Such coupling, in some embodiments, may take place in vivo, by the addition of a single cysteine residue at or around the C-terminus of the ELP. Such ELP components may each be fused to one or more therapeutic components, so as to increase activity or avidity at the target.

Polynucleotides, Vectors, and Host Cells

In another aspect, the invention provides polynucleotides comprising a nucleotide sequence encoding the therapeutic agent of the invention. Such polynucleotides further comprise, in addition to sequences encoding the elastic peptide and therapeutic components, one or more expression control elements. For example, the polynucleotide, may comprise one or more promoters or transcriptional enhancers, ribosomal binding sites, transcription termination signals, and polyadenylation signals, as expression control elements. The polynucleotide may be inserted within any suitable vector, which may be contained within any suitable host cell for expression.

A vector comprising the polynucleotide can be introduced into a cell for expression of the therapeutic agent. The vector can remain episomal or become chromosomally integrated, as long as the insert encoding the therapeutic agent can be transcribed. Vectors can be constructed by standard recombinant DNA technology. Vectors can be plasmids, phages, cosmids, phagemids, viruses, or any other types known in the art, which are used for replication and expression in prokaryotic or eukaryotic cells. It will be appreciated by one of skill in the art that a wide variety of components known in the art (such as expression control elements) may be included in such vectors, including a wide variety of transcription signals, such as promoters and other sequences that regulate the binding of RNA polymerase onto the promoter. Any promoter known to be effective in the cells in which the vector will be expressed can be used to initiate expression of the therapeutic agent. Suitable promoters may be inducible or constitutive. Examples of suitable promoters include the SV40 early promoter region, the promoter contained in the 3' long terminal repeat of Rous sarcoma virus, the HSV-1 (herpes simplex virus-1) thymidine kinase promoter, the regulatory sequences of the metallothionein gene, etc., as well as the following animal transcriptional control regions, which exhibit tissue specificity and have been utilized in transgenic animals: elastase I gene control region which is active in pancreatic acinar cells; insulin gene control region which is active in pancreatic beta cells, immunoglobulin gene control region which is active in lymphoid cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in erythroid cells, myelin basic protein gene control region which is active in oligodendrocyte cells in the brain, myosin light chain-2 gene control region which is active in skeletal muscle, and gonadotropin releasing hormone gene control region which is active in the hypothalamus.

Pharmaceutical Compositions

The present invention further provides pharmaceutical compositions comprising the therapeutic agents of the invention (as described above) together with a pharmaceutically acceptable carrier or excipient. Such pharmaceutical compositions may be employed in the methods of treatment as described above, for each of the therapeutic proteins, e.g., the therapeutic proteins listed in Table 1, GLP-1 receptor agonists, insulin, and Factor VII/VIIa embodiments.

The therapeutic agents of the invention may overcome certain deficiencies of peptide agents when administered (e.g., parenterally), including in some embodiments, the limitation that such peptides may be easily metabolized by plasma proteases or cleared from circulation by kidney filtration. Traditionally, the oral route of administration of peptide agents may also be problematic, because in addition to proteolysis in the stomach, the high acidity of the stomach destroys such peptide agents before they reach their intended target tissue. Peptides and peptide fragments produced by the action of gastric and pancreatic enzymes are cleaved by exo and endopeptidases in the intestinal brush border membrane to yield di- and tripeptides, and even if proteolysis by pancreatic enzymes is avoided, polypeptides are subject to degradation by brush border peptidases. Any of the peptide agents that survive passage through the stomach are further subjected to metabolism in the intestinal mucosa where a penetration barrier prevents entry into the cells. In certain embodiments, the therapeutic agents of the invention may overcome such deficiencies, and provide compositional forms having enhanced efficacy, bioavailability, therapeutic half-life, persistence, degradation assistance, etc. The therapeutic agents of the invention thus include oral and parenteral dose forms, as well as various other dose forms, by which peptide agents can be utilized in a highly effective manner. For example, in some embodiments, such agents may achieve high mucosal absorption, and the concomitant ability to use lower doses to elicit an optimum therapeutic effect.

The therapeutic agents of the present invention may be administered in smaller doses and/or less frequently than unfused or unconjugated counterparts. While one of skill in the art can determine the desirable dose in each case, a suitable dose of the therapeutic agent for achievement of therapeutic benefit, may, for example, be in a range of about 1 microgram (µg) to about 100 milligrams (mg) per kilogram body weight of the recipient per day, preferably in a range of about 10 µg to about 50 mg per kilogram body weight per day and most preferably in a range of about 10 µg to about 50 mg per kilogram body weight per day. The desired dose may be presented as one dose or two or more sub-doses administered at appropriate intervals throughout the day. These sub-doses can be administered in unit dosage forms, for example, containing from about 10 µg to about 1000 mg, preferably from about 50 µg to about 500 mg, and most preferably from about 50 µg to about 250 mg of active ingredient per unit dosage form. Alternatively, if the condition of the recipient so requires, the doses may be administered as a continuous infusion.

The mode of administration and dosage forms will of course affect the therapeutic amount of the peptide active therapeutic agent that is desirable and efficacious for a given treatment application. For example, orally administered dosages can be at least twice, e.g., 2-10 times, the dosage levels used in parenteral administration methods.

The therapeutic agents of the invention may be administered per se as well as in various forms including pharmaceutically acceptable esters, salts, and other physiologically functional derivatives thereof. The present invention also contemplates pharmaceutical formulations, both for veterinary and for human medical use, which include therapeutic agents of the invention. In such pharmaceutical and medicament formulations, the therapeutic agents can be used together with one or more pharmaceutically acceptable carrier(s) therefore and optionally any other therapeutic ingredients. The carrier(s) must be pharmaceutically acceptable in the sense of being compatible with the other ingredients of the formulation and not unduly deleterious to the recipient thereof. The therapeutic agents are provided in an amount effective to achieve the desired pharmacological effect, as described above, and in a quantity appropriate to achieve the desired daily dose.

The formulations of the therapeutic agent include those suitable for parenteral as well as non-parenteral administration, and specific administration modalities include oral, rectal, buccal, topical, nasal, ophthalmic, subcutaneous, intramuscular, intravenous, transdermal, intrathecal, intra-articular, intra-arterial, sub-arachnoid, bronchial, lymphatic, vaginal, and intra-uterine administration. Formulations suitable for oral and parenteral administration are preferred.

When the therapeutic agent is used in a formulation including a liquid solution, the formulation advantageously can be administered orally or parenterally. When the therapeutic agent is employed in a liquid suspension formulation or as a powder in a biocompatible carrier formulation, the formulation may be advantageously administered orally, rectally, or bronchially.

When the therapeutic agent is used directly in the form of a powdered solid, the active agent can be advantageously administered orally. Alternatively, it may be administered bronchially, via nebulization of the powder in a carrier gas, to form a gaseous dispersion of the powder which is inspired by the patient from a breathing circuit comprising a suitable nebulizer device.

The formulations comprising the therapeutic agent of the present invention may conveniently be presented in unit dosage forms and may be prepared by any of the methods well known in the art of pharmacy. Such methods generally include the step of bringing the therapeutic agents into association with a carrier which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation.

Formulations suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the therapeutic agent being in a free-flowing form such as a powder or granules which optionally is mixed with a binder, disintegrant, lubricant, inert diluent, surface active agent, or discharging agent. Molded tablets comprised of a mixture of the powdered peptide active therapeutic agent-elastic peptide construct(s) with a suitable carrier may be made by molding in a suitable machine.

A syrup may be made by adding the peptide active therapeutic agent-ELP construct(s) to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the therapeutic agent, which preferably is isotonic with the blood of the recipient (e.g., physiological saline solution). Such formulations may include suspending agents and thickening agents or other microparticulate systems which are designed to target the peptide active therapeutic agent to blood components or one or more organs. The formulations may be presented in unit-dose or multi-dose form.

Nasal spray formulations comprise purified aqueous solutions of the therapeutic agent with preservative agents and isotonic agents. Such formulations are preferably adjusted to a pH and isotonic state compatible with the nasal mucus membranes.

Formulations for rectal administration may be presented as a suppository with a suitable carrier such as cocoa butter, hydrogenated fats, or hydrogenated fatty carboxylic acid.

Topical formulations comprise the therapeutic agent dissolved or suspended in one or more media, such as mineral oil, petroleum, polyhydroxy alcohols, or other bases used for topical pharmaceutical formulations.

In addition to the aforementioned ingredients, the formulations of this invention may further include one or more accessory ingredient(s) selected from diluents, buffers, flavoring agents, disintegrants, surface active agents, thickeners, lubricants, preservatives (including antioxidants), and the like.

The features and advantages of the present invention are more fully shown with respect to the following non-limiting examples.

EXAMPLES

Example 1

Construction of Various ELP Component Constructs

Cloning steps were conducted in *Escherichia coli* strain XL1-Blue (rec A1, endA1, gyrA96, thi-1, hsdR17 ($r_k^-$, $m_k$+), supE44, relA1, lac[F', proAB, /acl$^q$ZΔM15, Tn10 (Tet$^r$)] (Stratagene La Jolla, Calif.). pUC19 (NEB, Beverly, Mass.) was used as the cloning vector for the ELP construction (Meyer and Chilkoti, *Nat. Biotechnol.*, 17(11):1112-5, 1999). Modified forms of pET15b and pET24d vectors (Novagen) were used to express ELP and ELP-fusion proteins in BL21 Star (DE3) strain (F$^-$, ompT, hsdS$_B$ ($r_B^- m_B^-$), gal, dcm, rne131, (DE3)) (Invitrogen Carlsbad, Calif.) or BLR(DE3) (F$^-$, ompT, hsdS$_B$ ($r_B^- m_B^-$), gal, dcm, Δ(srl-recA) 306::Tn10 (TcR)(DE3)) (Novagen Madison, Wis.). Synthetic DNA oligos were purchased from Integrated DNA Technologies, Coralville, Iowa. All vector constructs were made using standard molecular biology protocols (e.g., *Current Protocols in Molecular Biology*, ed. Ausubel, et al., 1995).

Construction of ELP1 [$V_5A_2G_3$] Gene Series

The ELP1 [$V_5A_2G_3$] series designate polypeptides containing multiple repeating units of the pentapeptide VPGXG (SEQ ID NO: 3), where X is valine, alanine, and glycine at a relative ratio of 5:2:3.

The ELP1 [$V_5A_2G_3$] series monomer, ELP1 [$V_5A_2G_3$-10], was created by annealing four 5' phosphorylated, PAGE purified synthetic oligos to form double stranded DNA with EcoRI and HindIII compatible ends (Meyer and Chilkoti, *Nat. Biotechnol.*, 17(11):1112-5, 1999). The oligos were annealed in a 1 μM mixture of the four oligos in 50 μl IX ligase buffer (Invitrogen) to 95° C. in a heating block than the block was allowed to cool slowly to room temperature. The ELP1 [$V_5A_2G_3$-10]/EcoRI-HindIII DNA segment was ligated into a pUC19 vector digested with EcoRI and HindIII and CIAP dephosphorylated (Invitrogen) to form pUC19-ELP1 [$V_5A_2G_3$-10]. Building of the ELP1 [$V_5A_2G_3$] series library began by inserting ELP1 [$V_5A_2G_3$-10] PflMI/BgII fragment from pUC19-ELP1 [$V_5A_2G_3$-10] into pUC19-ELP1 [$V_5A_2G_3$-10] linearized with PflMI and dephosphorylated with CIAP to create pUC19-ELP1 [$V_5A_2G_3$-20]. pUC19-ELP1 [$V_5A_2G_3$-20] was then built up to pUC19-ELP1 [$V_5A_2G_3$-30] and pUC19-ELP1 [$V_5A_2G_3$-40] by ligating ELP1 [$V_5A_2G_3$-10] or ELP1 [$V_5A_2G_3$-20] PflMI/BgII fragments respectively into PflMI digested pUC 19-ELP1 [$V_5A_2G_3$-20]. This procedure was used to expand the ELP1 [$V_5A_2G_3$] series to create pUC19-ELP1 [$V_5A_2G_3$-60], pUC19-ELP1 [$V_5A_2G_3$-90] and pUC19-ELP1 [$V_5A_2G_3$-180] genes.

Construction of ELP1 [$K_1V_2F_1$] Gene Series

The ELP1 [$K_1V_2F_1$] series designate polypeptides containing multiple repeating units of the pentapeptide VPGXG (SEQ ID NO: 3), where X is lysine, valine, and phenylalanine at a relative ratio of 1:2:1.

The ELP1 [$K_1V_2F_1$] series monomer, ELP1 [$K_1V_2F_1$-4], was created by annealing two 5' phosphorylated, PAGE purified synthetic oligos to form double stranded DNA with EcoRI and HindIII compatible ends (Meyer and Chilkoti, 1999). The oligos were annealed in a 1 μM mixture of the four oligos in 50 μl 1× ligase buffer (Invitrogen) to 95° C. in a heating block then the block was allowed to cool slowly to room temperature. The ELP1 [$K_1V_2F_1$-4]/EcoRI-HindIII DNA segment was ligated into a pUC19 vector digested with EcoRI and HindIII and CIAP dephosphorylated (Invitrogen) to form pUC19-ELP1 [$K_1V_2F_1$-4]. Building of the ELP1 [$K_1V_2F_1$] series library began by inserting ELP1 [$K_1V_2F_1$-4] PflM1/BglI fragment from pUC19-ELP1 [$K_1V_2F_1$-4] into pUC19-ELP1 [$K_1V_2F_1$-4] linearized with PflM1 and dephosphorylated with CIAP to create pUC19-ELP1 [$K_1V_2F_1$-8]. Using the same procedure the ELP1 [$K_1V_2F_1$] series was doubled at each ligation to form pUC19-ELP1 [$K_1V_2F_1$-I6], pUC19-ELP1 [$K_1V_2F_1$-32], pUC19-ELP1 [$K_1V_2F_1$-64] and pUC19-ELP1 [$K_1V_2F_1$-128].

Construction of ELP1 [K$_1$V$_7$F$_1$] Gene Series

The ELP1 [K$_1$V$_7$F$_1$] series designate polypeptides containing multiple repeating units of the pentapeptide VPGXG (SEQ ID NO: 3), where X is lysine, valine, and phenylalanine at a relative ratio of 1:7:1.

The ELP1 [K$_1$V$_7$F$_1$] series monomer, ELP1 [K$_1$V$_7$F$_1$-9], was created by annealing four 5' phosphorylated, PAGE purified synthetic oligos to form double stranded DNA with PflMI and HindIII compatible ends. The ELP1 [K$_1$V$_7$F$_1$-9] DNA segment was than ligated into PflM1/HindIII dephosphorylated PUC19-ELP1 [V$_5$A$_2$G$_3$-180] vector thereby substituting ELP1 [V$_5$A$_2$G$_3$-180] for ELP1 [K$_1$V$_7$F$_1$-9] to create the pUC19-ELP1 [K$_1$V$_7$F$_1$-9] monomer. The ELP1 [K$_1$V$_7$F$_1$] series was expanded in the same manner as the ELP1 [K$_1$V$_2$F$_1$] series to create pUC19-ELP1 [K$_1$V$_7$F$_1$-18], PUC19-ELP1 [K$_1$V$_7$F$_1$-36], pUC19-ELP1 [K$_1$V$_7$F$_1$-72] and pUC19-ELP1 [K$_1$V$_7$F$_1$-144].

Construction of ELP1 [V] Gene Series

The ELP1 [V] series designate polypeptides containing multiple repeating units of the pentapeptide VPGXG (SEQ ID NO: 3), where X is exclusively valine.

The ELP1 [V] series monomer, ELP1 [V-5], was created by annealing two 5' phosphorylated, PAGE purified synthetic oligos to form double stranded DNA with EcoRI and HindIII compatible ends. The ELP1 [V-5] DNA segment was than ligated into EcoRI/HindIII dephosphorylated pUC19 vector to create the pUC19-ELP1 [V-5] monomer. The ELP1 [V] series was created in the same manner as the ELP1 [V$_5$A$_2$G$_3$] series, ultimately expanding pUC19-ELP1 [V-5] to pUC19-ELP1 [V-60] and pUC19-ELP1 [V-120].

Construction of ELP2 Gene Series

The ELP2 series designate polypeptides containing multiple repeating units of the pentapeptide AVGVP.

The ELP2 series monomer, ELP2 [5], was created by annealing two 5' phosphorylated, PAGE purified synthetic oligos to form double stranded DNA with EcoRI and HindIII compatible ends. The ELP2 [5] DNA segment was than ligated into EcoRI/HindIII dephosphorylated pUC19 vector to create the pUC19-ELP2[5] monomer. The ELP2 series was expanded in the same manner as the ELP1 [K$_1$V$_2$F$_1$] series to create pUC19-ELP2[10], pUC19-ELP2 [30], pUC 19-ELP2 [60] and pUC 19-ELP2 [120].

Construction of ELP3 [V] Gene Series

The ELP3 [V] series designate polypeptides containing multiple repeating units of the pentapeptide IPGXG (SEQ ID NO: 5), where X is exclusively valine.

The ELP3 [V] series monomer, ELP3 [V-5], was created by annealing two 5' phosphorylated, PAGE purified synthetic oligos to form double stranded DNA with PflM1 amino terminal and GGC carboxyl terminal compatible ends due to the lack of a convenient carboxyl terminal restriction site but still enable seamless addition of the monomer. The ELP3 [V-5] DNA segment was then ligated into PflM1/BglII dephosphorylated pUC19-ELP4[V-5], thereby substituting ELP4 [V-5] for ELP3 [V-5] to create the pUC19-ELP3 [V-5] monomer. The ELP3 [V] series was expanded by ligating the annealed ELP3 oligos into pUC19-ELP3[V-5] digested with PflMI. Each ligation expands the ELP3 [V] series by 5 to create ELP3 [V-10], ELP3 [V-15], etc.

Construction of the ELP4 [V] Gene Series

The ELP4 [V] series designate polypeptides containing multiple repeating units of the pentapeptide LPGXG (SEQ ID NO: 7), where X is exclusively valine.

The ELP4 [V] series monomer, ELP4 [V-5], was created by annealing two 5' phosphorylated, PAGE purified synthetic oligos to form double stranded DNA with EcoRI and HindIII compatible ends. The ELP4 [V-5] DNA segment was than ligated into EcoRI/HindIII dephosphorylated pUC19 vector to create the pUC19-ELP4[V-5] monomer. The ELP4 [V] series was expanded in the same manner as the ELP1 [K$_1$V$_2$F$_1$] series to create pUC19-ELP4[V-10], pUC19-ELP4 [V-30], pUC19-ELP4[V-60] and pUC19-ELP4[V-120].

The ELP genes were also inserted into other vectors such as pET15b-SD0, pET15b-SD3, pET15b-SD5, pET15b-SD6, and pET24d-SD21. The pET vector series are available from Novagen, San Diego, Calif.

The pET15b-SD0 vector was formed by modifying the pET15b vector using SD0 double-stranded DNA segment containing the multicloning restriction site (SacI-NdeI-NcoI-XhoI-SnaBI-BamHI). The SD0 double-stranded DNA segment had XbaI and BamHI compatible ends and was ligated into XbaI/BamHI linearized and 5'-dephosphorylated pET15b to form the pet15b-SD0 vector.

The pET15b-SD3 vector was formed by modifying the pET15b-SD0 vector using SD3 double-stranded DNA segment containing a SfiI restriction site upstream of a hinge region-thrombin cleavage site followed by the multicloning site (NdeI-NcoI-XhoI-SnaBI-BamHI). The SD3 double-stranded DNA segment had SacI and NdeI compatible ends and was ligated into SacI/NdeI linearized and 5'-dephosphorylated pET15b-SD0 to form the pET15b-SD3 vector.

The pET15b-SD5 vector was formed by modifying the pET15b-SD3 vector using the SD5 double-stranded DNA segment containing a SM restriction site upstream of a thrombin cleavage site followed by a hinge and the multicloning site (NdeI-NcoI-XhoI-SnaBI-BamHI). The SD5 double-stranded DNA segment had SfiI and NdeI compatible ends and was ligated into SfiI/NdeI linearized and 5'-dephosphorylated pET15b-SD3 to form the pET15b-SD5 vector.

The pET15b-SD6 vector was formed by modifying the pET15b-SD3 vector using the SD6 double-stranded DNA segment containing a SfiI restriction site upstream of a linker region-TEV cleavage site followed by the multicloning site (NdeI-NcoI-XhoI-SnaBI-BamHI). The SD6 double-stranded DNA segment had SfiI and NheI compatible ends and was ligated into SfiI/NdeI linearized and 5'-dephosphorylated pET15b-SD3 to form the pET15b-SD6 vector.

The pET24d-SD21 vector was formed by modifying the pET24d vector using the SD21 double-stranded DNA segment with NcoI and NheI compatible ends. The SD21 double-stranded DNA segment was ligated into NcoI/NheI linearized and 5' dephosphorylated pET24d to create the pET24d-SD21 vector, which contained a new multicloning site NcoI-SfiI-NheI-BamHI-EcoRI-SacI-SalI-HindIII-NotI-XhoI with two stop codons directly after the SfiI site for insertion and expression of ELP with the minimum number of extra amino acids.

The pUC19-ELP1 [V$_5$A$_2$G$_3$-60], pUC19-ELP1 [V$_5$A$_2$G$_3$-90], and pUC19-ELP1 [V$_5$A$_2$G$_3$-180] plasmids produced in XL1-Blue were digested with PflMI and BglI, and the ELP-containing fragments were ligated into the SfiI site of the pET15b-SD3 expression vector as described hereinabove to create pET15b-SD3-ELP1 [V$_5$A$_2$G$_3$-60], pET15b-SD5-ELP1 [V$_5$A$_2$G$_3$-90] and pET15b-SD5-ELP1 [V$_5$A$_2$G$_3$-180], respectively.

The pUC19-ELP1 [V$_5$A$_2$G$_3$-90], pUC19-ELP1 [V$_5$A$_2$G$_3$-180], pUC19-ELP1 [V-60] and pUC19-ELP1 [V-120] plasmids produced in XL1-Blue were digested with PflMI and BglI, and the ELP-containing fragments were ligated into the SfiI site of the pET15b-SD5 expression vector as described hereinabove to create pET15b-SD5-ELP1 [V$_5$A$_2$G$_3$-90], pET15b-SD5-ELP1 [V$_5$A$_2$G$_3$-180], pET15b-SD5-ELP1 [V-60] and pET15b-SD5-ELP1 [V-120], respectively.

The pUC19-ELP1 [V$_5$A$_2$G$_3$-90] plasmid produced in XL1-Blue was digested with PflMI and BglI, and the ELP-containing fragment was ligated into the SfiI site of the pET15b-SD6 expression vector as described hereinabove to create pET15b-SD6-ELP1 [$V_5A_2G_3$-90].

The pUC19-ELP1 [$K_1V_2F_1$-64], and pUC19-ELP1 [$K_1V_2F_1$-128] plasmids produced in XL1-Blue were digested with PflMI and BglII, and the ELP-containing fragments were ligated into the SfiI site of the pET24d-SD21 expression vector as described hereinabove to create pET24d-SD21-ELP1 [$K_1V_2F_1$-64] and pET24d-SD21-ELP1 [$K_1V_2F_1$-128], respectively.

The pUC19-ELP1 [$K_1V_7F_1$-72] and pUC19-ELP1 [$K_1V_7F_1$-144] plasmids produced in XL1-Blue were digested with PflMI and BglII, and the ELP-containing fragments were ligated into the SfiI site of the pET24d-SD21 expression vector as described hereinabove to create pET24d-SD21-ELP1 [$K_1V_7F_1$-72], pET24d-SD21-ELP1 [$K_1V_7F_1$-144], respectively.

The pUC19-ELP2[60] and pUC19-ELP2[120] plasmids produced in XL1-Blue were digested with NcoI and HindIII, and the ELP-containing fragments were ligated into the NcoI and HindIII sites of the pET24d-SD21 expression vector as described hereinabove to create pET24d-SD21-ELP2[60], pET24d-SD21-ELP2[120], respectively.

The pUC19-ELP4[V-60] and pUC19-ELP4[V-120] plasmids produced in XL1-Blue were digested with NcoI and HindIII, and the ELP-containing fragments were ligated into the NcoI and HindIII sites of the pET24d-SD21 expression vector as described hereinabove to create pET24d-SD21-ELP4[V-60], pET24d-SD21-ELP4[V-120], respectively.

Example 2

Isolation and Purification of Fusion Proteins Containing Insulin A Peptide (InsA)

ELP-InsA fusion proteins included the following:
Insulin A peptide and ELP1 [V-60] polypeptide with an enterokinase protease cleavage site therebetween.
Insulin A peptide and ELP1 [$V_5A_2G_3$-90] polypeptide with an enterokinase protease cleavage site therebetween.
Insulin A peptide and ELP1 [V-120] polypeptide with an enterokinase protease cleavage site therebetween.
Insulin A peptide and ELP1 [$V_5A_2G_3$-180] polypeptide with an enterokinase protease cleavage site therebetween.

A single colony of E. coli strain BLR (DE3) (Novagen) containing the respective ELP-InsA fusion protein was inoculated into 5 ml CircleGrow (Q-BIOgene, San Diego, Calif.) supplemented with 100 µg/ml ampicillin (Sigma) and grown at 37° C. with shaking at 250 rpm for 5 hours. The 5 ml culture was then inoculated into a 500 ml culture and allowed to grow at 25° C. for 16 hours before inducing with 1 mM IPTG for 4 hours at 25° C. The culture was harvested and suspended in 40 ml 20 mM Tris-HCl pH 7.4, 50 mM NaCl, 1 mM DTT and 1 Complete EDTA free Protease inhibitor pellet (Roche, Indianapolis, Ind.). Cells were lysed by ultrasonic disruption on ice for 3 minutes, which consisted of 10 seconds bursts at 35% power separated by 30 second cooling down intervals. Cell debris was removed by centrifugation at 20,000 g, 4° C. for 30 minutes.

Inverse phase transition was induced by adding NaCl to the cell lysate at room temperature to achieve a final concentration of 1.0 M therein, followed by centrifugation at 20,000 g for 15 minutes at room temperature. The resulting pellet contained the respective ELP-InsA fusion protein and non-specifically NaCl precipitated proteins.

The pellet was re-suspended in 40 ml ice-cold ml 20 mM Tris-HCl pH 7.4, 50 mM NaCl, 1 mM DTT and re-centrifuged at 20,000 g, 4° C. for 15 minutes to remove the non-specifically NaCl precipitated proteins. The inverse transition cycle was repeated two additional times to increase the purity of the respective ELP-InsA fusion protein and reduce the final volume to 0.5 ml.

Example 3

Half-Life of ELP1

The pharmacokinetics of ELP1 were determined by intravenously administering [$^{14}$C]ELP1 to nude mice (Balb/c nu/nu) bearing a leg/flank FaDu xenograft and collecting blood samples at various time intervals after administration. The blood pharmacokinetics exhibited a characteristic distribution and elimination response for large macromolecules, which was well described by a bi-exponential process.

The plasma concentration time-course curve was fit to the analytical solution of a two-compartment model to approximate both an elimination and distribution response. Certain pharmakinetic parameters are shown in Table 1 below. The distribution volume of the ELP (1.338 µl) was nearly identical to the hypothetical plasma volume of 1.363 µl (Barbee, R. W., et al., Am. J. Physio. 263(3) (1992) R728-R733), indicating that the ELP did not rapidly distribute or bind to specific organs and tissues directly after administration. The AUC is a measure of the cumulative exposure to ELP in the central compartment or the blood plasma. The body clearance is defined as the rate of ELP elimination in the body relative to its plasma concentration and is the summation of clearance through all organs including the kidney, liver and others.

TABLE 1

| | Pharmacokinetic parameters calculated for [$^{14}$C]ELP1 | | | | | |
|---|---|---|---|---|---|---|
| | $k_1$ (hr$^{-1}$) | $k_2$ (hr$^{-1}$) | $k_e$ (hr$^{-1}$) | $V_d$ (µL) | AUC (mg ELP hr/ml) | $Cl_B$ (µL/hr) |
| ELP1-150 | 3.54 | 1.99 | 0.24 | 1,338 | 7.1 | 317 |

The mass transfer rate constants are from a standard two-compartment model ($k_1$; from central to peripheral compartment; $k_2$, from peripheral to central compartment; and $k_e$, elimination from central compartment). The distribution volume ($V_d$), central compartment concentration time-course area under the curve (AUC) and body clearance ($Cl_B$) are displayed. Data are shown as the mean values (n=5, except $V_d$ and initial plasma concentration ($C_O$) was calculated from a similar cohort with n=3).

Example 4

Biodistribution of ELPs in Nude Mice $^{14}$C Labeled ELP1-150 and/or $^{14}$C Labeled ELP2-160

$^{14}$C labeled ELP1-150 and/or $^{14}$C labeled ELP2-160 were administered to nude mice with a FaDu tumor (mean+/−SD, n=6). The tumor was heated post administration of the ELP in a water bath at 41.5° C. The distribution was highest to the organs with the highest blood content: liver, kidneys, spleen, and lungs.

$^{14}$C Labeled ELP2-[$V_1A_8G_7$-160]

$^{14}$C labeled ELP2-[$V_1A_8G_7$-160] ($T_t$>60° C.) was administered to nude mice for a plasma concentration of 15 µM. ELP concentrations were determined following 1 hour of heating (41° C.) of an implanted FaDu tumor, located in the right hind leg of the nude mouse. Data are shown as the mean, plus the 95% confidence interval. N=6.

ELP concentration was measured 1.5 hours following systemic administration of $^{14}$C labeled ELP2-[$V_1A_8G_7$-160]. The highest distribution is seen in organs with the highest blood content: liver, kidneys, spleen, and lungs.

Example 5

Exendin-4 ELP Fusion

Figure 2A:
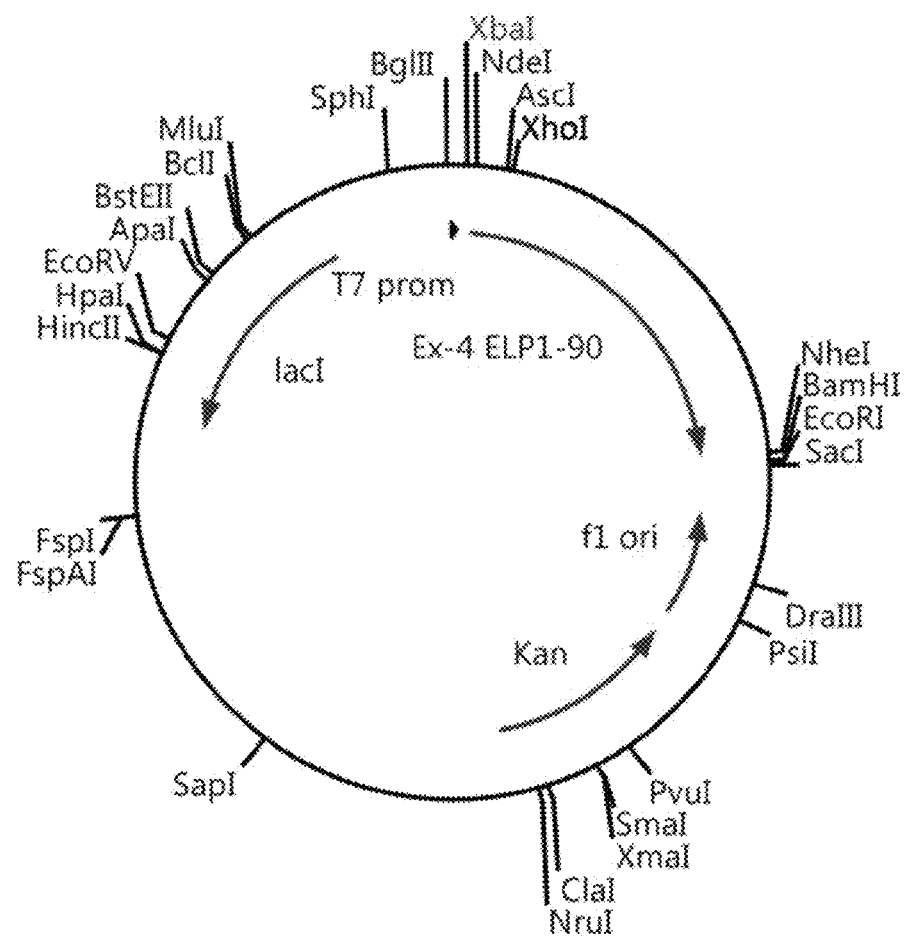
FIG. 2A depicts plasmid pET24d-Ex-4 ELP1-90 encoding an ELP component with VPGXG (SEQ ID NO: 3) repeat motif (as in FIG. 1) cloned in frame with an N-terminal exendin-4 component.

The DNA sequence for Exendin-4 (Ex-4) (SEQ ID NO: 14) was reverse translated from the amino acid sequence using codons optimized for *E. coli* expression. The DNA sequence encoding Exendin-4 was constructed by annealing together synthetic oligonucleotides with overhanging 5' and 3' ends compatible with the restriction sites NdeI and XhoI in the plasmid pET24d-ELP1-90 (FIG. 1). This plasmid was digested with the restriction enzymes NdeI and XhoI and the annealed DNA sequence was ligated into the cut vector. Insertion was confirmed by restriction digest and DNA sequencing. The resulting plasmid was designated as pET24d-Ex-4 ELP1-90 (FIG. 2A), and the sequence of the resulting Exendin-4-ELP fusion shown in FIG. 2B. Primers for construction of the fusion are also indicated.

pET24d-Ex-4 ELP1-90 was used to transform the *E. coli* strain BRL (Invitrogen) and selected transformants were grown in media 3(1.2% Tryptone Peptone, 2.4% yeast extract, 5 g/L casamino acids, 2% glycerol, 2.313 g Potassium phosphate dibasic/L, 12.541 g Potassium phosphate monobasic/L) in shake flasks. Production proceeded by autoinduction by inoculating 1 OD cells into 1 L of media 3 and allowing growth to proceed for 17 hr at 37° C. without addition of inducer. The product was recovered by collection of the cell pellet, sonicated to disrupt the cells and recovered by thermal and/or salt induced transition modulated by the ELP moiety (*Improved Non-chromatographic Purification of a Recombinant Protein by Cationic Elastin-like Polypeptides*, Dong Woo Lim, Kimberly Trabbic-Carlson, J. Andrew MacKay, and Ashutosh Chilkoti. *Biomacromolecules* 2007, 8, 1417-1424).

This example is with the ELP designated 1-90. This is based on the VPGXG (SEQ ID NO: 3) motif where X is a V, G or A in the ratio 5:3:2 in a 10 unit repeat, repeated 8× with a final (C-terminal) 10-unit repeat where X is a V, G, A and W in the ratio 4:3:2:1.

[(VPGXG)10]$_9$ where the X residue in the ten sequential iterations of the repeat unit (numerical subscript) can be described as [($V_{1, 4, 5, 6, 10}G_{2, 7, 9}A_{3, 8}$)$_8$ ($V_{1, 4, 5, 6}G_{2, 7, 9}A_{3, 8}W_{10}$)].

The ELP may be any combination of VPGXG (SEQ ID NO: 3) units where X is any of the 20 natural amino, acids, except proline, in any combination of repeat units of any length. In addition, the amino acid may be an unnatural amino acid for which the host strain has been engineered to accept an engineered tRNA for incorporation at specific codon (Wang L, Brock A, Herberich B, Schultz P G. *Expanding the genetic code of Escherichia coli.* [2001] Science 292, 498-500).

This construct was produced in the cytosol with an N-terminal methionine, which is normally removed by methionine aminopeptidase. Complete and accurate processing of the methionine, however, cannot be assumed; this enzyme may also remove the N-terminal histidine of the Exendin-4 moiety. This could result in a mixture of, unprocessed, processed and incorrectly processed products. Consequently, further constructs were developed to generate products with correctly processed N-termini.

Primers were designed to add a Tev protease (Tobacco Etch Virus cysteine protease) cleavage site between the N-terminal methionine and the histidine at the N-terminus of Exendin-4. This allows for removal of the methionine and the Tev recognition sequence to give the mature N-terminus of Exendin-4 (histidine). This can be done post-production or the Tev protease can be co-expressed to cleave the recognition sequence during production, for instance, as an intein (Ge, X., Yang, D. S. C., Trabbic-Carlson, K., Kim, B., Chilkoti, A. and Filipe, C. D. M. *Self-Cleavable Stimulus Responsive Tags for Protein Purification without Chromatography. J. Am. Chem. Soc.* 127, 11228-11229, 2005). The Tev Exendin-4 sequence is shown in FIG. 3A. FIG. 3B shows additional sequences added, labeled as "Linker Tev," provide a better target for the Tev protease.

Figure 4B:
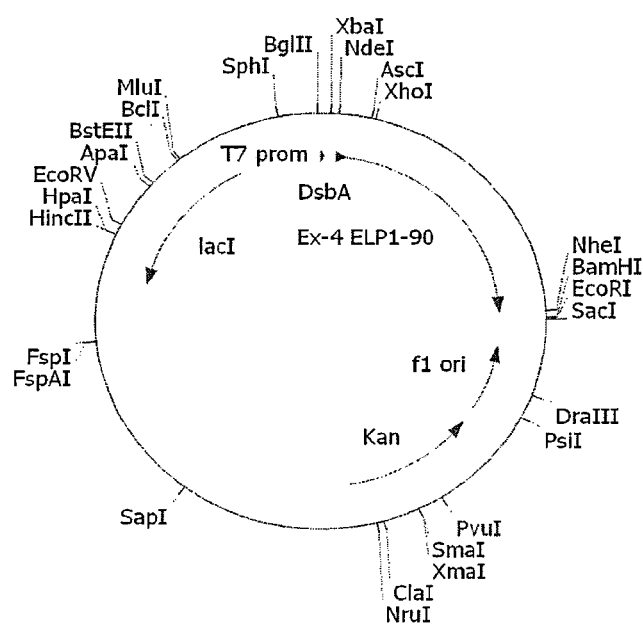
FIG. 4B depicts plasmid pET24d-DsbA-Ex-4 ELP1-90 encoding the fusion of FIG. 4A.

An alternative route to obtaining a correctly processed N-terminus for Ex-4 is to use a leader or signal sequence that directs the product to the periplasm and which is cleaved by a signal peptidase in the process. In this instance, a signal sequence, DsbA, that directs the transcript to the signal recognition particle for direct secretion of the polypeptide into the periplasm is given. (See FIG. 4A). The plasmid pET24d-DsbA-Ex-4 ELP1-90 is shown in FIG. 4B.

While this example illustrates the preparation of therapeutic agents with Exendin-4 sequences, such sequences can be replaced with GLP-1, insulin, Factor VII/VIIa, or other therapeutic protein listed in Table 1, generated in exactly or a similar manner as detailed for Exendin-4.

Example 6

GLP1-ELP Fusion Protein

Figure 5A:
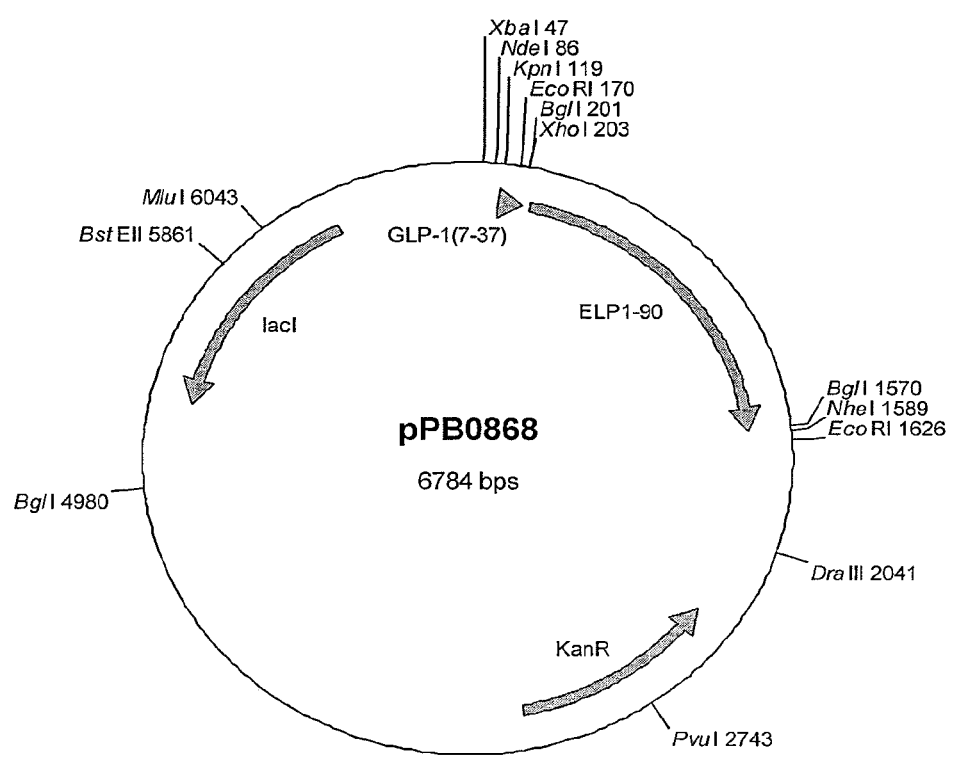
FIG. 5A depicts pPB0868, which encodes GLP-1(A8G,7-37)ELP1-90.
Figure 6A:
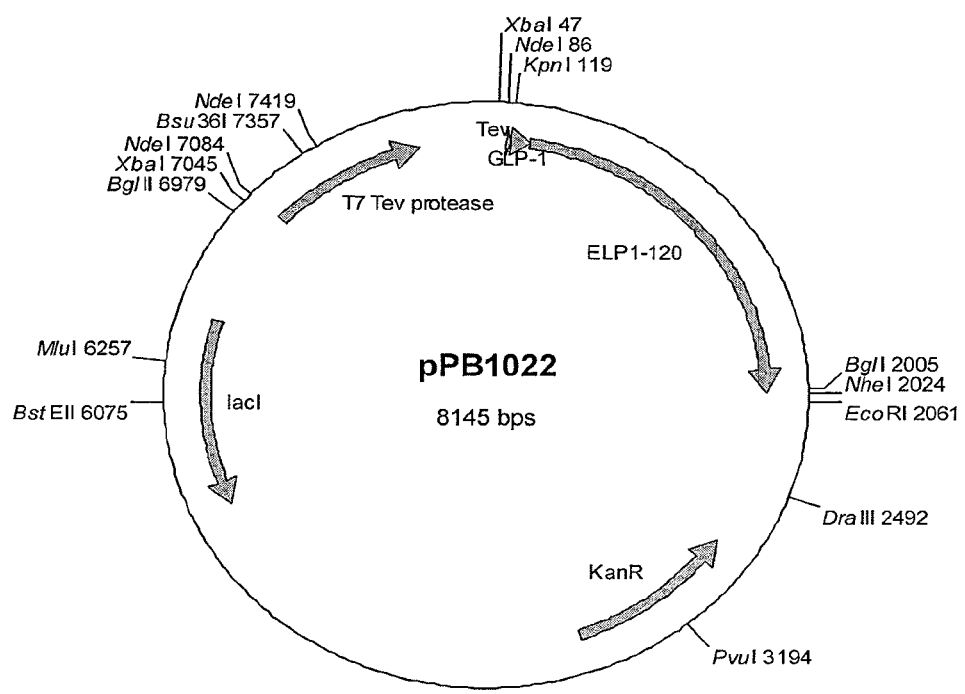
FIG. 6A depicts pPB1022, which encodes GLP-1(A8G,7-37)ELP1-120.

The ELP plasmid constructs were used to prepare two GLP1-ELP fusion proteins, GLP1(A8G,7-37)ELP1-90 and GLP1(A8G,7-37)ELP1-120. The plasmid constructs, fusion-encoding nucleotide sequence, as well as the amino acid sequence of the resulting fusion proteins are shown in FIGS. 5 and 6.

Both constructs contain an N-terminal Tev protease site to allow processing to the mature form where His$^7$ of GLP1 is at the N-terminus. The processed fusion proteins have calculated molecular weights of about 39,536 and about 50,828, respectively.

Example 7

FVII ELP Fusion Protein

The coagulation factor VII (FVII) gene was modified by PCR from a cDNA clone (Oragene) to add restriction sites at the 5' and 3' ends for cloning into the ELP-containing vector. At the 5' end an NheI site was added and at the 3' end a NotI site was added. The DNA and amino acid sequences of the Factor VII gene are shown in the accompanying Sequence Listing as SEQ ID NOS: 34 and 33, respectively. The DNA sequences of the 5' and 3' primers used to PCR amplify the factor VII (FVII) gene were:

```
P13:
                                        (SEQ ID NO.: 49)
CTAGCTAGCATGGTCTCCCAGGCCCTC

P14:
                                        (SEQ ID NO.: 50)
TATTCTTGCGGCCGCGGGAAATGGGGCTCGCAG
```

Figure 7A:
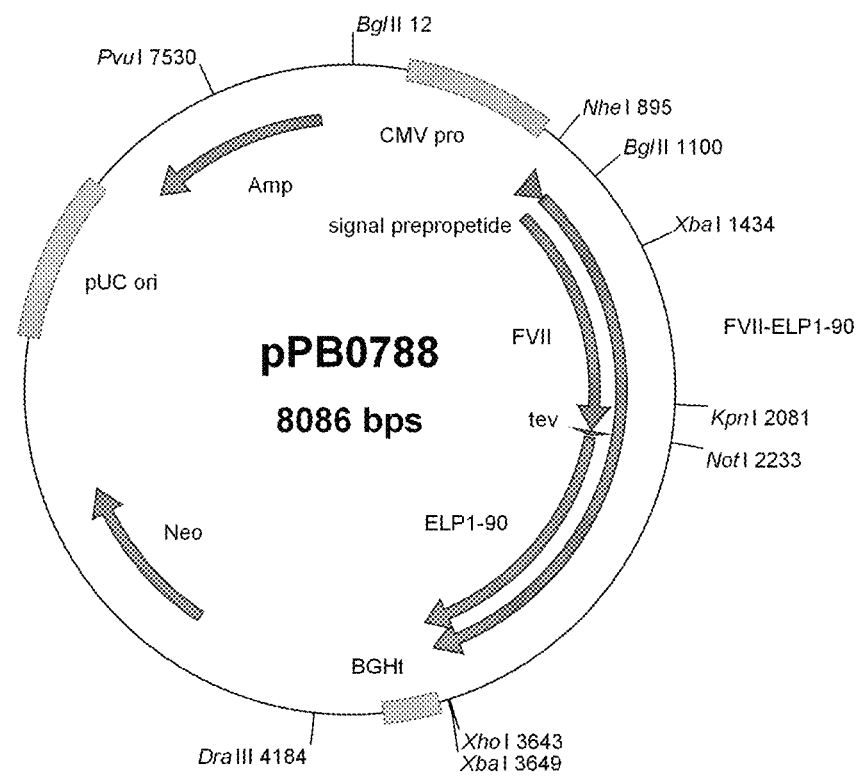
FIG. 7A depicts pPB0788, which encodes Factor VII-ELP1-90.

The resulting PCR fragment was digested with the restriction enzymes NheI and NotI and ligated into the plasmid pcDNA3.1+ELP1-90 previously digested with the restriction enzymes NheI and NotI (FIG. 7A).

Figure 9:
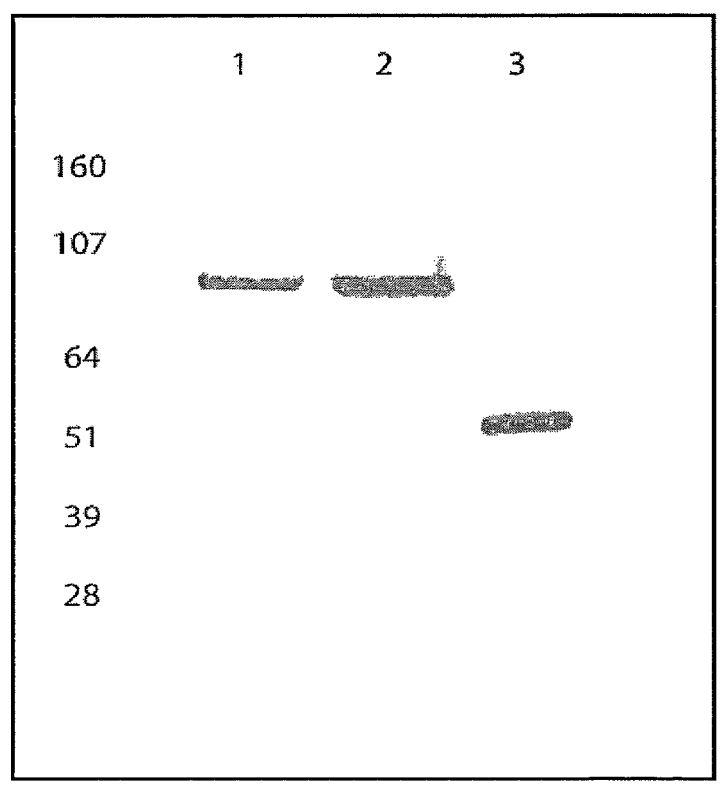
FIG. 9 is a Western blot for FVII-ELP1-90 from transient transfection of Freestyle HEK293, detected with mouse anti-human FVII monoclonal antibody. Lanes are: (1) culture media; (2) FVII ELP1-90 after purification by phase transition; and FVII control.
Figure 10:
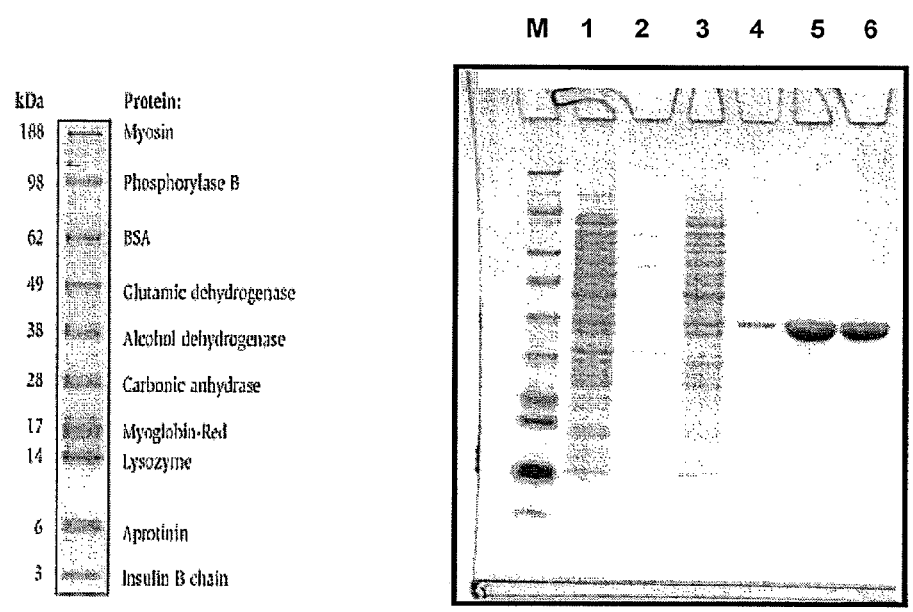
FIG. 10 is an SDS-PAGE showing recombinant production of an Exendin-4/ELP4-60 fusion. Lanes are: (M) Protein markers; (1) Exendin-4 ELP4-60 from total lysate; (2) Exendin-4 ELP4-60 from insoluble lysate; (3) Exendin-4 ELP4-60 from soluble lysate; (4) Exendin-4 ELP4-60 from 1st transition (equal volume); (5) Exendin-4 ELP4-60 from 2nd transition (concentrated); (6) Exendin-4 ELP4-60 from 3rd transition (concentrated).

The resulting plasmid, pcDNA3.1+FVII-ELP1-90, was transiently transfected into HEK293 cells and culture media harvested. The ELP fusion was purified by phase transition (FIGS. 9 and 10).

The nucleotide and amino acid sequences of the FactorVII-ELP fusion is shown in FIG. 7B. As shown, the FactorVII-ELP fusion protein contains a Tev protease linker between the Factory VII component and the ELP component. This linker is optional.

Example 8

Insulin ELP Fusion Protein

The cDNA for the human insulin gene is modified at the 5' and 3' ends for insertion in to pET24d-ELP1-90. The 5' primer adds an N-terminal methionine for bacterial expression and an NdeI restriction enzyme site. The 3' primer adds an XhoI restriction enzyme site. The PCR product and the plasmid are both digested with the restriction enzymes NdeI and XhoI and ligated together. The sequence of the insulin (Chains B, C, and A fused to ELP1 is shown in FIG. 8A.

Figure 8B:
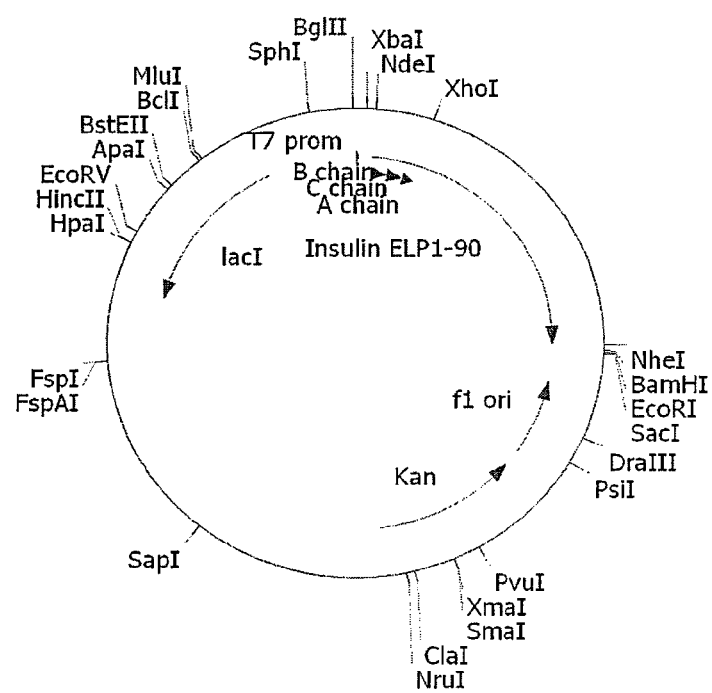
FIG. 8B depicts plasmid pET24d Insulin-ELP1-90 expressing the insulin/ELP fusion of FIG. 8A.

Correct insertion is determined by restriction digest and DNA sequencing. The resulting plasmid, designated pET24d Insulin-ELP1-90, is shown in FIG. 8B.

The native insulin form is generated after recovery from *E. coli* by treatment with trypsin and carboxypeptidase B to remove the C-peptide chain.

For correct processing of the N-terminus of the B-chain similar modifications to those made for the Exendin-4 fusion (protease cleavage site, signal sequence) can be implemented (see Example 4). Alternatively, the first two residues can be Met-Arg, which can also be removed by trypsin digestion in production of the final material (R. M. Belagaje, S. G. Reams, S. C. Ly and W. F. Prouty, *Increased production of low molecular weight recombinant proteins in Escherichia coli. Protein Sci.* 6, 1953-1962, 1997).

Additional constructs would place the insulin cDNA at the 3' end of the ELP for a C-terminal fusion, add linkers between the Insulin and ELP sequences, and/or use modified forms of insulin which have no C-peptide (single chain insulins as described) removing the need for additional processing.

Example 9

Synthesis of the ELP Gene for Conjugation

A gene encoding a 50 amino acid sequence was constructed from chemically-synthesized oligonucleotides using standard molecular biology protocols. The 50 amino acid sequence contained 10 repeats of the pentapeptide VPGXG (SEQ ID NO: 3), where the guest residues (V, G, and A in a 5:3:2 molar ratio) were selected to provide a Tt of 40° C. The gene was oligomerized end-to-end by standard molecular biology techniques, to produce an oligomeric ELP gene. Additionally a single 50 amino acid sequence was constructed containing the 10 repeat pentapeptide VPGXG (SEQ ID NO: 3) polypeptide where the guest residues were V, G, A and C in a 4:3:2:1 molar ratio. This sequence could be added at any cycle of the oligomerization process to introduce a single cysteine residue into the final construct at a chosen point along the length of the construct.

The example given here is with the ELP designated 1-90. This is based on the VPGXG (SEQ ID NO: 3) motif where X is a V, G or A in the ratio 5:3:2 in a 10-unit repeat, repeated 8× with a final (C-terminal) 10-unit repeat where X is a V, G, A and C in the ratio 4:3:2:1, i.e., [(VPGXG)10]9 (SEQ ID NO.: 3).

Alternatively, the residue could be one of either arginine, lysine, aspartic acid or glutamic acid. The purpose of these amino acids is to provide a reactive side chain for the chemical conjugation of, for example, insulin. In this particular case the use of an ELP would be to extend the circulating half-life of the therapeutic protein (e.g., insulin) to provide prolonged basal glucose control. Conjugated to an ELP that transitions at body temperature, the insulin would form a precipitated depot at the site of injection in a similar manner to Lantus® (Sanofi Aventis) but without the requirement for formulation in acidic (pH 4.0) conditions with m-cresol for a more tolerable injection.

Example 10

Potency and Half-Life of Factor VII-ELP

Figure 11:
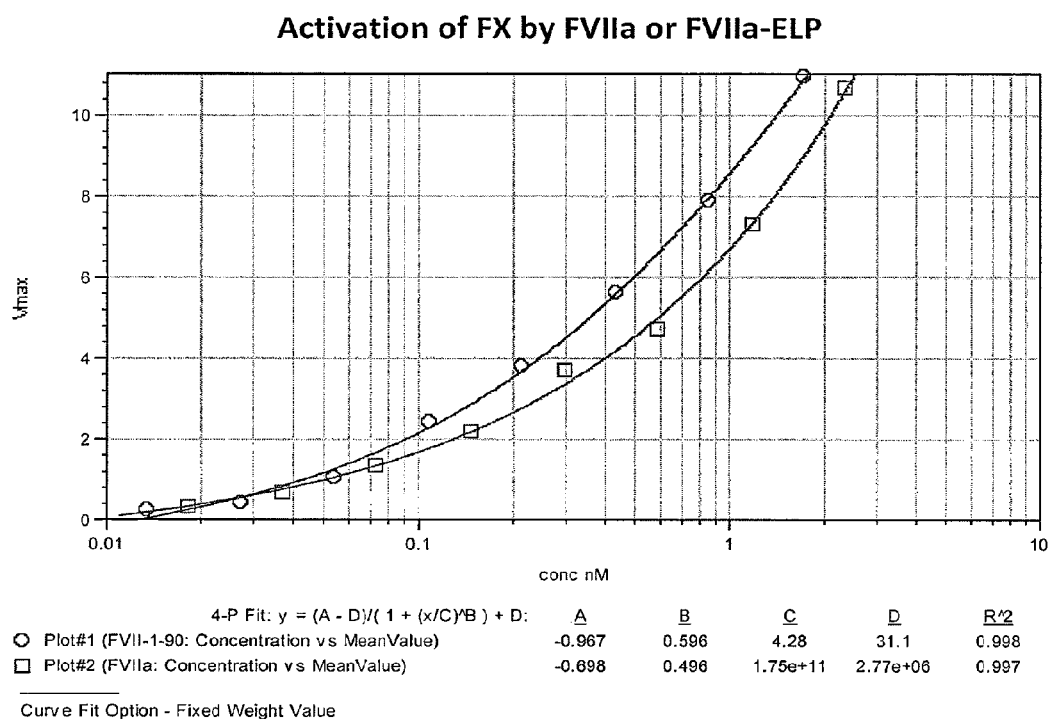
FIG. 11 shows the activation of Factor X by FactorVIIa-ELP1-90, and by Factor VIIa as a comparison. As shown, FactorVIIa-ELP retains full activity.

FIG. 11 shows the activation of Factor X by FactorVIIa-ELP1-90, and by Factor VIIa as a comparison. Factor VII-ELP was produced in HEK cells. Factor VIIa was derived from human plasma. As shown, FactorVIIa-ELP retains full activity.

Figure 12:
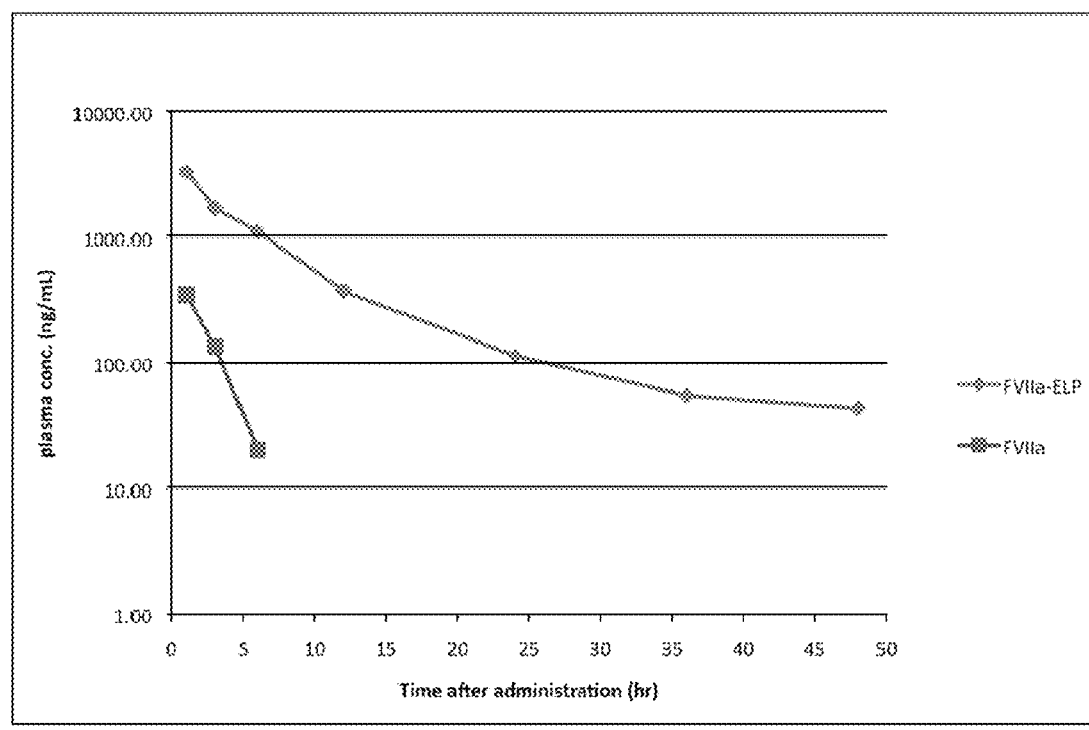
FIG. 12 shows that Factor VIIa-ELP1-90 has a long PK when administered by i.v. in rats. FactorVIIa has a $T_{1/2}$ of about 690 min. as compared to about 45-60 min, for Factor VIIa.

When administered to rats by i.v., Factor VII-ELP demonstrated a half-life of about 690 minutes. In contrast, Factor VII demonstrated a half-life of 45-60 minutes. Half-life in this example was measured by sandwich ELISA for FactorVII. FIG. 12.

Also in contrast, the reported half-life for NovoSeven™ is 45 minutes, the reported half-life for FactorVIIa-albumin fusion is 263 minutes, and the reported half-life for Factor VIIa-PEG is 300 minutes in mice and 600 minutes in dog.

Example 11

GLP-1 (or Exendin-4) In Vitro Bioassay

Activation of the GLP-1 receptor (GLP1R) results in production of cAMP secondary messenger within the cell. Therefore, GLP-1 or Exendin-4 analogs and corresponding therapeutic agents may be tested by their ability to activate GLP1R on the cell surface and produce cAMP.

For this bioassay CHO cells transfected with cDNA coding for GLP1R are used. These cells respond to stimulation by GLP-1 and produce high levels of cAMP. Log phase growing cells are plated and increasing concentrations of test compounds (e.g., therapeutic agent of the invention, or GLP-1 or exendin-4 functional analog) are added to the cells. After an appropriate incubation period (usually 15-60 min) in physiological buffer at 37° C. the cAMP produced is measured using a CatchPoint cAMP assay kit from Molecular Devices (Sunnyvale, Calif.). The $EC_{50}$ of each test compound as compared to GLP-1 peptide or Exendin-4 peptide (or as compared to an unfused or unconjugated counterpart of a therapeutic agent of the invention) is indicative of the changes in activity due to a specific modifications introduced into the peptide, or due to particular chemical or recombinant coupling to an ELP component.

Figure 13:
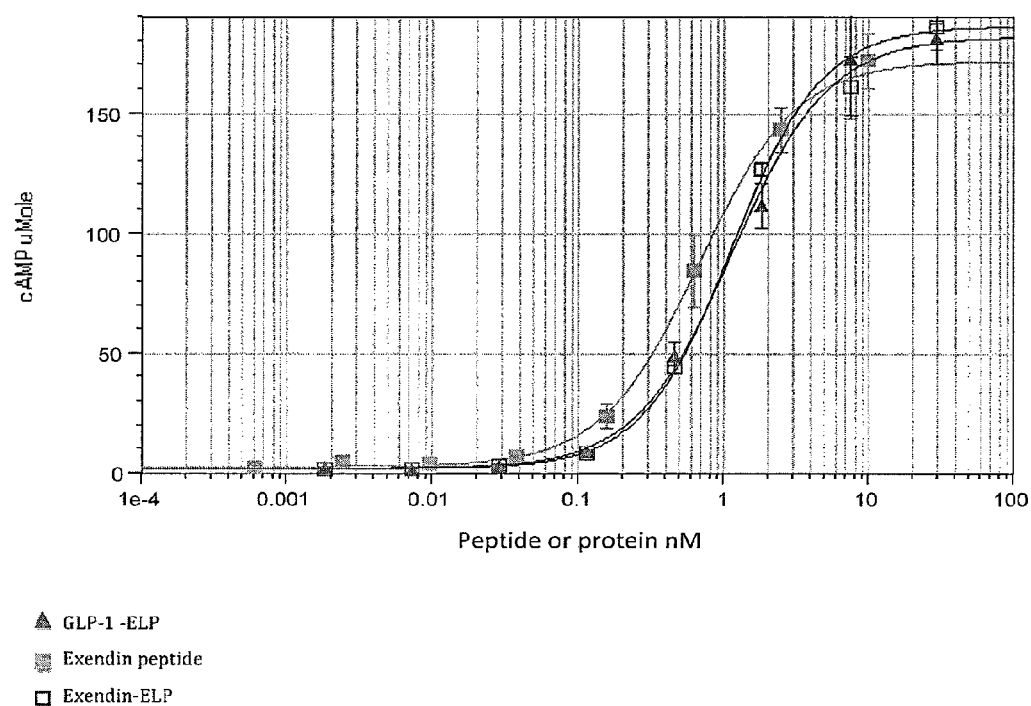
FIG. 13 shows the high in vitro activity of GLP1-ELP and Exendin-4-ELP, when compared to the activity of Exendin peptide.

As shown in FIG. 13, both GLP1-ELP (PB0868) and Exendin-4-ELP (PB 0859) maintain high activity in vitro, shown in comparison to Exendin alone. It is of note that the specific activity of Albugon® and Liraglutide® run 50-100 fold less than the exendin peptide.

Example 12

GLP-1 (or Exendin-4) In Vivo Bioassay

The activity of GLP-1 or Exendin analogues or corresponding therapeutic agents may be tested in animals. For this assay, normal or diabetic animals may be used. Diabetic animals with blood glucose concentration 300-500 mg/dl are injected with different doses of GLP-1 or Exendin analogues or corresponding therapeutic agent, and changes in blood glucose monitored with a glucometer. The drop in glucose at different times points post administration is compared to that resulting with standard amounts of GLP-1 or Exendin-4 peptide, or compared to an unfused or unconjugated counterpart of a therapeutic agent of the invention. Alternatively, the blood glucose excursion in normal or diabetic animals during specific time period after administration of exogenous glucose is compared to GLP-1 or Exendin-4 (or to unfused or unconjugated counterparts of therapeutic agents). In this way the activity of the analogues and fusion proteins can be compared to the natural peptides.

Figure 14:
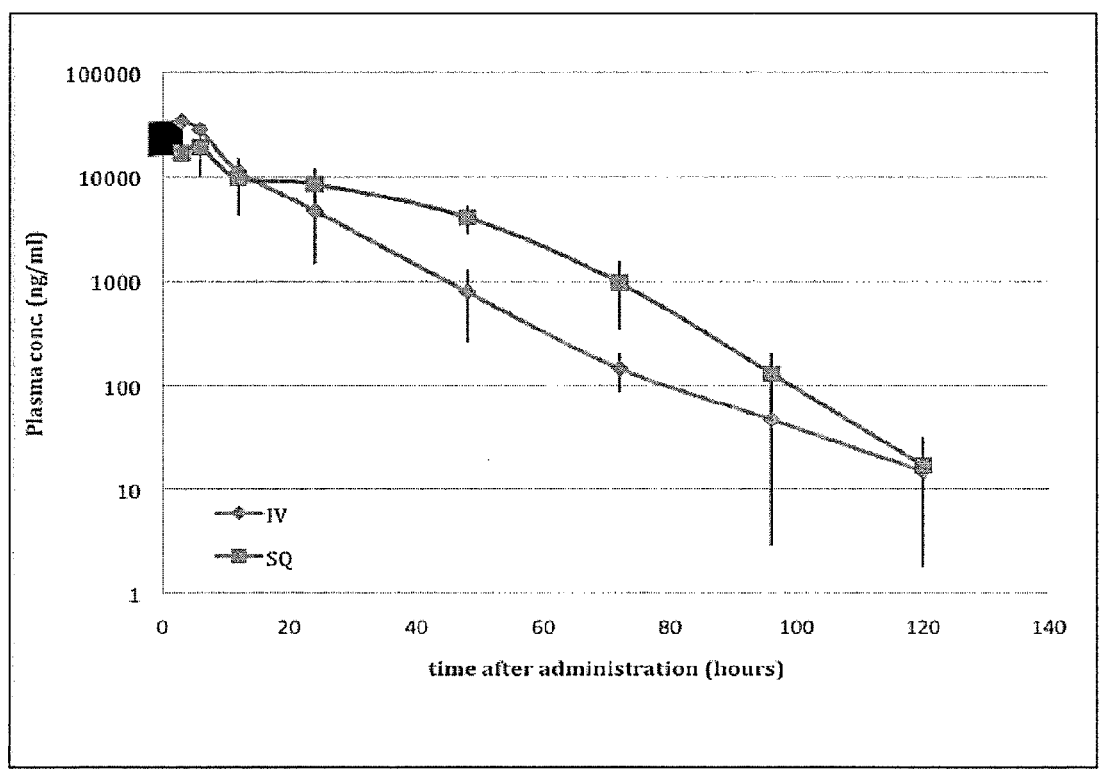
FIG. 14 shows that GLP1-ELP has a $T_{1/2}$ of about 12.9 hours when administered by i.v. to rats, and a $T_{1/2}$ of about 8.6 hours when administered subcutaneously (SQ).

FIG. 14 shows the pharmacokinetics of GLP1-ELP1-120 in rats administered both by i.v. and subcutaneously. Three rats were used for each time point. The dose was ~10 mg/kg. The $T_{1/2}$ when administered by i.v. was about 12.9 hours. The $T_{1/2}$ when administered subcutaneously was about 8.6 hours.

Figure 15:
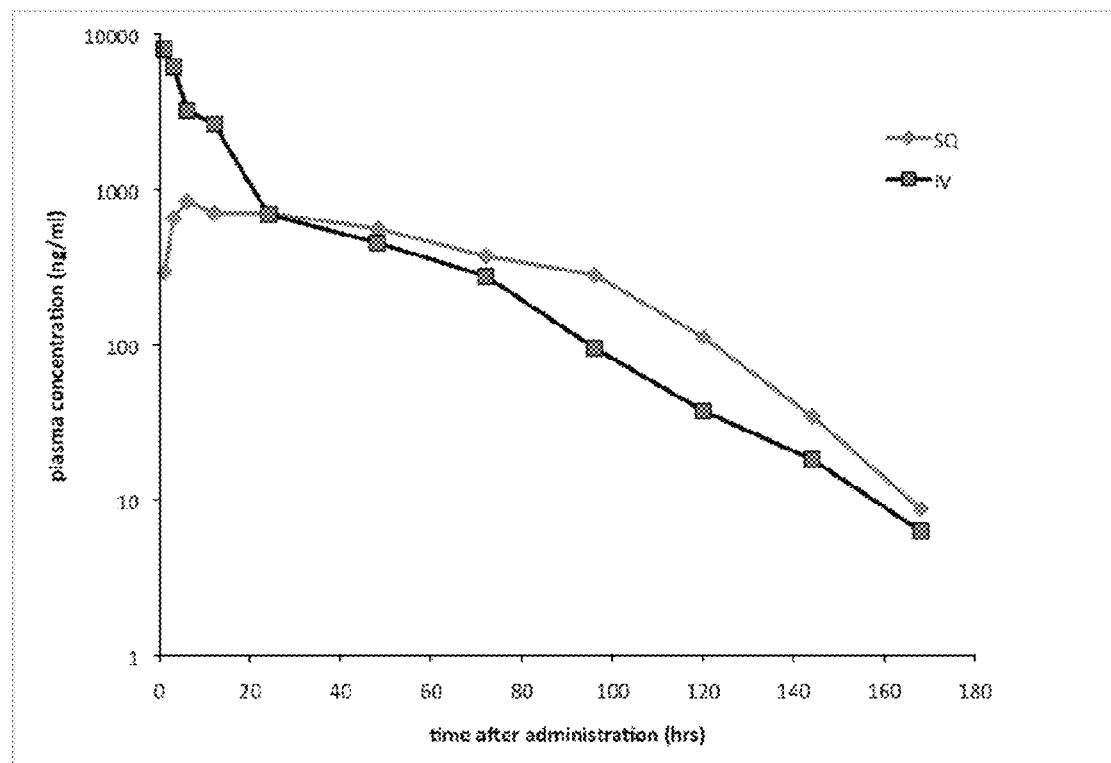
FIG. 15 shows that GLP-1 ELP has a long half-life in rabbits of about 20 hours when administered i.v., and about 24 hours when administered sub-cutaneously.

FIG. 15 shows the pharmacokinetics of GLP1-ELP1-120 in rabbits administered both by i.v. and subcutaneously. Three rabbits were used for each time point. The dose was ~1 mg/kg. The $T_{1/2}$ when administered by i.v. was about 20 hours. The $T_{1/2}$ when administered subcutaneously was about 24 hours.

Figure 16:
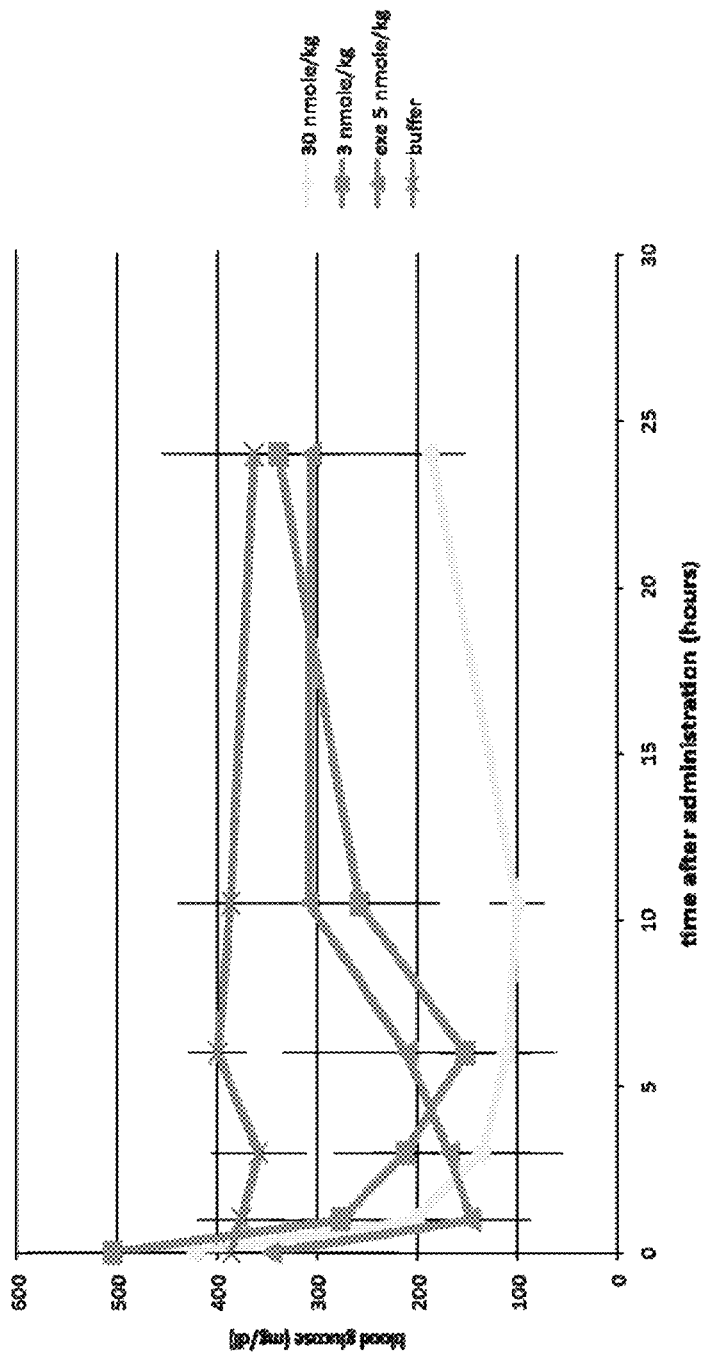
FIG. 16 shows sustained glycemic control in diabetic mice with GLP-1-ELP.

FIG. 16 shows the sustained glycemic control in diabetic mice with GLP1-ELP1-90.

All reference cited herein are hereby incorporated by reference in their entireties. While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein.

What is claimed is:

1. A therapeutic agent comprising a recombinant fusion between an elastic polypeptide and a therapeutic peptide, the therapeutic agent being formulated with a pharmaceutically acceptable carrier or excipient suitable for parenteral administration, and the therapeutic agent having an extended circulatory half-life when compared to the therapeutic peptide alone, wherein:
the therapeutic peptide comprises growth hormone; and
the elastic polypeptide has a pattern of proline-containing beta-turns forming an extended, non-globular structure, with no tertiary structure.

2. The therapeutic agent of claim 1, wherein the elastic polypeptide forms a spiral conformation.

3. The therapeutic agent of claim 1, wherein the elastic polypeptide comprises repeat amino acid motifs.

4. The therapeutic agent of claim 1, wherein the therapeutic agent is formulated for injection.

5. The therapeutic agent of claim 4 wherein the therapeutic agent is formulated for subcutaneous injection.

6. The therapeutic agent of claim 5, wherein the therapeutic agent is formulated for injection from about once to about five times per month.

7. The therapeutic agent of claim 4, wherein the therapeutic agent is formulated for intramuscular injection.

8. The therapeutic agent of claim 7 wherein the therapeutic agent is formulated for injection from about once to about five times per month.

9. The therapeutic agent of claim 1, wherein the growth hormone optionally has from 1 to 3 amino acid modifications independently selected from an insertion, deletion, and/or substitution.

10. The therapeutic agent of claim 1, wherein the growth hormone is flanked on each terminus by an elastin-like peptide.

11. A therapeutic agent comprising a recombinant fusion between an elastic polypeptide and a therapeutic peptide, the therapeutic agent being formulated with a pharmaceutically acceptable carrier or excipient suitable for parenteral administration, and the therapeutic agent having an extended circulatory half-life when compared to the therapeutic peptide alone, wherein:
the therapeutic peptide comprises growth hormone;
the elastic polypeptide has a pattern of proline-containing beta-turns forming an extended, non-globular structure, with no tertiary structure, and
the elastic polypeptide consists essentially of glycine and hydrophobic amino acids selected from alanine, valine, leucine, isoleucine, proline, phenylalanine, tryptophan, and methionine, and optionally serine, threonine, and glutamic acid.

12. The therapeutic agent of claim 11, wherein the elastic polypeptide contains amino acids selected from alanine, valine, glycine, serine, threonine, and glutamic acid.

13. The therapeutic agent of claim 11, wherein the elastic polypeptide forms a spiral conformation.

14. The therapeutic agent of claim 11, wherein the elastic polypeptide comprises repeat amino acid motifs.

15. The therapeutic agent of claim 11 wherein the therapeutic agent is formulated for injection.

16. The therapeutic agent of claim 15, wherein the therapeutic agent is formulated for subcutaneous injection.

17. The therapeutic agent of claim 16, wherein the therapeutic agent is formulated for injection from about once to about five times per month.

18. The therapeutic agent of claim 15, wherein the therapeutic agent is formulated for intramuscular injection.

19. The therapeutic agent of claim 18, wherein the therapeutic agent is formulated for injection from about once to about five times per month.

20. The therapeutic agent of claim 11, wherein the growth hormone optionally has from 1 to 3 amino acid modifications independently selected from an insertion, deletion, and/or substitution.

21. The therapeutic agent of claim 11, wherein the growth hormone is flanked on each terminus by an elastin-like peptide.

* * * * *

SEQUENCE LISTING

```
<160> NUMBER OF SEQ ID NOS: 59

<210> SEQ ID NO 1
<211> LENGTH: 4
<212> TYPE: PRT
<213> ORGANISM: Artificial Sequence
<220> FEATURE:
<223> OTHER INFORMATION: ELP component sequence

<400> SEQUENCE: 1

Val Pro Gly Gly
1

<210> SEQ ID NO 2
<211> LENGTH: 4
<212> TYPE: PRT
<213> ORGANISM: Artificial Sequence
<220> FEATURE:
<223> OTHER INFORMATION: ELP component sequence

<400> SEQUENCE: 2

Ile Pro Gly Gly
1

<210> SEQ ID NO 3
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (4)..(4)
<223> OTHER INFORMATION: Xaa can be any naturally occurring or
      non-natural amino acid

<400> SEQUENCE: 3

Val Pro Gly Xaa Gly
1               5

<210> SEQ ID NO 4
<211> LENGTH: 5
```

```
<212> TYPE: PRT
<213> ORGANISM: Artificial Sequence
<220> FEATURE:
<223> OTHER INFORMATION: ELP component sequence

<400> SEQUENCE: 4

Ala Val Gly Val Pro
1               5

<210> SEQ ID NO 5
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (4)..(4)
<223> OTHER INFORMATION: Xaa can be any naturally occurring or
      non-natural amino acid

<400> SEQUENCE: 5

Ile Pro Gly Xaa Gly
1               5

<210> SEQ ID NO 6
<211> LENGTH: 5
<212> TYPE: PRT
<213> ORGANISM: Artificial Sequence
<220> FEATURE:
<223> OTHER INFORMATION: ELP component sequence

<400> SEQUENCE: 6

Ile Pro Gly Val Gly
1               5

<210> SEQ ID NO 7
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (4)..(4)
<223> OTHER INFORMATION: Xaa can be any naturally occurring or
      non-natural amino acid

<400> SEQUENCE: 7

Leu Pro Gly Xaa Gly
1               5

<210> SEQ ID NO 8
<211> LENGTH: 5
<212> TYPE: PRT
<213> ORGANISM: Artificial Sequence
<220> FEATURE:
<223> OTHER INFORMATION: ELP component sequence

<400> SEQUENCE: 8

Leu Pro Gly Val Gly
1               5

<210> SEQ ID NO 9
<211> LENGTH: 6
<212> TYPE: PRT
<213> ORGANISM: Artificial Sequence
<220> FEATURE:
<223> OTHER INFORMATION: ELP component sequence
```

```
<400> SEQUENCE: 9

Val Ala Pro Gly Val Gly
1               5

<210> SEQ ID NO 10
<211> LENGTH: 8
<212> TYPE: PRT
<213> ORGANISM: Artificial Sequence
<220> FEATURE:
<223> OTHER INFORMATION: ELP component sequence

<400> SEQUENCE: 10

Gly Val Gly Val Pro Gly Val Gly
1               5

<210> SEQ ID NO 11
<211> LENGTH: 9
<212> TYPE: PRT
<213> ORGANISM: Artificial Sequence
<220> FEATURE:
<223> OTHER INFORMATION: ELP component sequence

<400> SEQUENCE: 11

Val Pro Gly Phe Gly Val Gly Ala Gly
1               5

<210> SEQ ID NO 12
<211> LENGTH: 9
<212> TYPE: PRT
<213> ORGANISM: Artificial Sequence
<220> FEATURE:
<223> OTHER INFORMATION: ELP component sequence

<400> SEQUENCE: 12

Val Pro Gly Val Gly Val Pro Gly Gly
1               5

<210> SEQ ID NO 13
<211> LENGTH: 30
<212> TYPE: PRT
<213> ORGANISM: Homo sapiens

<400> SEQUENCE: 13

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 14
<211> LENGTH: 38
<212> TYPE: PRT
<213> ORGANISM: Homo sapiens

<400> SEQUENCE: 14

His Gly Glu Gly Thr Phe Thr Ser Asp Leu Ser Lys Gln Met Glu Glu
1               5                   10                  15

Glu Ala Val Arg Leu Phe Glu Trp Leu Lys Asn Gly Gly Pro Ser Ser
            20                  25                  30

Gly Ala Pro Pro Pro Ser
            35

<210> SEQ ID NO 15
<211> LENGTH: 21
```

```
<212> TYPE: PRT
<213> ORGANISM: Homo sapiens

<400> SEQUENCE: 15

Gly Ile Val Glu Gln Cys Cys Ala Ser Val Cys Ser Leu Tyr Gln Leu
1               5                   10                  15

Glu Asn Tyr Cys Asn
            20

<210> SEQ ID NO 16
<211> LENGTH: 30
<212> TYPE: PRT
<213> ORGANISM: Homo sapiens

<400> SEQUENCE: 16

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30

<210> SEQ ID NO 17
<211> LENGTH: 30
<212> TYPE: PRT
<213> ORGANISM: Homo sapiens

<400> SEQUENCE: 17

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 18
<211> LENGTH: 44
<212> TYPE: PRT
<213> ORGANISM: Unknown
<220> FEATURE:
<223> OTHER INFORMATION: GLP-1 receptor agonist

<400> SEQUENCE: 18

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 19
<211> LENGTH: 31
<212> TYPE: PRT
<213> ORGANISM: Unknown
<220> FEATURE:
<223> OTHER INFORMATION: GLP-1 receptor agonist

<400> SEQUENCE: 19

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Arg Gly
            20                  25                  30

<210> SEQ ID NO 20
<211> LENGTH: 12
<212> TYPE: PRT
<213> ORGANISM: Artificial Sequence
```

<220> FEATURE:
<223> OTHER INFORMATION: Peptide linker sequence

<400> SEQUENCE: 20

Lys Asp Asp Asn Pro Asn Leu Pro Arg Leu Val Arg
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Peptide linker sequence

<400> SEQUENCE: 21

Gly Ala Gly Ser Ser Ser Arg Arg Ala Pro Gln Thr
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Non-cleavable spacer sequence
<220> FEATURE:
<221> NAME/KEY: MISC_FEATURE
<222> LOCATION: (2)..(4)
<223> OTHER INFORMATION: Gly residue is optional
<220> FEATURE:
<221> NAME/KEY: MISC_FEATURE
<222> LOCATION: (6)..(8)
<223> OTHER INFORMATION: Ser residue is optional

<400> SEQUENCE: 22

Gly Gly Gly Gly Ser Ser Ser Ser
1               5

<210> SEQ ID NO 23
<211> LENGTH: 300
<212> TYPE: DNA
<213> ORGANISM: Artificial Sequence
<220> FEATURE:
<223> OTHER INFORMATION: Exendin-4/ELP sequence

<400> SEQUENCE: 23
aattaatacg actcactata ggggaattgt gagcggataa caattcccct ctagaaataa      60
ttttgtttaa ctttaagaag gagatataca tatgcatggc gaaggcacct ttaccagcga     120
tctgagcaaa cagatggaag aagaagcggt gcgcctgttt attgaatggc tgaaaaacgg     180
cggcccgagc agcggcgcgc cgccgccgag cctcgagggc atgggtgggc gggcgtggg      240 tgttccgggc gtgggtgttc cgggtggcgg tgtgccgggc gcaggtgttc ctggtgtagg     300

<210> SEQ ID NO 24
<211> LENGTH: 69
<212> TYPE: PRT
<213> ORGANISM: Artificial Sequence
<220> FEATURE:
<223> OTHER INFORMATION: Exendin-4/ELP sequence

<400> SEQUENCE: 24

Met His Gly Glu Gly Thr Phe Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser Leu Glu Gly Met Gly Gly Pro Gly

-continued

```
                35                  40                  45
Val Gly Val Pro Gly Val Gly Val Pro Gly Gly Val Pro Gly Ala
            50                  55                  60

Gly Val Pro Gly Val
65

<210> SEQ ID NO 25
<211> LENGTH: 140
<212> TYPE: DNA
<213> ORGANISM: Artificial Sequence
<220> FEATURE:
<223> OTHER INFORMATION: Exendin-4/ELP sequence with N-terminal Tev
      cleavage site

<400> SEQUENCE: 25
tatggaaaac ctgtatttcc aacatggcga aggcaccttt accagcgatc tgagcaaaca      60
gatggaagaa gaagcggtgc gcctgtttat tgaatggctg aaaaacggcg gcccgagcag     120
cggcgcgccg ccgccgagcc                                                 140

<210> SEQ ID NO 26
<211> LENGTH: 46
<212> TYPE: PRT
<213> ORGANISM: Artificial Sequence
<220> FEATURE:
<223> OTHER INFORMATION: Exendin-4/ELP sequence with N-terminal Tev
      cleavage site

<400> SEQUENCE: 26

Met Glu Asn Leu Tyr Phe Gln His Gly Glu Gly Thr Phe Thr Ser Asp
1               5                   10                  15

Leu Ser Lys Gln Met Glu Glu Glu Ala Val Arg Leu Phe Ile Glu Trp
            20                  25                  30

Leu Lys Asn Gly Gly Pro Ser Ser Gly Ala Pro Pro Pro Ser
        35                  40                  45

<210> SEQ ID NO 27
<211> LENGTH: 155
<212> TYPE: DNA
<213> ORGANISM: Artificial Sequence
<220> FEATURE:
<223> OTHER INFORMATION: Exendin-4/ELP sequence with N-terminal Tev
      cleavage site and additional N-terminal sequence

<400> SEQUENCE: 27
tatggatatc ccaacgaccg aaaacctgta tttccaacat ggcgaaggca cctttaccag      60
cgatctgagc aaacagatgg aagaagaagc ggtgcgcctg tttattgaat ggctgaaaaa     120
cggcggcccg agcagcggcg cgccgccgcc gagcc                                155

<210> SEQ ID NO 28
<211> LENGTH: 51
<212> TYPE: PRT
<213> ORGANISM: Artificial Sequence
<220> FEATURE:
<223> OTHER INFORMATION: Exendin-4/ELP sequence with N-terminal Tev
      cleavage site and additional N-terminal sequence

<400> SEQUENCE: 28

Met Asp Ile Pro Thr Thr Glu Asn Leu Tyr Phe Gln His Gly Glu Gly
1               5                   10                  15

Thr Phe Thr Ser Asp Leu Ser Lys Gln Met Glu Glu Glu Ala Val Arg
            20                  25                  30
```

Leu Phe Ile Glu Trp Leu Lys Asn Gly Gly Pro Ser Ser Gly Ala Pro
            35                  40                  45

Pro Pro Ser
    50

<210> SEQ ID NO 29
<211> LENGTH: 176
<212> TYPE: DNA
<213> ORGANISM: Artificial Sequence
<220> FEATURE:
<223> OTHER INFORMATION: Exendin-4/ELP sequence with DsbA leader
      sequence

<400> SEQUENCE: 29
tatgaaaaag atttggctgg cgctggctgg tttagtttta gcgtttagcg catcggcgca      60
tggcgaaggc acctttacca gcgatctgag caaacagatg gaagaagaag cggtgcgcct     120
gtttattgaa tggctgaaaa acggcggccc gagcagcggc gcgccgccgc cgagcc        176

<210> SEQ ID NO 30
<211> LENGTH: 58
<212> TYPE: PRT
<213> ORGANISM: Artificial Sequence
<220> FEATURE:
<223> OTHER INFORMATION: Exendin-4/ELP sequence with DsbA leader
      sequence

<400> SEQUENCE: 30

Met Lys Lys Ile Trp Leu Ala Leu Ala Gly Leu Val Leu Ala Phe Ser
1               5                   10                  15

Ala Ser Ala His Gly Glu Gly Thr Phe Thr Ser Asp Leu Ser Lys Gln
            20                  25                  30

Met Glu Glu Glu Ala Val Arg Leu Phe Ile Glu Trp Leu Lys Asn Gly
        35                  40                  45

Gly Pro Ser Ser Gly Ala Pro Pro Pro Ser
    50                  55

<210> SEQ ID NO 31
<211> LENGTH: 400
<212> TYPE: DNA
<213> ORGANISM: Artificial Sequence
<220> FEATURE:
<223> OTHER INFORMATION: Insulin/ELP sequence

<400> SEQUENCE: 31
ctagaaataa ttttgtttaa ctttaagaag gagatataca tatgtttgtg aaccaacacc      60
tgtgcggctc acacctggtg gaagctctct acctagtgtg cggggaacga ggcttcttct     120
acacacccaa gacccgccgg gaggcagagg acctgcaggt ggggcaggtg gagctgggcg     180
ggggccctgg tgcaggcagc ctgcagccct tggccctgga ggggtccctg cagaagcgtg     240
gcattgtgga acaatgctgt accagcatct gctccctcta ccagctggag aactactgca     300
acctcgaggg catgggtggg ccgggcgtgg gtgttccggg cgtgggtgtt ccgggtggcg     360
gtgtgccggg cgcaggtgtt cctggtgtag gtgtgccggg                          400

<210> SEQ ID NO 32
<211> LENGTH: 119
<212> TYPE: PRT
<213> ORGANISM: Artificial Sequence
<220> FEATURE:
<223> OTHER INFORMATION: Insulin/ELP sequence

<400> SEQUENCE: 32

```
Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Arg
            20                  25                  30

Arg Glu Ala Glu Asp Leu Gln Val Gly Gln Val Glu Leu Gly Gly Gly
        35                  40                  45

Pro Gly Ala Gly Ser Leu Gln Pro Leu Ala Leu Glu Gly Ser Leu Gln
    50                  55                  60

Lys Arg Gly Ile Val Glu Gln Cys Cys Thr Ser Ile Cys Ser Leu Tyr
65                  70                  75                  80

Gln Leu Glu Asn Tyr Cys Asn Leu Glu Gly Met Gly Gly Pro Gly Val
                85                  90                  95

Gly Val Pro Gly Val Gly Val Pro Gly Gly Gly Val Pro Gly Ala Gly
            100                 105                 110

Val Pro Gly Val Gly Val Pro
            115
```

```
<210> SEQ ID NO 33
<211> LENGTH: 406
<212> TYPE: PRT
<213> ORGANISM: Homo sapiens

<400> SEQUENCE: 33

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
```

His Val Val Pro Leu Cys Leu Pro Glu Arg Thr Phe Ser Glu Arg Thr
            245                 250                 255
Leu Ala Phe Val Arg Phe Ser Leu Val Ser Gly Trp Gly Gln Leu Leu
        260                 265                 270
Asp Arg Gly Ala Thr Ala Leu Glu Leu Met Val Leu Asn Val Pro Arg
    275                 280                 285
Leu Met Thr Gln Asp Cys Leu Gln Gln Ser Arg Lys Val Gly Asp Ser
290                 295                 300
Pro Asn Ile Thr Glu Tyr Met Phe Cys Ala Gly Tyr Ser Asp Gly Ser
305                 310                 315                 320
Lys Asp Ser Cys Lys Gly Asp Ser Gly Gly Pro His Ala Thr His Tyr
            325                 330                 335
Arg Gly Thr Trp Tyr Leu Thr Gly Ile Val Ser Trp Gly Gln Gly Cys
        340                 345                 350
Ala Thr Val Gly His Phe Gly Val Tyr Thr Arg Val Ser Gln Tyr Ile
    355                 360                 365
Glu Trp Leu Gln Lys Leu Met Arg Ser Glu Pro Arg Pro Gly Val Leu
370                 375                 380
Leu Arg Ala Pro Phe Pro
385                 390                 395                 400

405

<210> SEQ ID NO 34
<211> LENGTH: 1218
<212> TYPE: DNA
<213> ORGANISM: Homo sapiens

<400> SEQUENCE: 34

```
gccaacgcgt tcctggagga gctgcggccg ggctccctgg agagggagtg caaggaggag    60
cagtgctcct cgaggaggc ccgggagatc ttcaaggacg cggagaggac gaagctgttc   120
tggatttctt acagtgatgg ggaccagtgt gcctcaagtc catgccagaa tgggggctcc   180
tgcaaggacc agctccagtc ctatatctgc ttctgcctcc ctgccttcga gggccggaac   240
tgtgagacgc acaaggatga ccagctgatc tgtgtgaacg agaacggcgg ctgtgagcag   300
tactgcagtg accacacggg caccaagcgc tcctgtcggt gccacgaggg gtactctctg   360
ctggcagacg gggtgtcctg cacacccaca gttgaatatc catgtggaaa atacctatt   420
ctagaaaaaa gaaatgccag caaacccaa ggccgaattg tggggggcaa ggtgtgcccc   480
aaagggagt gtccatggca ggtcctgttg ttggtgaatg gagctcagtt gtgtggggg   540
acctgatca acaccatctg ggtggtctcc gcggccact gttcgacaa atcaagaac   600
tggaggaacc tgatcgcggt gctgggcgag cacgacctca gcgagcacga cggggatgag   660
cagagccggc gggtggcgca ggtcatcatc cccagcacgt acgtcccggg caccaccaac   720
cacgacatcg cgctgctccg cctgcaccag cccgtggtcc tcactgacca tgtggtgccc   780
ctctgcctgc ccgaacggac gttctctgag aggacgctgg ccttcgtgcg cttctcattg   840
gtcagcggct ggggccagct gctggaccgt ggcgccacgg ccctggagct catggtgctc   900
aacgtgcccc ggctgatgac ccaggactgc ctgcagcagt cacggaaggt gggagactcc   960
ccaaatatca cggagtacat gttctgtgcc ggctactcgg atggcagcaa ggactcctgc  1020
aaggggggaca gtggaggccc acatgccacc cactaccggg gcacgtggta cctgacgggc  1080
atcgtcagct ggggccaggg ctgcgcaacc gtgggccact tgggggtgta caccagggtc  1140
tcccagtaca tcgagtggct gcaaaagctc atgcgctcag agccacgccc aggagtcctc  1200
```
ctgcgagccc catttccc 1218

<210> SEQ ID NO 35
<211> LENGTH: 33
<212> TYPE: DNA
<213> ORGANISM: Homo sapiens

<400> SEQUENCE: 35
tatgcatggc gaaggcacct ttaccagcga tct 33

<210> SEQ ID NO 36
<211> LENGTH: 62
<212> TYPE: DNA
<213> ORGANISM: Homo sapiens

<400> SEQUENCE: 36
gagcaaacag atggaagaag aagcggtgcg cctgtttatt gaatggctga aaacggcgg 60 cc 62

<210> SEQ ID NO 37
<211> LENGTH: 27
<212> TYPE: DNA
<213> ORGANISM: Homo sapiens

<400> SEQUENCE: 37
cgagcagcgg cgcgccgccg ccgagcc 27

<210> SEQ ID NO 38
<211> LENGTH: 35
<212> TYPE: DNA
<213> ORGANISM: Homo sapiens

<400> SEQUENCE: 38
tcgaggctcg gcggcggcgc gccgctgctc gggcc 35

<210> SEQ ID NO 39
<211> LENGTH: 63
<212> TYPE: DNA
<213> ORGANISM: Homo sapiens

<400> SEQUENCE: 39
gccgtttttc agccattcaa taaacaggcg caccgcttct tcttccatct gtttgctcag 60
atc 63

<210> SEQ ID NO 40
<211> LENGTH: 26
<212> TYPE: DNA
<213> ORGANISM: Homo sapiens

<400> SEQUENCE: 40
gctggtaaag gtgccttcgc catgca 26

<210> SEQ ID NO 41
<211> LENGTH: 51
<212> TYPE: DNA
<213> ORGANISM: Artificial Sequence
<220> FEATURE:
<223> OTHER INFORMATION: Primer for Exendin-4/ELP sequence with
      N-terminal Tev cleavage site

<400> SEQUENCE: 41
tatggaaaac ctgtatttcc aacatggcga aggcaccttt accagcgatc t 51

<210> SEQ ID NO 42
<211> LENGTH: 44
<212> TYPE: DNA
<213> ORGANISM: Artificial Sequence
<220> FEATURE:
<223> OTHER INFORMATION: Primer for Exendin-4/ELP sequence with
      N-terminal Tev cleavage site

<400> SEQUENCE: 42
gctggtaaag gtgccttcgc catgttggaa atacaggttt tcca                    44

<210> SEQ ID NO 43
<211> LENGTH: 66
<212> TYPE: DNA
<213> ORGANISM: Artificial Sequence
<220> FEATURE:
<223> OTHER INFORMATION: Primer for Exendin-4/ELP sequence with
      N-terminal Tev cleavage site and additional N-terminal sequence

<400> SEQUENCE: 43
tatggatatc ccaacgaccg aaaacctgta tttccaacat ggcgaaggca cctttaccag    60
cgatct                                                              66

<210> SEQ ID NO 44
<211> LENGTH: 59
<212> TYPE: DNA
<213> ORGANISM: Artificial Sequence
<220> FEATURE:
<223> OTHER INFORMATION: Primer for Exendin-4/ELP sequence with
      N-terminal Tev cleavage site and additional N-terminal sequence

<400> SEQUENCE: 44
gctggtaaag gtgccttcgc catgttggaa atacaggttt tcggtcgttg ggatatcca    59

<210> SEQ ID NO 45
<211> LENGTH: 87
<212> TYPE: DNA
<213> ORGANISM: Artificial Sequence
<220> FEATURE:
<223> OTHER INFORMATION: Primer for Exendin-4/ELP sequence with DsbA
      leader sequence

<400> SEQUENCE: 45
tatgaaaaag atttggctgg cgctggctgg tttagtttta gcgtttagcg catcggcgca    60
tggcgaaggc acctttacca gcgatct                                       87

<210> SEQ ID NO 46
<211> LENGTH: 80
<212> TYPE: DNA
<213> ORGANISM: Artificial Sequence
<220> FEATURE:
<223> OTHER INFORMATION: Primer for Exendin-4/ELP sequence with DsbA
      leader sequence

<400> SEQUENCE: 46
gctggtaaag gtgccttcgc catgcgccga tgcgctaaac gctaaaacta aaccagccag    60
cgccagccaa atcttttca                                                80

<210> SEQ ID NO 47
<211> LENGTH: 39
<212> TYPE: DNA
<213> ORGANISM: Artificial Sequence
<220> FEATURE:
<223> OTHER INFORMATION: Primer for Insulin/ELP sequence

<400> SEQUENCE: 47
gaaggagata tacatatgtt tgtgaaccaa cacctgtgc                                39

<210> SEQ ID NO 48
<211> LENGTH: 30
<212> TYPE: DNA
<213> ORGANISM: Artificial Sequence
<220> FEATURE:
<223> OTHER INFORMATION: Primer for Insulin/ELP sequence

<400> SEQUENCE: 48
cccatgccct cgaggttgca gtagttctcc                                          30

<210> SEQ ID NO 49
<211> LENGTH: 27
<212> TYPE: DNA
<213> ORGANISM: Homo sapiens

<400> SEQUENCE: 49
ctagctagca tggtctccca ggccctc                                             27

<210> SEQ ID NO 50
<211> LENGTH: 33
<212> TYPE: DNA
<213> ORGANISM: Homo sapiens

<400> SEQUENCE: 50
tattcttgcg gccgcgggaa atggggctcg cag                                      33

<210> SEQ ID NO 51
<211> LENGTH: 261
<212> TYPE: DNA
<213> ORGANISM: Homo sapiens

<400> SEQUENCE: 51
atgtttgtga accaacacct gtgcggctca cacctggtgg aagctctcta cctagtgtgc         60
ggggaacgag gcttcttcta cacacccaag acccgccggg aggcagagga cctgcaggtg        120
gggcaggtgg agctgggcgg gggccctggt gcaggcagcc tgcagccctt ggccctggag        180
gggtccctgc agaagcgtgg cattgtggaa caatgctgta ccagcatctg ctccctctac        240
cagctggaga actactgcaa c                                                  261

<210> SEQ ID NO 52
<211> LENGTH: 87
<212> TYPE: PRT
<213> ORGANISM: Homo sapiens

<400> SEQUENCE: 52

Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Arg
            20                  25                  30

Arg Glu Ala Glu Asp Leu Gln Val Gly Gln Val Glu Leu Gly Gly Gly
        35                  40                  45

Pro Gly Ala Gly Ser Leu Gln Pro Leu Ala Leu Glu Gly Ser Leu Gln
    50                  55                  60

Lys Arg Gly Ile Val Glu Gln Cys Cys Thr Ser Ile Cys Ser Leu Tyr
65                  70                  75                  80

Gln Leu Glu Asn Tyr Cys Asn

<210> SEQ ID NO 53
<211> LENGTH: 1700
<212> TYPE: DNA
<213> ORGANISM: Artificial Sequence
<220> FEATURE:
<223> OTHER INFORMATION: pPB0868 DNA sequence

<400> SEQUENCE: 53

```
taatacgact cactataggg gaattgtgag cggataacaa ttcccctcta gaaataattt     60
tgtttaactt taagaaggag atatacatat ggagaacctg tatttccaac atggcgaagg    120
taccttaca agcgatgtta gttcatatct ggagggccag gcggcaaagg aattcattgc    180
gtggctggtg aaaggccgcg gcctcgaggg catgggtggg ccgggcgtgg gtgttccggg    240
cgtgggtgtt ccgggtggcg gtgtgccggg cgcaggtgtt cctggtgtag gtgtgccggg    300
tgttggtgtg ccgggtgttg gtgtaccagg tggcggtgtt ccgggtgcag gcgttccggg    360
tggcggtgtg ccgggcgtgg gtgttccggg cgtgggtgtt ccgggtggcg gtgtgccggg    420
cgcaggtgtt cctggtgtag gtgtgccggg tgttggtgtg ccgggtgttg gtgtaccagg    480
tggcggtgtt ccgggtgcag gcgttccggg tggcggtgtg ccgggcgtgg gtgttccggg    540
cgtgggtgtt ccgggtggcg gtgtgccggg cgcaggtgtt cctggtgtag gtgtgccggg    600
tgttggtgtg ccgggtgttg gtgtaccagg tggcggtgtt ccgggtgcag gcgttccggg    660
tggcggtgtg ccgggcgtgg gtgttccggg cgtgggtgtt ccgggtggcg gtgtgccggg    720
cgcaggtgtt cctggtgtag gtgtgccggg tgttggtgtg ccgggtgttg gtgtaccagg    780
tggcggtgtt ccgggtgcag gcgttccggg tggcggtgtg ccgggcgtgg gtgttccggg    840
cgtgggtgtt ccgggtggcg gtgtgccggg cgcaggtgtt cctggtgtag gtgtgccggg    900
tgttggtgtg ccgggtgttg gtgtaccagg tggcggtgtt ccgggtgcag gcgttccggg    960
tggcggtgtg ccgggcgtgg gtgttccggg cgtgggtgtt ccgggtggcg gtgtgccggg   1020
cgcaggtgtt cctggtgtag gtgtgccggg tgttggtgtg ccgggtgttg gtgtaccagg   1080
tggcggtgtt ccgggtgcag gcgttccggg tggcggtgtg ccgggcgtgg gtgttccggg   1140
cgtgggtgtt ccgggtggcg gtgtgccggg cgcaggtgtt cctggtgtag gtgtgccggg   1200
tgttggtgtg ccgggtgttg gtgtaccagg tggcggtgtt ccgggtgcag gcgttccggg   1260
tggcggtgtg ccgggcgtgg gtgttccggg cgtgggtgtt ccgggtggcg gtgtgccggg   1320
cgcaggtgtt cctggtgtag gtgtgccggg tgttggtgtg ccgggtgttg gtgtaccagg   1380
tggcggtgtt ccgggtgcag gcgttccggg tggcggtgtg ccgggcgtgg gtgttccggg   1440
cgtgggtgtt ccgggtggcg gtgtgccggg cgcaggtgtt cctggtgtag gtgtgccggg   1500
tgttggtgtg ccgggtgttg gtgtaccagg tggcggtgtt ccgggtgcag gcgttccggg   1560
tggcggtgtg ccgggctggc cgtgataagc tagcatgact ggtggacagc aaatgggtcg   1620
gatccgaatt cgagctccgt cgagcaccac caccaccacc actgagatcc ggctgctaac   1680
aaagcccgaa aggaagctga                                              1700
```

<210> SEQ ID NO 54
<211> LENGTH: 498
<212> TYPE: PRT
<213> ORGANISM: Artificial Sequence
<220> FEATURE:
<223> OTHER INFORMATION: GLP-1(A8G,7-37)ELP1-90 amino acid sequence

<400> SEQUENCE: 54

-continued

```
Met Glu Asn Leu Tyr Phe Gln His Gly Glu Gly Thr Phe Thr Ser Asp
1               5                   10                  15

Val Ser Ser Tyr Leu Glu Gly Gln Ala Ala Lys Glu Phe Ile Ala Trp
            20                  25                  30

Leu Val Lys Gly Arg Gly Leu Glu Gly Met Gly Gly Pro Gly Val Gly
            35                  40                  45

Val Pro Gly Val Gly Val Pro Gly Gly Val Pro Gly Ala Gly Val
50                  55                  60

Pro Gly Val Gly Val Pro Gly Val Gly Val Pro Gly Val Gly Val Pro
65                  70                  75                  80

Gly Gly Gly Val Pro Gly Ala Gly Val Pro Gly Gly Val Pro Gly
                85                  90                  95

Val Gly Val Pro Gly Val Gly Val Pro Gly Gly Val Pro Gly Ala
            100                 105                 110

Gly Val Pro Gly Val Gly Val Pro Gly Val Gly Val Pro Gly Val Gly
            115                 120                 125

Val Pro Gly Gly Gly Val Pro Gly Ala Gly Val Pro Gly Gly Val
            130                 135                 140

Pro Gly Val Gly Val Pro Gly Val Gly Val Pro Gly Gly Gly Val Pro
145                 150                 155                 160

Gly Ala Gly Val Pro Gly Val Gly Val Pro Gly Val Gly Val Pro Gly
                165                 170                 175

Val Gly Val Pro Gly Gly Gly Val Pro Gly Ala Gly Val Pro Gly Gly
            180                 185                 190

Gly Val Pro Gly Val Gly Val Pro Gly Val Gly Val Pro Gly Gly Gly
            195                 200                 205

Val Pro Gly Ala Gly Val Pro Gly Val Gly Val Pro Gly Val Gly Val
            210                 215                 220

Pro Gly Val Gly Val Pro Gly Gly Gly Val Pro Gly Ala Gly Val Pro
225                 230                 235                 240

Gly Gly Gly Val Pro Gly Val Gly Val Pro Gly Val Gly Val Pro Gly
                245                 250                 255

Gly Gly Val Pro Gly Ala Gly Val Pro Gly Val Gly Val Pro Gly Val
            260                 265                 270

Gly Val Pro Gly Val Gly Val Pro Gly Gly Gly Val Pro Gly Ala Gly
            275                 280                 285

Val Pro Gly Gly Gly Val Pro Gly Val Gly Val Pro Gly Val Gly Val
            290                 295                 300

Pro Gly Gly Gly Val Pro Gly Ala Gly Val Pro Gly Gly Val Pro
305                 310                 315                 320

Gly Val Gly Val Pro Gly Val Gly Val Pro Gly Gly Gly Val Pro Gly
                325                 330                 335

Ala Gly Val Pro Gly Gly Gly Val Pro Gly Gly Val Pro Gly Val
            340                 345                 350

Gly Val Pro Gly Val Gly Val Pro Gly Ala Gly Val Pro Gly Gly Gly
            355                 360                 365

Val Pro Gly Val Gly Val Pro Gly Val Gly Val Pro Gly Gly Gly Val
            370                 375                 380

Pro Gly Ala Gly Val Pro Gly Gly Val Pro Gly Val Gly Val Pro
385                 390                 395                 400

Gly Val Gly Val Pro Gly Gly Val Pro Gly Ala Gly Val Pro Gly
                405                 410                 415
```

Val Gly Val Pro Gly Val Gly Val Pro Gly Val Gly
            420                 425                 430

Gly Val Pro Gly Ala Gly Val Pro Gly Gly Val Pro Gly Val Gly
            435                 440                 445

Val Pro Gly Val Gly Val Pro Gly Gly Val Pro Gly Ala Gly Val
450                 455                 460

Pro Gly Val Gly Val Pro Gly Val Gly Val Pro Gly Val Gly Val Pro
465                 470                 475                 480

Gly Gly Gly Val Pro Gly Ala Gly Val Pro Gly Gly Gly Val Pro Gly
            485                 490                 495

Trp Pro

<210> SEQ ID NO 55
<211> LENGTH: 2050
<212> TYPE: DNA
<213> ORGANISM: Artificial Sequence
<220> FEATURE:
<223> OTHER INFORMATION: pPB1022 DNA sequence

<400> SEQUENCE: 55

```
taatacgact cactataggg gaattgtgag cggataacaa ttcccctcta gaaataattt      60
tgtttaactt taagaaggag atatacatat ggagaacctg tatttccaac atggcgaagg    120
tacctttaca agcgatgtta gttcatatct ggagggccag gcggcaaagg aattattgc    180
gtggctggtg aaaggccgcg gcgtgccggg cgtgggtgtt ccgggcgtgg gtgttccggg    240
tggcggtgtg ccgggcgcag gtgttcctgg tgtaggtgtg ccgggtgttg gtgtgccggg    300
tgttggtgta ccaggtggcg gtgttccggg tgcaggcgtt ccgggtggcg gtgtgccggg    360
cgtgggtgtt ccgggcgtgg gtgttccggg tggcggtgtg ccgggcgcag gtgttcctgg    420
tgtaggtgtg ccgggtgttg gtgtgccggg tgttggtgta ccaggtggcg gtgttccggg    480
tgcaggcgtt ccgggtggcg gtgtgccggg cgtgggtgtt ccgggcgtgg gtgttccggg    540
tggcggtgtg ccgggcgcag gtgttcctgg tgtaggtgtg ccgggtgttg gtgtgccggg    600
tgttggtgta ccaggtggcg gtgttccggg tgcaggcgtt ccgggtggcg gtgtgccggg    660
cgtgggtgtt ccgggcgtgg gtgttccggg tggcggtgtg ccgggcgcag gtgttcctgg    720
tgtaggtgtg ccgggtgttg gtgtgccggg tgttggtgta ccaggtggcg gtgttccggg    780
tgcaggcgtt ccgggtggcg gtgtgccggg cgtgggtgtt ccgggcgtgg gtgttccggg    840
tggcggtgtg ccgggcgcag gtgttcctgg tgtaggtgtg ccgggtgttg gtgtgccggg    900
tgttggtgta ccaggtggcg gtgttccggg tgcaggcgtt ccgggtggcg gtgtgccggg    960
cgtgggtgtt ccgggcgtgg gtgttccggg tggcggtgtg ccgggcgcag gtgttcctgg   1020
tgtaggtgtg ccgggtgttg gtgtgccggg tgttggtgta ccaggtggcg gtgttccggg   1080
tgcaggcgtt ccgggtggcg gtgtgccggg cgtgggtgtt ccgggcgtgg gtgttccggg   1140
tggcggtgtg ccgggcgcag gtgttcctgg tgtaggtgtg ccgggtgttg gtgtgccggg   1200
tgttggtgta ccaggtggcg gtgttccggg tgcaggcgtt ccgggtggcg gtgtgccggg   1260
cgtgggtgtt ccgggcgtgg gtgttccggg tggcggtgtg ccgggcgcag gtgttcctgg   1320
tgtaggtgtg ccgggtgttg gtgtgccggg tgttggtgta ccaggtggcg gtgttccggg   1380
tgcaggcgtt ccgggtggcg gtgtgccggg cgtgggtgtt ccgggcgtgg gtgttccggg   1440
tggcggtgtg ccgggcgcag gtgttcctgg tgtaggtgtg ccgggtgttg gtgtgccggg   1500
tgttggtgta ccaggtggcg gtgttccggg tgcaggcgtt ccgggtggcg gtgtgccggg   1560
```

```
cgtgggtgtt ccgggcgtgg ggtgttccggg tggcggtgtg ccgggcgcag gtgttcctgg      1620
tgtaggtgtg ccgggtgttg gtgtgccggg tgttggtgta ccaggtggcg gtgttccggg      1680
tgcaggcgtt ccgggtggcg gtgtgccggg cgtgggtgtt ccgggcgtgg gtgttccggg      1740
tggcggtgtg ccgggcgcag gtgttcctgg tgtaggtgtg ccgggtgttg gtgtgccggg      1800
tgttggtgta ccaggtggcg gtgttccggg tgcaggcgtt ccgggtggcg gtgtgccggg      1860
cgtgggtgtt ccgggcgtgg gtgttccggg tggcggtgtg ccgggcgcag gtgttcctgg      1920
tgtaggtgtg ccgggtgttg gtgtgccggg tgttggtgta ccaggtggcg gtgttccggg      1980
tgcaggcgtt ccgggtggcg gtgtgccggg ctggccgtga taagctagca tgactggtgg      2040
acagcaaatg                                                            2050
```

<210> SEQ ID NO 56
<211> LENGTH: 643
<212> TYPE: PRT
<213> ORGANISM: Artificial Sequence
<220> FEATURE:
<223> OTHER INFORMATION: GLP-1(A8G,7-37)ELP1-120 amino acid sequence

<400> SEQUENCE: 56

```
Met Glu Asn Leu Tyr Phe Gln His Gly Glu Gly Thr Phe Thr Ser Asp
1               5                   10                  15

Val Ser Ser Tyr Leu Glu Gly Gln Ala Ala Lys Glu Phe Ile Ala Trp
            20                  25                  30

Leu Val Lys Gly Arg Gly Val Pro Gly Val Gly Val Pro Gly Val Gly
        35                  40                  45

Val Pro Gly Gly Gly Val Pro Gly Ala Gly Val Pro Gly Val Gly Val
    50                  55                  60

Pro Gly Val Gly Val Pro Gly Val Gly Val Pro Gly Gly Gly Val Pro
65                  70                  75                  80

Gly Ala Gly Val Pro Gly Gly Val Pro Gly Val Gly Val Pro Gly
                85                  90                  95

Val Gly Val Pro Gly Gly Val Pro Gly Ala Gly Val Pro Gly Val
            100                 105                 110

Gly Val Pro Gly Val Gly Val Pro Gly Val Gly Val Pro Gly Gly Gly
        115                 120                 125

Val Pro Gly Ala Gly Val Pro Gly Gly Val Pro Gly Val Gly Val
    130                 135                 140

Pro Gly Val Gly Val Pro Gly Gly Gly Val Pro Gly Ala Gly Val Pro
145                 150                 155                 160

Gly Val Gly Val Pro Gly Val Gly Val Pro Gly Val Gly Val Pro Gly
                165                 170                 175

Gly Gly Val Pro Gly Ala Gly Val Pro Gly Gly Gly Val Pro Gly Val
            180                 185                 190

Gly Val Pro Gly Val Gly Val Pro Gly Gly Gly Val Pro Gly Ala Gly
        195                 200                 205

Val Pro Gly Val Gly Val Pro Gly Val Gly Val Pro Gly Val Gly Val
    210                 215                 220

Pro Gly Gly Gly Val Pro Gly Ala Gly Val Pro Gly Gly Gly Val Pro
225                 230                 235                 240

Gly Val Gly Val Pro Gly Val Gly Val Pro Gly Val Gly Val Pro Gly
                245                 250                 255

Ala Gly Val Pro Gly Val Gly Val Pro Gly Val Gly Val Pro Gly Val
            260                 265                 270
```

-continued

Gly Val Pro Gly Gly Val Pro Gly Ala Gly Val Pro Gly Gly Gly
            275                 280                 285

Val Pro Gly Val Gly Val Pro Gly Val Gly Val Pro Gly Gly Gly Val
290                 295                 300

Pro Gly Ala Gly Val Pro Gly Val Gly Val Pro Gly Val Gly Val Pro
305                 310                 315                 320

Gly Val Gly Val Pro Gly Gly Val Pro Gly Ala Gly Val Pro Gly
            325                 330                 335

Gly Gly Val Pro Gly Val Gly Val Pro Gly Val Gly Val Pro Gly Gly
            340                 345                 350

Gly Val Pro Gly Ala Gly Val Pro Gly Val Gly Val Pro Gly Val Gly
            355                 360                 365

Val Pro Gly Val Gly Val Pro Gly Gly Val Pro Gly Ala Gly Val
370                 375                 380

Pro Gly Gly Gly Val Pro Gly Val Gly Val Pro Gly Val Gly Val Pro
385                 390                 395                 400

Gly Gly Gly Val Pro Gly Ala Gly Val Pro Gly Val Gly Val Pro Gly
            405                 410                 415

Val Gly Val Pro Gly Val Gly Val Pro Gly Gly Gly Val Pro Gly Ala
            420                 425                 430

Gly Val Pro Gly Gly Gly Val Pro Gly Val Gly Val Pro Gly Val Gly
            435                 440                 445

Val Pro Gly Gly Gly Val Pro Gly Ala Gly Val Pro Gly Val Gly Val
450                 455                 460

Pro Gly Val Gly Val Pro Gly Gly Gly Val Pro Gly Gly Gly Val Pro
465                 470                 475                 480

Gly Ala Gly Val Pro Gly Gly Val Pro Gly Val Gly Val Pro Gly
            485                 490                 495

Val Gly Val Pro Gly Gly Gly Val Pro Gly Ala Gly Val Pro Gly Val
            500                 505                 510

Gly Val Pro Gly Val Gly Val Pro Gly Val Gly Val Pro Gly Gly Gly
            515                 520                 525

Val Pro Gly Ala Gly Val Pro Gly Gly Val Pro Gly Val Gly Val
530                 535                 540

Pro Gly Val Gly Val Pro Gly Gly Val Pro Gly Ala Gly Val Pro
545                 550                 555                 560

Gly Val Gly Val Pro Gly Val Gly Val Pro Gly Val Gly Val Pro Gly
            565                 570                 575

Gly Gly Val Pro Gly Ala Gly Val Pro Gly Gly Gly Val Pro Gly Val
            580                 585                 590

Gly Val Pro Gly Val Gly Val Pro Gly Gly Gly Val Pro Gly Ala Gly
            595                 600                 605

Val Pro Gly Val Gly Val Pro Gly Val Gly Val Pro Gly Val Gly Val
610                 615                 620

Pro Gly Gly Gly Val Pro Gly Ala Gly Val Pro Gly Gly Gly Val Pro
625                 630                 635                 640

Gly Trp Pro

<210> SEQ ID NO 57
<211> LENGTH: 3700
<212> TYPE: DNA
<213> ORGANISM: Artificial Sequence
<220> FEATURE:
<223> OTHER INFORMATION: pPB0788 DNA sequence

```
<400> SEQUENCE: 57
gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg     780
gtaggcgtgt acggtgggag gtctatataa gcagagctct ctggctaact agagaaccca    840
ctgcttactg gcttatcgaa attaatacga ctcactatag ggagacccaa gctggctagc    900
atggtctccc aggccctcag gctcctctgc cttctgcttg gcttcaggg ctgcctggct      960
gcagtcttcg taacccagga ggaagcccac ggcgtcctgc accggcgccg gcgcgccaac    1020
gcgttcctgg aggagctacg gccgggctcc ctggagaggg agtgcaagga ggagcagtgc    1080
tccttcgagg aggcccggga gatcttcaag gacgcggaga ggacgaagct gttctggatt    1140
tcttacagtg atgggaccca gtgtgcctca gtccatgcc agaatggggg ctcctgcaag    1200
gaccagctcc agtcctatat ctgcttctgc ctccctgcct tcgagggccg gaactgtgag    1260
acgcacaagg atgaccagct gatctgtgtg aacgagaacg gcggctgtga gcagtactgc    1320
agtgaccaca cgggcaccaa gcgctcctgt cggtgccacg agggtactc tctgctggca     1380
gacggggtgt cctgcacacc cacagttgaa tatccatgtg gaaaaatacc tattctagaa    1440
aaaagaaatg ccagcaaacc ccaaggccga attgtggggg gcaaggtgtg ccccaaaggg    1500
gagtgtccat ggcaggtcct gttgttggtg aatggagctc agttgtgtgg ggggaccctg    1560
atcaacacca tctgggtggt ctccgcggcc cactgtttcg acaaaatcaa gaactggagg    1620
aacctgatcg cggtgctggg cgagcacgac ctcagcgagc acgacgggga tgagcagagc    1680
cggcgggtgg cgcaggtcat catccccagc acgtacgtcc cgggcaccac caaccacgac    1740
atcgcgctgc tccgcctgca ccagcccgtg gtcctcactg accatgtggt gccctctgc    1800
ctgcccgaac ggacgttctc tgagaggacg ctggccttcg tgcgcttctc attggtcagc    1860
ggctggggcc agctgctgga ccgtggcgcc acgccctgg agctcatggt cctcaacgtg    1920
cccggctga tgacccagga ctgcctgcag cagtcacgga aggtgggaga ctccccaaat    1980
atcacggagt acatgttctg tgccggctac tcggatggca gcaaggactc ctgcaagggg    2040
gacagtggag gccacatgc cacccactac cggggcacgt ggtacctgac gggcatcgtc    2100
agctgggggc agggctgcgc aaccgtgggc cactttgggg tgtacaccag ggtctcccag    2160
tacatcgagt ggctgcaaaa gctcatgcgc tcagagccac gcccaggagt cctcctgcga    2220
gccccatttc ccgcggccgc tgaaaacctg tattttcagg gtggggccgc tgggccgggc    2280
gtgggagttc ccggcgtggg agttcccgga ggcggagtgc ccggcgcagg agttcctgga    2340
```

```
gtcggagtgc cggagttgg agtgcccgga gttggagtcc caggaggcgg agtccccgga    2400
gcaggcgtcc ccggaggcgg agtgccgggc gtgggagttc ccggcgtggg agttcccgga    2460
ggcggagtgc ccggcgcagg agttcctgga gtcggagtgc ccggagttgg agtgcccgga    2520
gttggagtcc caggaggcgg agtccccgga gcaggcgtcc ccggaggcgg agtgccgggc    2580
gtgggagttc ccggcgtggg agtcccgga ggcggagtgc ccggcgcagg agttcctgga    2640
gtcggagtgc ccggagttgg agtgcccgga gttggagtcc caggaggcgg agtccccgga    2700
gcaggcgtcc ccggaggcgg agtgccgggc gtgggagttc ccggcgtggg agttcccgga    2760
ggcggagtgc ccggcgcagg agttcctgga gtcggagtgc ccggagttgg agtgcccgga    2820
gttggagtcc caggaggcgg agtccccgga gcaggcgtcc ccggaggcgg agtgccgggc    2880
gtgggagttc ccggcgtggg agtcccgga ggcggagtgc ccggcgcagg agttcctgga    2940
gtcggagtgc ccggagttgg agtgcccgga gttggagtcc caggaggcgg agtccccgga    3000
gcaggcgtcc ccggaggcgg agtgccgggc gtgggagttc ccggcgtggg agttcccgga    3060
ggcggagtgc ccggcgcagg agttcctgga gtcggagtgc ccggagttgg agtgcccgga    3120
gttggagtcc caggaggcgg agtccccgga gcaggcgtcc ccggaggcgg agtgccgggc    3180
gtgggagttc ccggcgtggg agtcccgga ggcggagtgc ccggcgcagg agttcctgga    3240
gtcggagtgc ccggagttgg agtgcccgga gttggagtcc caggaggcgg agtccccgga    3300
gcaggcgtcc ccggaggcgg agtgccgggc gtgggagttc ccggcgtggg agttcccgga    3360
ggcggagtgc ccggcgcagg agttcctgga gtcggagtgc ccggagttgg agtgcccgga    3420
gttggagtcc caggaggcgg agtccccgga gcaggcgtcc ccggaggcgg agtgccgggc    3480
gtgggagttc ccggcgtggg agtcccgga ggcggagtgc ccggcgcagg agttcctgga    3540
gtcggagtgc ccggagttgg agtgcccgga gttggagtcc caggaggcgg agtccccgga    3600
gcaggcgtcc ccggaggcgg agtgccgggc tggccttgat gactcgagtc tagagggccc    3660
gtttaaaccc gctgatcagc ctcgactgtg ccttctagtt                          3700
```

<210> SEQ ID NO 58
<211> LENGTH: 912
<212> TYPE: PRT
<213> ORGANISM: Artificial Sequence
<220> FEATURE:
<223> OTHER INFORMATION: Factor VII-ELP 1-90 amino acid sequence

<400> SEQUENCE: 58

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile

-continued

```
            115                 120                 125
Cys Val Asn Glu Asn Gly Gly Cys Glu Gln Tyr Cys Ser Asp His Thr
            130                 135                 140
Gly Thr Lys Arg Ser Cys Arg Cys His Glu Gly Tyr Ser Leu Leu Ala
145                 150                 155                 160
Asp Gly Val Ser Cys Thr Pro Thr Val Glu Tyr Pro Cys Gly Lys Ile
                165                 170                 175
Pro Ile Leu Glu Lys Arg Asn Ala Ser Lys Pro Gln Gly Arg Ile Val
                180                 185                 190
Gly Gly Lys Val Cys Pro Lys Gly Glu Cys Pro Trp Gln Val Leu Leu
            195                 200                 205
Leu Val Asn Gly Ala Gln Leu Cys Gly Gly Thr Leu Ile Asn Thr Ile
            210                 215                 220
Trp Val Val Ser Ala Ala His Cys Phe Asp Lys Ile Lys Asn Trp Arg
225                 230                 235                 240
Asn Leu Ile Ala Val Leu Gly Glu His Asp Leu Ser Glu His Asp Gly
                245                 250                 255
Asp Glu Gln Ser Arg Arg Val Ala Gln Val Ile Ile Pro Ser Thr Tyr
                260                 265                 270
Val Pro Gly Thr Thr Asn His Asp Ile Ala Leu Leu Arg Leu His Gln
                275                 280                 285
Pro Val Val Leu Thr Asp His Val Val Pro Leu Cys Leu Pro Glu Arg
            290                 295                 300
Thr Phe Ser Glu Arg Thr Leu Ala Phe Val Arg Phe Ser Leu Val Ser
305                 310                 315                 320
Gly Trp Gly Gln Leu Leu Asp Arg Gly Ala Thr Ala Leu Glu Leu Met
                325                 330                 335
Val Leu Asn Val Pro Arg Leu Met Thr Gln Asp Cys Leu Gln Gln Ser
                340                 345                 350
Arg Lys Val Gly Asp Ser Pro Asn Ile Thr Glu Tyr Met Phe Cys Ala
            355                 360                 365
Gly Tyr Ser Asp Gly Ser Lys Asp Ser Cys Lys Gly Asp Ser Gly Gly
            370                 375                 380
Pro His Ala Thr His Tyr Arg Gly Thr Trp Tyr Leu Thr Gly Ile Val
385                 390                 395                 400
Ser Trp Gly Gln Gly Cys Ala Thr Val Gly His Phe Gly Val Tyr Thr
                405                 410                 415
Arg Val Ser Gln Tyr Ile Glu Trp Leu Gln Lys Leu Met Arg Ser Glu
                420                 425                 430
Pro Arg Pro Gly Val Leu Leu Arg Ala Pro Phe Pro Ala Ala Ala Glu
            435                 440                 445
Asn Leu Tyr Phe Gln Gly Gly Ala Ala Gly Pro Gly Val Gly Val Pro
            450                 455                 460
Gly Val Gly Val Pro Gly Gly Val Pro Gly Ala Gly Val Pro Gly
465                 470                 475                 480
Val Gly Val Pro Gly Val Gly Val Pro Gly Val Gly Val Pro Gly Gly
                485                 490                 495
Gly Val Pro Gly Ala Gly Val Pro Gly Gly Val Pro Gly Val Gly
            500                 505                 510
Val Pro Gly Val Gly Val Pro Gly Gly Val Pro Gly Ala Gly Val
            515                 520                 525
Pro Gly Val Gly Val Pro Gly Val Gly Val Pro Gly Val Gly Val Pro
            530                 535                 540
```

Gly Gly Gly Val Pro Gly Ala Gly Val Pro Gly Gly Val Pro Gly
545                 550                 555                 560

Val Gly Val Pro Gly Val Gly Val Pro Gly Gly Val Pro Gly Ala
                565                 570                 575

Gly Val Pro Gly Val Gly Val Pro Gly Val Gly Val Pro Gly Val Gly
                580                 585                 590

Val Pro Gly Gly Gly Val Pro Gly Ala Gly Val Pro Gly Gly Val
                595                 600                 605

Pro Gly Val Gly Val Pro Gly Val Gly Val Pro Gly Gly Val Pro
    610                 615                 620

Gly Ala Gly Val Pro Gly Val Gly Val Pro Gly Val Gly Val Pro Gly
625                 630                 635                 640

Val Gly Val Pro Gly Gly Gly Val Pro Gly Ala Gly Val Pro Gly Gly
                645                 650                 655

Gly Val Pro Gly Val Gly Val Pro Gly Val Gly Val Pro Gly Gly Gly
                660                 665                 670

Val Pro Gly Ala Gly Val Pro Gly Val Gly Val Pro Gly Val Gly Val
                675                 680                 685

Pro Gly Val Gly Val Pro Gly Gly Val Pro Gly Ala Gly Val Pro
    690                 695                 700

Gly Gly Gly Val Pro Gly Val Gly Val Pro Gly Val Gly Val Pro Gly
705                 710                 715                 720

Gly Gly Val Pro Gly Ala Gly Val Pro Gly Val Gly Val Pro Gly Val
                725                 730                 735

Gly Val Pro Gly Val Gly Val Pro Gly Gly Gly Val Pro Gly Ala Gly
                740                 745                 750

Val Pro Gly Gly Gly Val Pro Gly Val Gly Val Pro Gly Val Gly Val
                755                 760                 765

Pro Gly Gly Gly Val Pro Gly Ala Gly Val Pro Gly Val Gly Val Pro
    770                 775                 780

Gly Val Gly Val Pro Gly Val Gly Val Pro Gly Gly Gly Val Pro Gly
785                 790                 795                 800

Ala Gly Val Pro Gly Gly Gly Val Pro Gly Val Gly Val Pro Gly Val
                805                 810                 815

Gly Val Pro Gly Gly Gly Val Pro Gly Ala Gly Val Pro Gly Val Gly
                820                 825                 830

Val Pro Gly Val Gly Val Pro Gly Val Gly Val Pro Gly Gly Gly Val
                835                 840                 845

Pro Gly Ala Gly Val Pro Gly Gly Gly Val Pro Gly Val Gly Val Pro
    850                 855                 860

Gly Val Gly Val Pro Gly Gly Gly Val Pro Gly Ala Gly Val Pro Gly
865                 870                 875                 880

Val Gly Val Pro Gly Val Gly Val Pro Gly Val Gly Val Pro Gly Gly
                885                 890                 895

Gly Val Pro Gly Ala Gly Val Pro Gly Gly Gly Val Pro Gly Trp Pro
                900                 905                 910

<210> SEQ ID NO 59
<211> LENGTH: 31
<212> TYPE: PRT
<213> ORGANISM: Unknown
<220> FEATURE:
<223> OTHER INFORMATION: GLP-1 receptor agonist

<400> SEQUENCE: 59

```
His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20              25              30
```